United States Patent [19]
Matsunaga et al.

[11] Patent Number: 5,852,011
[45] Date of Patent: Dec. 22, 1998

[54] BENZIMIDAZOLE DERIVATIVES

[75] Inventors: Akio Matsunaga; Yuki Nakajima; Hiroshi Kohno, all of Mobara, Japan; Hironori Komatsu, San Diego, Calif.; Hajime Edatsugi, Mobara, Japan; Daiji Iwata, Mobara, Japan; Kimiko Takezawa, Mobara, Japan

[73] Assignee: Mitsui Chemicals, Inc., Tokyo, Japan

[21] Appl. No.: 581,608

[22] PCT Filed: May 30, 1995

[86] PCT No.: PCT/JP95/01034

§ 371 Date: Jan. 19, 1996

§ 102(e) Date: Jan. 19, 1996

[87] PCT Pub. No.: WO95/32960

PCT Pub. Date: Dec. 7, 1995

[30] Foreign Application Priority Data

| May 31, 1994 | [JP] | Japan | 6-118984 |
| Feb. 23, 1995 | [JP] | Japan | 7-035562 |
| Apr. 17, 1995 | [JP] | Japan | 7-090522 |

[51] Int. Cl.$^6$ ............... C07D 403/04; C07D 409/04; A61K 31/44; A61K 31/415

[52] U.S. Cl. ............... 514/228.2; 514/234.5; 514/255; 514/323; 514/338; 514/394; 544/134; 544/138; 544/139; 544/140; 544/141; 544/62; 544/367; 544/372; 544/374; 546/199; 546/273.4; 548/304.7; 548/306.1

[58] Field of Search ............... 548/518, 304.7, 548/306.1; 514/394, 228.2, 234.5, 255, 323, 338; 546/199, 273.4; 544/134, 138, 139, 140, 141, 62, 367, 372, 374

[56] References Cited

U.S. PATENT DOCUMENTS 4,053,472  10/1977  Ruter et al. ............... 544/139

FOREIGN PATENT DOCUMENTS 1094903  12/1967  United Kingdom.

OTHER PUBLICATIONS

Rufer et al., Chem. Abstract 75:140764, 1971.

Journal of Medicinal Chemistry, vol. 33, No. 2, 1990, Washington, U.S., pp. 814–819, XP002007402, W.A. Denny et al., "Potential Antitumor Agents . . . ".

Journal of Medicinal Chemistry, vol. 36, No. 2, 1993, Washington, U.S., pp. 1746–1753, XP002007403, T.A. Fairley et al, "Structure, DNA Minor Groove Binding, and . . . ".

Primary Examiner—Mukund J. Shah
Assistant Examiner—Deepak R. Rao
Attorney, Agent, or Firm—Burns, Doane, Swecker & Mathis, L.L.P.

[57] ABSTRACT

Disclosed are compounds represented by the following chemical formula (I) and pharmacologically acceptable salts thereof which are novel compounds useful as anticancer agents, antiviral agents or antimicrobial agents.

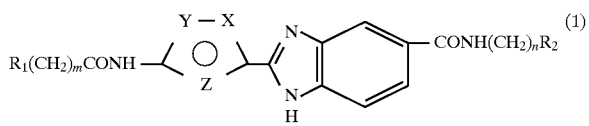

18 Claims, No Drawings

BENZIMIDAZOLE DERIVATIVES

BACKGROUND OF THE INVENTION

1. Field of the Invention

This invention relates to novel benzimidazole derivatives bondable to DNAs to inhibit proliferation of cells, and also to pharmaceutical compositions containing same, especially their use as anticancer agents, antiviral agents, antimicrobial agents or the like.

2. Description of the Related Art

DNA-acting compounds include those useful as anticancer agents. For example, adriamycin is useful as an anticancer agent which intercalates into DNA. Further, DNA-reacting compounds such as cisplatin and mitomycin are also employed widely. Anticancer effects which are derived from such action on DNA are considered to have been ascertained although their mechanisms have not been fully elucidated. In the meantime, it has come to be known that distamycin and netropsin are substances bondable to DNA and having anti-tumor activities (Nature, 203, 1064–65 (1964)). These substances have attracted attention as groove binders which are different in their manner of bonding with DNA compared to conventional anticancer agents.

According to the conventional knowledge of anticancer agents, it is presently by no means possible to foresee which structural part of a compound is really needed for interaction with DNA or what other structures can substitute for the part of the compound. It is however meaningful to predict the presence of other compounds having a desired structure and to make a search for them. A strong demand is therefore believed to exist for the search of such a new structure so that a novel anticancer agent can be created.

Also known are compounds in which the structure of an alkylating agent has been bonded to distamycin derivatives. Typical examples are found inter alia in J. Am. Chem. Soc., 107, 8266(1985), EP 246868, WO 93-13739, J. Med. Chem., 32, 774(1989). Compounds in each of which the structure of an alkylating agent has been bound to a compound similar to distamycin by bonding N-methyl-imidazole as a partial structure via an amide bond are also known (U.S. Pat. No. 5,273,991). These compounds include those making use of a bis(2-chloroethyl)amino residual group as an alkylating agent. This residual group is already known to be a structural part of anticancer agents. For example, chlorambucil is known as an anticancer agent which contains a bis(2-chloroethyl)amino residual group in its molecule. The anticancer activities of this compound are presumed to result from alkylation of DNA, enzymes or the like. However the value of addition of the structure of an alkylating agent, for example, the structure of chloroethylamine, as a part of the structure of a DNA-bonding anticancer agent is still hardly considered to have been ascertained.

SUMMARY OF THE INVENTION

An object of the present invention is to provide a novel compound which acts on DNA or contains a structural part capable of acting on DNA and which is useful as an anticancer agent, an antiviral agent, an antimicrobial agent or the like.

The above-described distamycin is a typical example of compounds which bind to DNA. Distamycin is characterized in that a pyrrole ring is bonded via an amide bond. As DNA-binding compounds include several other types of compounds, the present inventors made a search for a new structure under the assumption of existence of compounds which have a structure different from the known compounds and exhibit anticancer action. As a result, novel compounds having the structure created from the direct bonding of a 5-membered aromatic ring with benzimidazole have been chosen as compounds useful as anticancer agents. Preferred examples include 1H-2-[1-methyl-(substituted)pyrrol-2-yl] benzimidazole-5-carboxamide derivatives, 1H-2-[(substituted)pyrrol-2-yl]benzimidazole-5-carboxamide derivatives, 1H-2-[(substituted)imidazol-2-yl] benzimidazole-5-carboxamide derivatives, 1H-2-[1-methyl-(substituted)imidazol-2-yl]benzimidazole-5-carboxamide derivatives, 1H-2-[(substituted)furan-2-yl]benzimidazole-5-carboxamide derivatives, 1H-2-[(substituted)thiophen-2-yl] benzimidazole-5-carboxamide derivatives and 1H-2-[(substituted)thiophen-3-yl]benzimidazole-5-carboxamide derivatives. These compounds have novel structures and are not known at all as useful anticancer agents. These compounds, for example, 1H-2-(4-formyl-1-methyl-pyrrol-2-yl)benzimidazol-5-[N-(2-amidinoethyl)]-carboxamide have been found to bind to DNA, indicated by the measurement of an increased Tm value (Tm: the melting temperature of double-stranded DNA) and, when tested in vitro, showed a similar degree of proliferation-inhibiting activity against tumor cells as distamycin.

Compounds in which structure of an alkylating agent has been bonded to distamycin derivatives are known so that there is the chance that their activities as anticancer agents may be enhanced by the addition of an alkylating moiety. In this regard, an investigation was also conducted at the same time. Compounds containing chlorambucil or another alkylating partial structure showed much higher anticancer activities than distamycin or chlorambucil. From this, the compound having a structure in which an aromatic 5-membered ring is bound directly to benzimidazole has been found to provide a highly active anticancer agent when an alkylating agent is added into the same molecule.

DETAILED DESCRIPTION OF THE INVENTION AND PREFERRED EMBODIMENTS

The present invention therefore provides a compound represented by the following chemical formula (1) or a pharmacologically acceptable salt thereof:

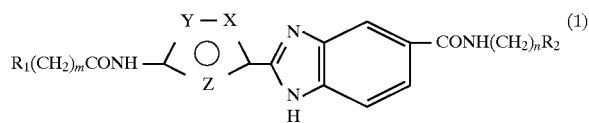

wherein X, Y and Z each independently means CH, N, NH, $N(CH_2)_t CH_3$, S or O with the proviso that X, Y and Z do not have the same meaning at the same time and t stands for an integer of 0–5, m and n are integers of 0–5, $R_1$ and $R_2$ each independently means a hydrogen atom, a $C_{1-20}$ alkyl group, a $C_{1-10}$ haloalkyl group, a $C_{1-10}$ alkoxyl group, an oxyethylene group, an ethyleneimino group, a hydroxyl group, a $C_{1-10}$ alkylthio group, a substituted or unsubstituted amino group, a substituted or unsubstituted ammonium group, a substituted or unsubstituted sulfonium group, a substituted or un substituted phenyl group, a substituted or unsubstituted 5-membered heteroring, a substituted or unsubstituted 6-membered heteroring, a substituted or unsubstituted fused heteroring, a substituted or unsubstituted amidino group, a substituted or unsubstituted guanidino group, an amino acid residual group, or a group represented by the following chemical formula (2):

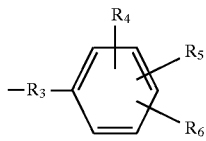

(2)

wherein $R_3$ means $(CH_2)_r$ or $(CH_2)_rO$ in which r stands for an integer of 0–5 and the O atom is located closer to the phenyl group, $R_4$ means a hydrogen atom, a $C_{1-10}$ alkyl group, a $C_{1-10}$ alkoxyl group, a halogen atom, a trifluoromethyl group, a cyano group, an amidino group, a guanidino group, a carboxyl group or —$COR_7$ in which $R_7$ means a $C_{1-5}$ alkyl group, an alkylamino group which may be substituted by a substituted amino group, an amino group which may be substituted by a substituted or unsubstituted phenyl group or a substituted or unsubstituted benzylamino group, $R_5$ means a hydrogen atom, a $C_{1-10}$ alkyl group, a $C_{1-10}$ alkoxyl group, a halogen atom, or —$(CH_2)_pN(R_8)_2$ or —$(CH_2)_pNR_8R_9$ in which p stands for an integer of 0–5, or $R_4$ and $R_5$ may form a ring when $R_4$ and $R_5$ take mutually adjacent positions, $R_6$ means a hydrogen atom, —$(CH_2)_pN(R_8)_2$— or —$(CH_2)_pNR_8R_9$ wherein in each case of $R_5$ and $R_6$, $R_8$ means —$CH_2CH_2W$, $R_9$ means a $C_{1-5}$ alkyl group or a mesyl group, W means a halogen atom, a hydroxyl group, a mesyloxy group, a tosyloxy group or —$OCOR_7$ in which $R_7$ and p have the same meanings as defined above.

The present invention will hereinafter be described in further detail.

Desired examples of the 5-membered ring which contains X, Y and Z in the compound of the chemical formula (1) include pyrrole, 1-methylpyrrole, imidazole, 1-methylimidazole, furan, thiophene, oxazole, isooxazole, pyrazole and isothiazole.

Preferred examples of the $C_{1-20}$ alkyl group represented by $R_1$ or $R_2$ include methyl, ethyl, n-propyl, i-propyl, n-butyl, i-butyl, t-butyl, n-pentyl, n-hexyl, n-heptyl, n-octyl and stearyl.

Desired examples of the $C_{1-10}$ haloalkyl group include chloromethyl, chloroethyl, chloropropyl, chlorobutyl, chloropentyl, chlorohexyl, chloroheptyl, bromomethyl, bromoethyl, bromopropyl, bromobutyl, bromopentyl, bromohexyl and bromoheptyl.

The substituted or unsubstituted amino group can desirably be an amino group or a monoalkylamino or dialkylamino group which has been substituted by a linear or branched $C_{1-10}$ alkyl group. Desired examples include methylamino, ethylamino, n-propylamino, i-propylamino, n-butylamino, dimethylamino, diethylamino, dipropylamino and diisopropylamino groups.

Desired examples of the $C_{1-10}$ alkoxyl group include methoxyl, ethoxyl, n-propyloxy, i-propyloxy, n-butoxy, i-butoxy, t-butoxy, n-pentyloxy, n-hexyloxy, n-heptyloxy and n-octyloxy.

Desired examples of the $C_{1-10}$ alkylthio group include methylthio, ethylthio, n-propylthio, i-propylthio, n-butylthio, i-butylthio, t-butylthio, n-pentylthio, n-hexylthio, n-heptylthio and n-octylthio.

The substituted or unsubstituted ammonium group can be a trialkylammonium group which has been substituted by a linear or branched $C_{1-4}$ alkyl group, for example, trimethylammonium or triethylammonium, or an ammonium group represented by the chemical formula (9). In the formula (9), $U^-$ can be any anion insofar as the anion is pharmacologically acceptable (for example, $Cl^-$, $I^-$, $OSO_3^-$, $NO_3^-$, $HOOCCH=CHCOO^-$ or the like). $R_{11}$ and $R_{12}$ independently mean a linear or branched $C_{1-10}$ alkyl group with methyl, ethyl, n-propyl, i-propyl, n-butyl, i-butyl, t-butyl, n-pentyl, n-hexyl, n-heptyl or n-octyl being desired.

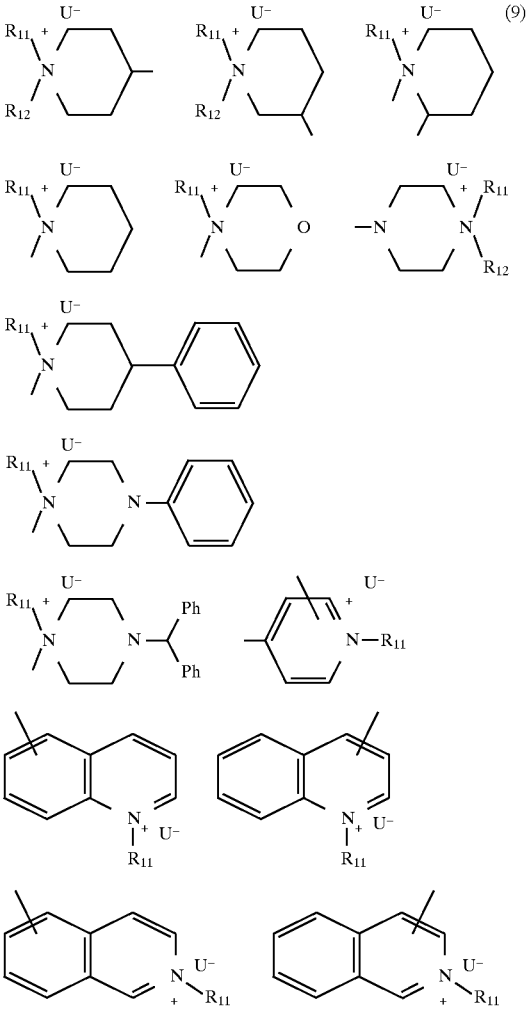

(9)

The terms "substituted or unsubstituted sulfonium group" means a sulfonium group; or a sulfonium group substituted by a linear or branched $C_{1-4}$ alkyl group, for example, a dimethylsulfonium, diethylsulfonium, methylethylsulfonium, methylpropylsulfonium, diisopropylsulfonium or methylisopropylsulfonium group, or a sulfonium group represented by the following formula (10). In the formula (10), $U^-$ can be any anion insofar as the anion is pharmacologically acceptable (for example, $Cl^-$, $I^-$, $OSO_3^-$, $NO_3^-$, $HOOCCH=CHCOO^-$ or the like). $R_{11}$ means a linear or branched $C_{1-10}$ alkyl group with methyl, ethyl, n-propyl, i-propyl, n-butyl, i-butyl, t-butyl, n-pentyl, n-hexyl, n-heptyl or n-octyl being desired.:

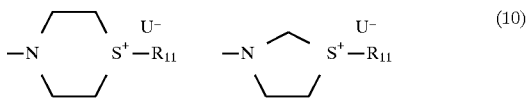

(10)

Illustrative of the substituted or unsubstituted phenyl group include a phenyl group which may be substituted by a halogen atom (fluorine atom, chlorine atom, bromine atom or iodine atom), a linear or branched $C_{1-5}$ alkyl group, a linear or branched $C_{1-5}$ alkoxyl group, a $C_{1-3}$ alkoxycarbonyl group, a $C_{1-3}$ haloalkyl group, a cyano group, an amidino group, and a $C_{1-3}$ dialkylamino group. Desired examples of the substituted or unsubstituted phenyl group include chlorophenyl, dichlorophenyl, trichlorophenyl, bromophenyl, dibromophenyl, tribromophenyl, fluorophenyl, difluorophenyl, trifluorophenyl, methylphenyl, ethylphenyl, n-propylphenyl, i-propylphenyl, n-butylphenyl, i-butylphenyl, t-butylphenyl, methoxyphenyl, ethoxyphenyl, methoxycarbonylphenyl, methylcarboxyphenyl, trifluoromethylphenyl, cyanophenyl, amidinophenyl, dimethylaminophenyl, dimethylaminophenyl, and 3,4,5-trimethoxyphenyl. The substituting position of each of the above substituents can be the 2-, 3- or 4-position in the case of the mono-substitution, any two of the 2-, 3-, 4-, 5- and 6-positions in the di-substitution and any three of the 2-, 3-, 4-, 5- and 6-positions in the tri-substitution unless otherwise specifically indicated.

Desired examples of the 5-membered heteroring of the substituted or unsubstituted 5-membered heteroring include pyrrolyl, furyl, thienyl, imidazolyl, oxazolyl, pyrazolyl, thiazolyl, isothiazolyl, isooxazolyl, pyrrolinyl, imidazolidinyl, pyrazolidinyl, pyrazolinyl, furazanyl, tetrahydrofuranyl, triazolyl and tetrazolyl.

Desired examples of the 6-membered heteroring of the substituted or unsubstituted 6-membered heteroring include pyridyl, pyrimidinyl, pyranyl, pyradinyl, pyridazinyl, piperidyl, piperidinyl, piperazinyl, thiomorpholino, 4-methyl-1-piperazino, 4-benzyl-1-piperazino, 1-morpholino, 1-piperidino, 4-piperidino, and 4-methyl-1-piperidino.

Desired examples of the fused heteroring of the substituted or unsubstituted fused heteroring include quinolyl, isoquinolyl, indolyl, isoindolyl, phthalazinyl, quinoxalyl, quinazolyl, cinnolyl, indolinyl, isoindolinyl, carbazolyl, acridinyl, benzotriazolyl, benzisooxazolyl, azaindolyl, azabenzindolyl, benzodioxanyl, piperinyl, and xanthenyl.

In the substituted or unsubstituted 5-membered heteroring, the substituted or unsubstituted 6-membered heteroring, or the substituted or unsubstituted fused heteroring, examples of substituents indicated by the term "substituted" include halogen atoms (fluorine atom, chlorine atom, bromine atom and iodine atom), linear or branched $C_{1-5}$ alkyl groups, linear or branched $C_{1-5}$ alkoxyl groups, $C_{1-3}$ alkoxycarbonyl groups, $C_{1-3}$ haloalkyl groups, a cyano group, an amidino group, and $C_{1-3}$ dialkylamino groups.

The substituted or unsubstituted amidino group can desirably be a group represented by the chemical formula (11). $R_{11}$ means a $C_{1-10}$ alkyl group with methyl, ethyl, n-propyl, i-propyl, n-butyl, i-butyl, t-butyl, n-pentyl, n-hexyl, n-heptyl or n-octyl being desired.

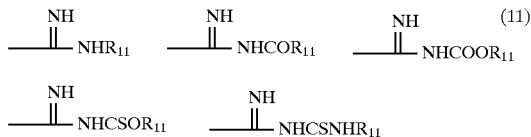

The substituted or unsubstituted guanidino group can desirably be a group represented by the chemical formula (12). $R_{11}$ means a $C_{1-10}$ alkyl group with methyl, ethyl, n-propyl, i-propyl, n-butyl, i-butyl, t-butyl, n-pentyl, n-hexyl, n-heptyl or n-octyl being desired.

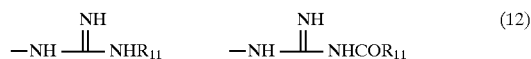

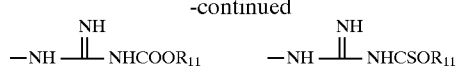

The term "amino acid residual group" means a carboxyl-removed moiety of an amino group and desired examples of the amino acid include arginine, histidine and lysine.

The term "halogen atom" as $R_4$, $R_6$ and $R_7$ means F, Cl, Br or I.

Desired examples of the halogen atom as W are Cl and Br.

Preferred examples of the $C_{1-10}$ alkyl group represented by $R_5$ include methyl, ethyl, n-propyl, i-propyl, n-butyl, i-butyl, t-butyl, n-pentyl, n-hexyl, n-heptyl and n-octyl groups.

Desired examples of the $C_{1-10}$ alkoxyl group represented by $R_5$ include methoxy, ethoxy, n-propyloxy, i-propyloxy, n-butoxy, i-butoxy, t-butoxy, n-pentyloxy, n-hexyloxy, n-heptyloxy and n-octyloxy.

When $R_4$ and $R_5$ take mutually adjacent positions and form a ring, the ring can desirably be represented by the following formula (13):

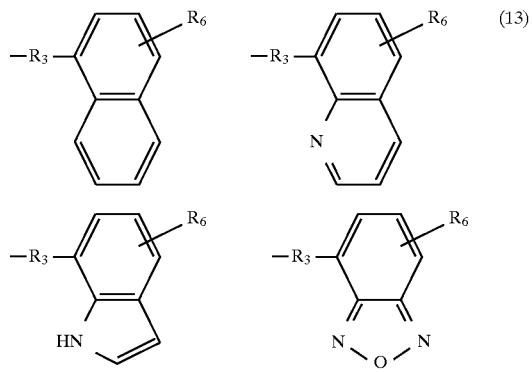

Desired examples of the alkylamino group which is represented by $R_7$ and may be substituted by a substituted amino group include dimethylaminoethylamino, dimethylaminopropylamino, dimethylaminobutylamino, diethylaminoethylamino, diethylaminopropylamino, diethylaminobutylamino, dipropylaminoethylamino, dipropylaminopropylamino, dipropylaminobutylamino, diisopropylaminoethylamino, diisopropylaminopropylamino and diisopropylaminobutylamino.

The amino group which is represented by $R_7$ and may be substituted by a substituted or unsubstituted phenyl group can desirably be aniline, 4-dimethyl-aminoaniline or 4-chloroaniline.

The substituted or unsubstituted benzylamino group represented by $R_7$ can desirably be benzylamine or 4-dimethylaminobenzylamine.

The term "pharmacologically acceptable salt" means an inorganic acid salt or an organic acid salt such as the hydrochloride, sulfate, nitrate, acetate, fumarate, maleate, citrate or oxalate.

BEST MODES FOR CARRYING OUT THE INVENTION

A group of compounds, which can be represented by the chemical formula (1), will hereinafter be described by dividing them into the following three groups A, B and C.

Incidentally, compound numbers which appear in this specification indicate the numbers of compounds shown in Tables 1–4.

Group A: Among the compounds represented by the chemical formula (1), those not classified to Group B or Group C and pharmacologically acceptable salts thereof.

Group B: Among the compounds represented by the chemical formula (1), the compounds in which $R_2$ is an oxoethylene group, an ethyleneimino group, a halogen-substituted $C_{1-10}$ alkyl group or a group represented by the formula (2), and pharmacologically acceptable salts thereof.

Group C: Among the compounds represented by the chemical formula (1), the compounds in which $R_1$ and $R_2$ are individually a group represented by the formula (2), and pharmacologically acceptable salts thereof.

A description will next be made of syntheses of these compounds. In the following description and Examples, DCC stands for N,N'-dicyclohexylcarbodiimide, CDI for N,N'-carbonyldiimidazole, HOSu for N-hydroxysuccinimide, EDCI for 1-(3-dimethylaminopropyl)-3-ethylcarbodiimide hydrochloride, DECP for diethyl cyanophosphonate, HOBt for 1-hydroxybenzotriazole, DMAP for 4-dimethylaminopyridine, DMF for dimethylformamide, THF for tetrahydrofuran, DMSO for dimethylsulfoxide, and IPA for isopropanol. Pd/C indicates Pd on charcoal, in which the palladium generally accounts for 5 to 10%.

A description will now be made of a process for the synthesis of the compound represented by the chemical formula (3), which is a principal intermediate.

As will be shown below by Reaction scheme (1), the aldehyde of the formula (5) and the 3,4-diaminobenzoic acid of the formula (6) or its ester are heated in nitrobenzene at 100° C. to a reflux temperature, preferably at 130° to 200° C., the reaction mixture is allowed to cool down to room temperature, and the reaction product of the formula (3), that is, 1H-2-benzimidazole- 5-carboxylic acid or its ester derivative can then be collected by filtration. As will be shown below by Reaction scheme (2), when the ester is obtained here, hydrolysis of it can provide the corresponding 1H-2-benzimidazole-5-carboxylic acid derivative represented by the chemical formula (14). Although no particular limitation is imposed on the amounts of the aldehyde of the formula (5) and the 3,4-diaminobenzoate of the formula (6), the latter may be reacted generally in an amount of 80–120 mole parts per 100 mole parts of the former. The reaction in nitrobenzene is carried out under heat until the raw materials are used up while the progress of the reaction is observed. A heating time in a range of 5–100 hours can bring about good results. The heating can be conducted continuously or intermittently until the total heating time reaches the above-described time. The hydrolysis of the ester can be conducted by heating it in a mixed solvent of water and ethanol or water and methanol while using sodium hydroxide or potassium hydroxide. Although the proportion of water in the mixed solvent can be from 5 to 90 wt. %, 40 to 60 wt. % can give good results. The heating temperature can range from 50° C. to the reflux temperature.

Reaction scheme (1)

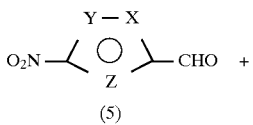

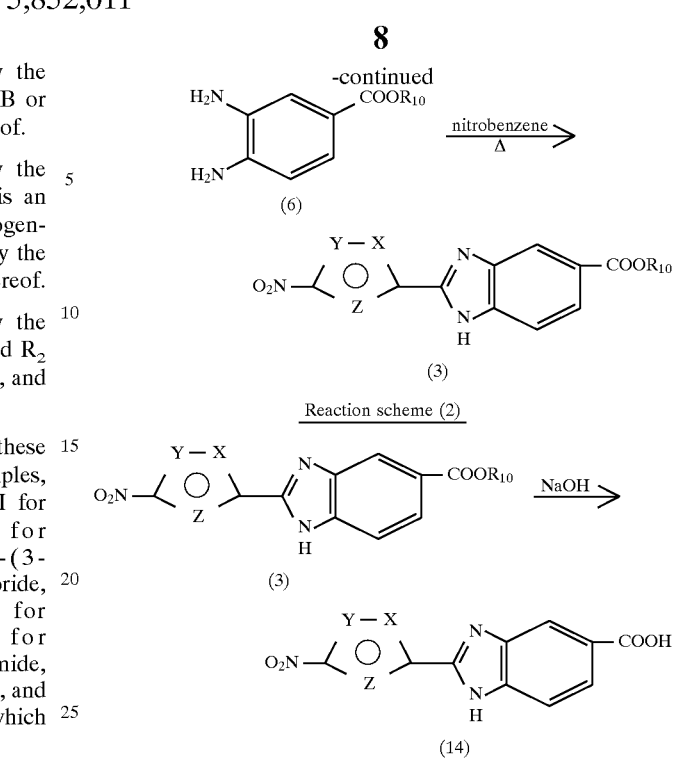

For example, selection of 1-methyl-4-nitropyrrole-2-carboxyaldehyde, 4-nitropyrrole-2-carboxyaldehyde, 5-nitropyrrole-2-carboxyaldehyde, 1-methyl-4-nitroimidazole-2-carboxyaldehyde, 4-nitroimidazole-2-carboxyaldehyde, 5-nitrofuran-2-carboxyaldehyde, 4-nitrothiophene-2-carboxyaldehyde and 2-nitrothiophene-4-carboxyaldehyde as starting materials makes it possible to synthesize, by similar procedures, 1H-2-[1-methyl-4-nitropyrrol-2-yl]benzimidazole-5-carboxylic acid, 1H-2-[4-nitropyrrol-2-yl]benzimidazole-5-carboxylic acid, 1H-2-[5-nitropyrrol-2-yl]benzimidazol- 5-carboxylic acid, 1H-2-[1-methyl-4-nitroimidazol-2-yl]benzimidazole-5-carboxylic acid, 1H-2-[4-nitroimidazol-2-yl]benzimidazole-5-carboxylic acid, 1H-2-[5-nitrofuran-2-yl]benzimidazole-5-carboxylic acid, 1H-2-[4-nitrothiophen-2-yl]benzimidazole-5-carboxylic acid and 1H-2-[2-nitrothiophen-4-yl]benzimidazole-5-carboxylic acid, respectively.

Incidentally, to heat a substituted benzaldehyde and 3,4-diaminobenzoic acid in nitrobenzene for the preparation of a corresponding 1H-2-phenylbenzimidazole has already been disclosed in Syn. Commun., 20, 955–963(1990). Use of the above-described aromatic 5-membered aldehyde derivatives having a nitro group is however novel.

As a further alternative, the compound of the formula (14) can also be synthesized as will be described next. For example, 1-methyl-4-nitro-2-pyrrolecarboxylic acid is reacted, by using the process disclosed in Tetrahedron, 34, 2389–2391(1978), with thionyl chloride into 1-methyl-4-nitro-2-pyrrolecarboxylic acid chloride, which is then reacted with a 3,4-diaminobenzoic acid to obtain 3-amino-4-(1-methyl-4-nitro-2-pyrrolecarboxamido)benzoic acid or 4-amino-3-(1-methyl-4-nitro-2-pyrrolecarboxamido) benzoic acid as the exemplified compound. Here, the reaction product can also be a mixture of both the benzoic acids. Methylene chloride, chloroform, DMF or the like can be used as a solvent. Other solvents are also usable as long as they do not take part in the reactions. Heating of the thus-obtained amide compound with trifluoroacetic acid with any solvent, which do not participate in the reaction, provides 1H-2-(1-methyl-4-nitropyrrol-2-yl)benzimidazole-5-carboxylic acid. Further, 1-methyl-4-nitro-2-trichloroacetylpyrrole which is a known compound disclosed in Heterocycles, 27, 1945–1952(1988) is likewise reacted with 3,4-diaminobenzoic acid to obtain 3-amino-4-(1-methyl-4-nitro-2-pyrrolecarboxamido)-benzoic acid or 4-amino-3-(1-methyl-4-nitro-2-pyrrolecarboxamido) benzoic acid. Here, the reaction product can also be a mixture of both the benzoic acids. The reaction product can also be converted into 1H-2-(1-methyl-4-nitropyrrole-2-yl) benzimidazole-5-carboxylic acid likewise. The reaction can also be conducted similarly by using as a starting material an equivalent carboxylic acid other than 1-methylpyrrole-2-carboxylic acid.

The above-described reactions can be summarized as follows (Reaction scheme (3)):

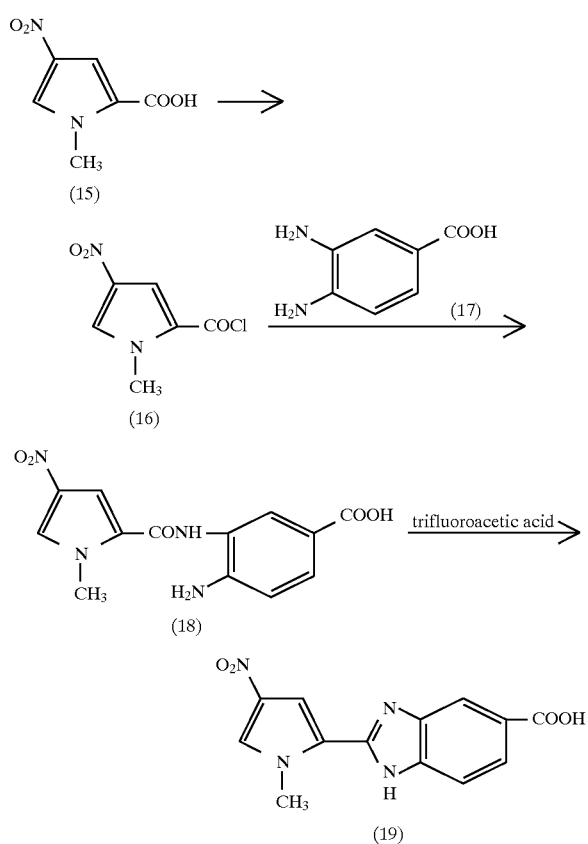

A description will next be made of the syntheses of the compounds in the respective groups.

As will be shown below in Reaction scheme (4), syntheses of the compounds in Group A can be conducted generally by uniting an amino compound, which is represented by the formula (20) and generally contains the moiety designated by $R_2$, with the carboxylic acid of the formula (14) in the presence of a suitable condensing agent, for example, DCC, CDI, EDCI, DECP or the like, subjecting the so-obtained intermediate of the formula (21) to catalytic hydrogenation to reduce its nitro group into an amino compound and then, reacting a carbonyl compound containing the moiety designated by $R_1$ to the resultant amino compound.

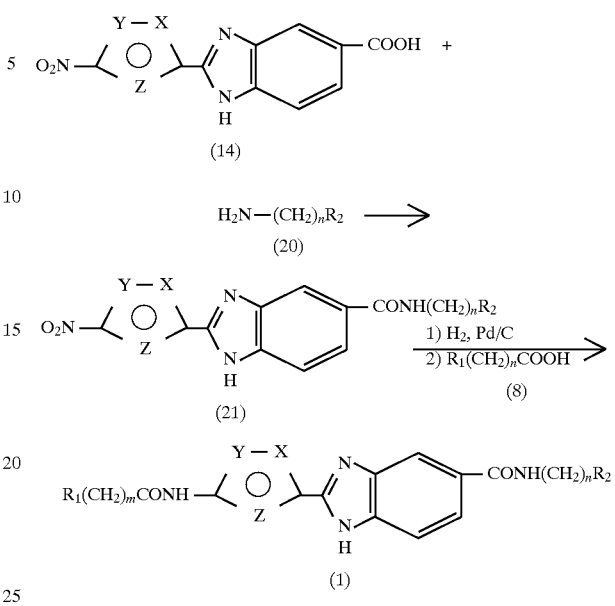

The amino compound which is represented by the formula (20) and contains the moiety designated by $R_2$ can be either one available as a reagent or one synthesizable through several steps by combining known reactions. Usable amino compounds include alkylamino compounds, for example, methylamine, ethylamine, 1-aminopropane, 2-aminopropane, 1-aminobutane and 2-aminobutane. Examples of substituted amino compounds include dimethylaminopropylamine, diethylaminopropylamine and dipropylaminopropylamine. Examples of amino compounds using as a substituent an alkylthio group include methylthiopropylamine, ethylthiopropylamine, propylthiopropylamine, butylthiopropylamine and the like. Examples of amino compounds using as the substituent an ammonium group include aminopropyltrimethylammonium, aminopropyltriethylammonium and the like. When amino-containing derivatives substituted by the substituted or unsubstituted phenyl group, the substituted or unsubstituted 5-membered heteroring, the substituted or unsubstituted 6-membered heteroring and the substituted or unsubstituted fused heteroring are used in the reaction, compounds which contain, as a substituent represented by $R_2$, the substituted or unsubstituted phenyl group, substituted or unsubstituted 5-membered heteroring, substituted or unsubstituted 6-membered heteroring and substituted or unsubstituted fused heteroring can be synthesized, respectively. Upon uniting these amino compounds with the carboxylic acid of the formula (14) by using a suitable condensing agent, for example, DCC, CDI, EDCI, DECP or the like, an ordinary solvent can be used as a reaction solvent. DMF or a mixed solvent containing DMF can however provide relatively good results. The reaction temperature may preferably range from –5° C. to 30° C. The reaction is allowed to proceed while observing its progress. The reaction time generally ranges from 1 hour to 50 hours.

Synthesis of compounds which contain an amidino group as $R_2$ can be conducted as will be described below. As will be shown below in Reaction scheme (5), the compound of the formula (14) (e.g., 1H-2-(1-methyl-4-nitropyrrol-2-yl) benzimidazole-5-carboxylic acid; other intermediates are treated similarly) and 3-amino-propionitrile are first united together. At this time, a general condensing agent such as DCC, CDI, EDCI or DECP can be used. It is also possible to add HOBt or HOSu to DCC. The reaction can desirably be conducted at 0°–30° C. The reaction mixture is suspended in ethanol, followed by bubbling of hydrogen chloride gas, so that the crystals so formed are collected by filtration. The crystals are then dissolved or suspended in a solvent. Ammonia gas is bubbled through the resulting solution or suspension, whereby the target amidino compound (e.g., 1H-2-(1-methyl-4-nitropyrrol-2-yl)benzimidazole-5-[N-(2-amidinoethyl)]carboxamide; this applies equally to other intermediates) is obtained. As a reaction solvent for the above reaction, ethanol or a mixed solvent of ethanol and methanol is desired. The proportion of ethanol can be freely chosen in a range of 10–100%.

1H-2-[1-methyl-(nitro-substituted)imidazol-2-yl] benzimidazole-5-carboxylic acid, 1H-2-[(nitro-substituted) imidazol-2-yl]benzimidazole-5-carboxylic acid, 1H-2-[(nitro-substituted)-furan- 2-yl]benzimidazole-5-carboxylic acid, 1H-2-[(nitro-substituted)thiophen-2-yl]benzimidazole-5-carboxylic acid, or 1H-2-[(nitro-substituted)thiophene-4-yl]benzimidazole-5-carboxylic acid.

A description will next be made of a method for synthesizing the side chain corresponding to $R_1$.

First, the synthesis of, as a side chain corresponding to $R_1$, the substituent represented by the formula (2) will be described. As a nitro-containing carboxylic acid derivative to be used in the synthesis, a compound which can be synthesized by using a commercially-available reagent or a known reaction can be employed. The nitro-containing

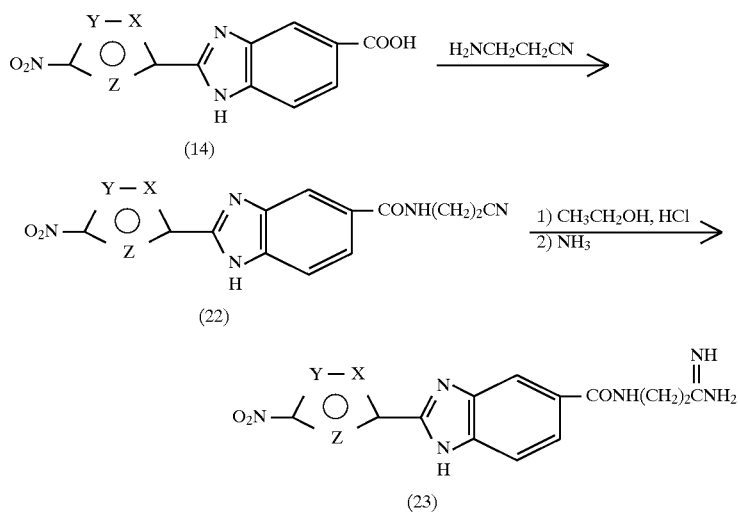

Reactions with amines such as methylamine and ethylamine instead of the bubbling of ammonia gas provide substituted amidino compounds, respectively, as shown in Reaction scheme (6):

carboxylate ester derivative of the formula (25) in Reaction scheme (7) is reduced into the corresponding amino compound of the formula (26) by catalytic hydrogenation while using Pd/C as a catalyst. Here, methanol, ethanol, DMF and

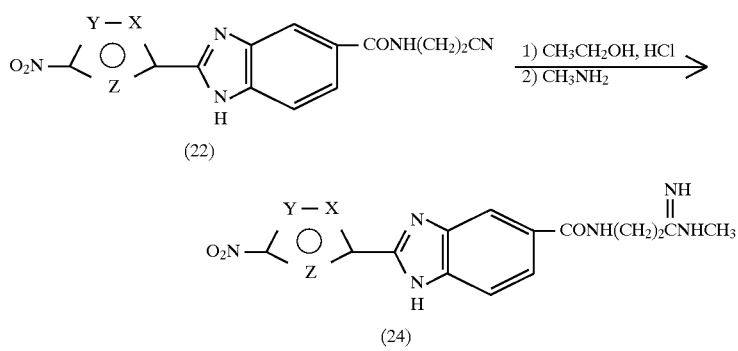

The above-described reactions shown in Reaction schemes (4)–(6) can be conducted using, as a precursor, the compound of the formula (14). Specific examples of the compound include 1H-2-[1-methyl-(nitro-substituted) pyrrol-2-yl]benzimidazole-5-carboxylic acid, 1H-2-[(nitro-substituted)pyrrol-2-yl]benzimidazole-5-carboxylic acid, the like can be used either singly or in combination as a reaction solvent. It is preferred to conduct the reaction at a temperature of 0°–30° C. The reaction time ranges from 30 minutes to 2 hours. As shown in the below-described reaction scheme, ethylene oxide is reacted to the amino compound of the formula (26) so formed to obtain the compound of the formula (27). For this reaction, 10–80% acetic acid can be used as a reaction solvent. The reaction is conducted at a temperature in a range of from −20° C. to 50° C. The reaction time may preferably range from 1 hour to 50 hours. The compound of the formula (27) is then chlorinated with an appropriate chlorinating agent such as thionyl chloride, oxalyl chloride, phosphorus pentachloride, phosphorus oxychloride, mesyl chloride (in DMF), a combination of mesyl chloride and sodium chloride, a combination of mesyl chloride and lithium chloride, dichlorotriphenylphosphoran, or the like, whereby the compound of the formula (28) can be obtained by changing OH group into $Ci^-$ radical. The reaction can be conducted at 0°–100° C. and the reaction time can range from 20 minutes to 5 hours. An ordinary solvent such as chloroform, benzene or toluene can be used as a reaction solvent. Further, DMF can be mixed with these solvents. In the case of thionyl chloride or oxalyl chloride, on the other hand, the reaction can be conducted in a solventless manner. The compound represented by the formula (28) is subjected to hydrolysis with an acid to obtain a carboxylic acid derivative of the formula (29). This can be achieved, for example, by heating the compound at 80° C. to the reflux temperature in the presence of concentrated hydrochloric acid. Desired reaction time is 30 minutes to 5 hours.

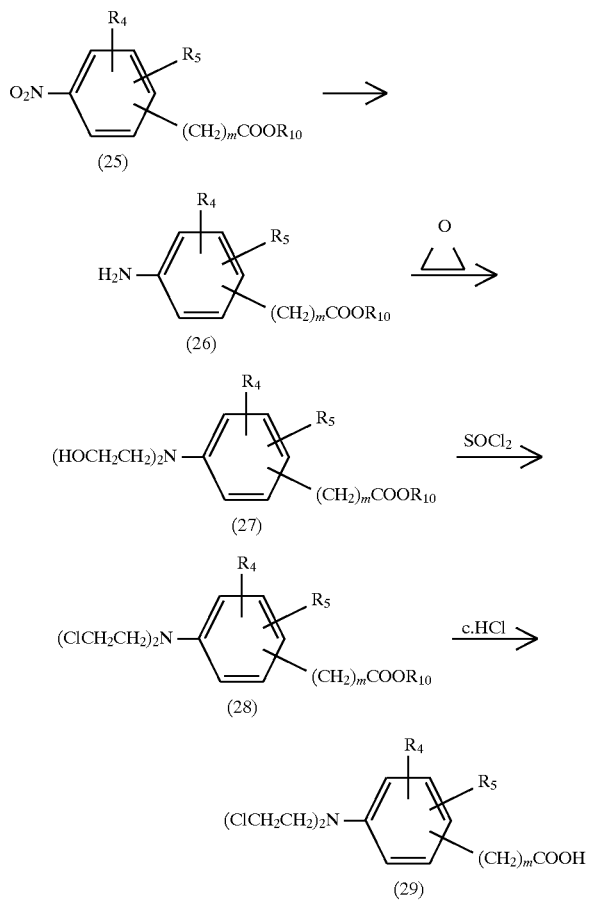

Side chains other than those described above can be prepared by using commercially-available reagents or conducting known reactions in several steps.

For example, the compound of the formula (7) and the compound of the formula (29) can be united using an appropriate condensing agent such as DCC, CDI, EDCI, DECP or the like. An ordinary solvent can be used as a reaction solvent. DMF or a mixed solvent containing DMF can however provide relatively good results. The reaction temperature may preferably range from −5° C. to 30° C. The reaction is allowed to proceed while observing its progress. The reaction time generally ranges from 1 hour to 50 hours. Alternatively, after the compound of the formula (29) is converted to a corresponding acid chloride by using thionyl chloride, oxalyl chloride or the like in an ordinary solvent (ex. methylene chloride, chloroform, toluene, DMF or the like. These solvents can be used either singly or in combination) and the acid chloride so obtained can be united with the compound represented by the formula (7). The reaction temperature may preferably range from −5° C. to 30° C. The reaction is allowed to proceed while observing its progress. The reaction time generally ranges from 1 hour to 50 hours. In the above reactions, the partial structure of $R_1$ can be united.

A description will next be made of syntheses of the compounds in Group B.

First, the synthesis of a side chain corresponding to $R_2$ will be described. A nitro-containing aniline derivative or a nitro-containing aminoalkylbenzene derivative is selected as a starting material. A derivative containing an appropriate substituent can be obtained by using a commercially-available reagent or a known reaction, or can also be synthesized in accordance with the following manner.

As will be shown below in Reaction scheme (8), the amino compound of the formula (31) is synthesized from the carboxylic acid of the formula (30) in accordance with the process disclosed in J. Med. Chem. 33, 3014–3019(1990). Use of this process makes it possible to synthesize a methylene chain derivative in which two or more methylene groups are contains as $R_3$. (A substituent corresponding to R6, which will be described next, supposed to have already been introduced to the compound of the formula (30))

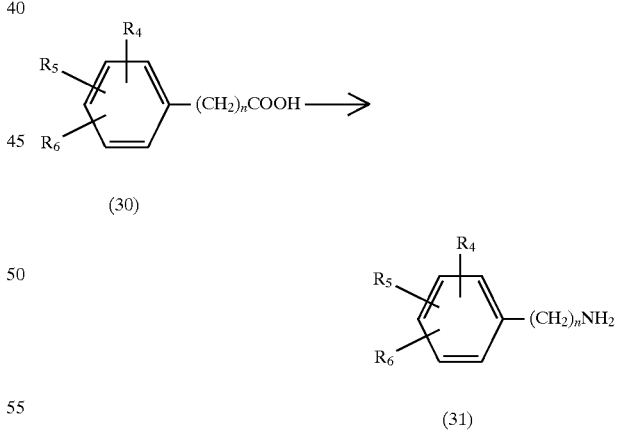

A description will next be made of the introduction of the moiety corresponding to $R_6$ to the side chain corresponding to $R_2$.

The reaction can be generally conducted in accordance with the following two processes:

As is shown in Reaction scheme (9), N,N-bis (hydroxyethyl)amine is first allowed to act on the halogenated benzene derivative of the formula (32) which contains a nitro group and an appropriate substituent (in the formula (32), a halogen atom is illustrated by F as an example), whereby the compound of the formula (33) is obtained. Here, DMSO can be used as a reaction solvent. The reaction temperature can range from 20° C. to 100° C. The reaction time can preferably range from 10 minutes to 4 hours. The chloride of the formula (34) can be obtained by reacting, with the intermediate of the formula (33), an appropriate chlorinating agent such as thionyl chloride, oxalyl chloride, phosphorus pentachloride, phosphorus oxychloride, mesyl chloride, a combination of mesyl chloride (in DMF) and sodium chloride or the like. The reaction can be conducted at 0°–100° C. and the reaction time can range from 20 minutes to 5 hours. An ordinary solvent such as chloroform, benzene or toluene can be used as a reaction solvent. Further, DMF can be mixed to these solvents. The reaction can also be conducted in a solventless manner.

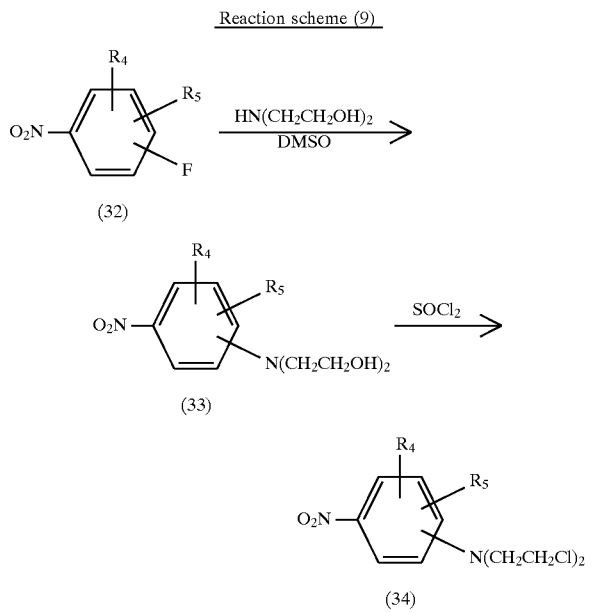

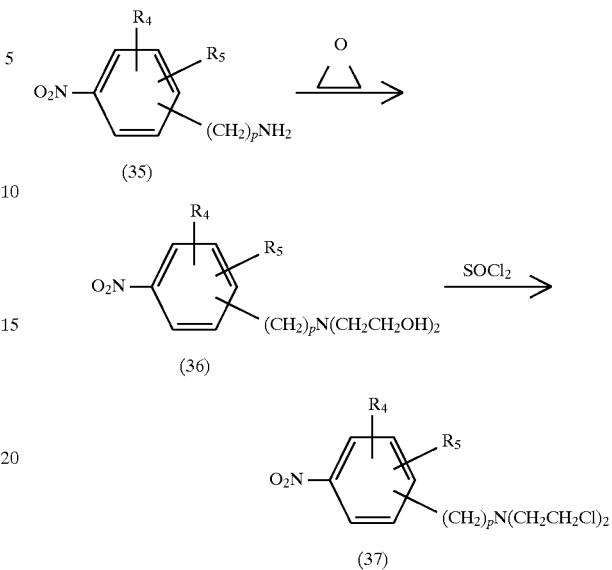

As an alternative, the compound of the formula (36) is obtained by reacting ethylene oxide with the nitro-containing aniline derivative (in the case of p=0) or the aminoalkylbenzene derivative (in the case that p is 1 or greater), each represented by the formula (35) shown below in Reaction scheme (10). For this reaction, 10–80% acetic acid (or a solution of p-toluenesulfonic acid in methanol) can be used as a reaction solvent. The reaction is conducted at a temperature in a range of from −20° C. to 50° C. The reaction time may preferably range from 1 hour to 50 hours. The compound of the formula (36) so obtained is chlorinated by an appropriate chlorinating agent such as thionyl chloride, oxalyl chloride, phosphorus pentachloride, phosphorus oxychloride, mesyl chloride (in DMF) or a combination of mesyl chloride and sodium chloride, whereby the compound of the formula (37) can be obtained. The reaction can be conducted at 0°–100° C. and the reaction time can range from 20 minutes to 5 hours. An ordinary solvent such as chloroform, benzene or toluene can be used as a reaction solvent. Further, DMF can be mixed to these solvents. In the case of thionyl chloride or oxalyl chloride, on the other hand, the reaction can be conducted in a solventless manner.

Upon synthesis of the amino compound from the corresponding nitrobenzene derivative, it is the common practice to conduct the synthesis by catalytic hydrogenation making use of Pd/C as a catalyst or by a reducing reaction making use of tin chloride and hydrochloric acid. As a reduction process especially in the case of the above-described nitrobenzene derivative with an N,N-bis(chloroethyl)amino group bonded thereto, the reduction process making use of tin chloride and hydrochloric acid was known widely, for example, as disclosed in J. Chem. Soc. 1972–83(1949) or J. Med. Chem. 33, 112–121(1990). This reduction can be effectively conducted in accordance with the following reaction and the treatment after the reaction can be conducted more easily. Namely, a nitro compound as a starting material is dissolved in a suitable solvent, for example, ethanol, methanol, ethyl acetate, THF or DMF, or a mixed solvent of at least two of them. Pd/C is added in an amount equivalent to 0.5–50 wt. % based on the nitro compound, followed by hydrogenation at room temperature under normal pressure so that the corresponding amino compound is obtained. At this time, hydrochloric acid can also be added in an amount equi-molar to or greater than the amount of the nitro derivative, generally in a molar amount 1 to 1.2 times as much as the nitro derivative. The catalyst is removed by filtration, the solvent is distilled out, and the residue is then treated by using a suitable solvent, for example, ethanol, IPA or ethyl ether or a mixed solvent of at least two of them, whereby the target compound can be obtained easily in the form of its hydrochloride.

As shown in Reaction scheme (11), the nitro compound of the formula (34) obtained by the above reactions (Reaction schemes (9), (10)) is converted to the corresponding amino compound of the formula (38) by catalytic hydrogenation. The nitro compound of the formula (37) can also be converted to the corresponding amino compound. Upon conducting the catalytic hydrogenation, hydrochloric acid can be added in an amount equimolar to or greater than the amount of the nitro derivative, generally in a molar amount 1–1.2 times as much as the nitro derivative to obtain the corresponding amino compound stably. Desirably, the catalytic hydrogenation can be conducted at 5°–30° C. An ordinary solvent is used as a reaction solvent. Desired is, for example, DMF or a mixed solvent of DMF and methanol. The proportion of DMF in the mixed solvent can be chosen from a range of 5–100%, with 20–100% being desired.

Reaction scheme (11)

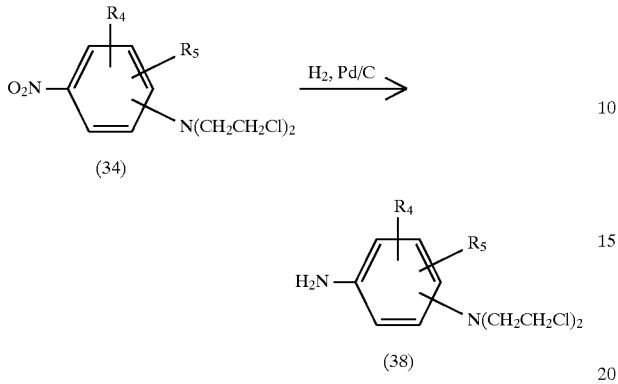

As shown in the below-described reaction scheme (12), the compound of the formula (39) can be obtained by uniting the amino compound obtained above and the compound of the formula (14) using an appropriate condensing agent such as DCC, EDCI, DECP or the like. At this time, an ordinary solvent can be used as a reaction solvent. DMF or a mixed solvent containing DMF can however provide relatively good results. The reaction temperature may preferably range from −5° C. to 30° C. The reaction is allowed to proceed while observing its progress. The reaction time generally ranges from 1 hour to 50 hours.

Similarly, as will be shown below in Reaction scheme (13), the compound of the formula (40) can be synthesized by uniting the benzimidazole derivative of the formula (14) with the amino compound of the formula (31), which had been obtained in the reduction reaction shown above in Reaction scheme (8), using an ordinary condensing agent such as CDI, DECP, DCC, a combination of DCC and HOBt, or the like. DMF is desired as a reaction solvent, although other general solvents can also be used. End of the reaction can be confirmed by proceeding with the reaction while checking its progress by TLC or the like. It is desired to bring the reaction into completion in 1–40 hours. The reaction temperature may desirably range from −5° C. to 40° C.

Reaction scheme (12)

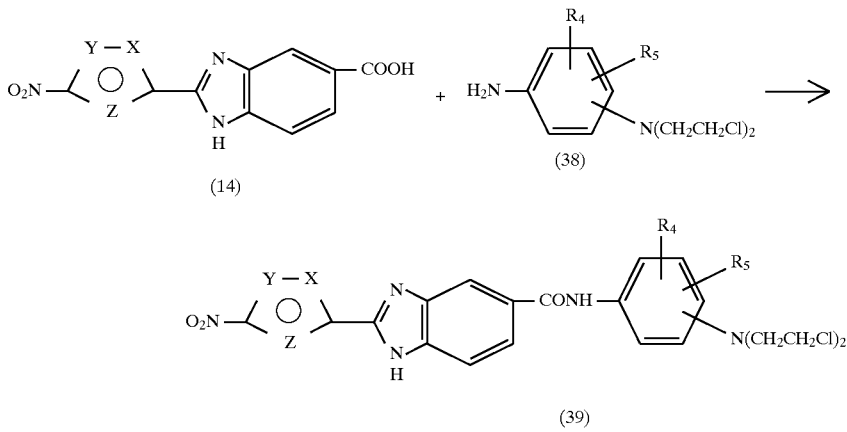

Reaction scheme (13)

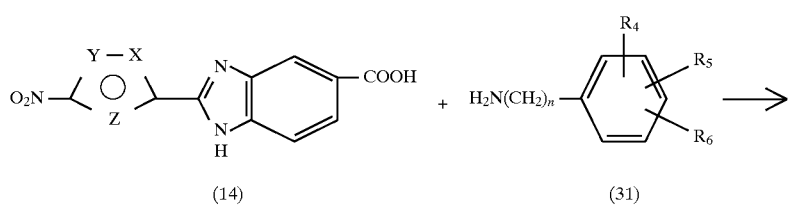

-continued
Reaction scheme (13)

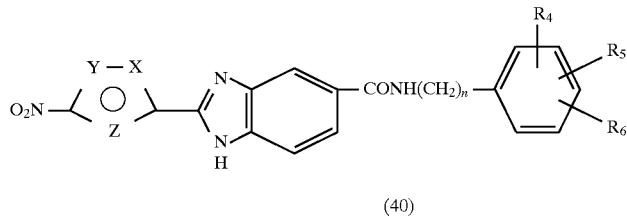

(40)

In the above reaction scheme, it is possible to treat the compound of the formula (39) as the compound of the formula (40) wherein n=0. This also applies to the description until Reaction scheme (19).

As will be shown below in Reaction scheme (14), the nitro group of the compound of the formula (40) can be reduced into the corresponding amino group by conducting catalytic hydrogenation while using Pd/C as a catalyst. The reaction proceeds in a substantially quantitative manner. As a solvent for the above reaction, ethanol, methanol and DMF can be used either singly or in combination. At this time, hydrochloric acid can be added in an amount equimolar to or greater than the amount of the nitro derivative, generally in an amount 1–1.2 times in moles as much as the nitro derivative. It is desired to perform the reaction for 10 minutes to 20 hours. The desired reaction temperature can range from 0° C. to 40° C.

nese Patent Laid-Open No. 92933/1994. In this publication, too, the distamycin moiety is synthesized in advance and the bonding reaction of N,N-bis(2-chloroethyl)-1,4-phenylenediamine is conducted at the end. This means that the bonding of the N,N-bis(2-chloroethyl)amino group having chemically high reactivity is deferred until the end. In the mean time, the present inventors have demonstrated that the target compound can be obtained at a high yield even when the aniline derivative moiety is introduced beforehand into the molecule in contrast to the above-described apparently reasonable reaction route.

As will be shown below by Reaction scheme (15), the carboxylic acid derivative of the formula (8) is condensed with the amino compound of the formula (41), which had been obtained in the above reduction reaction, using a conventional condensing agent (for example, DCC, CDI, Reaction scheme (14)

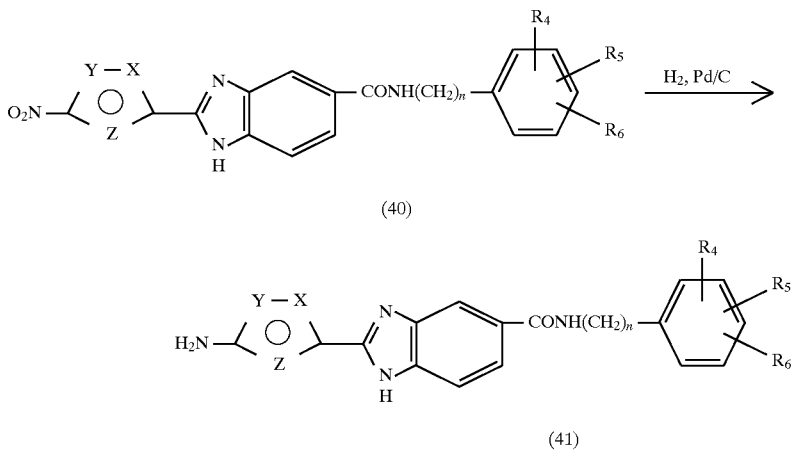

The above-described bonding of the aniline derivative in Reaction scheme (13) and the subsequent reducing reaction in Reaction scheme (14) constitute a new synthesis route not seen in any publications available to date. For example, a bonding reaction between a distamycin derivative and N,N-bis(2-chloroethyl)-1,4-phenylenediamine is found in Japa- EDCI, DECP or the like), whereby the carboxylic acid derivative can be bonded as the moiety $R_1$. Although a general solvent can be used in this reaction, DMF or a mixed solvent containing DMF provides good results. The desired reaction time can range from 30 minutes to 40 hours. It is desired to conduct the reaction at 020 C. to 40° C.

Reaction scheme (15)

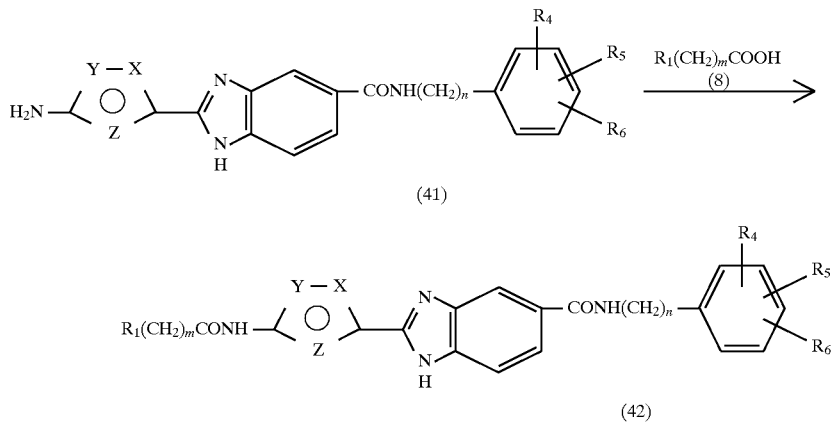

Use of N,N-dimethylaminopropionic acid, N,N-dimethylaminobutyric acid or the like as an example of the carboxylic acid derivative permits introduction of a substituted amino group into the moiety $R_1$. Further, use of carboxypropyltrimethylammonium makes it possible to introduce an ammonium group into the moiety $R_1$. Use of methylthiopropionic acid or the like can introduce an alkylthio group. On the other hand, use of 4-amidinobenzoic acid, 3-pyridinecarboxylic acid, 4-piperidinecarboxylic acid, pyrrole-2-carboxylic acid, indole-2-carboxylic acid or the like makes it possible to introduce a substituted or unsubstituted phenyl group, a substituted or unsubstituted 5-membered heteroring, a substituted or unsubstituted 6-membered heteroring or a substituted or unsubstituted fused heteroring.

As will be shown in Reaction scheme (16), for example, 1H-2-[4-(3-methylthiopropionylamino)-1-methylpyrrol-2-yl]benzimidazole-5-[N-[4-[N,N-bis(2-chloroethyl)amino]phenylamino]]carboxamide hydrochloride can be methylated further as disclosed in J. Org. Chem., 25, 804–807 (1960) or methylated by an ordinary methylating agent such as methyliodide, dimethylsulfonic acid or the like to obtain its sulfonium derivative of the formula (44). As a reaction solvent, formic acid, acetic acid, methanol or the like can be used. Its desired reaction time can range from 1 hour to 60 hours. It is desired to conduct the reaction at 0° C. to 60° C.

Counter anions ($I^-$) of the sulfonium compound obtained above can be converted to other anions by a known process. For example, counter anions $I^-$ can be converted to $Cl^-$ by using, for example, an ion exchange resin ("DOWEX" 1×8, $Cl^-$ type).

Likewise, further alkylation of a compound, which has as $R_1$ an amino group substituted by two alkyl groups, makes it possible to obtain an ammonium compound.

Further, the compound of the formula (46) can be obtained by reacting a pyridine derivative of the formula (45) shown in Reaction scheme (17) with the compound of the formula (41). At this time, the pyridine derivative is first converted into its acid chloride by using an ordinary reagent such as thionyl chloride and then united using an ordinary base such as triethylamine in an ordinary solvent such as methylene chloride, chloroform or the like. It is desired to conduct reaction at −5° C. to 50° C. The reaction time is preferably ranges from 1 hour to 50 hours. Alternatively, the pyridine derivative can be condensed with the compound of the formula (41) by using an appropriate condensing agent such as DCC, CDI, EDCI, DECP or the like. An ordinary solvent such as DMF, chloroform, methylene chloride or the like is employed as a reaction solvent. The reaction is conducted preferably at −5° C. to 50° C. The desired reaction time ranges from 1 hour to 50 hours.

Reaction scheme (16)

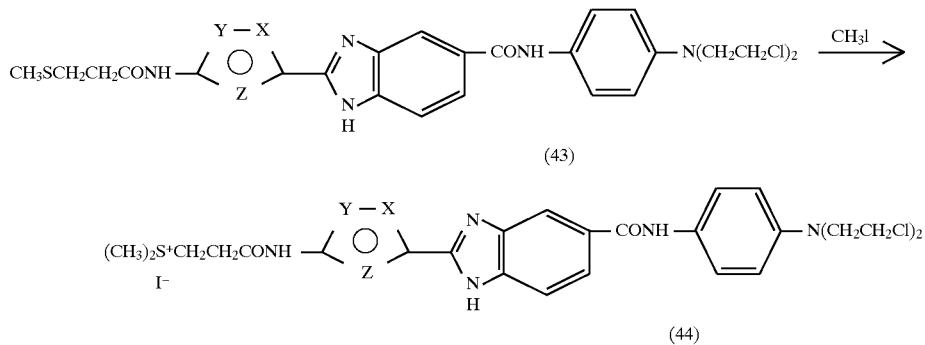

Reaction scheme (17)

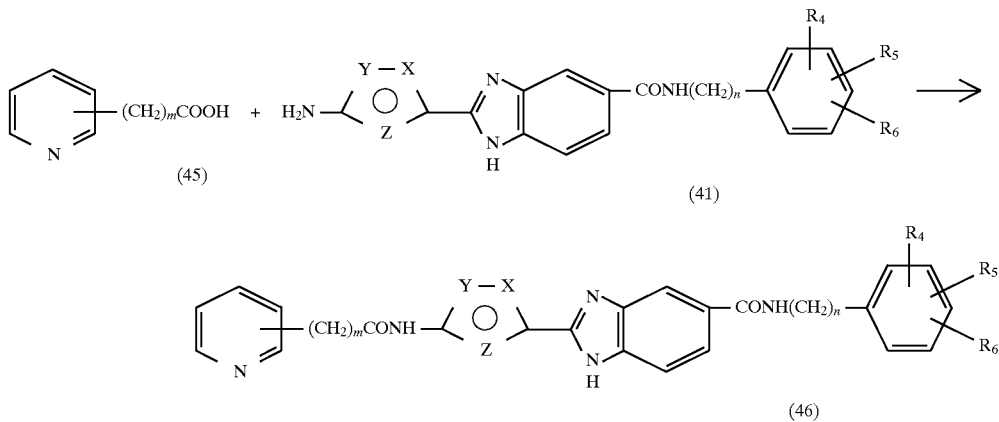

As will be described below in Reaction scheme (18), the compound of the formula (47) can be obtained by subjecting the compound of the formula (46) to methylation with methyl iodide. At this time, an ordinary solvent such as methanol, acetone, chloroform, methylene chloride or the like is employed. The reaction is preferably conducted at −5° C. to 50° C. The desired reaction time is 1 hour to 50 hours.

As will be shown below in Reaction scheme (19), the compound of the formula (48) with guanidine introduced into $R_1$ can be synthesized by reacting a guanidinoacetic acid to the amino compound of the formula (41)

Reaction scheme (18)

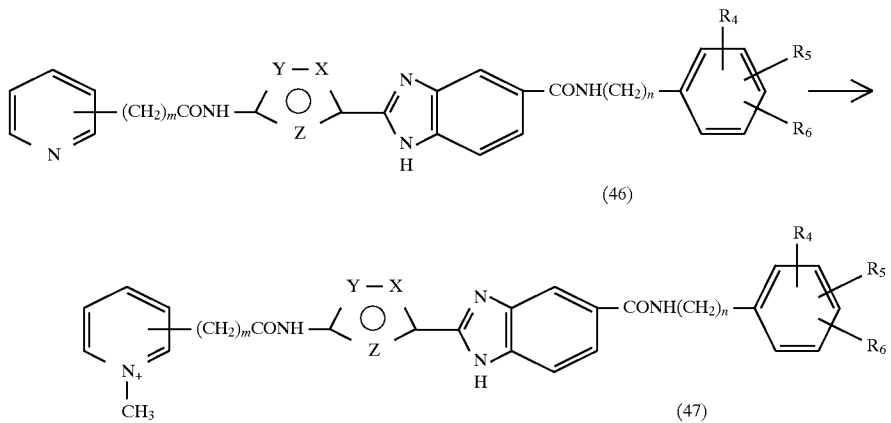

Reaction scheme (19)

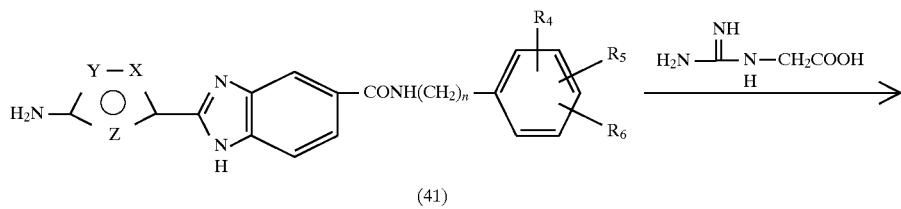

-continued
Reaction scheme (19)

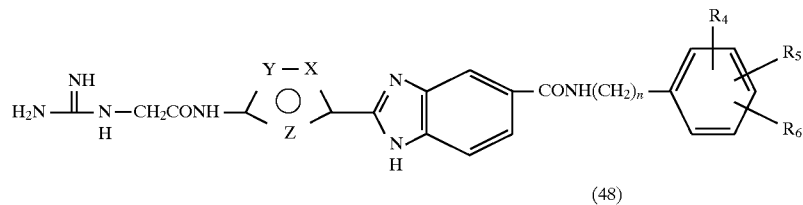

(48)

This guanidino group can be easily acylated. A reaction with an acid anhydride or an acid chloride makes it possible to introduce a substituted guanidine derivative into $R_1$. The reaction temperature can range from $-5°$ C. to $30°$ C. As a reaction solvent, ordinary solvents such as chloroform, benzene, toluene and DMF can be used either singly or in combination. The reaction time can range from 1 hour to 50 hours.

A cyano-containing carboxylic acid derivative such as 3-cyanopropionic acid is bonded by an ordinary condensing agent (DCC, CDI, EDCI, DECP or the like). Although an ordinary solvent can be used as a reaction solvent in the above reaction, DMF or a mixed solvent containing DMF provides good results. The reaction time can desirably range from 1 hour to 24 hours. The desired reaction temperature can range from $0°$ C. to $40°$ C. The reaction product can be dissolved in ethanol, followed by bubbling of hydrogen chloride gas ($0°$–$30°$ C., 20 minutes to 2 hours). A further reaction with an amino compound makes it possible to synthesize a substituted or unsubstituted amidino compound. For example, an amidino compound can be synthesized by reacting ammonium acetate or bubbling ammonia gas. Use of methylamine, for example, can synthesize a methyl-substituted amidino compound. As a solvent usable in this reaction, ethanol, methanol or a mixed solvent thereof can be used. The desired reaction time may range from 30 minutes to 24 hours.

Other compounds can be synthesized under the above-described conditions provided that the starting materials are changed.

A description will next be made of the compounds in Group C.

As will be shown below in Reaction scheme (20), a compound of the formula (49) is subjected to catalytic hydrogenation at room temperature under normal pressure, whereby the compound is reduced into a corresponding amino compound (50). As a solvent for this reaction, ethanol, methanol and DMF can be used either singly or in combination. Here, hydrochloric acid can be added in an amount equimolar to or greater than the amount of the nitro derivative, generally in a molar amount 1–1.2 times as much as the nitro derivative. The desired reaction time can range from 10 minutes to 20 hours. It is desired to conduct the reaction at a reaction temperature in a range of from $0°$ C. to $40°$ C. Subsequent to the reduction, a carboxylic acid derivative of the formula (51) is reacted with an amino compound of the formula (50) as shown in Reaction scheme (21), whereby a compound of the formula (52) can be obtained. At this time, a conventional condensing agent (for example, DCC, CDI, EDCI, DECP or the like) can be used. Although a general solvent can be used in this reaction, DMF or a mixed solvent containing DMF provides good results. The desired reaction time can range from 30 minutes to 40 hours. It is desired to conduct the reaction at $0°$ C. to $40°$ C. In essence, this synthesis process is not different from those described above for groups A and B, and for group C the chemical formula (2) is bonded to the moieties $R_1$ and $R_2$.

Reaction scheme (21)

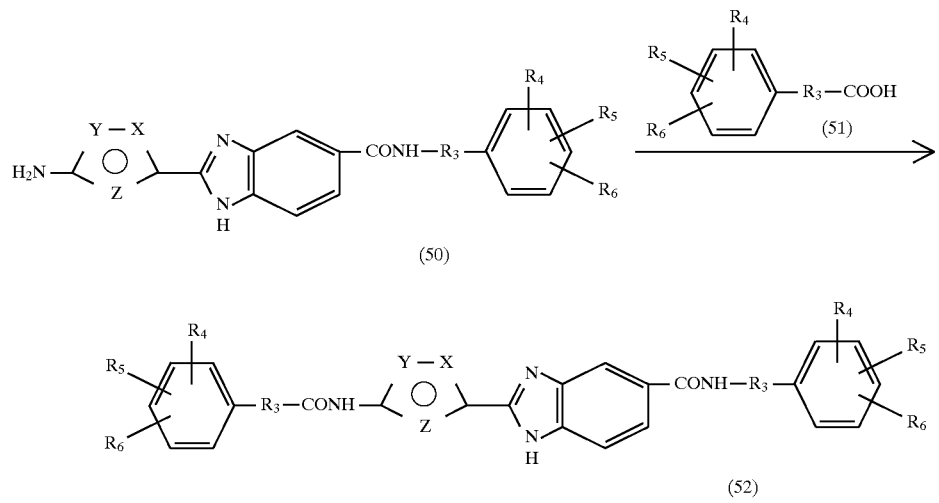

Reaction scheme (20)

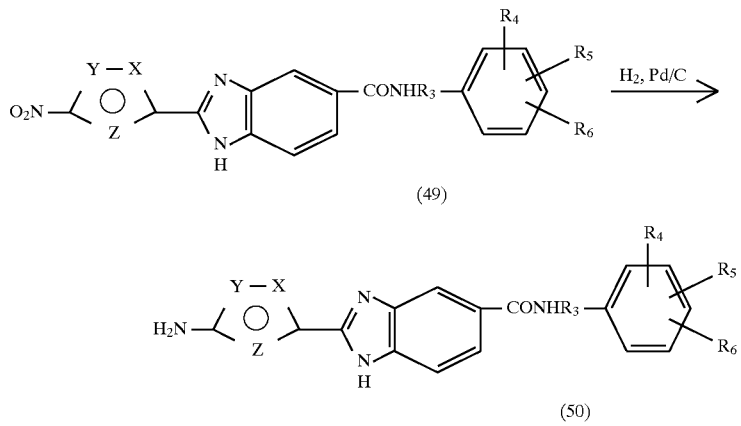

(49)

(50)

Examples of the compounds embraced by the formula (1) of the present invention will be shown in Tables 1–4. In these tables, counter anions of the ammonium group or the sulfonium group are not indicated. Any counter anions can be used insofar as they are recognized as pharmacologically acceptable. When it is necessary to specify the counter anions, they are described specifically.

The compounds according to the present invention are useful as anticancer agents having excellent activities. Applicable cancers include leukemia, osteosarcoma, breast cancer, ovarian cancer, stomach cancer, colon cancer, lung cancer, head and neck cancer, and the like. Further, these compounds can also be used as antibacterial agents and antiviral agents.

Their formulation into dosable preparations can be conducted by methods known per se in the art.

As dosage forms, various dosage forms can be chosen depending on the objects of treatments. Representative dosage forms include solid preparations, liquid preparations, suppositories, etc. More specifically, there are various preparations as will be described next.

These preparations are considered to include, as solid preparations, tablets, pills, powders, granules and capsules; as liquid preparations, injections in the form of solutions, and suspensions, syrups and emulsions; and as other preparations, suppositories and the like.

Upon formation into tablets, a variety of additives well known as carriers for many years in the present field of art can be used. Illustrative carriers include excipients lactose, sucrose, sodium chloride, glucose, urea, starch, calcium carbonate, kaolin, crystalline cellulose and silicic acid; binders such as water, ethanol, propanol, simple syrup, glucose solution, starch solution, gelatin solution, shellac solution, methylcellulose solution, hydroxypropylcellulose solution, polyvinylpyrrolidone solution, and carboxymethylcellulose solution; disintegrants such as dried starch, sodium arginate, agar powder, sodium hydrogencarbonate, calcium carbonate, polyoxyethylene sorbitan fatty acid esters, sodium lauryl sulfate, stearic monoglyceride, starch, and lactose; disintegration inhibitors such as sucrose, stearic acid, cacao butter, and hydrogenated oils; absorption promoters such as quaternary ammonium salts and lauryl sodium sulfate; moisturizers such as glycerin and starch; adsorbents such as starch, lactose, kaolin, bentonite, colloidal silicic acid, crystalline cellulose, and light anhydrous silicic acid; and lubricants such as talc, stearate salts, boric acid powder, and polyethylene glycol.

In the case of tablets, they can be formed, as needed, into tablets applied with a conventional coating, for example, into sugar coated tablets, gelatin coated tablets, enteric coated tablets or film coated tablets; or they can be formed into double layer tablets or multiple layer tablets.

Upon formation into pills, a variety of additives well known as carriers for many years in the present field of art can be used. Illustrative carriers include excipients such as glucose, lactose, starch, cacao butter, hydrogenated vegetable oils, kaolin and talc; binders such as gum arabic powder, tragacanth powder and gelatin; and disintegrants such as calmerose calcium and agar.

Capsules are formulated generally by mixing a compound of the present invention as an active ingredient with one of the above-exemplified various carriers and then filling the resultant mixture in hard gelatin capsules, soft capsules or the like.

To form as an injection, it is possible to use, upon formation into a solution, emulsion or suspension, a liquid widely employed as a diluent in the present field of art, for example, water, ethanol, macrogol, propylene glycol, ethoxylated isostearyl alcohol, polyoxylated isostearyl alcohol, a polyoxyethylene sorbitan fatty acid ester, cotton seed oil, corn oil, peanut oil, olive oil or the like. Further, each compound of the present invention can be used as a suspension or an emulsion by adding water to the compound and then forming the mixture into an aqueous suspension in the presence of an appropriate surfactant or into an emulsion by using a surfactant such as "HCO-60". Further, sodium chloride, glucose or glycerin can be incorporated in pharmaceutical preparations. In addition, an ordinary solubilizer, buffer, smoothing agent or the like can also be added.

Upon forming suppositories, a wide variety of additives conventionally known as carriers can be used. Illustrative usable examples of such additives include polyethylene glycol, cacao butter, higher alcohols, esters of higher alcohols, gelatin, and semi-synthetic glyceride.

One or more of colorants, preservatives, perfumes, corrigents, sweeteners and other drugs can be incorporated in pharmaceutical preparations as needed.

No particular limitation is imposed on the content of each compound of the present invention contained as an active ingredient in such pharmaceutical preparations. Its content can be chosen suitably from a wide range. In general, however, it is desired to contain a compound of the present invention in an amount of about 1–70 wt. %, preferably about 5–50 wt. % in each preparation composition.

No particular limitation is imposed on the manner of administration of these pharmaceutical preparations according to the present invention. Each preparation can be administered to a patient in a manner commensurate with the form of the preparation, the age, sex, other conditions, the seriousness of disease of the patient. For example, tablets, pills, solutions, suspensions, emulsions, powders, granules, syrups and capsules can be administered orally. Injections can be intravenously administered either singly or as mixtures with an ordinary fluid replacement such as a glucose solution or an amino acid solution. These injections can also be administered singly by an intramuscular, subcutaneous or intraperitoneal route. Suppositories are rectally administered. The dose of each pharmaceutical preparation according to the present invention can be suitably chosen depending on the manner of its administration and the age, sex, other conditions and the seriousness of disease of each patient. In general, it is however desired to control the daily dosage at about 0.001–1,000 mg or so in terms of the amount of the compound as the active ingredient. Further, the compound as the effective ingredient can desirably be contained in a range of about 0.001–1,000 mg in each preparation which is in the form of a dosage unit.

Generally speaking, an anticancer agent, even in the case of a widely used drug such as adriamycin or cisplatin, can hardly be considered to have small side effects. In view of the current level of technology, these side effects should be considered in relation to the strength of its action. The side effects are therefore unavoidable to some extent. Side effects of each compound according to the present invention are of such level that no problem will arise as long as the compound is used as an anticancer agent.

TABLE 1

| Compd. No. | $R_1$ | m | $R_2$ | n |
|---|---|---|---|---|

Structure: $R_1(CH_2)_mCONH$—[pyrrole with N–CH$_3$]—[benzimidazole with NH]—$CONH(CH_2)_nR_2$

| Compd. No. | $R_1$ | m | $R_2$ | n |
|---|---|---|---|---|
| 1 | $(ClCH_2CH_2)_2N$—C$_6$H$_4$— | 0 | —C(=NH)NH$_2$ | 2 |
| 2 | $(ClCH_2CH_2)_2N$—C$_6$H$_4$— | 1 | —C(=NH)NH$_2$ | 2 |
| 3 | $(ClCH_2CH_2)_2N$—C$_6$H$_4$— | 2 | —C(=NH)NH$_2$ | 2 |
| 4 | $(ClCH_2CH_2)_2N$—C$_6$H$_4$— | 3 | —C(=NH)NH$_2$ | 2 |
| 5 | $(ClCH_2CH_2)_2N$—C$_6$H$_3$(CH$_3$)— | 0 | —C(=NH)NH$_2$ | 2 |
| 6 | $(ClCH_2CH_2)_2N$—C$_6$H$_3$(OCH$_3$)— | 0 | —C(=NH)NH$_2$ | 2 |
| 7 | $(ClCH_2CH_2)_2N$—C$_6$H$_3$(Cl)— | 0 | —C(=NH)NH$_2$ | 2 |
| 8 | $(ClCH_2CH_2)_2N$—C$_6$H$_3$(CN)— | 0 | —C(=NH)NH$_2$ | 2 |

TABLE 1-continued

| Compd. No. | $R_1$ | m | $R_2$ | n |
|---|---|---|---|---|
| 9 | (ClCH$_2$CH$_2$)$_2$N—C$_6$H$_3$(CH$_3$)— (with CH$_3$ ortho) | 0 | —C(=NH)NH$_2$ | 2 |
| 10 | (ClCH$_2$CH$_2$)$_2$N—C$_6$H$_3$(OCH$_3$)— | 0 | —C(=NH)NH$_2$ | 2 |
| 11 | (ClCH$_2$CH$_2$)$_2$N—C$_6$H$_3$(Cl)— | 0 | —C(=NH)NH$_2$ | 2 |
| 12 | (ClCH$_2$CH$_2$)$_2$N—C$_6$H$_3$(CN)— | 0 | —C(=NH)NH$_2$ | 2 |
| 13 | (ClCH$_2$CH$_2$)$_2$N—C$_6$H$_4$—O— | 1 | —C(=NH)NH$_2$ | 2 |
| 14 | (ClCH$_2$CH$_2$)$_2$N—CH$_2$—C$_6$H$_4$— | 0 | —C(=NH)NH$_2$ | 2 |
| 15 | (ClCH$_2$CH$_2$)$_2$N—C$_6$H$_4$— | 0 | —C(=NH)NH$_2$ | 2 |
| 16 | Br— | 5 | —C(=NH)NH$_2$ | 2 |
| 17 | (ClCH$_2$CH$_2$)$_2$N—C$_6$H$_4$— | 0 | —S$^+$(CH$_3$)CH$_3$ | 2 |
| 18 | (ClCH$_2$CH$_2$)$_2$N—C$_6$H$_4$— | 1 | —S$^+$(CH$_3$)CH$_3$ | 2 |
| 19 | (ClCH$_2$CH$_2$)$_2$N—C$_6$H$_4$— | 2 | —S$^+$(CH$_3$)CH$_3$ | 2 |
| 20 | (ClCH$_2$CH$_2$)$_2$N—C$_6$H$_4$— | 3 | —S$^+$(CH$_3$)CH$_3$ | 2 |
| 21 | (ClCH$_2$CH$_2$)$_2$N—C$_6$H$_3$(CH$_3$)— | 0 | —S$^+$(CH$_3$)CH$_3$ | 2 |

TABLE 1-continued

| Compd. No. | R$_1$ | m | R$_2$ | n |
|---|---|---|---|---|
| 22 | (ClCH$_2$CH$_2$)$_2$N—⟨C$_6$H$_3$⟩— (CH$_3$O) | 0 | —S$^+$(CH$_3$)—CH$_3$ | 2 |
| 23 | (ClCH$_2$CH$_2$)$_2$N—⟨C$_6$H$_3$⟩— (Cl) | 0 | —S$^+$(CH$_3$)—CH$_3$ | 2 |
| 24 | (ClCH$_2$CH$_2$)$_2$N—⟨C$_6$H$_3$⟩— (NC) | 0 | —S$^+$(CH$_3$)—CH$_3$ | 2 |
| 25 | (ClCH$_2$CH$_2$)$_2$N—⟨C$_6$H$_4$⟩— | 0 | —S$^+$(CH$_3$)—CH$_3$ | 3 |
| 26 | (ClCH$_2$CH$_2$)$_2$N—⟨C$_6$H$_4$⟩— | 1 | —S$^+$(CH$_3$)—CH$_3$ | 3 |
| 27 | (ClCH$_2$CH$_2$)$_2$N—⟨C$_6$H$_4$⟩— | 2 | —S$^+$(CH$_3$)—CH$_3$ | 3 |
| 28 | (ClCH$_2$CH$_2$)$_2$N—⟨C$_6$H$_4$⟩— | 3 | —S$^+$(CH$_3$)—CH$_3$ | 3 |
| 29 | (ClCH$_2$CH$_2$)$_2$N—⟨C$_6$H$_3$⟩— (CH$_3$) | 0 | —S$^+$(CH$_3$)—CH$_3$ | 3 |
| 30 | (ClCH$_2$CH$_2$)$_2$N—⟨C$_6$H$_3$⟩— (CH$_3$O) | 0 | —S$^+$(CH$_3$)—CH$_3$ | 3 |
| 31 | (ClCH$_2$CH$_2$)$_2$N—⟨C$_6$H$_3$⟩— (Cl) | 0 | —S$^+$(CH$_3$)—CH$_3$ | 3 |
| 32 | (ClCH$_2$CH$_2$)$_2$N—⟨C$_6$H$_3$⟩— (NC) | 0 | —S$^+$(CH$_3$)—CH$_3$ | 3 |
| 33 | (ClCH$_2$CH$_2$)$_2$N—⟨C$_6$H$_3$⟩— (CH$_3$) | 0 | —S$^+$(CH$_3$)—CH$_3$ | 2 |

TABLE 1-continued

| Compd. No. | R₁ | m | R₂ | n |
|---|---|---|---|---|
| 34 | (ClCH₂CH₂)₂N—C₆H₃(OCH₃)— | 0 | —S⁺(CH₃)—CH₃ | 2 |
| 35 | (ClCH₂CH₂)₂N—C₆H₃(Cl)— | 0 | —S⁺(CH₃)—CH₃ | 2 |
| 36 | (ClCH₂CH₂)₂N—C₆H₃(CN)— | 0 | —S⁺(CH₃)—CH₃ | 2 |
| 37 | (ClCH₂CH₂)₂N—C₆H₄—O— | 1 | —S⁺(CH₃)—CH₃ | 2 |
| 38 | (ClCH₂CH₂)₂N—CH₂—C₆H₄— | 0 | —S⁺(CH₃)—CH₃ | 2 |
| 39 | (ClCH₂CH₂)₂N—C₆H₄— | 0 | —S⁺(CH₃)—CH₃ | 2 |
| 40 | Br— | 5 | —S⁺(CH₃)—CH₃ | 2 |
| 41 | (ClCH₂CH₂)₂N—C₆H₃(CH₃)— | 0 | —S⁺(CH₃)—CH₃ | 3 |
| 42 | (ClCH₂CH₂)₂N—C₆H₃(OCH₃)— | 0 | —S⁺(CH₃)—CH₃ | 3 |
| 43 | (ClCH₂CH₂)₂N—C₆H₃(Cl)— | 0 | —S⁺(CH₃)—CH₃ | 3 |
| 44 | (ClCH₂CH₂)₂N—C₆H₃(CN)— | 0 | —S⁺(CH₃)—CH₃ | 3 |
| 45 | (ClCH₂CH₂)₂N—C₆H₄—O— | 1 | —S⁺(CH₃)—CH₃ | 3 |

TABLE 1-continued

| Compd. No. | R₁ | m | R₂ | n |
|---|---|---|---|---|
| 46 | (ClCH₂CH₂)₂N—CH₂—C₆H₄— | 0 | —S⁺(CH₃)—CH₃ | 3 |
| 47 | (ClCH₂CH₂)₂N—C₆H₄— (meta) | 0 | —S⁺(CH₃)—CH₃ | 3 |
| 48 | Br— | 5 | —S⁺(CH₃)—CH₃ | 3 |
| 49 | (ClCH₂CH₂)₂N—C₆H₄— | 0 | —S—CH₃ | 2 |
| 50 | (ClCH₂CH₂)₂N—C₆H₄— | 1 | —S—CH₃ | 2 |
| 51 | (ClCH₂CH₂)₂N—C₆H₄— | 2 | —S—CH₃ | 2 |
| 52 | (ClCH₂CH₂)₂N—C₆H₄— | 3 | —S—CH₃ | 2 |
| 53 | (ClCH₂CH₂)₂N—C₆H₃(CH₃)— | 0 | —S—CH₃ | 2 |
| 54 | (ClCH₂CH₂)₂N—C₆H₃(OCH₃)— | 0 | —S—CH₃ | 2 |
| 55 | (ClCH₂CH₂)₂N—C₆H₃(Cl)— | 0 | —S—CH₃ | 2 |
| 56 | (ClCH₂CH₂)₂N—C₆H₃(CN)— | 0 | —S—CH₃ | 2 |
| 57 | (ClCH₂CH₂)₂N—C₆H₄— | 0 | —S—CH₃ | 3 |
| 58 | (ClCH₂CH₂)₂N—C₆H₄— | 1 | —S—CH₃ | 3 |

TABLE 1-continued
| Compd. No. | R₁ | m | R₂ | n |
|---|---|---|---|---|
| 59 | 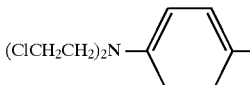 | 2 | $-S-CH_3$ | 3 |
| 60 | 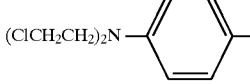 | 3 | $-S-CH_3$ | 3 |
| 61 | 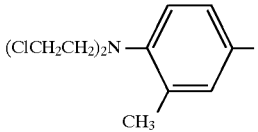 | 0 | $-S-CH_3$ | 3 |
| 62 | 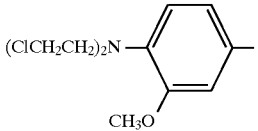 | 0 | $-S-CH_3$ | 3 |
| 63 | 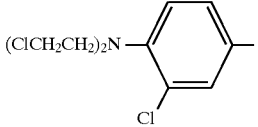 | 0 | $-S-CH_3$ | 3 |
| 64 | 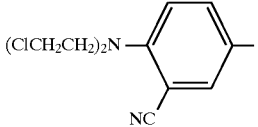 | 0 | $-S-CH_3$ | 3 |
| 65 | 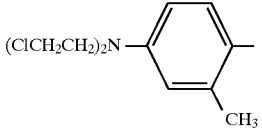 | 0 | $-S-CH_3$ | 2 |
| 66 | 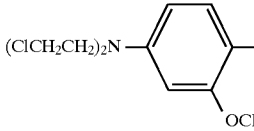 | 0 | $-S-CH_3$ | 2 |
| 67 | 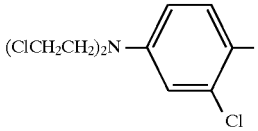 | 0 | $-S-CH_3$ | 2 |
| 68 | 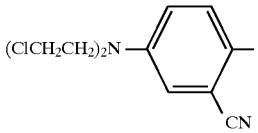 | 0 | $-S-CH_3$ | 2 |
| 69 | 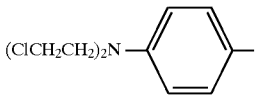 | 1 | $-S-CH_3$ | 2 |
| 70 | 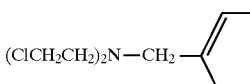 | 0 | $-S-CH_3$ | 2 |

TABLE 1-continued

| Compd. No. | R₁ | m | R₂ | n |
|---|---|---|---|---|
| 71 | (ClCH₂CH₂)₂N—⟨phenyl⟩— | 0 | —S—CH₃ | 2 |
| 72 | Br— | 5 | —S—CH₃ | 2 |
| 73 | (ClCH₂CH₂)₂N—⟨phenyl-CH₃⟩— | 0 | —S—CH₃ | 3 |
| 74 | (ClCH₂CH₂)₂N—⟨phenyl-OCH₃⟩— | 0 | —S—CH₃ | 3 |
| 75 | (ClCH₂CH₂)₂N—⟨phenyl-Cl⟩— | 0 | —S—CH₃ | 3 |
| 76 | (ClCH₂CH₂)₂N—⟨phenyl-CN⟩— | 0 | —S—CH₃ | 3 |
| 77 | (ClCH₂CH₂)₂N—⟨phenyl⟩—O— | 1 | —S—CH₃ | 3 |
| 78 | (ClCH₂CH₂)₂N—CH₂—⟨phenyl⟩— | 0 | —S—CH₃ | 3 |
| 79 | (ClCH₂CH₂)₂N—⟨phenyl⟩— | 0 | —S—CH₃ | 3 |
| 80 | Br— | 5 | —S—CH₃ | 3 |
| 81 | (ClCH₂CH₂)₂N—⟨phenyl⟩— | 0 | —N(CH₃)—CH₃ | 3 |
| 82 | (ClCH₂CH₂)₂N—⟨phenyl⟩— | 1 | —N(CH₃)—CH₃ | 3 |
| 83 | (ClCH₂CH₂)₂N—⟨phenyl⟩— | 2 | —N(CH₃)—CH₃ | 3 |
| 84 | (ClCH₂CH₂)₂N—⟨phenyl⟩— | 3 | —N(CH₃)—CH₃ | 3 |

TABLE 1-continued

| Compd. No. | R₁ | m | R₂ | n |
|---|---|---|---|---|
| 85 | (ClCH₂CH₂)₂N—[phenyl with CH₃ substituent]— | 0 | —N(CH₃)CH₃ | 3 |
| 86 | (ClCH₂CH₂)₂N—[phenyl with CH₃O substituent]— | 0 | —N(CH₃)CH₃ | 3 |
| 87 | (ClCH₂CH₂)₂N—[phenyl with Cl substituent]— | 0 | —N(CH₃)CH₃ | 3 |
| 88 | (ClCH₂CH₂)₂N—[phenyl with NC substituent]— | 0 | —N(CH₃)CH₃ | 3 |
| 89 | (ClCH₂CH₂)₂N—[phenyl with CH₃ substituent]— | 0 | —N(CH₃)CH₃ | 3 |
| 90 | (ClCH₂CH₂)₂N—[phenyl with OCH₃ substituent]— | 0 | —N(CH₃)CH₃ | 3 |
| 91 | (ClCH₂CH₂)₂N—[phenyl with Cl substituent]— | 0 | —N(CH₃)CH₃ | 3 |
| 92 | (ClCH₂CH₂)₂N—[phenyl with CN substituent]— | 0 | —N(CH₃)CH₃ | 3 |
| 93 | (ClCH₂CH₂)₂N—[phenyl]—O— | 1 | —N(CH₃)CH₃ | 3 |
| 94 | (ClCH₂CH₂)₂N—CH₂—[phenyl]— | 0 | —N(CH₃)CH₃ | 3 |
| 95 | (ClCH₂CH₂)₂N—[phenyl]— | 0 | —N(CH₃)CH₃ | 3 |
| 96 | Br— | 5 | —N(CH₃)CH₃ | 3 |

TABLE 1-continued

| Compd. No. | R₁ | m | R₂ | n |
|---|---|---|---|---|
| 97 | (ClCH₂CH₂)₂N—⟨C₆H₄⟩— | 0 | —N⁺(CH₃)₃ | 3 |
| 98 | (ClCH₂CH₂)₂N—⟨C₆H₄⟩— | 1 | —N⁺(CH₃)₃ | 3 |
| 99 | (ClCH₂CH₂)₂N—⟨C₆H₄⟩— | 2 | —N⁺(CH₃)₃ | 3 |
| 100 | (ClCH₂CH₂)₂N—⟨C₆H₄⟩— | 3 | —N⁺(CH₃)₃ | 3 |
| 101 | (ClCH₂CH₂)₂N—⟨C₆H₃(CH₃)⟩— | 0 | —N⁺(CH₃)₃ | 3 |
| 102 | (ClCH₂CH₂)₂N—⟨C₆H₃(OCH₃)⟩— | 0 | —N⁺(CH₃)₃ | 3 |
| 103 | (ClCH₂CH₂)₂N—⟨C₆H₃(Cl)⟩— | 0 | —N⁺(CH₃)₃ | 3 |
| 104 | (ClCH₂CH₂)₂N—⟨C₆H₃(CN)⟩— | 0 | —N⁺(CH₃)₃ | 3 |
| 105 | (ClCH₂CH₂)₂N—⟨C₆H₃(CH₃)⟩— | 0 | —N⁺(CH₃)₃ | 3 |
| 106 | (ClCH₂CH₂)₂N—⟨C₆H₃(OCH₃)⟩— | 0 | —N⁺(CH₃)₃ | 3 |
| 107 | (ClCH₂CH₂)₂N—⟨C₆H₃(Cl)⟩— | 0 | —N⁺(CH₃)₃ | 3 |

TABLE 1-continued

| Compd. No. | R$_1$ | m | R$_2$ | n |
|---|---|---|---|---|
| 108 | (ClCH$_2$CH$_2$)$_2$N—[phenyl with CN]— | 0 | —N$^+$(CH$_3$)$_3$ | 3 |
| 109 | (ClCH$_2$CH$_2$)$_2$N—[phenyl]—O— | 1 | —N$^+$(CH$_3$)$_3$ | 3 |
| 110 | (ClCH$_2$CH$_2$)$_2$N—CH$_2$—[phenyl]— | 0 | —N$^+$(CH$_3$)$_3$ | 3 |
| 111 | (ClCH$_2$CH$_2$)$_2$N—[phenyl]— | 0 | —N$^+$(CH$_3$)$_3$ | 3 |
| 112 | Br— | 5 | —N$^+$(CH$_3$)$_3$ | 3 |
| 113 | (ClCH$_2$CH$_2$)$_2$N—[phenyl]— | 0 | —NH—C(=NH)—NH$_2$ | 1 |
| 114 | (ClCH$_2$CH$_2$)$_2$N—[phenyl]— | 1 | —NH—C(=NH)—NH$_2$ | 1 |
| 115 | (ClCH$_2$CH$_2$)$_2$N—[phenyl]— | 2 | —NH—C(=NH)—NH$_2$ | 1 |
| 116 | (ClCH$_2$CH$_2$)$_2$N—[phenyl]— | 3 | —NH—C(=NH)—NH$_2$ | 1 |
| 117 | (ClCH$_2$CH$_2$)$_2$N—[phenyl with CH$_3$]— | 0 | —NH—C(=NH)—NH$_2$ | 1 |
| 118 | (ClCH$_2$CH$_2$)$_2$N—[phenyl with CH$_3$O]— | 0 | —NH—C(=NH)—NH$_2$ | 1 |
| 119 | (ClCH$_2$CH$_2$)$_2$N—[phenyl with Cl]— | 0 | —NH—C(=NH)—NH$_2$ | 1 |

TABLE 1-continued
| Compd. No. | R₁ | m | R₂ | n |
|---|---|---|---|---|
| 120 | 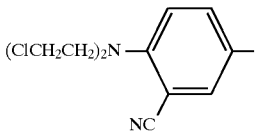 | 0 | —NH—C(=NH)—NH₂ | 1 |
| 121 | 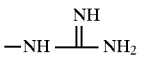 | 0 | —NH—C(=NH)—NH₂ | 1 |
| 122 | 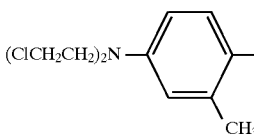 | 0 | —NH—C(=NH)—NH₂ | 1 |
| 123 | 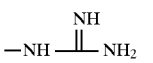 | 0 | —NH—C(=NH)—NH₂ | 1 |
| 124 | 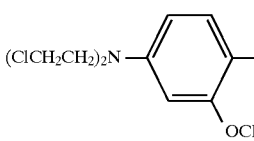 | 0 | —NH—C(=NH)—NH₂ | 1 |
| 125 | 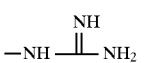 | 1 | —NH—C(=NH)—NH₂ | 1 |
| 126 | 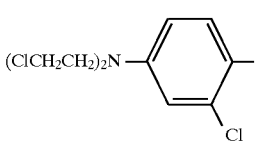 | 0 | —NH—C(=NH)—NH₂ | 1 |
| 127 | 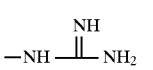 | 0 | —NH—C(=NH)—NH₂ | 1 |
| 128 | Br— | 5 | —NH—C(=NH)—NH₂ | 1 |
| 129 | 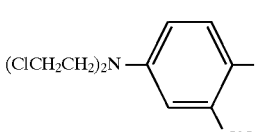 | 0 | —NH₂ | 2 |
| 130 | 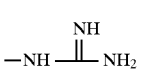 | 1 | —NH₂ | 2 |
| 131 | 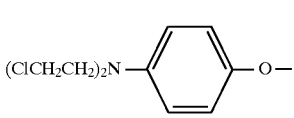 | 2 | —NH₂ | 2 |
| 132 | 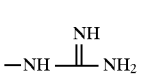 | 3 | —NH₂ | 2 |

TABLE 1-continued

| Compd. No. | R₁ | m | R₂ | n |
|---|---|---|---|---|
| 133 | (ClCH₂CH₂)₂N—[phenyl with CH₃]— | 0 | —NH₂ | 2 |
| 134 | (ClCH₂CH₂)₂N—[phenyl with CH₃O]— | 0 | —NH₂ | 2 |
| 135 | (ClCH₂CH₂)₂N—[phenyl with Cl]— | 0 | —NH₂ | 2 |
| 136 | (ClCH₂CH₂)₂N—[phenyl with NC]— | 0 | —NH₂ | 2 |
| 137 | (ClCH₂CH₂)₂N—[phenyl with CH₃]— | 0 | —NH₂ | 2 |
| 138 | (ClCH₂CH₂)₂N—[phenyl with OCH₃]— | 1 | —NH₂ | 2 |
| 139 | (ClCH₂CH₂)₂N—[phenyl with Cl]— | 2 | —NH₂ | 2 |
| 140 | (ClCH₂CH₂)₂N—[phenyl with CN]— | 3 | —NH₂ | 2 |
| 141 | (ClCH₂CH₂)₂N—[phenyl]—O— | 1 | —NH₂ | 2 |
| 142 | (ClCH₂CH₂)₂N—CH₂—[phenyl]— | 0 | —NH₂ | 2 |
| 143 | (ClCH₂CH₂)₂N—[phenyl]— | 0 | —NH₂ | 2 |
| 144 | (ClCH₂CH₂)₂N—[phenyl]— | 0 | —OH | 2 |

TABLE 1-continued

| Compd. No. | R₁ | m | R₂ | n |
|---|---|---|---|---|
| 145 | (ClCH₂CH₂)₂N—C₆H₄— | 1 | —OH | 2 |
| 146 | (ClCH₂CH₂)₂N—C₆H₄— | 2 | —OH | 2 |
| 147 | (ClCH₂CH₂)₂N—C₆H₄— | 3 | —OH | 2 |
| 148 | (ClCH₂CH₂)₂N—C₆H₃(CH₃)— | 0 | —OH | 2 |
| 149 | (ClCH₂CH₂)₂N—C₆H₃(OCH₃)— | 0 | —OH | 2 |
| 150 | (ClCH₂CH₂)₂N—C₆H₃(Cl)— | 0 | —OH | 2 |
| 151 | (ClCH₂CH₂)₂N—C₆H₃(CN)— | 0 | —OH | 2 |
| 152 | (ClCH₂CH₂)₂N—C₆H₃(CH₃)— | 0 | —OH | 2 |
| 153 | (ClCH₂CH₂)₂N—C₆H₃(OCH₃)— | 1 | —OH | 2 |
| 154 | (ClCH₂CH₂)₂N—C₆H₃(Cl)— | 2 | —OH | 2 |
| 155 | (ClCH₂CH₂)₂N—C₆H₃(CN)— | 3 | —OH | 2 |
| 156 | (ClCH₂CH₂)₂N—C₆H₄—O— | 1 | —OH | 2 |

TABLE 1-continued

| Compd. No. | R₁ | m | R₂ | n |
|---|---|---|---|---|
| 157 | (ClCH₂CH₂)₂N—CH₂—C₆H₄— | 0 | —OH | 2 |
| 158 | (ClCH₂CH₂)₂N—C₆H₄— | 0 | —OH | 2 |
| 159 | (ClCH₂CH₂)₂N—C₆H₄— | 0 | —C₆H₄—C(=NH)NH₂ | 0 |
| 160 | (ClCH₂CH₂)₂N—C₆H₄— | 1 | —C₆H₄—C(=NH)NH₂ | 0 |
| 161 | (ClCH₂CH₂)₂N—C₆H₄— | 2 | —C₆H₄—C(=NH)NH₂ | 0 |
| 162 | (ClCH₂CH₂)₂N—C₆H₄— | 3 | —C₆H₄—C(=NH)NH₂ | 0 |
| 163 | (ClCH₂CH₂)₂N—C₆H₃(CH₃)— | 0 | —C₆H₄—C(=NH)NH₂ | 0 |
| 164 | (ClCH₂CH₂)₂N—C₆H₃(OCH₃)— | 0 | —C₆H₄—C(=NH)NH₂ | 0 |
| 165 | (ClCH₂CH₂)₂N—C₆H₃(Cl)— | 0 | —C₆H₄—C(=NH)NH₂ | 0 |
| 166 | (ClCH₂CH₂)₂N—C₆H₃(CN)— | 0 | —C₆H₄—C(=NH)NH₂ | 0 |
| 167 | (ClCH₂CH₂)₂N—C₆H₃(CH₃)— | 0 | —C₆H₄—C(=NH)NH₂ | 0 |
| 168 | (ClCH₂CH₂)₂N—C₆H₃(OCH₃)— | 1 | —C₆H₄—C(=NH)NH₂ | 0 |

TABLE 1-continued

| Compd. No. | R₁ | m | R₂ | n |
|---|---|---|---|---|
| 169 | (ClCH₂CH₂)₂N—C₆H₃(Cl)— | 2 | 4-(H₂N(HN=)C)-C₆H₄— | 0 |
| 170 | (ClCH₂CH₂)₂N—C₆H₃(CN)— | 3 | 4-(H₂N(HN=)C)-C₆H₄— | 0 |
| 171 | (ClCH₂CH₂)₂N—C₆H₄—O— | 1 | 4-(H₂N(HN=)C)-C₆H₄— | 0 |
| 172 | (ClCH₂CH₂)₂N—CH₂—C₆H₄— | 0 | 4-(H₂N(HN=)C)-C₆H₄— | 0 |
| 173 | (ClCH₂CH₂)₂N—C₆H₄— (meta) | 0 | 4-(H₂N(HN=)C)-C₆H₄— | 0 |
| 174 | Br— | 5 | 4-(H₂N(HN=)C)-C₆H₄— | 0 |
| 175 | (ClCH₂CH₂)₂N—C₆H₄— | 0 | piperidin-1-yl | 2 |
| 176 | (ClCH₂CH₂)₂N—C₆H₄— | 1 | piperidin-1-yl | 2 |
| 177 | (ClCH₂CH₂)₂N—C₆H₄— | 2 | piperidin-1-yl | 2 |
| 178 | (ClCH₂CH₂)₂N—C₆H₄— | 3 | piperidin-1-yl | 2 |
| 179 | (ClCH₂CH₂)₂N—C₆H₃(CH₃)— | 0 | piperidin-1-yl | 2 |
| 180 | (ClCH₂CH₂)₂N—C₆H₃(OCH₃)— | 0 | piperidin-1-yl | 2 |
| 181 | (ClCH₂CH₂)₂N—C₆H₃(Cl)— | 0 | piperidin-1-yl | 2 |

TABLE 1-continued

| Compd. No. | R₁ | m | R₂ | n |
|---|---|---|---|---|
| 182 | (ClCH₂CH₂)₂N–C₆H₃(CN)– (2-CN) | 0 | –N(piperidine) | 2 |
| 183 | (ClCH₂CH₂)₂N–C₆H₃(CH₃)– (3-CH₃) | 0 | –N(piperidine) | 2 |
| 184 | (ClCH₂CH₂)₂N–C₆H₃(OCH₃)– (3-OCH₃) | 1 | –N(piperidine) | 2 |
| 185 | (ClCH₂CH₂)₂N–C₆H₃(Cl)– (4-Cl) | 2 | –N(piperidine) | 2 |
| 186 | (ClCH₂CH₂)₂N–C₆H₃(CN)– (3-CN) | 3 | –N(piperidine) | 2 |
| 187 | (ClCH₂CH₂)₂N–C₆H₄–O– | 1 | –N(piperidine) | 2 |
| 188 | (ClCH₂CH₂)₂N–CH₂–C₆H₄– | 0 | –N(piperidine) | 2 |
| 189 | (ClCH₂CH₂)₂N–C₆H₄– | 0 | –N(piperidine) | 2 |
| 190 | Br– | 0 | –N(piperidine) | 2 |
| 191 | (ClCH₂CH₂)₂N–C₆H₄– | 0 | furan-2-yl | 0 |
| 192 | (ClCH₂CH₂)₂N–C₆H₄– | 1 | furan-2-yl | 0 |
| 193 | (ClCH₂CH₂)₂N–C₆H₄– | 2 | furan-2-yl | 0 |

TABLE 1-continued

| Compd. No. | R₁ | m | R₂ | n |
|---|---|---|---|---|
| 194 | (ClCH₂CH₂)₂N—C₆H₄— | 3 | furan-2-yl | 0 |
| 195 | (ClCH₂CH₂)₂N—C₆H₃(CH₃)— | 0 | furan-2-yl | 0 |
| 196 | (ClCH₂CH₂)₂N—C₆H₃(OCH₃)— | 0 | furan-2-yl | 0 |
| 197 | (ClCH₂CH₂)₂N—C₆H₃(Cl)— | 0 | furan-2-yl | 0 |
| 198 | (ClCH₂CH₂)₂N—C₆H₃(CN)— | 0 | furan-2-yl | 0 |
| 199 | (ClCH₂CH₂)₂N—C₆H₃(CH₃)— | 0 | furan-2-yl | 0 |
| 200 | (ClCH₂CH₂)₂N—C₆H₃(OCH₃)— | 1 | furan-2-yl | 0 |
| 201 | (ClCH₂CH₂)₂N—C₆H₃(Cl)— | 2 | furan-2-yl | 0 |
| 202 | (ClCH₂CH₂)₂N—C₆H₃(CN)— | 3 | furan-2-yl | 0 |
| 203 | (ClCH₂CH₂)₂N—C₆H₄—O— | 1 | furan-2-yl | 0 |
| 204 | (ClCH₂CH₂)₂N—CH₂—C₆H₄— | 0 | furan-2-yl | 0 |
| 205 | (ClCH₂CH₂)₂N—C₆H₄— | 0 | furan-2-yl | 0 |

TABLE 1-continued
| Compd. No. | R₁ | m | R₂ | n |
|---|---|---|---|---|
| 206 | Br— | 0 | 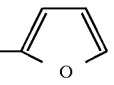 | 0 |
| 207 |  (ClCH₂CH₂)₂N— | 0 | 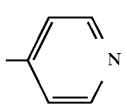 | 1 |
| 208 | (ClCH₂CH₂)₂N— | 3 | 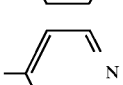 | 1 |
| 209 | (ClCH₂CH₂)₂N— (CH₃) | 0 | 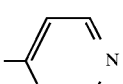 | 1 |
| 200 | (ClCH₂CH₂)₂N— (Cl) | 0 | 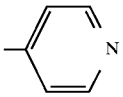 | 1 |
| 211 | (ClCH₂CH₂)₂N— (CH₃) | 0 | 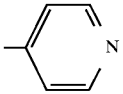 | 1 |
| 212 | (ClCH₂CH₂)₂N— (CH₃O) | 0 | 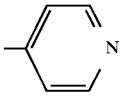 | 1 |
| 213 | (ClCH₂CH₂)₂N— (Cl) | 0 | 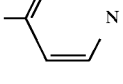 | 1 |
| 214 | (ClCH₂CH₂)₂N— (NC) | 0 | 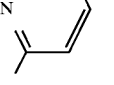 | 1 |
| 215 | (ClCH₂CH₂)₂N— | 0 | 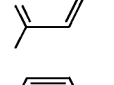 | 1 |
| 216 | (ClCH₂CH₂)₂N— | 3 | 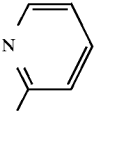 | 1 |
| 217 | (ClCH₂CH₂)₂N— (CH₃) | 0 | 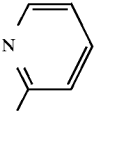 | 1 |

TABLE 1-continued

| Compd. No. | R$_1$ | m | R$_2$ | n |
|---|---|---|---|---|
| 218 | (ClCH$_2$CH$_2$)$_2$N—⟨phenyl-3-Cl⟩— | 0 | 2-pyridyl | 1 |
| 219 | (ClCH$_2$CH$_2$)$_2$N—⟨phenyl-2-CH$_3$⟩— | 0 | 2-pyridyl | 1 |
| 220 | (ClCH$_2$CH$_2$)$_2$N—⟨phenyl-2-OCH$_3$⟩— | 0 | 2-pyridyl | 1 |
| 221 | (ClCH$_2$CH$_2$)$_2$N—⟨phenyl-2-Cl⟩— | 0 | 2-pyridyl | 1 |
| 222 | (ClCH$_2$CH$_2$)$_2$N—⟨phenyl-2-CN⟩— | 0 | 2-pyridyl | 1 |
| 223 | (ClCH$_2$CH$_2$)$_2$N—⟨phenyl⟩— | 0 | 3-pyridyl | 1 |
| 224 | (ClCH$_2$CH$_2$)$_2$N—⟨phenyl⟩— | 3 | 3-pyridyl | 1 |
| 225 | (ClCH$_2$CH$_2$)$_2$N—⟨phenyl-3-CH$_3$⟩— | 0 | 3-pyridyl | 1 |
| 226 | (ClCH$_2$CH$_2$)$_2$N—⟨phenyl-3-Cl⟩— | 0 | 3-pyridyl | 1 |
| 227 | (ClCH$_2$CH$_2$)$_2$N—⟨phenyl-2-CH$_3$⟩— | 0 | 3-pyridyl | 1 |
| 228 | (ClCH$_2$CH$_2$)$_2$N—⟨phenyl-3-OCH$_3$⟩— | 0 | 3-pyridyl | 1 |

TABLE 1-continued

| Compd. No. | R₁ | m | R₂ | n |
|---|---|---|---|---|
| 229 | (ClCH₂CH₂)₂N—(2-Cl-phenyl)— | 0 | 3-pyridyl | 1 |
| 230 | (ClCH₂CH₂)₂N—(2-CN-phenyl)— | 0 | 3-pyridyl | 1 |
| 231 | (ClCH₂CH₂)₂N—(phenyl)— | 0 | N-methylpyridinium Cl⁻ | 1 |
| 232 | (ClCH₂CH₂)₂N—(phenyl)— | 3 | N-methylpyridinium Cl⁻ | 1 |
| 233 | (ClCH₂CH₂)₂N—(3-CH₃-phenyl)— | 0 | N-methylpyridinium Cl⁻ | 1 |
| 234 | (ClCH₂CH₂)₂N—(3-Cl-phenyl)— | 0 | N-methylpyridinium Cl⁻ | 1 |
| 235 | (ClCH₂CH₂)₂N—(2-CH₃-phenyl)— | 0 | N-methylpyridinium Cl⁻ | 1 |
| 236 | (ClCH₂CH₂)₂N—(3-CH₃O-phenyl)— | 0 | N-methylpyridinium Cl⁻ | 1 |
| 237 | (ClCH₂CH₂)₂N—(2-Cl-phenyl)— | 0 | N-methylpyridinium Cl⁻ | 1 |
| 238 | (ClCH₂CH₂)₂N—(2-CN-phenyl)— | 0 | N-methylpyridinium Cl⁻ | 1 |
| 239 | (ClCH₂CH₂)₂N—(phenyl)— | 0 | 2-methyl-N-methylpyridinium Cl⁻ | 1 |

TABLE 1-continued
| Compd. No. | R₁ | m | R₂ | n |
|---|---|---|---|---|
| 240 | 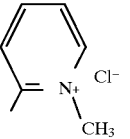 | 3 | 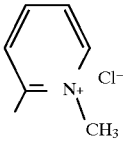 | 1 |
| 241 | 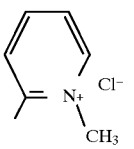 | 0 | 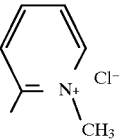 | 1 |
| 242 | 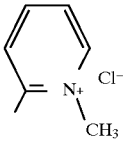 | 0 | 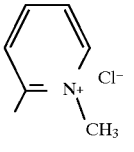 | 1 |
| 243 | 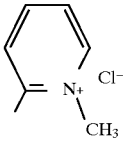 | 0 | 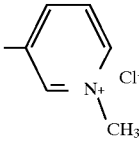 | 1 |
| 244 | 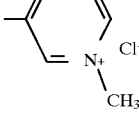 | 0 | 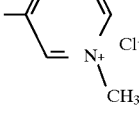 | 1 |
| 245 | (ClCH₂CH₂)₂N—⟨phenyl-Cl⟩— | 0 | pyridinium-CH₃ Cl⁻ | 1 |
| 246 | (ClCH₂CH₂)₂N—⟨phenyl-CN⟩— | 0 | pyridinium-CH₃ Cl⁻ | 1 |
| 247 | (ClCH₂CH₂)₂N—⟨phenyl⟩— | 0 | pyridinium-CH₃ Cl⁻ | 1 |
| 248 | (ClCH₂CH₂)₂N—⟨phenyl⟩— | 3 | pyridinium-CH₃ Cl⁻ | 1 |
| 249 | (ClCH₂CH₂)₂N—⟨phenyl-CH₃⟩— | 0 | pyridinium-CH₃ Cl⁻ | 1 |

TABLE 1-continued

| Compd. No. | R$_1$ | m | R$_2$ | n |
|---|---|---|---|---|
| 250 | (ClCH$_2$CH$_2$)$_2$N—[phenyl with Cl]— | 0 | [N-methylpyridinium Cl$^-$] | 1 |
| 251 | (ClCH$_2$CH$_2$)$_2$N—[phenyl with CH$_3$]— | 0 | [N-methylpyridinium Cl$^-$] | 1 |
| 252 | (ClCH$_2$CH$_2$)$_2$N—[phenyl with CH$_3$O]— | 0 | [N-methylpyridinium Cl$^-$] | 1 |
| 253 | (ClCH$_2$CH$_2$)$_2$N—[phenyl with Cl]— | 0 | [N-methylpyridinium Cl$^-$] | 1 |
| 254 | (ClCH$_2$CH$_2$)$_2$N—[phenyl with NC]— | 0 | [N-methylpyridinium Cl$^-$] | 1 |
| 255 | (ClCH$_2$CH$_2$)$_2$N—[phenyl with CF$_3$]— | 0 | —C(=NH)NH$_2$ | 2 |
| 256 | (ClCH$_2$CH$_2$)$_2$N—[phenyl with CONHCH$_2$CH$_2$N(CH$_3$)$_2$]— | 0 | —C(=NH)NH$_2$ | 2 |
| 257 | (ClCH$_2$CH$_2$)$_2$N—[phenyl with CF$_3$]— | 0 | —C(=NH)NH$_2$ | 2 |
| 258 | (ClCH$_2$CH$_2$)$_2$N—[phenyl with CONHCH$_2$CH$_2$N(CH$_3$)$_2$]— | 0 | —C(=NH)NH$_2$ | 2 |
| 259 | (ClCH$_2$CH$_2$)$_2$N—[phenyl]—O— | 2 | —C(=NH)NH$_2$ | 2 |
| 260 | (BrCH$_2$CH$_2$)$_2$N—[phenyl]— | 0 | —C(=NH)NH$_2$ | 2 |

TABLE 1-continued

| Compd. No. | R₁ | m | R₂ | n |
|---|---|---|---|---|
| 261 | 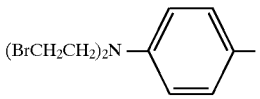 (BrCH₂CH₂)₂N—⟨phenyl⟩— | 3 |  $-\overset{NH}{\underset{}{\|}}-NH_2$ | 2 |
| 262 | 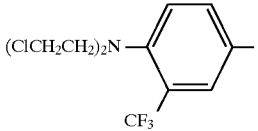 (ClCH₂CH₂)₂N—⟨phenyl, CF₃⟩— | 0 | $-N(CH_3)-CH_3$ | 3 |
| 263 |  (ClCH₂CH₂)₂N—⟨phenyl, CONHCH₂CH₂N(CH₃)₂⟩— | 0 | $-N(CH_3)-CH_3$ | 3 |
| 264 | 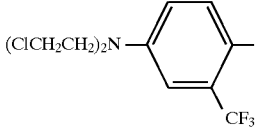 (ClCH₂CH₂)₂N—⟨phenyl, CF₃⟩— | 0 | $-N(CH_3)-CH_3$ | 3 |
| 265 |  (ClCH₂CH₂)₂N—⟨phenyl, CONHCH₂CH₂N(CH₃)₂⟩— | 0 | $-N(CH_3)-CH_3$ | 3 |
| 266 | 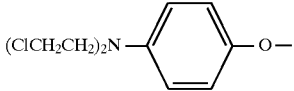 (ClCH₂CH₂)₂N—⟨phenyl⟩—O— | 2 | $-N(CH_3)-CH_3$ | 3 |
| 267 | 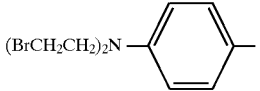 (BrCH₂CH₂)₂N—⟨phenyl⟩— | 0 | $-N(CH_3)-CH_3$ | 3 |
| 268 | 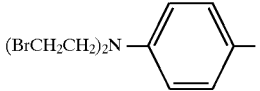 (BrCH₂CH₂)₂N—⟨phenyl⟩— | 3 | $-N(CH_3)-CH_3$ | 3 |
| 269 | 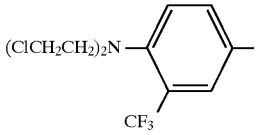 (ClCH₂CH₂)₂N—⟨phenyl, CF₃⟩— | 0 | $-N^+(CH_3)_3$ | 3 |
| 270 | 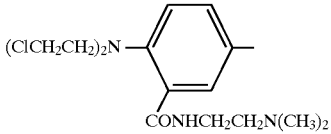 (ClCH₂CH₂)₂N—⟨phenyl, CONHCH₂CH₂N(CH₃)₂⟩— | 0 | $-N^+(CH_3)_3$ | 3 |
| 271 | 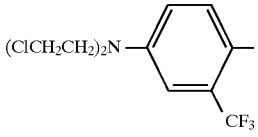 (ClCH₂CH₂)₂N—⟨phenyl, CF₃⟩— | 0 | $-N^+(CH_3)_3$ | 3 |
| 272 |  (ClCH₂CH₂)₂N—⟨phenyl, CONHCH₂CH₂N(CH₃)₂⟩— | 0 | $-N^+(CH_3)_3$ | 3 |

TABLE 1-continued

| Compd. No. | R₁ | m | R₂ | n |
|---|---|---|---|---|
| 273 | (ClCH₂CH₂)₂N—⟨C₆H₄⟩—O— | 2 | —N⁺(CH₃)₃ | 3 |
| 274 | (BrCH₂CH₂)₂N—⟨C₆H₄⟩— | 0 | —N⁺(CH₃)₃ | 3 |
| 275 | (BrCH₂CH₂)₂N—⟨C₆H₄⟩— | 3 | —N⁺(CH₃)₃ | 3 |
| 276 | (ClCH₂CH₂)₂N—⟨C₆H₃(CF₃)⟩— | 0 | —S⁺(CH₃)₂ | 2 |
| 277 | (ClCH₂CH₂)₂N—⟨C₆H₃(CONHCH₂CH₂N(CH₃)₂)⟩— | 0 | —S⁺(CH₃)₂ | 2 |
| 278 | (ClCH₂CH₂)₂N—⟨C₆H₃(CF₃)⟩— | 0 | —S⁺(CH₃)₂ | 2 |
| 279 | (ClCH₂CH₂)₂N—⟨C₆H₃(CONHCH₂CH₂N(CH₃)₂)⟩— | 0 | —S⁺(CH₃)₂ | 2 |
| 280 | (ClCH₂CH₂)₂N—⟨C₆H₄⟩—O— | 2 | —S⁺(CH₃)₂ | 2 |
| 281 | (BrCH₂CH₂)₂N—⟨C₆H₄⟩— | 0 | —S⁺(CH₃)₂ | 2 |
| 282 | (BrCH₂CH₂)₂N—⟨C₆H₄⟩— | 3 | —S⁺(CH₃)₂ | 2 |
| 283 | (ClCH₂CH₂)₂N—⟨C₆H₃(CF₃)⟩— | 0 | —S—CH₃ | 2 |
| 284 | (ClCH₂CH₂)₂N—⟨C₆H₃(CONHCH₂CH₂N(CH₃)₂)⟩— | 0 | —S—CH₃ | 2 |

TABLE 1-continued
| Compd. No. | R₁ | m | R₂ | n |
|---|---|---|---|---|
| 285 | 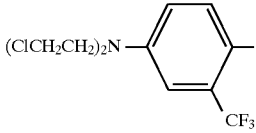 (ClCH₂CH₂)₂N—⌬—CF₃ | 0 | —S—CH₃ | 2 |
| 286 | 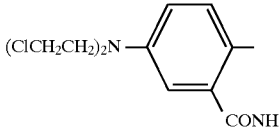 (ClCH₂CH₂)₂N—⌬—CONHCH₂CH₂N(CH₃)₂ | 0 | —S—CH₃ | 2 |
| 287 | 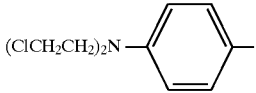 (ClCH₂CH₂)₂N—⌬—O— | 2 | —S—CH₃ | 2 |
| 288 | 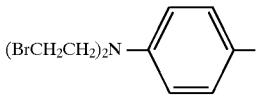 (BrCH₂CH₂)₂N—⌬— | 0 | —S—CH₃ | 2 |
| 289 | 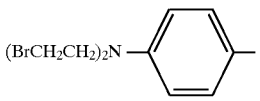 (BrCH₂CH₂)₂N—⌬— | 3 | —S—CH₃ | 2 |
| 290 | 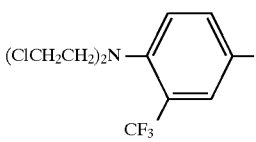 (ClCH₂CH₂)₂N—⌬—CF₃ | 0 | —NH—C(=NH)—NH₂ | 1 |
| 291 |  (ClCH₂CH₂)₂N—⌬—CONHCH₂CH₂N(CH₃)₂ | 0 | —NH—C(=NH)—NH₂ | 1 |
| 292 | 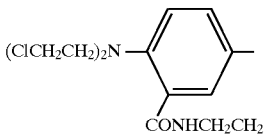 (ClCH₂CH₂)₂N—⌬—CF₃ | 0 | —NH—C(=NH)—NH₂ | 1 |
| 293 |  (ClCH₂CH₂)₂N—⌬—CONHCH₂CH₂N(CH₃)₂ | 0 | —NH—C(=NH)—NH₂ | 1 |
| 294 | 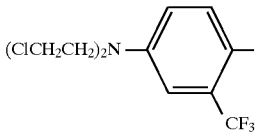 (ClCH₂CH₂)₂N—⌬—O— | 2 | —NH—C(=NH)—NH₂ | 1 |
| 295 |  (BrCH₂CH₂)₂N—⌬— | 0 | —NH—C(=NH)—NH₂ | 1 |
| 296 | 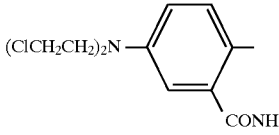 (BrCH₂CH₂)₂N—⌬— | 3 | —NH—C(=NH)—NH₂ | 1 |

TABLE 1-continued

| Compd. No. | R₁ | m | R₂ | n |
|---|---|---|---|---|
| 297 | (ClCH₂CH₂)₂N—⟨phenyl with CF₃⟩— | 0 | —NH₂ | 3 |
| 298 | (ClCH₂CH₂)₂N—⟨phenyl with CONHCH₂CH₂N(CH₃)₂⟩— | 0 | —NH₂ | 3 |
| 299 | (ClCH₂CH₂)₂N—⟨phenyl with CF₃⟩— | 0 | —NH₂ | 3 |
| 300 | (ClCH₂CH₂)₂N—⟨phenyl with CONHCH₂CH₂N(CH₃)₂⟩— | 0 | —NH₂ | 3 |
| 301 | (ClCH₂CH₂)₂N—⟨phenyl⟩—O— | 2 | —NH₂ | 3 |
| 302 | (BrCH₂CH₂)₂N—⟨phenyl⟩— | 0 | —NH₂ | 3 |
| 303 | (BrCH₂CH₂)₂N—⟨phenyl⟩— | 3 | —NH₂ | 3 |
| 304 | (ClCH₂CH₂)₂N—⟨phenyl with Cl, Cl⟩— | 0 | —C(=NH)NH₂ | 2 |
| 305 | ⟨phenyl⟩—N(CH₂CH₂Cl)₂ | 0 | —C(=NH)NH₂ | 2 |
| 306 | (BrCH₂CH₂)₂N—⟨phenyl⟩— | 0 | —C(=NH)NH₂ | 2 |
| 307 | CH₃CH₂, ClCH₂CH₂—N—⟨phenyl⟩— | 0 | —C(=NH)NH₂ | 2 |
| 308 | CH₃CH₂, ClCH₂CH₂—N—⟨phenyl⟩— | 0 | —C(=NH)NH₂ | 2 |

TABLE 1-continued
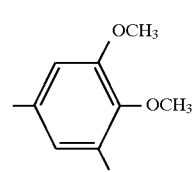

TABLE 1-continued

| Compd. No. | R₁ | m | R₂ | n |
|---|---|---|---|---|
| 321 | H | 0 | —N(CH₃)CH₃ | 3 |
| 322 | H | 0 | —N⁺(CH₃)(CH₃)CH₃ | 3 |
| 323 | H | 0 | —NH—C(=NH)—NH₂ | 1 |
| 324 | H | 0 | —NH₂ | 3 |
| 325 | H | 0 | 3-pyridyl | 1 |
| 326 | Ph | 0 | —C(=NH)NH₂ | 2 |
| 327 | Ph | 0 | —S⁺(CH₃)CH₃ | 2 |
| 328 | Ph | 0 | 3,4,5-tri(OCH₃)phenyl | 0 |
| 329 | Ph | 0 | —N(CH₃)CH₃ | 3 |
| 330 | Ph | 0 | —N⁺(CH₃)(CH₃)CH₃ | 3 |
| 331 | Ph | 0 | —NH—C(=NH)—NH₂ | 1 |
| 332 | Ph | 0 | —NH₂ | 2 |
| 333 | Ph | 0 | 3-pyridyl | 1 |
| 334 | H | 0 | —CH₃ | 3 |
| 335 | Ph | 0 | —CH₃ | 3 |

TABLE 1-continued

| Compd. No. | R₁ | m | R₂ | n |
|---|---|---|---|---|
| 336 | (ClCH₂CH₂)₂N—C₆H₄— | 0 | —CH₃ | 3 |
| 337 | H | 0 | —CH₃ | 17 |
| 338 | C₆H₅— | 0 | —CH₃ | 17 |
| 339 | (ClCH₂CH₂)₂N—C₆H₄— | 0 | —CH₃ | 17 |
| 340 | H₂N—C(=NH)—NH— | 1 | —N(CH₃)CH₃ | 3 |
| 341 | H₂N—C(=NH)—NH— | 1 | —C(=NH)NH₂ | 2 |
| 342 | (ClCH₂CH₂)₂N—C₆H₄— | 0 | —C(=NH)NH₂ | 2 |
| 343 | (ClCH₂CH₂)₂N—C₆H₄— | 1 | —C(=NH)NH₂ | 2 |
| 344 | (ClCH₂CH₂)₂N—C₆H₄— | 2 | —C(=NH)NH₂ | 2 |
| 345 | (ClCH₂CH₂)₂N—C₆H₄— | 3 | —C(=NH)NH₂ | 2 |
| 346 | (ClCH₂CH₂)₂N—C₆H₃(CH₃)— | 0 | —C(=NH)NH₂ | 2 |
| 347 | (ClCH₂CH₂)₂N—C₆H₃(OCH₃)— | 0 | —C(=NH)NH₂ | 2 |
| 348 | (ClCH₂CH₂)₂N—C₆H₃(Cl)— | 0 | —C(=NH)NH₂ | 2 |
| 349 | (ClCH₂CH₂)₂N—C₆H₃(CN)— | 0 | —C(=NH)NH₂ | 2 |

TABLE 1-continued

| Compd. No. | R₁ | m | R₂ | n |
|---|---|---|---|---|
| 350 |  (ClCH₂CH₂)₂N—⟨phenyl-CH₃⟩— | 0 | 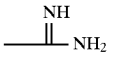 NH=C—NH₂ | 2 |
| 351 | (ClCH₂CH₂)₂N—⟨phenyl-OCH₃⟩— | 0 | NH=C—NH₂ | 2 |
| 352 | (ClCH₂CH₂)₂N—⟨phenyl-Cl⟩— | 0 | NH=C—NH₂ | 2 |
| 353 | (ClCH₂CH₂)₂N—⟨phenyl-CN⟩— | 0 | NH=C—NH₂ | 2 |
| 354 | (ClCH₂CH₂)₂N—⟨phenyl⟩—O— | 1 | NH=C—NH₂ | 2 |
| 355 | (ClCH₂CH₂)₂N—CH₂—⟨phenyl⟩— | 0 | NH=C—NH₂ | 2 |
| 356 | (ClCH₂CH₂)₂N—⟨phenyl⟩— | 0 | NH=C—NH₂ | 2 |
| 357 | Br— | 5 | NH=C—NH₂ | 2 |
| 358 | H | 0 | NH=C—NH₂ | 2 |
| 359 | (ClCH₂CH₂)₂N—⟨phenyl⟩— | 0 | —S⁺—CH₃ \| CH₃ | 2 |
| 360 | (ClCH₂CH₂)₂N—⟨phenyl⟩— | 1 | —S⁺—CH₃ \| CH₃ | 2 |
| 361 | (ClCH₂CH₂)₂N—⟨phenyl⟩— | 2 | —S⁺—CH₃ \| CH₃ | 2 |
| 362 | (ClCH₂CH₂)₂N—⟨phenyl⟩— | 3 | —S⁺—CH₃ \| CH₃ | 2 |

TABLE 1-continued

| Compd. No. | R₁ | m | R₂ | n |
|---|---|---|---|---|
| 363 | 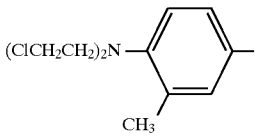 | 0 | $-\overset{\underset{\displaystyle CH_3}{\mid}}{S^+}-CH_3$ | 2 |
| 364 | 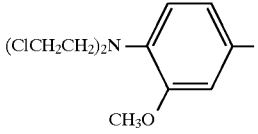 | 0 | $-\overset{\underset{\displaystyle CH_3}{\mid}}{S^+}-CH_3$ | 2 |
| 365 | 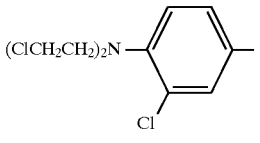 | 0 | $-\overset{\underset{\displaystyle CH_3}{\mid}}{S^+}-CH_3$ | 2 |
| 366 | 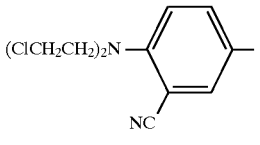 | 0 | $-\overset{\underset{\displaystyle CH_3}{\mid}}{S^+}-CH_3$ | 2 |
| 367 |  | 0 | $-\overset{\underset{\displaystyle CH_3}{\mid}}{S^+}-CH_3$ | 2 |
| 368 | 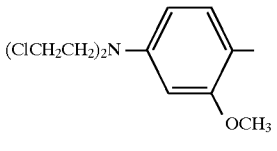 | 0 | $-\overset{\underset{\displaystyle CH_3}{\mid}}{S^+}-CH_3$ | 2 |
| 369 | 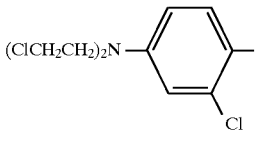 | 0 | $-\overset{\underset{\displaystyle CH_3}{\mid}}{S^+}-CH_3$ | 2 |
| 370 | 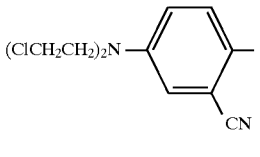 | 0 | $-\overset{\underset{\displaystyle CH_3}{\mid}}{S^+}-CH_3$ | 2 |
| 371 | 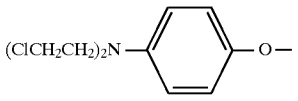 | 1 | $-\overset{\underset{\displaystyle CH_3}{\mid}}{S^+}-CH_3$ | 2 |
| 372 | 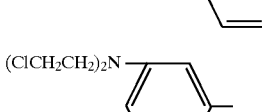 | 0 | $-\overset{\underset{\displaystyle CH_3}{\mid}}{S^+}-CH_3$ | 2 |
| 373 |  | 0 | $-\overset{\underset{\displaystyle CH_3}{\mid}}{S^+}-CH_3$ | 2 |
| 374 | Br— | 5 | $-\overset{\underset{\displaystyle CH_3}{\mid}}{S^+}-CH_3$ | 2 |

TABLE 1-continued
| Compd. No. | R₁ | m | R₂ | n |
|---|---|---|---|---|
| 375 | 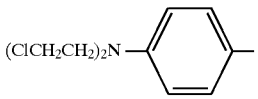 | 0 | —N(CH₃)—CH₃ | 3 |
| 376 | 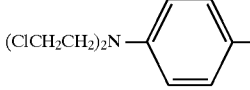 | 1 | —N(CH₃)—CH₃ | 3 |
| 377 | 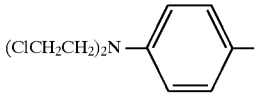 | 2 | —N(CH₃)—CH₃ | 3 |
| 378 | 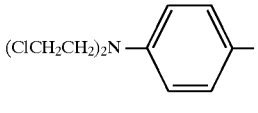 | 3 | —N(CH₃)—CH₃ | 3 |
| 379 | 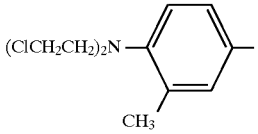 | 0 | —N(CH₃)—CH₃ | 3 |
| 380 | 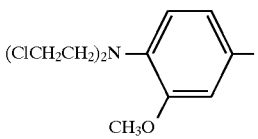 | 0 | —N(CH₃)—CH₃ | 3 |
| 381 |  | 0 | —N(CH₃)—CH₃ | 3 |
| 382 |  | 0 | —N(CH₃)—CH₃ | 3 |
| 383 | 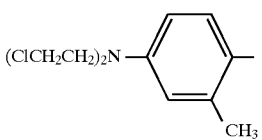 | 0 | —N(CH₃)—CH₃ | 3 |
| 384 | 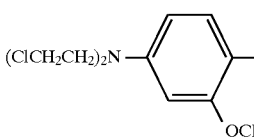 | 0 | —N(CH₃)—CH₃ | 3 |
| 385 | 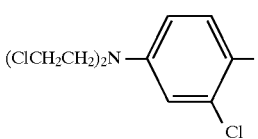 | 0 | —N(CH₃)—CH₃ | 3 |
| 386 | 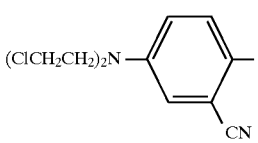 | 0 | —N(CH₃)—CH₃ | 3 |

TABLE 1-continued

| Compd. No. | R₁ | m | R₂ | n |
|---|---|---|---|---|
| 387 | (ClCH₂CH₂)₂N—⟨C₆H₄⟩—O— | 1 | —N(CH₃)—CH₃ | 3 |
| 388 | (ClCH₂CH₂)₂N—CH₂—⟨C₆H₄⟩— | 0 | —N(CH₃)—CH₃ | 3 |
| 389 | (ClCH₂CH₂)₂N—⟨C₆H₄⟩— | 0 | —N(CH₃)—CH₃ | 3 |
| 390 | (ClCH₂CH₂)₂N—⟨C₆H₄⟩— | 0 | —N⁺(CH₃)₃ | 3 |
| 391 | (ClCH₂CH₂)₂N—⟨C₆H₄⟩— | 1 | —N⁺(CH₃)₃ | 3 |
| 392 | (ClCH₂CH₂)₂N—⟨C₆H₄⟩— | 2 | —N⁺(CH₃)₃ | 3 |
| 393 | (ClCH₂CH₂)₂N—⟨C₆H₄⟩— | 3 | —N⁺(CH₃)₃ | 3 |
| 394 | (ClCH₂CH₂)₂N—⟨C₆H₃(H₃C)⟩— | 0 | —N⁺(CH₃)₃ | 3 |
| 395 | (ClCH₂CH₂)₂N—⟨C₆H₃(H₃CO)⟩— | 0 | —N⁺(CH₃)₃ | 3 |
| 396 | (ClCH₂CH₂)₂N—⟨C₆H₃(Cl)⟩— | 0 | —N⁺(CH₃)₃ | 3 |
| 397 | (ClCH₂CH₂)₂N—⟨C₆H₃(NC)⟩— | 0 | —N⁺(CH₃)₃ | 3 |
| 398 | (ClCH₂CH₂)₂N—⟨C₆H₃(CH₃)⟩— | 0 | —N⁺(CH₃)₃ | 3 |

TABLE 1-continued
| Compd. No. | R₁ | m | R₂ | n |
|---|---|---|---|---|
| 399 | 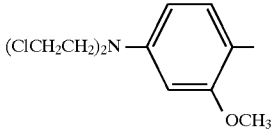 | 0 | 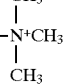 | 3 |
| 400 | 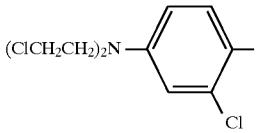 | 0 | 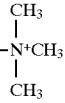 | 3 |
| 401 | 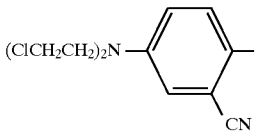 | 0 | 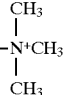 | 3 |
| 402 | 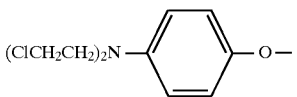 | 1 | 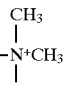 | 3 |
| 403 | 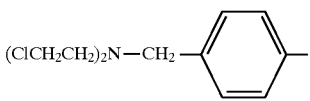 | 0 | 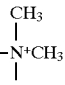 | 3 |
| 404 | 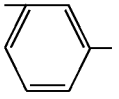 | 0 | 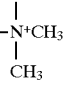 | 3 |
| 405 | 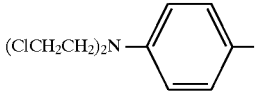 | 0 | 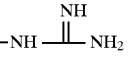 | 1 |
| 406 | 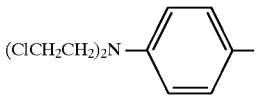 | 1 | 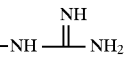 | 1 |
| 407 | 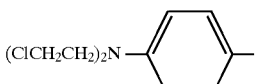 | 2 | 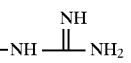 | 1 |
| 408 | 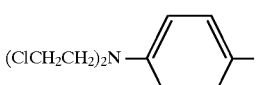 | 3 | 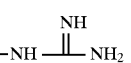 | 1 |
| 409 | 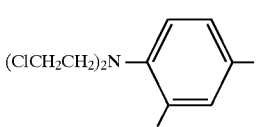 | 0 | 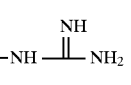 | 1 |
| 410 | 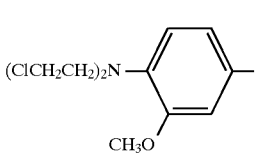 | 0 | 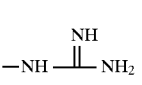 | 1 |

TABLE 1-continued

| Compd. No. | R₁ | m | R₂ | n |
|---|---|---|---|---|
| 411 | (ClCH₂CH₂)₂N—[phenyl with Cl]— | 0 | —NH—C(=NH)—NH₂ | 1 |
| 412 | (ClCH₂CH₂)₂N—[phenyl with NC]— | 0 | —NH—C(=NH)—NH₂ | 1 |
| 413 | (ClCH₂CH₂)₂N—[phenyl with CH₃]— | 0 | —NH—C(=NH)—NH₂ | 1 |
| 414 | (ClCH₂CH₂)₂N—[phenyl with OCH₃]— | 0 | —NH—C(=NH)—NH₂ | 1 |
| 415 | (ClCH₂CH₂)₂N—[phenyl with Cl]— | 0 | —NH—C(=NH)—NH₂ | 1 |
| 416 | (ClCH₂CH₂)₂N—[phenyl with CN]— | 0 | —NH—C(=NH)—NH₂ | 1 |
| 417 | (ClCH₂CH₂)₂N—[phenyl]—O— | 1 | —NH—C(=NH)—NH₂ | 1 |
| 418 | (ClCH₂CH₂)₂N—CH₂—[phenyl]— | 0 | —NH—C(=NH)—NH₂ | 1 |
| 419 | (ClCH₂CH₂)₂N—[phenyl]— | 0 | —NH—C(=NH)—NH₂ | 1 |
| 420 | Br— | 5 | —NH—C(=NH)—NH₂ | 1 |

R₁(CH₂)ₘCONH—[thiophene]—[benzimidazole]—CONH(CH₂)ₙR₂

| 421 | (ClCH₂CH₂)₂N—[phenyl]— | 0 | —C(=NH)—NH₂ | 2 |
| 422 | (ClCH₂CH₂)₂N—[phenyl]— | 1 | —C(=NH)—NH₂ | 2 |

TABLE 1-continued
| Compd. No. | R₁ | m | R₂ | n |
|---|---|---|---|---|
| 423 | 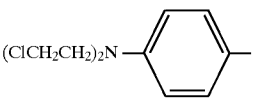 | 2 | 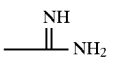 | 2 |
| 424 | 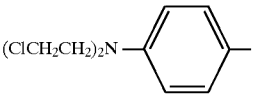 | 3 | 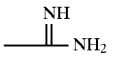 | 2 |
| 425 | 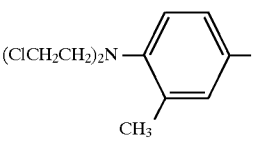 | 0 | 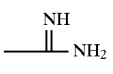 | 2 |
| 426 | 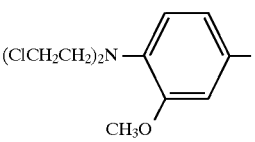 | 0 | 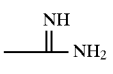 | 2 |
| 427 | 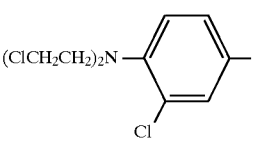 | 0 | 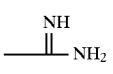 | 2 |
| 428 | 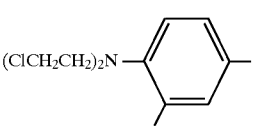 | 0 | 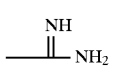 | 2 |
| 429 | H | 0 | 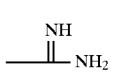 | 2 |
| 430 | 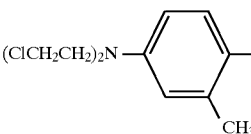 | 0 | 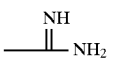 | 2 |
| 431 | 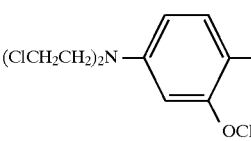 | 0 | 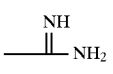 | 2 |
| 432 | 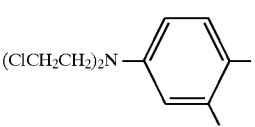 | 0 | 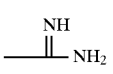 | 2 |
| 433 | 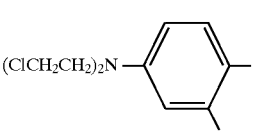 | 0 | 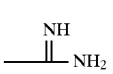 | 2 |
| 434 | 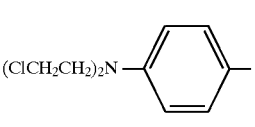 | 1 | 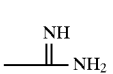 | 2 |

TABLE 1-continued

| Compd. No. | R₁ | m | R₂ | n |
|---|---|---|---|---|
| 435 | (ClCH₂CH₂)₂N—CH₂—(C₆H₄)— | 0 | —C(=NH)NH₂ | 2 |
| 436 | (ClCH₂CH₂)₂N—(C₆H₄)— | 0 | —C(=NH)NH₂ | 2 |
| 437 | Br— | 5 | —C(=NH)NH₂ | 2 |
| 438 | C₆H₅— | 0 | —C(=NH)NH₂ | 2 |
| 439 | (ClCH₂CH₂)₂N—(C₆H₄)— | 0 | —S⁺(CH₃)—CH₃ | 2 |
| 440 | (ClCH₂CH₂)₂N—(C₆H₄)— | 1 | —S⁺(CH₃)—CH₃ | 2 |
| 441 | (ClCH₂CH₂)₂N—(C₆H₄)— | 2 | —S⁺(CH₃)—CH₃ | 2 |
| 442 | (ClCH₂CH₂)₂N—(C₆H₄)— | 3 | —S⁺(CH₃)—CH₃ | 2 |
| 443 | (ClCH₂CH₂)₂N—(C₆H₃)(CH₃)— | 0 | —S⁺(CH₃)—CH₃ | 2 |
| 444 | (ClCH₂CH₂)₂N—(C₆H₃)(OCH₃)— | 0 | —S⁺(CH₃)—CH₃ | 2 |
| 445 | (ClCH₂CH₂)₂N—(C₆H₃)(Cl)— | 0 | —S⁺(CH₃)—CH₃ | 2 |
| 446 | (ClCH₂CH₂)₂N—(C₆H₃)(CN)— | 0 | —S⁺(CH₃)—CH₃ | 2 |
| 447 | (ClCH₂CH₂)₂N—(C₆H₃)(CH₃)— | 0 | —S⁺(CH₃)—CH₃ | 2 |

TABLE 1-continued

| Compd. No. | R₁ | m | R₂ | n |
|---|---|---|---|---|
| 448 | (ClCH₂CH₂)₂N—[phenyl with OCH₃]— | 0 | —S⁺(CH₃)—CH₃ | 2 |
| 449 | (ClCH₂CH₂)₂N—[phenyl with Cl]— | 0 | —S⁺(CH₃)—CH₃ | 2 |
| 450 | (ClCH₂CH₂)₂N—[phenyl with CN]— | 0 | —S⁺(CH₃)—CH₃ | 2 |
| 451 | (ClCH₂CH₂)₂N—[phenyl]—O— | 1 | —S⁺(CH₃)—CH₃ | 2 |
| 452 | (ClCH₂CH₂)₂N—CH₂—[phenyl]— | 0 | —S⁺(CH₃)—CH₃ | 2 |
| 453 | (ClCH₂CH₂)₂N—[phenyl]— | 0 | —S⁺(CH₃)—CH₃ | 2 |
| 454 | Br— | 5 | —S⁺(CH₃)—CH₃ | 2 |
| 455 | (ClCH₂CH₂)₂N—[phenyl]— | 0 | —N(CH₃)—CH₃ | 3 |
| 456 | (ClCH₂CH₂)₂N—[phenyl]— | 1 | —N(CH₃)—CH₃ | 3 |
| 457 | (ClCH₂CH₂)₂N—[phenyl]— | 2 | —N(CH₃)—CH₃ | 3 |
| 458 | (ClCH₂CH₂)₂N—[phenyl]— | 3 | —N(CH₃)—CH₃ | 3 |
| 459 | (ClCH₂CH₂)₂N—[phenyl with CH₃]— | 0 | —N(CH₃)—CH₃ | 3 |
| 460 | (ClCH₂CH₂)₂N—[phenyl with CH₃O]— | 0 | —N(CH₃)—CH₃ | 3 |

TABLE 1-continued

| Compd. No. | R₁ | m | R₂ | n |
|---|---|---|---|---|
| 461 |  (ClCH₂CH₂)₂N—⟨benzene, 2-Cl⟩— | 0 | —N(CH₃)—CH₃ | 3 |
| 462 | (ClCH₂CH₂)₂N—⟨benzene, 2-CN⟩— | 0 | —N(CH₃)—CH₃ | 3 |
| 463 | (ClCH₂CH₂)₂N—⟨benzene, 3-CH₃⟩— | 0 | —N(CH₃)—CH₃ | 3 |
| 464 | (ClCH₂CH₂)₂N—⟨benzene, 3-OCH₃⟩— | 0 | —N(CH₃)—CH₃ | 3 |
| 465 | (ClCH₂CH₂)₂N—⟨benzene, 3-Cl⟩— | 0 | —N(CH₃)—CH₃ | 3 |
| 466 | (ClCH₂CH₂)₂N—⟨benzene, 3-CN⟩— | 0 | —N(CH₃)—CH₃ | 3 |
| 467 | (ClCH₂CH₂)₂N—⟨benzene⟩—O— | 1 | —N(CH₃)—CH₃ | 3 |
| 468 | (ClCH₂CH₂)₂N—CH₂—⟨benzene⟩— | 0 | —N(CH₃)—CH₃ | 3 |
| 469 | (ClCH₂CH₂)₂N—⟨benzene, meta⟩— | 0 | —N(CH₃)—CH₃ | 3 |
| 470 | Br— | 5 | —N(CH₃)—CH₃ | 3 |
| 471 | (ClCH₂CH₂)₂N—⟨benzene⟩— | 0 | —N⁺(CH₃)₃ | 3 |
| 472 | (ClCH₂CH₂)₂N—⟨benzene⟩— | 1 | —N⁺(CH₃)₃ | 3 |

TABLE 1-continued

| Compd. No. | R₁ | m | R₂ | n |
|---|---|---|---|---|
| 473 | (ClCH₂CH₂)₂N—C₆H₄— | 2 | —N⁺(CH₃)₃ | 3 |
| 474 | (ClCH₂CH₂)₂N—C₆H₄— | 3 | —N⁺(CH₃)₃ | 3 |
| 475 | (ClCH₂CH₂)₂N—C₆H₃(CH₃)— | 0 | —N⁺(CH₃)₃ | 3 |
| 476 | (ClCH₂CH₂)₂N—C₆H₃(OCH₃)— | 0 | —N⁺(CH₃)₃ | 3 |
| 477 | (ClCH₂CH₂)₂N—C₆H₃(Cl)— | 0 | —N⁺(CH₃)₃ | 3 |
| 478 | (ClCH₂CH₂)₂N—C₆H₃(CN)— | 0 | —N⁺(CH₃)₃ | 3 |
| 479 | (ClCH₂CH₂)₂N—C₆H₃(CH₃)— | 0 | —N⁺(CH₃)₃ | 3 |
| 480 | (ClCH₂CH₂)₂N—C₆H₃(OCH₃)— | 0 | —N⁺(CH₃)₃ | 3 |
| 481 | (ClCH₂CH₂)₂N—C₆H₃(Cl)— | 0 | —N⁺(CH₃)₃ | 3 |
| 482 | (ClCH₂CH₂)₂N—C₆H₃(CN)— | 0 | —N⁺(CH₃)₃ | 3 |
| 483 | (ClCH₂CH₂)₂N—C₆H₄—O— | 1 | —N⁺(CH₃)₃ | 3 |

TABLE 1-continued

| Compd. No. | R₁ | m | R₂ | n |
|---|---|---|---|---|
| 484 | (ClCH₂CH₂)₂N—CH₂—<phenyl>— | 0 | —N⁺(CH₃)₃ | 3 |
| 485 | (ClCH₂CH₂)₂N—<phenyl>— | 0 | —N⁺(CH₃)₃ | 3 |
| 486 | (ClCH₂CH₂)₂N—<phenyl>— | 0 | —NH—C(=NH)—NH₂ | 1 |
| 487 | (ClCH₂CH₂)₂N—<phenyl>— | 1 | —NH—C(=NH)—NH₂ | 1 |
| 488 | (ClCH₂CH₂)₂N—<phenyl>— | 2 | —NH—C(=NH)—NH₂ | 1 |
| 489 | (ClCH₂CH₂)₂N—<phenyl>— | 3 | —NH—C(=NH)—NH₂ | 1 |
| 490 | (ClCH₂CH₂)₂N—<phenyl, CH₃>— | 0 | —NH—C(=NH)—NH₂ | 1 |
| 491 | (ClCH₂CH₂)₂N—<phenyl, CH₃O>— | 0 | —NH—C(=NH)—NH₂ | 1 |
| 492 | (ClCH₂CH₂)₂N—<phenyl, Cl>— | 0 | —NH—C(=NH)—NH₂ | 1 |
| 493 | (ClCH₂CH₂)₂N—<phenyl, CN>— | 0 | —NH—C(=NH)—NH₂ | 1 |
| 494 | (ClCH₂CH₂)₂N—<phenyl, CH₃>— | 0 | —NH—C(=NH)—NH₂ | 1 |
| 495 | (ClCH₂CH₂)₂N—<phenyl, OCH₃>— | 0 | —NH—C(=NH)—NH₂ | 1 |

TABLE 1-continued

| Compd. No. | R₁ | m | R₂ | n |
|---|---|---|---|---|
| 496 | (ClCH₂CH₂)₂N—⟨phenyl-Cl⟩— | 0 | —NH—C(=NH)—NH₂ | 1 |
| 497 | (ClCH₂CH₂)₂N—⟨phenyl-CN⟩— | 0 | —NH—C(=NH)—NH₂ | 1 |
| 498 | (ClCH₂CH₂)₂N—⟨phenyl⟩—O— | 1 | —NH—C(=NH)—NH₂ | 1 |
| 499 | (ClCH₂CH₂)₂N—CH₂—⟨phenyl⟩— | 0 | —NH—C(=NH)—NH₂ | 1 |
| 500 | (ClCH₂CH₂)₂N—⟨phenyl⟩— | 0 | —NH—C(=NH)—NH₂ | 1 |
| 501 | Br— | 5 | —NH—C(=NH)—NH₂ | 1 |

R₁(CH₂)ₘCONH—⟨thiophene⟩—⟨benzimidazole⟩—CONH(CH₂)ₙR₂

| Compd. No. | R₁ | m | R₂ | n |
|---|---|---|---|---|
| 502 | (ClCH₂CH₂)₂N—⟨phenyl⟩— | 0 | —C(=NH)—NH₂ | 2 |
| 503 | (ClCH₂CH₂)₂N—⟨phenyl⟩— | 1 | —C(=NH)—NH₂ | 2 |
| 504 | (ClCH₂CH₂)₂N—⟨phenyl⟩— | 2 | —C(=NH)—NH₂ | 2 |
| 505 | (ClCH₂CH₂)₂N—⟨phenyl⟩— | 3 | —C(=NH)—NH₂ | 2 |
| 506 | (ClCH₂CH₂)₂N—⟨phenyl-CH₃⟩— | 0 | —C(=NH)—NH₂ | 2 |
| 507 | (ClCH₂CH₂)₂N—⟨phenyl-OCH₃⟩— | 0 | —C(=NH)—NH₂ | 2 |

TABLE 1-continued
| Compd. No. | R₁ | m | R₂ | n |
|---|---|---|---|---|
| 508 | 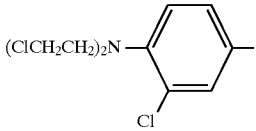 | 0 | 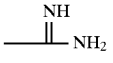 | 2 |
| 509 | 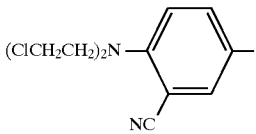 | 0 | 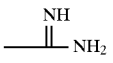 | 2 |
| 510 | 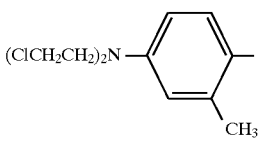 | 0 | 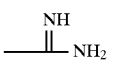 | 2 |
| 511 | 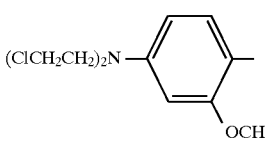 | 0 | 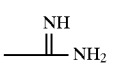 | 2 |
| 512 | 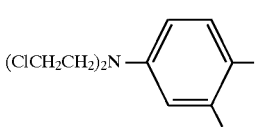 | 0 | 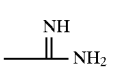 | 2 |
| 513 | 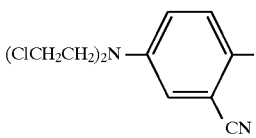 | 0 | 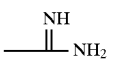 | 2 |
| 514 | 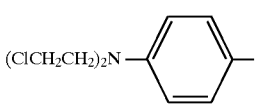 | 1 | 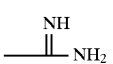 | 2 |
| 515 | 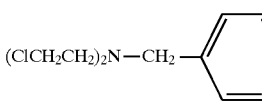 | 0 | 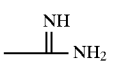 | 2 |
| 516 | 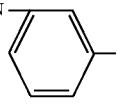 | 0 | 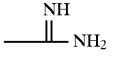 | 2 |
| 517 | Br— | 5 | 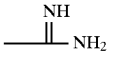 | 2 |
| 518 | H | 0 | 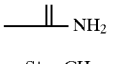 | 2 |
| 519 | 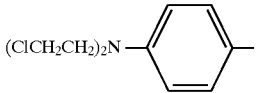 | 0 | 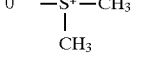 | 2 |
| 520 | 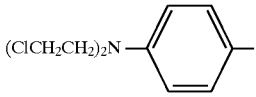 | 1 | 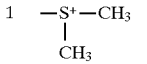 | 2 |

TABLE 1-continued

| Compd. No. | R₁ | m | R₂ | n |
|---|---|---|---|---|
| 521 | 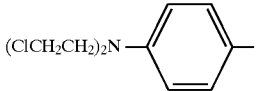 (ClCH₂CH₂)₂N— | 2 | $-S^+-CH_3$<br>$\|$<br>$CH_3$ | 2 |
| 522 | (ClCH₂CH₂)₂N— | 3 | $-S^+-CH_3$<br>$\|$<br>$CH_3$ | 2 |
| 523 | (ClCH₂CH₂)₂N—<br>CH₃ | 0 | $-S^+-CH_3$<br>$\|$<br>$CH_3$ | 2 |
| 524 | (ClCH₂CH₂)₂N—<br>CH₃O | 0 | $-S^+-CH_3$<br>$\|$<br>$CH_3$ | 2 |
| 525 | (ClCH₂CH₂)₂N—<br>Cl | 0 | $-S^+-CH_3$<br>$\|$<br>$CH_3$ | 2 |
| 526 | (ClCH₂CH₂)₂N—<br>NC | 0 | $-S^+-CH_3$<br>$\|$<br>$CH_3$ | 2 |
| 527 | (ClCH₂CH₂)₂N—<br>Cl   Cl | 0 | $-S^+-CH_3$<br>$\|$<br>$CH_3$ | 2 |
| 528 | (ClCH₂CH₂)₂N—<br>CH₃ | 0 | $-S^+-CH_3$<br>$\|$<br>$CH_3$ | 2 |
| 529 | (ClCH₂CH₂)₂N—<br>OCH₃ | 0 | $-S^+-CH_3$<br>$\|$<br>$CH_3$ | 2 |
| 530 | (ClCH₂CH₂)₂N—<br>Cl | 0 | $-S^+-CH_3$<br>$\|$<br>$CH_3$ | 2 |
| 531 | (ClCH₂CH₂)₂N—<br>CN | 0 | $-S^+-CH_3$<br>$\|$<br>$CH_3$ | 2 |

TABLE 1-continued

| Compd. No. | R₁ | m | R₂ | n |
|---|---|---|---|---|
| 532 | (ClCH₂CH₂)₂N—⟨C₆H₄⟩—O— | 1 | —S⁺(CH₃)—CH₃ | 2 |
| 533 | (ClCH₂CH₂)₂N—CH₂—⟨C₆H₄⟩— | 0 | —S⁺(CH₃)—CH₃ | 2 |
| 534 | (ClCH₂CH₂)₂N—⟨C₆H₄⟩— | 0 | —S⁺(CH₃)—CH₃ | 2 |
| 535 | Br— | 5 | —S⁺(CH₃)—CH₃ | 2 |
| 536 | H— | 0 | —S⁺(CH₃)—CH₃ | 2 |
| 537 | (ClCH₂CH₂)₂N—⟨C₆H₄⟩— | 0 | —N(CH₃)—CH₃ | 3 |
| 538 | (ClCH₂CH₂)₂N—⟨C₆H₄⟩— | 1 | —N(CH₃)—CH₃ | 3 |
| 539 | (ClCH₂CH₂)₂N—⟨C₆H₄⟩— | 2 | —N(CH₃)—CH₃ | 3 |
| 540 | (ClCH₂CH₂)₂N—⟨C₆H₄⟩— | 3 | —N(CH₃)—CH₃ | 3 |
| 541 | (ClCH₂CH₂)₂N—⟨C₆H₃(CH₃)⟩— | 0 | —N(CH₃)—CH₃ | 3 |
| 542 | (ClCH₂CH₂)₂N—⟨C₆H₃(OCH₃)⟩— | 0 | —N(CH₃)—CH₃ | 3 |
| 543 | (ClCH₂CH₂)₂N—⟨C₆H₃(Cl)⟩— | 0 | —N(CH₃)—CH₃ | 3 |
| 544 | (ClCH₂CH₂)₂N—⟨C₆H₃(CN)⟩— | 0 | —N(CH₃)—CH₃ | 3 |

TABLE 1-continued

| Compd. No. | R₁ | m | R₂ | n |
|---|---|---|---|---|
| 545 | 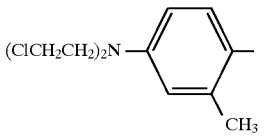 | 0 | $-\underset{\underset{CH_3}{\mid}}{N}-CH_3$ | 3 |
| 546 | 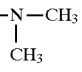 | 0 | $-\underset{\underset{CH_3}{\mid}}{N}-CH_3$ | 3 |
| 547 | 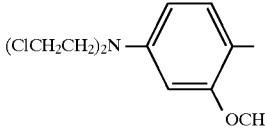 | 0 | $-\underset{\underset{CH_3}{\mid}}{N}-CH_3$ | 3 |
| 548 | 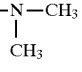 | 0 | $-\underset{\underset{CH_3}{\mid}}{N}-CH_3$ | 3 |
| 549 | 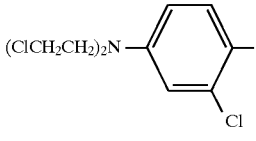 | 1 | $-\underset{\underset{CH_3}{\mid}}{N}-CH_3$ | 3 |
| 550 |  | 0 | $-\underset{\underset{CH_3}{\mid}}{N}-CH_3$ | 3 |
| 551 | 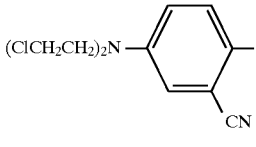 | 0 | $-\underset{\underset{CH_3}{\mid}}{N}-CH_3$ | 3 |
| 552 | Br— | 5 | $-\underset{\underset{CH_3}{\mid}}{N}-CH_3$ | 3 |
| 553 |  | 0 | $\underset{\underset{CH_3}{\mid}}{\overset{\overset{CH_3}{\mid}}{-N^+CH_3}}$ | 3 |
| 554 | 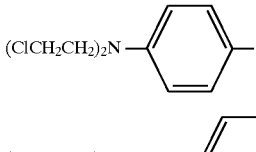 | 1 | $\underset{\underset{CH_3}{\mid}}{\overset{\overset{CH_3}{\mid}}{-N^+CH_3}}$ | 3 |
| 555 |  | 2 | $\underset{\underset{CH_3}{\mid}}{\overset{\overset{CH_3}{\mid}}{-N^+CH_3}}$ | 3 |
| 556 | 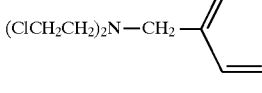 | 3 | $\underset{\underset{CH_3}{\mid}}{\overset{\overset{CH_3}{\mid}}{-N^+CH_3}}$ | 3 |
| 557 |  | 0 | $\underset{\underset{CH_3}{\mid}}{\overset{\overset{CH_3}{\mid}}{-N^+CH_3}}$ | 3 |

TABLE 1-continued

| Compd. No. | R₁ | m | R₂ | n |
|---|---|---|---|---|
| 558 | (ClCH₂CH₂)₂N—C₆H₃(OCH₃)— | 0 | —N⁺(CH₃)₃ | 3 |
| 559 | (ClCH₂CH₂)₂N—C₆H₃(Cl)— | 0 | —N⁺(CH₃)₃ | 3 |
| 560 | (ClCH₂CH₂)₂N—C₆H₃(CN)— | 0 | —N⁺(CH₃)₃ | 3 |
| 561 | (ClCH₂CH₂)₂N—C₆H₃(CH₃)— | 0 | —N⁺(CH₃)₃ | 3 |
| 562 | (ClCH₂CH₂)₂N—C₆H₃(OCH₃)— | 0 | —N⁺(CH₃)₃ | 3 |
| 563 | (ClCH₂CH₂)₂N—C₆H₃(Cl)— | 0 | —N⁺(CH₃)₃ | 3 |
| 564 | (ClCH₂CH₂)₂N—C₆H₃(CN)— | 0 | —N⁺(CH₃)₃ | 3 |
| 565 | (ClCH₂CH₂)₂N—C₆H₄—O— | 1 | —N⁺(CH₃)₃ | 3 |
| 566 | (ClCH₂CH₂)₂N—CH₂—C₆H₄— | 0 | —N⁺(CH₃)₃ | 3 |
| 567 | (ClCH₂CH₂)₂N—C₆H₄— | 0 | —N⁺(CH₃)₃ | 3 |
| 568 | (ClCH₂CH₂)₂N—C₆H₄— | 0 | —NH—C(=NH)—NH₂ | 1 |
| 569 | (ClCH₂CH₂)₂N—C₆H₄— | 1 | —NH—C(=NH)—NH₂ | 1 |

TABLE 1-continued

| Compd. No. | R₁ | m | R₂ | n |
|---|---|---|---|---|
| 570 | (ClCH₂CH₂)₂N—C₆H₄— | 2 | —NH—C(=NH)—NH₂ | 1 |
| 571 | (ClCH₂CH₂)₂N—C₆H₄— | 3 | —NH—C(=NH)—NH₂ | 1 |
| 572 | (ClCH₂CH₂)₂N—C₆H₃(CH₃)— | 0 | —NH—C(=NH)—NH₂ | 1 |
| 573 | (ClCH₂CH₂)₂N—C₆H₃(OCH₃)— | 0 | —NH—C(=NH)—NH₂ | 1 |
| 574 | (ClCH₂CH₂)₂N—C₆H₃(Cl)— | 0 | —NH—C(=NH)—NH₂ | 1 |
| 575 | (ClCH₂CH₂)₂N—C₆H₃(CN)— | 0 | —NH—C(=NH)—NH₂ | 1 |
| 576 | (ClCH₂CH₂)₂N—C₆H₃(CH₃)— | 0 | —NH—C(=NH)—NH₂ | 1 |
| 577 | (ClCH₂CH₂)₂N—C₆H₃(OCH₃)— | 0 | —NH—C(=NH)—NH₂ | 1 |
| 578 | (ClCH₂CH₂)₂N—C₆H₃(Cl)— | 0 | —NH—C(=NH)—NH₂ | 1 |
| 579 | (ClCH₂CH₂)₂N—C₆H₃(CN)— | 0 | —NH—C(=NH)—NH₂ | 1 |
| 580 | (ClCH₂CH₂)₂N—C₆H₄—O— | 1 | —NH—C(=NH)—NH₂ | 1 |
| 581 | (ClCH₂CH₂)₂N—CH₂—C₆H₄— | 0 | —NH—C(=NH)—NH₂ | 1 |

TABLE 1-continued

| Compd. No. | R₁ | m | R₂ | n |
|---|---|---|---|---|
| 582 | (ClCH₂CH₂)₂N—⟨phenyl⟩— | 0 | —NH—C(=NH)—NH₂ | 1 |
| 583 | Br— | 5 | —NH—C(=NH)—NH₂ | 1 |

R₁(CH₂)ₘCONH—⟨furan⟩—⟨benzimidazole⟩—CONH(CH₂)ₙR₂

| Compd. No. | R₁ | m | R₂ | n |
|---|---|---|---|---|
| 584 | (ClCH₂CH₂)₂N—⟨phenyl⟩— | 0 | —C(=NH)—NH₂ | 2 |
| 585 | (ClCH₂CH₂)₂N—⟨phenyl⟩— | 1 | —C(=NH)—NH₂ | 2 |
| 586 | (ClCH₂CH₂)₂N—⟨phenyl⟩— | 2 | —C(=NH)—NH₂ | 2 |
| 587 | (ClCH₂CH₂)₂N—⟨phenyl⟩— | 3 | —C(=NH)—NH₂ | 2 |
| 588 | (ClCH₂CH₂)₂N—⟨phenyl, 3-CH₃⟩— | 0 | —C(=NH)—NH₂ | 2 |
| 589 | (ClCH₂CH₂)₂N—⟨phenyl, 3-OCH₃⟩— | 0 | —C(=NH)—NH₂ | 2 |
| 590 | (ClCH₂CH₂)₂N—⟨phenyl, 3-Cl⟩— | 0 | —C(=NH)—NH₂ | 2 |
| 591 | (ClCH₂CH₂)₂N—⟨phenyl, 3-CN⟩— | 0 | —C(=NH)—NH₂ | 2 |
| 592 | (ClCH₂CH₂)₂N—⟨phenyl, 3-CH₃⟩— | 0 | —C(=NH)—NH₂ | 2 |

TABLE 1-continued

| Compd. No. | R₁ | m | R₂ | n |
|---|---|---|---|---|
| 593 | (ClCH₂CH₂)₂N—C₆H₃(OCH₃)— | 0 | —C(=NH)NH₂ | 2 |
| 594 | (ClCH₂CH₂)₂N—C₆H₃(Cl)— | 0 | —C(=NH)NH₂ | 2 |
| 595 | (ClCH₂CH₂)₂N—C₆H₃(CN)— | 0 | —C(=NH)NH₂ | 2 |
| 596 | (ClCH₂CH₂)₂N—C₆H₄—O— | 1 | —C(=NH)NH₂ | 2 |
| 597 | (ClCH₂CH₂)₂N—CH₂—C₆H₄— | 0 | —C(=NH)NH₂ | 2 |
| 598 | (ClCH₂CH₂)₂N—C₆H₄— | 0 | —C(=NH)NH₂ | 2 |
| 599 | Br— | 5 | —C(=NH)NH₂ | 2 |
| 600 | H | 0 | —C(=NH)NH₂ | 2 |
| 601 | (ClCH₂CH₂)₂N—C₆H₄— | 0 | —S⁺(CH₃)CH₃ | 2 |
| 602 | (ClCH₂CH₂)₂N—C₆H₄— | 1 | —S⁺(CH₃)CH₃ | 2 |
| 603 | (ClCH₂CH₂)₂N—C₆H₄— | 2 | —S⁺(CH₃)CH₃ | 2 |
| 604 | (ClCH₂CH₂)₂N—C₆H₄— | 3 | —S⁺(CH₃)CH₃ | 2 |
| 605 | (ClCH₂CH₂)₂N—C₆H₃(CH₃)— | 0 | —S⁺(CH₃)CH₃ | 2 |

TABLE 1-continued

| Compd. No. | R₁ | m | R₂ | n |
|---|---|---|---|---|
| 606 | 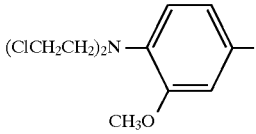 | 0 | $-S^+-CH_3$<br>$\phantom{-S^+-}|$<br>$\phantom{-S^+-}CH_3$ | 2 |
| 607 | 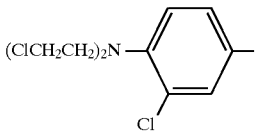 | 0 | $-S^+-CH_3$<br>$\phantom{-S^+-}|$<br>$\phantom{-S^+-}CH_3$ | 2 |
| 608 | 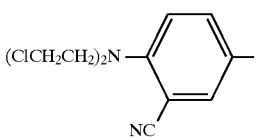 | 0 | $-S^+-CH_3$<br>$\phantom{-S^+-}|$<br>$\phantom{-S^+-}CH_3$ | 2 |
| 609 | 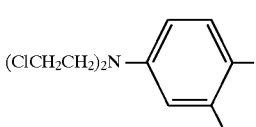 | 0 | $-S^+-CH_3$<br>$\phantom{-S^+-}|$<br>$\phantom{-S^+-}CH_3$ | 2 |
| 610 | 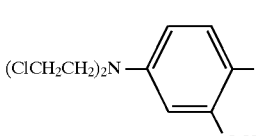 | 0 | $-S^+-CH_3$<br>$\phantom{-S^+-}|$<br>$\phantom{-S^+-}CH_3$ | 2 |
| 611 | 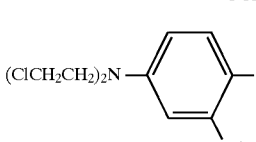 | 0 | $-S^+-CH_3$<br>$\phantom{-S^+-}|$<br>$\phantom{-S^+-}CH_3$ | 2 |
| 612 | 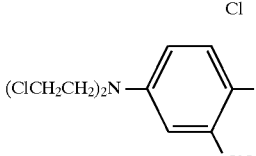 | 0 | $-S^+-CH_3$<br>$\phantom{-S^+-}|$<br>$\phantom{-S^+-}CH_3$ | 2 |
| 613 | 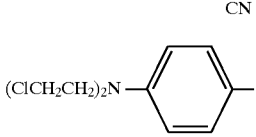 | 1 | $-S^+-CH_3$<br>$\phantom{-S^+-}|$<br>$\phantom{-S^+-}CH_3$ | 2 |
| 614 | 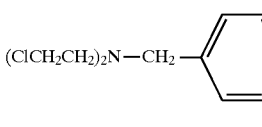 | 0 | $-S^+-CH_3$<br>$\phantom{-S^+-}|$<br>$\phantom{-S^+-}CH_3$ | 2 |
| 615 | 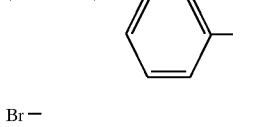 | 0 | $-S^+-CH_3$<br>$\phantom{-S^+-}|$<br>$\phantom{-S^+-}CH_3$ | 2 |
| 616 | Br— | 5 | $-S^+-CH_3$<br>$\phantom{-S^+-}|$<br>$\phantom{-S^+-}CH_3$ | 2 |
| 617 | 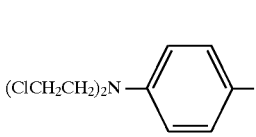 | 0 | $-N-CH_3$<br>$\phantom{-N-}|$<br>$\phantom{-N-}CH_3$ | 3 |

TABLE 1-continued
| Compd. No. | R₁ | m | R₂ | n |
|---|---|---|---|---|
| 618 | 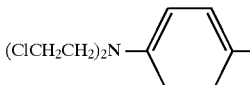 | 1 | —N(CH₃)—CH₃ | 3 |
| 619 | 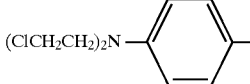 | 2 | —N(CH₃)—CH₃ | 3 |
| 620 | 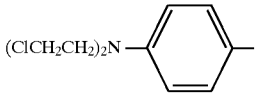 | 3 | —N(CH₃)—CH₃ | 3 |
| 621 | 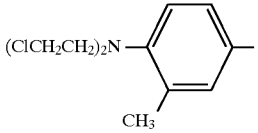 | 0 | —N(CH₃)—CH₃ | 3 |
| 622 | 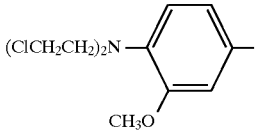 | 0 | —N(CH₃)—CH₃ | 3 |
| 623 | 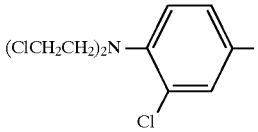 | 0 | —N(CH₃)—CH₃ | 3 |
| 624 | 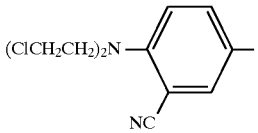 | 0 | —N(CH₃)—CH₃ | 3 |
| 625 | 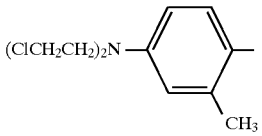 | 0 | —N(CH₃)—CH₃ | 3 |
| 626 | 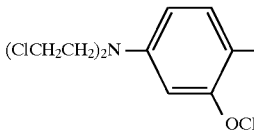 | 0 | —N(CH₃)—CH₃ | 3 |
| 627 | 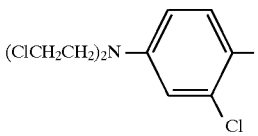 | 0 | —N(CH₃)—CH₃ | 3 |
| 628 | 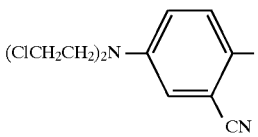 | 0 | —N(CH₃)—CH₃ | 3 |
| 629 | 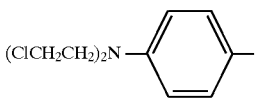 | 1 | —N(CH₃)—CH₃ | 3 |

TABLE 1-continued
| Compd. No. | R₁ | m | R₂ | n |
|---|---|---|---|---|
| 630 | (ClCH₂CH₂)₂N—CH₂—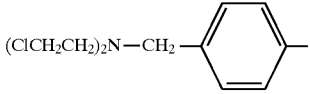— | 0 | —N(CH₃)CH₃ | 3 |
| 631 | (ClCH₂CH₂)₂N—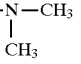— | 0 | —N(CH₃)CH₃ | 3 |
| 632 | Br— | 5 | —N(CH₃)CH₃ | 3 |
| 633 | (ClCH₂CH₂)₂N—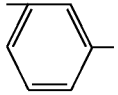— | 0 | —N⁺(CH₃)₃ | 3 |
| 634 | (ClCH₂CH₂)₂N—— | 1 | —N⁺(CH₃)₃ | 3 |
| 635 | (ClCH₂CH₂)₂N—— | 2 | —N⁺(CH₃)₃ | 3 |
| 636 | (ClCH₂CH₂)₂N—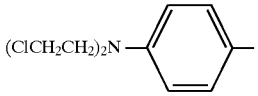— | 3 | —N⁺(CH₃)₃ | 3 |
| 637 | (ClCH₂CH₂)₂N—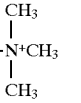— (H₃C) | 0 | —N⁺(CH₃)₃ | 3 |
| 638 | (ClCH₂CH₂)₂N—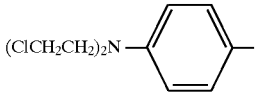— (H₃CO) | 0 | —N⁺(CH₃)₃ | 3 |
| 639 | (ClCH₂CH₂)₂N—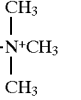— (Cl) | 0 | —N⁺(CH₃)₃ | 3 |
| 640 | (ClCH₂CH₂)₂N—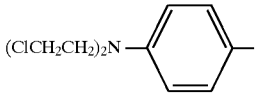— (NC) | 0 | —N⁺(CH₃)₃ | 3 |
| 641 | (ClCH₂CH₂)₂N—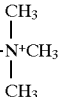— (CH₃) | 0 | —N⁺(CH₃)₃ | 3 |

TABLE 1-continued

| Compd. No. | R₁ | m | R₂ | n |
|---|---|---|---|---|
| 642 | (ClCH₂CH₂)₂N—C₆H₃(OCH₃)— | 0 | —N⁺(CH₃)₃ | 3 |
| 643 | (ClCH₂CH₂)₂N—C₆H₃(Cl)— | 0 | —N⁺(CH₃)₃ | 3 |
| 644 | (ClCH₂CH₂)₂N—C₆H₃(CN)— | 0 | —N⁺(CH₃)₃ | 3 |
| 645 | (ClCH₂CH₂)₂N—C₆H₄—O— | 1 | —N⁺(CH₃)₃ | 3 |
| 646 | (ClCH₂CH₂)₂N—CH₂—C₆H₄— | 0 | —N⁺(CH₃)₃ | 3 |
| 647 | (ClCH₂CH₂)₂N—C₆H₄— | 0 | —N⁺(CH₃)₃ | 3 |
| 648 | (ClCH₂CH₂)₂N—C₆H₄— | 0 | —NH—C(=NH)—NH₂ | 1 |
| 649 | (ClCH₂CH₂)₂N—C₆H₄— | 1 | —NH—C(=NH)—NH₂ | 1 |
| 650 | (ClCH₂CH₂)₂N—C₆H₄— | 2 | —NH—C(=NH)—NH₂ | 1 |
| 651 | (ClCH₂CH₂)₂N—C₆H₄— | 3 | —NH—C(=NH)—NH₂ | 1 |
| 652 | (ClCH₂CH₂)₂N—C₆H₃(CH₃)— | 0 | —NH—C(=NH)—NH₂ | 1 |
| 653 | (ClCH₂CH₂)₂N—C₆H₃(OCH₃)— | 0 | —NH—C(=NH)—NH₂ | 1 |

TABLE 1-continued

| Compd. No. | R₁ | m | R₂ | n |
|---|---|---|---|---|
| 654 | (ClCH₂CH₂)₂N—[phenyl with Cl]— | 0 | —NH—C(=NH)—NH₂ | 1 |
| 655 | (ClCH₂CH₂)₂N—[phenyl with CN]— | 0 | —NH—C(=NH)—NH₂ | 1 |
| 656 | (ClCH₂CH₂)₂N—[phenyl with CH₃]— | 0 | —NH—C(=NH)—NH₂ | 1 |
| 657 | (ClCH₂CH₂)₂N—[phenyl with OCH₃]— | 0 | —NH—C(=NH)—NH₂ | 1 |
| 658 | (ClCH₂CH₂)₂N—[phenyl with Cl]— | 0 | —NH—C(=NH)—NH₂ | 1 |
| 659 | (ClCH₂CH₂)₂N—[phenyl with CN]— | 0 | —NH—C(=NH)—NH₂ | 1 |
| 660 | (ClCH₂CH₂)₂N—[phenyl]—O— | 1 | —NH—C(=NH)—NH₂ | 1 |
| 661 | (ClCH₂CH₂)₂N—CH₂—[phenyl]— | 0 | —NH—C(=NH)—NH₂ | 1 |
| 662 | (ClCH₂CH₂)₂N—[phenyl]— | 0 | —NH—C(=NH)—NH₂ | 1 |
| 663 | Br— | 5 | —NH—C(=NH)—NH₂ | 1 |

R₁(CH₂)ₘCONH—[pyridine]—[benzimidazole]—CONH(CH₂)ₙR₂

| 664 | (ClCH₂CH₂)₂N—[phenyl]— | 0 | —C(=NH)—NH₂ | 2 |

TABLE 1-continued
| Compd. No. | R₁ | m | R₂ | n |
|---|---|---|---|---|
| 665 | 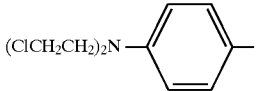 | 3 |  | 2 |
| 666 | 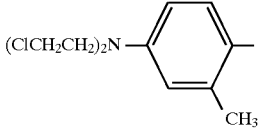 | 0 |  | 2 |
| 667 | 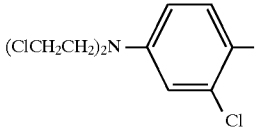 | 0 |  | 2 |
| 668 | 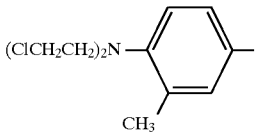 | 0 |  | 2 |
| 669 | 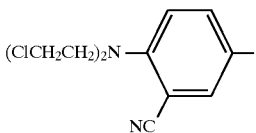 | 0 |  | 2 |
| 670 | 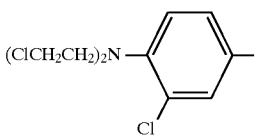 | 0 |  | 2 |
| 671 | H | 0 |  | 2 |
| 672 | 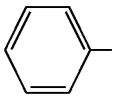 | 0 |  | 2 |
TABLE 2
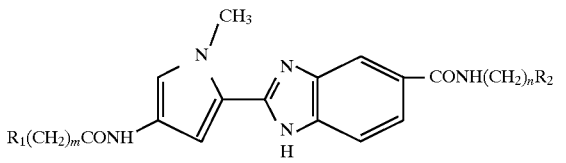
| Compd. No. | R₁ | m | R₂ | n |
|---|---|---|---|---|
| 1001 | 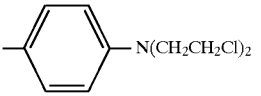 | 1 | 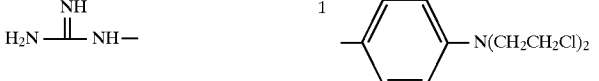 | 0 |
| 1002 | 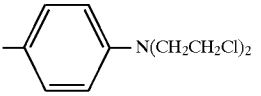 | 1 | | 1 |

TABLE 2-continued

| Compd. No. | R₁ | m | R₂ | n |
|---|---|---|---|---|
| 1003 | H₂N−C(=NH)−NH− | 1 | −C₆H₄−N(CH₂CH₂Cl)₂ (para) | 2 |
| 1004 | H₂N−C(=NH)−NH− | 1 | −C₆H₄−N(CH₂CH₂Cl)₂ (para) | 3 |
| 1005 | H₂N−C(=NH)−NH− | 1 | −C₆H₃(CH₃)−N(CH₂CH₂Cl)₂ | 0 |
| 1006 | H₂N−C(=NH)−NH− | 1 | −C₆H₃(CH₃)−N(CH₂CH₂Cl)₂ | 1 |
| 1007 | H₂N−C(=NH)−NH− | 1 | −C₆H₃(CH₃)−N(CH₂CH₂Cl)₂ | 2 |
| 1008 | H₂N−C(=NH)−NH− | 1 | −C₆H₃(CH₃)−N(CH₂CH₂Cl)₂ | 3 |
| 1009 | H₂N−C(=NH)−NH− | 1 | −C₆H₃(OCH₃)−N(CH₂CH₂Cl)₂ | 0 |
| 1010 | H₂N−C(=NH)−NH− | 1 | −C₆H₃(OCH₃)−N(CH₂CH₂Cl)₂ | 1 |
| 1011 | H₂N−C(=NH)−NH− | 1 | −C₆H₃(OCH₃)−N(CH₂CH₂Cl)₂ | 2 |
| 1012 | H₂N−C(=NH)−NH− | 1 | −C₆H₃(OCH₃)−N(CH₂CH₂Cl)₂ | 3 |
| 1013 | H₂N−C(=NH)−NH− | 1 | −C₆H₃(CN)−N(CH₂CH₂Cl)₂ | 0 |

TABLE 2-continued

| Compd. No. | R₁ | m | R₂ | n |
|---|---|---|---|---|
| 1014 | H₂N–C(=NH)–NH– | 1 | 4-N(CH₂CH₂Cl)₂, 3-CN phenyl | 1 |
| 1015 | H₂N–C(=NH)–NH– | 1 | 4-N(CH₂CH₂Cl)₂, 3-CN phenyl | 2 |
| 1016 | H₂N–C(=NH)–NH– | 1 | 4-N(CH₂CH₂Cl)₂, 3-CN phenyl | 3 |
| 1017 | H₂N–C(=NH)–NH– | 1 | 4-N(CH₂CH₂Cl)₂, 3-Cl phenyl | 0 |
| 1018 | H₂N–C(=NH)–NH– | 1 | 4-N(CH₂CH₂Cl)₂, 3-Cl phenyl | 1 |
| 1019 | H₂N–C(=NH)–NH– | 1 | 4-N(CH₂CH₂Cl)₂, 3-Cl phenyl | 2 |
| 1020 | H₂N–C(=NH)–NH– | 1 | 4-N(CH₂CH₂Cl)₂, 3-Cl phenyl | 3 |
| 1021 | H₂N–C(=NH)–NH– | 1 | 4-N(CH₂CH₂Cl)₂, 3-F phenyl | 0 |
| 1022 | H₂N–C(=NH)–NH– | 1 | 4-N(CH₂CH₂Cl)₂, 3-CF₃ phenyl | 0 |
| 1023 | H₂N–C(=NH)–NH– | 1 | 4-N(CH₂CH₂Cl)₂, 3-CONH(CH₂)₂N(CH₃)₂ phenyl | 0 |
| 1024 | H₂N–C(=NH)–NH– | 1 | 4-N(CH₂CH₂Cl)₂, 2-CH₃ phenyl | 0 |

TABLE 2-continued

| Compd. No. | R₁ | m | R₂ | n |
|---|---|---|---|---|
| 1025 | H₂N−C(=NH)−NH− | 1 | 4-N(CH₂CH₂Cl)₂-3-CH₃-phenyl | 1 |
| 1026 | H₂N−C(=NH)−NH− | 1 | 4-N(CH₂CH₂Cl)₂-3-CH₃-phenyl | 2 |
| 1027 | H₂N−C(=NH)−NH− | 1 | 4-N(CH₂CH₂Cl)₂-3-CH₃-phenyl | 3 |
| 1028 | H₂N−C(=NH)−NH− | 1 | 4-N(CH₂CH₂Cl)₂-3-OCH₃-phenyl | 0 |
| 1029 | H₂N−C(=NH)−NH− | 1 | 4-N(CH₂CH₂Cl)₂-3-OCH₃-phenyl | 1 |
| 1030 | H₂N−C(=NH)−NH− | 1 | 4-N(CH₂CH₂Cl)₂-3-OCH₃-phenyl | 2 |
| 1031 | H₂N−C(=NH)−NH− | 1 | 4-N(CH₂CH₂Cl)₂-3-OCH₃-phenyl | 3 |
| 1032 | H₂N−C(=NH)−NH− | 1 | 4-N(CH₂CH₂Cl)₂-3-CN-phenyl | 0 |
| 1033 | H₂N−C(=NH)−NH− | 1 | 4-N(CH₂CH₂Cl)₂-3-CN-phenyl | 1 |
| 1034 | H₂N−C(=NH)−NH− | 1 | 4-N(CH₂CH₂Cl)₂-3-CN-phenyl | 2 |
| 1035 | H₂N−C(=NH)−NH− | 1 | 4-N(CH₂CH₂Cl)₂-3-CN-phenyl | 3 |

TABLE 2-continued

| Compd. No. | R$_1$ | m | R$_2$ | n |
|---|---|---|---|---|
| 1036 | H$_2$N-C(=NH)-NH— | 1 | 4-N(CH$_2$CH$_2$Cl)$_2$-3-Cl-phenyl | 0 |
| 1037 | H$_2$N-C(=NH)-NH— | 1 | 4-N(CH$_2$CH$_2$Cl)$_2$-3-Cl-phenyl | 1 |
| 1038 | H$_2$N-C(=NH)-NH— | 1 | 4-N(CH$_2$CH$_2$Cl)$_2$-3-Cl-phenyl | 2 |
| 1039 | H$_2$N-C(=NH)-NH— | 1 | 4-N(CH$_2$CH$_2$Cl)$_2$-3-Cl-phenyl | 3 |
| 1040 | H$_2$N-C(=NH)-NH— | 1 | 4-N(CH$_2$CH$_2$Cl)$_2$-3-F-phenyl | 0 |
| 1041 | H$_2$N-C(=NH)-NH— | 1 | 4-N(CH$_2$CH$_2$Cl)$_2$-3-CF$_3$-phenyl | 0 |
| 1042 | H$_2$N-C(=NH)-NH— | 1 | 3-N(CH$_2$CH$_2$Cl)$_2$-5-CONH(CH$_2$)$_2$N(CH$_3$)$_2$-phenyl | 0 |
| 1043 | H$_2$N-C(=NH)-NH— | 1 | 4-N(CH$_2$CH$_2$Cl)$_2$-2,3-Cl$_2$-phenyl | 0 |
| 1044 | H$_2$N-C(=NH)-NH— | 1 | —O—C$_6$H$_4$—N(CH$_2$CH$_2$Cl)$_2$ | 1 |
| 1045 | H$_2$N-C(=NH)-NH— | 1 | —O—C$_6$H$_4$—N(CH$_2$CH$_2$Cl)$_2$ | 2 |
| 1046 | H$_2$N-C(=NH)-NH— | 1 | —C$_6$H$_4$—CH$_2$N(CH$_2$CH$_2$Cl)$_2$ | 0 |

TABLE 2-continued

| Compd. No. | R₁ | m | R₂ | n |
|---|---|---|---|---|
| 1047 | H₂N-C(=NH)-NH- | 1 | [3-N(CH₂CH₂Cl)₂-phenyl] | 0 |
| 1048 | H₂N-C(=NH)-NH- | 1 | [4-N(CH₂CH₃)(CH₂CH₂Cl)-phenyl] | 0 |
| 1049 | H₂N-C(=NH)-NH- | 1 | [3-N(CH₂CH₃)(CH₂CH₂Cl)-phenyl] | 0 |
| 1050 | H₂N-C(=NH)-NH- | 1 | [4-N(CH₂CH₂Br)₂-phenyl] | 0 |
| 1051 | H₂N-C(=NH)-NH- | 1 | [4-N(CH₂CH₂Br)₂-phenyl] | 3 |
| 1052 | H₂N-C(=NH)-NH- | 1 | [3-N(CH₂CH₂Br)₂-phenyl-O-] | 0 |
| 1053 | H₂N-C(=NH)-NH- | 1 | [4-N(CH₂CH₂OMs)₂-phenyl] | 0 |
| 1054 | H₂N-C(=NH)-NH- | 1 | [4-N(CH₂CH₂OAc)₂-phenyl] | 0 |
| 1055 | H₂N-C(=NH)-NH- | 1 | [N(CH₂CH₂Cl)₂-pyridyl] | 0 |
| 1056 | (CH₃)₃S⁺- | 2 | [4-N(CH₂CH₂Cl)₂-phenyl] | 0 |
| 1057 | (CH₃)₃S⁺- | 2 | [4-N(CH₂CH₂Cl)₂-phenyl] | 1 |
| 1058 | (CH₃)₃S⁺- | 2 | [4-N(CH₂CH₂Cl)₂-phenyl] | 2 |
| 1059 | (CH₃)₃S⁺- | 2 | [4-N(CH₂CH₂Cl)₂-phenyl] | 3 |

TABLE 2-continued

| Compd. No. | R₁ | m | R₂ | n |
|---|---|---|---|---|
| 1060 | H₃C—S⁺—, CH₃ | 2 |  —C₆H₃(CH₃)—N(CH₂CH₂Cl)₂ | 0 |
| 1061 | H₃C—S⁺—, CH₃ | 2 | 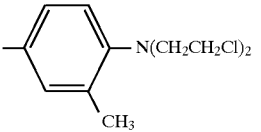 —C₆H₃(CH₃)—N(CH₂CH₂Cl)₂ | 1 |
| 1062 | H₃C—S⁺—, CH₃ | 2 |  —C₆H₃(CH₃)—N(CH₂CH₂Cl)₂ | 2 |
| 1063 | H₃C—S⁺—, CH₃ | 2 | 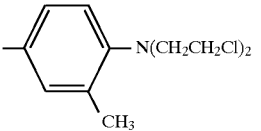 —C₆H₃(CH₃)—N(CH₂CH₂Cl)₂ | 3 |
| 1064 | H₃C—S⁺—, CH₃ | 2 |  —C₆H₃(OCH₃)—N(CH₂CH₂Cl)₂ | 0 |
| 1065 | H₃C—S⁺—, CH₃ | 2 | 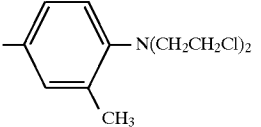 —C₆H₃(OCH₃)—N(CH₂CH₂Cl)₂ | 1 |
| 1066 | H₃C—S⁺—, CH₃ | 2 |  —C₆H₃(OCH₃)—N(CH₂CH₂Cl)₂ | 2 |
| 1067 | H₃C—S⁺—, CH₃ | 2 | 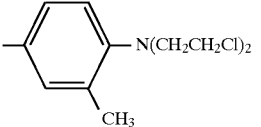 —C₆H₃(OCH₃)—N(CH₂CH₂Cl)₂ | 3 |
| 1068 | H₃C—S⁺—, CH₃ | 2 |  —C₆H₃(CN)—N(CH₂CH₂Cl)₂ | 0 |
| 1069 | H₃C—S⁺—, CH₃ | 2 | 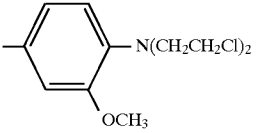 —C₆H₃(CN)—N(CH₂CH₂Cl)₂ | 1 |
| 1070 | H₃C—S⁺—, CH₃ | 2 |  —C₆H₃(CN)—N(CH₂CH₂Cl)₂ | 2 |

TABLE 2-continued

| Compd. No. | R₁ | m | R₂ | n |
|---|---|---|---|---|
| 1071 | H₃C—S⁺—  with CH₃ | 2 | phenyl with —N(CH₂CH₂Cl)₂ and CN | 3 |
| 1072 | H₃C—S⁺—  with CH₃ | 2 | phenyl with —N(CH₂CH₂Cl)₂ and Cl | 0 |
| 1073 | H₃C—S⁺—  with CH₃ | 2 | phenyl with —N(CH₂CH₂Cl)₂ and Cl | 1 |
| 1074 | H₃C—S⁺—  with CH₃ | 2 | phenyl with —N(CH₂CH₂Cl)₂ and Cl | 2 |
| 1075 | H₃C—S⁺—  with CH₃ | 2 | phenyl with —N(CH₂CH₂Cl)₂ and Cl | 3 |
| 1076 | H₃C—S⁺—  with CH₃ | 2 | phenyl with —N(CH₂CH₂Cl)₂ and F | 0 |
| 1077 | H₃C—S⁺—  with CH₃ | 2 | phenyl with —N(CH₂CH₂Cl)₂ and CF₃ | 0 |
| 1078 | H₃C—S⁺—  with CH₃ | 2 | phenyl with —N(CH₂CH₂Cl)₂ and CONH(CH₂)₂N(CH₃)₂ | 0 |
| 1079 | H₃C—S⁺—  with CH₃ | 2 | phenyl with —N(CH₂CH₂Cl)₂ and CH₃ | 0 |
| 1080 | H₃C—S⁺—  with CH₃ | 2 | phenyl with —N(CH₂CH₂Cl)₂ and H₃C | 1 |
| 1081 | H₃C—S⁺—  with CH₃ | 2 | phenyl with —N(CH₂CH₂Cl)₂ and H₃C | 2 |

TABLE 2-continued

| Compd. No. | R₁ | m | R₂ | n |
|---|---|---|---|---|
| 1082 | H₃C—S⁺— (CH₃) | 2 | 4-N(CH₂CH₂Cl)₂-3-methylphenyl | 3 |
| 1083 | H₃C—S⁺— (CH₃) | 2 | 4-N(CH₂CH₂Cl)₂-3-methoxyphenyl | 0 |
| 1084 | H₃C—S⁺— (CH₃) | 2 | 4-N(CH₂CH₂Cl)₂-3-methoxyphenyl | 1 |
| 1085 | H₃C—S⁺— (CH₃) | 2 | 4-N(CH₂CH₂Cl)₂-3-methoxyphenyl | 2 |
| 1086 | H₃C—S⁺— (CH₃) | 2 | 4-N(CH₂CH₂Cl)₂-3-methoxyphenyl | 3 |
| 1087 | H₃C—S⁺— (CH₃) | 2 | 4-N(CH₂CH₂Cl)₂-3-cyanophenyl | 0 |
| 1088 | H₃C—S⁺— (CH₃) | 2 | 4-N(CH₂CH₂Cl)₂-3-cyanophenyl | 1 |
| 1089 | H₃C—S⁺— (CH₃) | 2 | 4-N(CH₂CH₂Cl)₂-3-cyanophenyl | 2 |
| 1090 | H₃C—S⁺— (CH₃) | 2 | 4-N(CH₂CH₂Cl)₂-3-cyanophenyl | 3 |
| 1091 | H₃C—S⁺— (CH₃) | 2 | 4-N(CH₂CH₂Cl)₂-3-chlorophenyl | 0 |
| 1092 | H₃C—S⁺— (CH₃) | 2 | 4-N(CH₂CH₂Cl)₂-3-chlorophenyl | 1 |

TABLE 2-continued

| Compd. No. | R₁ | m | R₂ | n |
|---|---|---|---|---|
| 1093 | H₃C—S⁺— with CH₃ | 2 | 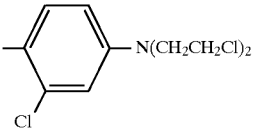 4-N(CH₂CH₂Cl)₂, 3-Cl phenyl | 2 |
| 1094 | H₃C—S⁺— with CH₃ | 2 | 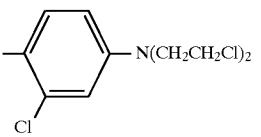 4-N(CH₂CH₂Cl)₂, 3-Cl phenyl | 3 |
| 1095 | H₃C—S⁺— with CH₃ | 2 | 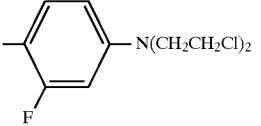 4-N(CH₂CH₂Cl)₂, 3-F phenyl | 0 |
| 1096 | H₃C—S⁺— with CH₃ | 2 | 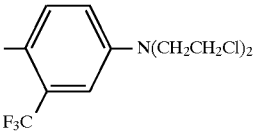 4-N(CH₂CH₂Cl)₂, 3-CF₃ phenyl | 0 |
| 1097 | H₃C—S⁺— with CH₃ | 2 | 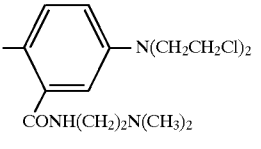 3-N(CH₂CH₂Cl)₂, CONH(CH₂)₂N(CH₃)₂ phenyl | 0 |
| 1098 | H₃C—S⁺— with CH₃ | 2 | 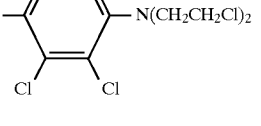 N(CH₂CH₂Cl)₂ with 2,3-diCl phenyl | 0 |
| 1099 | H₃C—S⁺— with CH₃ | 2 | —O—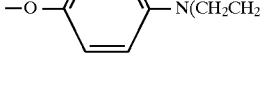—N(CH₂CH₂Cl)₂ | 1 |
| 1100 | H₃C—S⁺— with CH₃ | 2 | —O—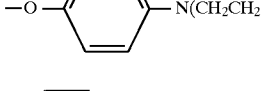—N(CH₂CH₂Cl)₂ | 2 |
| 1101 | H₃C—S⁺— with CH₃ | 2 | 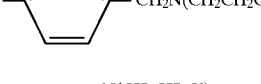—CH₂N(CH₂CH₂Cl)₂ | 0 |
| 1102 | H₃C—S⁺— with CH₃ | 2 | 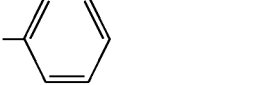 3-N(CH₂CH₂Cl)₂ phenyl | 0 |
| 1103 | H₃C—S⁺— with CH₃ | 2 | 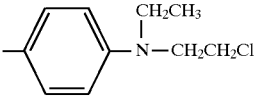 4-N(CH₂CH₃)(CH₂CH₂Cl) phenyl | 0 |

TABLE 2-continued

| Compd. No. | R₁ | m | R₂ | n |
|---|---|---|---|---|
| 1104 | H₃C—S⁺— with CH₃ substituent | 2 | 3-[N(CH₂CH₃)(CH₂CH₂Cl)]-phenyl- | 0 |
| 1105 | H₃C—S⁺— with CH₃ substituent | 2 | 4-[N(CH₂CH₂Br)₂]-phenyl- | 0 |
| 1106 | H₃C—S⁺— with CH₃ substituent | 2 | 4-[N(CH₂CH₂Br)₂]-phenyl- | 3 |
| 1107 | H₃C—S⁺— with CH₃ substituent | 2 | 3-[N(CH₂CH₂Br)₂]-phenoxy- | 0 |
| 1108 | H₃C—S⁺— with CH₃ substituent | 2 | 4-[N(CH₂CH₂OMs)₂]-phenyl- | 0 |
| 1109 | H₃C—S⁺— with CH₃ substituent | 2 | 4-[N(CH₂CH₂OAc)₂]-phenyl- | 0 |
| 1110 | H₃C—S⁺— with CH₃ substituent | 2 | 3-[N(CH₂CH₂Cl)₂]-pyridin-... | 0 |
| 1111 | H₃C—S⁺— with CH₃ substituent | 2 | —C(=NH)NH₂ | 2 |
| 1112 | H₂N—C(=NH)— | 2 | 4-[N(CH₂CH₂Cl)₂]-phenyl- | 0 |
| 1113 | H₂N—C(=NH)— | 2 | 4-[N(CH₂CH₂Cl)₂]-phenyl- | 1 |
| 1114 | H₂N—C(=NH)— | 2 | 4-[N(CH₂CH₂Cl)₂]-phenyl- | 2 |
| 1115 | H₂N—C(=NH)— | 2 | 4-[N(CH₂CH₂Cl)₂]-phenyl- | 3 |
| 1116 | H₂N—C(=NH)— | 2 | 4-[N(CH₂CH₂Cl)₂]-3-methyl-phenyl- | 0 |

TABLE 2-continued

| Compd. No. | R₁ | m | R₂ | n |
|---|---|---|---|---|
| 1117 | H₂N−C(=NH)− | 2 | 4-N(CH₂CH₂Cl)₂-3-CH₃-phenyl | 1 |
| 1118 | H₂N−C(=NH)− | 2 | 4-N(CH₂CH₂Cl)₂-3-CH₃-phenyl | 2 |
| 1119 | H₂N−C(=NH)− | 2 | 4-N(CH₂CH₂Cl)₂-3-CH₃-phenyl | 3 |
| 1120 | H₂N−C(=NH)− | 2 | 4-N(CH₂CH₂Cl)₂-3-OCH₃-phenyl | 0 |
| 1121 | H₂N−C(=NH)− | 2 | 4-N(CH₂CH₂Cl)₂-3-OCH₃-phenyl | 1 |
| 1122 | H₂N−C(=NH)− | 2 | 4-N(CH₂CH₂Cl)₂-3-OCH₃-phenyl | 2 |
| 1123 | H₂N−C(=NH)− | 2 | 4-N(CH₂CH₂Cl)₂-3-OCH₃-phenyl | 3 |
| 1124 | H₂N−C(=NH)− | 2 | 4-N(CH₂CH₂Cl)₂-3-CN-phenyl | 0 |
| 1125 | H₂N−C(=NH)− | 2 | 4-N(CH₂CH₂Cl)₂-3-CN-phenyl | 1 |
| 1126 | H₂N−C(=NH)− | 2 | 4-N(CH₂CH₂Cl)₂-3-CN-phenyl | 2 |
| 1127 | H₂N−C(=NH)− | 2 | 4-N(CH₂CH₂Cl)₂-3-CN-phenyl | 3 |

TABLE 2-continued

| Compd. No. | R₁ | m | R₂ | n |
|---|---|---|---|---|
| 1128 | H₂N−C(=NH)− | 2 | 4-N(CH₂CH₂Cl)₂-2-Cl-phenyl | 0 |
| 1129 | H₂N−C(=NH)− | 2 | 4-N(CH₂CH₂Cl)₂-2-Cl-phenyl | 1 |
| 1130 | H₂N−C(=NH)− | 2 | 4-N(CH₂CH₂Cl)₂-2-Cl-phenyl | 2 |
| 1131 | H₂N−C(=NH)− | 2 | 4-N(CH₂CH₂Cl)₂-2-Cl-phenyl | 3 |
| 1132 | H₂N−C(=NH)− | 2 | 4-N(CH₂CH₂Cl)₂-2-F-phenyl | 0 |
| 1133 | H₂N−C(=NH)− | 2 | 4-N(CH₂CH₂Cl)₂-2-CF₃-phenyl | 0 |
| 1134 | H₂N−C(=NH)− | 2 | 4-N(CH₂CH₂Cl)₂-2-CONH(CH₂)₂N(CH₃)₂-phenyl | 0 |
| 1135 | H₂N−C(=NH)− | 2 | 3-N(CH₂CH₂Cl)₂-5-CH₃-phenyl | 0 |
| 1136 | H₂N−C(=NH)− | 2 | 3-N(CH₂CH₂Cl)₂-5-CH₃-phenyl | 1 |
| 1137 | H₂N−C(=NH)− | 2 | 3-N(CH₂CH₂Cl)₂-5-CH₃-phenyl | 2 |
| 1138 | H₂N−C(=NH)− | 2 | 3-N(CH₂CH₂Cl)₂-5-CH₃-phenyl | 3 |

TABLE 2-continued

| Compd. No. | R₁ | m | R₂ | n |
|---|---|---|---|---|
| 1139 | H₂N–C(=NH)– | 2 | 4-N(CH₂CH₂Cl)₂-3-H₃CO-phenyl (methyl attached) | 0 |
| 1140 | H₂N–C(=NH)– | 2 | 4-N(CH₂CH₂Cl)₂-3-H₃CO-phenyl (methyl attached) | 1 |
| 1141 | H₂N–C(=NH)– | 2 | 4-N(CH₂CH₂Cl)₂-3-H₃CO-phenyl (methyl attached) | 2 |
| 1142 | H₂N–C(=NH)– | 2 | 4-N(CH₂CH₂Cl)₂-3-H₃CO-phenyl (methyl attached) | 3 |
| 1143 | H₂N–C(=NH)– | 2 | 4-N(CH₂CH₂Cl)₂-3-NC-phenyl (methyl attached) | 0 |
| 1144 | H₂N–C(=NH)– | 2 | 4-N(CH₂CH₂Cl)₂-3-NC-phenyl (methyl attached) | 1 |
| 1145 | H₂N–C(=NH)– | 2 | 4-N(CH₂CH₂Cl)₂-3-NC-phenyl (methyl attached) | 2 |
| 1146 | H₂N–C(=NH)– | 2 | 4-N(CH₂CH₂Cl)₂-3-NC-phenyl (methyl attached) | 3 |
| 1147 | H₂N–C(=NH)– | 2 | 4-N(CH₂CH₂Cl)₂-3-Cl-phenyl (methyl attached) | 0 |
| 1148 | H₂N–C(=NH)– | 2 | 4-N(CH₂CH₂Cl)₂-3-Cl-phenyl (methyl attached) | 1 |
| 1149 | H₂N–C(=NH)– | 2 | 4-N(CH₂CH₂Cl)₂-3-Cl-phenyl (methyl attached) | 2 |

TABLE 2-continued

| Compd. No. | R₁ | m | R₂ | n |
|---|---|---|---|---|
| 1150 | H₂N-C(=NH)- | 2 | 4-[N(CH₂CH₂Cl)₂]-3-Cl-C₆H₃- | 3 |
| 1151 | H₂N-C(=NH)- | 2 | 4-[N(CH₂CH₂Cl)₂]-3-F-C₆H₃- | 0 |
| 1152 | H₂N-C(=NH)- | 2 | 4-[N(CH₂CH₂Cl)₂]-3-CF₃-C₆H₃- | 0 |
| 1153 | H₂N-C(=NH)- | 2 | 4-[N(CH₂CH₂Cl)₂]-3-[CONH(CH₂)₂N(CH₃)₂]-C₆H₃- | 0 |
| 1154 | H₂N-C(=NH)- | 2 | 4-[N(CH₂CH₂Cl)₂]-2,3-Cl₂-C₆H₂- | 0 |
| 1155 | H₂N-C(=NH)- | 2 | -O-C₆H₄-N(CH₂CH₂Cl)₂ | 1 |
| 1156 | H₂N-C(=NH)- | 2 | -O-C₆H₄-N(CH₂CH₂Cl)₂ | 2 |
| 1157 | H₂N-C(=NH)- | 2 | -C₆H₄-CH₂N(CH₂CH₂Cl)₂ | 0 |
| 1158 | H₂N-C(=NH)- | 2 | 3-[N(CH₂CH₂Cl)₂]-C₆H₄- | 0 |
| 1159 | H₂N-C(=NH)- | 2 | 4-[N(CH₂CH₃)(CH₂CH₂Cl)]-C₆H₄- | 0 |
| 1160 | (CH₃)₃N⁺- | 3 | 4-[N(CH₂CH₂Cl)₂]-C₆H₄- | 0 |
| 1161 | (CH₃)₃N⁺- | 3 | 4-[N(CH₂CH₂Cl)₂]-C₆H₄- | 1 |

TABLE 2-continued

| Compd. No. | R₁ | m | R₂ | n |
|---|---|---|---|---|
| 1162 | H₃C—N⁺(CH₃)₂—CH₃ | 3 | —C₆H₄—N(CH₂CH₂Cl)₂ (para) | 2 |
| 1163 | H₃C—N⁺(CH₃)₂—CH₃ | 3 | —C₆H₄—N(CH₂CH₂Cl)₂ (para) | 3 |
| 1164 | H₃C—N⁺(CH₃)₂—CH₃ | 3 | —C₆H₃(CH₃)—N(CH₂CH₂Cl)₂ | 0 |
| 1165 | H₃C—N⁺(CH₃)₂—CH₃ | 3 | —C₆H₃(CH₃)—N(CH₂CH₂Cl)₂ | 1 |
| 1166 | H₃C—N⁺(CH₃)₂—CH₃ | 3 | —C₆H₃(CH₃)—N(CH₂CH₂Cl)₂ | 2 |
| 1167 | H₃C—N⁺(CH₃)₂—CH₃ | 3 | —C₆H₃(CH₃)—N(CH₂CH₂Cl)₂ | 3 |
| 1168 | H₃C—N⁺(CH₃)₂—CH₃ | 3 | —C₆H₃(OCH₃)—N(CH₂CH₂Cl)₂ | 0 |
| 1169 | H₃C—N⁺(CH₃)₂—CH₃ | 3 | —C₆H₃(OCH₃)—N(CH₂CH₂Cl)₂ | 1 |
| 1170 | H₃C—N⁺(CH₃)₂—CH₃ | 3 | —C₆H₃(OCH₃)—N(CH₂CH₂Cl)₂ | 2 |
| 1171 | H₃C—N⁺(CH₃)₂—CH₃ | 3 | —C₆H₃(OCH₃)—N(CH₂CH₂Cl)₂ | 3 |
| 1172 | H₃C—N⁺(CH₃)₂—CH₃ | 3 | —C₆H₃(CN)—N(CH₂CH₂Cl)₂ | 0 |

TABLE 2-continued

| Compd. No. | R₁ | m | R₂ | n |
|---|---|---|---|---|
| 1173 | (CH₃)₃N⁺— | 3 | 4-[N(CH₂CH₂Cl)₂]-2-CN-phenyl | 1 |
| 1174 | (CH₃)₃N⁺— | 3 | 4-[N(CH₂CH₂Cl)₂]-2-CN-phenyl | 2 |
| 1175 | (CH₃)₃N⁺— | 3 | 4-[N(CH₂CH₂Cl)₂]-2-CN-phenyl | 3 |
| 1176 | (CH₃)₃N⁺— | 3 | 4-[N(CH₂CH₂Cl)₂]-2-Cl-phenyl | 0 |
| 1177 | (CH₃)₃N⁺— | 3 | 4-[N(CH₂CH₂Cl)₂]-2-Cl-phenyl | 1 |
| 1178 | (CH₃)₃N⁺— | 3 | 4-[N(CH₂CH₂Cl)₂]-2-Cl-phenyl | 2 |
| 1179 | (CH₃)₃N⁺— | 3 | 4-[N(CH₂CH₂Cl)₂]-2-Cl-phenyl | 3 |
| 1180 | (CH₃)₃N⁺— | 3 | 4-[N(CH₂CH₂Cl)₂]-2-F-phenyl | 0 |
| 1181 | (CH₃)₃N⁺— | 3 | 4-[N(CH₂CH₂Cl)₂]-2-CF₃-phenyl | 0 |
| 1182 | (CH₃)₃N⁺— | 3 | 4-[N(CH₂CH₂Cl)₂]-2-CONH(CH₂)₂N(CH₃)₂-phenyl | 0 |
| 1183 | (CH₃)₃N⁺— | 3 | 4-[N(CH₂CH₂Cl)₂]-3-CH₃-phenyl | 0 |

TABLE 2-continued

| Compd. No. | R₁ | m | R₂ | n |
|---|---|---|---|---|
| 1184 | H₃C—N⁺(CH₃)₂—CH₃ | 3 | 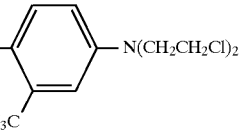 4-N(CH₂CH₂Cl)₂, 3-CH₃ phenyl | 1 |
| 1185 | H₃C—N⁺(CH₃)₂—CH₃ | 3 | 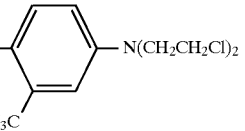 4-N(CH₂CH₂Cl)₂, 3-CH₃ phenyl | 2 |
| 1186 | H₃C—N⁺(CH₃)₂—CH₃ | 3 | 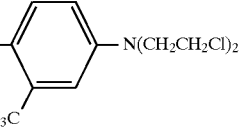 4-N(CH₂CH₂Cl)₂, 3-CH₃ phenyl | 3 |
| 1187 | H₃C—N⁺(CH₃)₂—CH₃ | 3 | 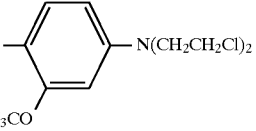 4-N(CH₂CH₂Cl)₂, 3-OCH₃ phenyl | 0 |
| 1188 | H₃C—N⁺(CH₃)₂—CH₃ | 3 | 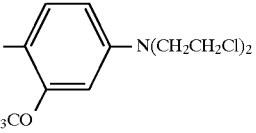 4-N(CH₂CH₂Cl)₂, 3-OCH₃ phenyl | 1 |
| 1189 | H₃C—N⁺(CH₃)₂—CH₃ | 3 | 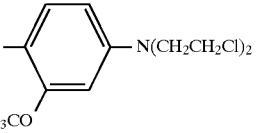 4-N(CH₂CH₂Cl)₂, 3-OCH₃ phenyl | 2 |
| 1190 | H₃C—N⁺(CH₃)₂—CH₃ | 3 | 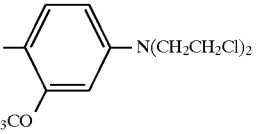 4-N(CH₂CH₂Cl)₂, 3-OCH₃ phenyl | 3 |
| 1191 | H₃C—N⁺(CH₃)₂—CH₃ | 3 | 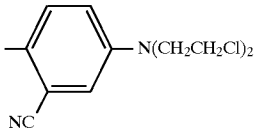 4-N(CH₂CH₂Cl)₂, 3-CN phenyl | 0 |
| 1192 | H₃C—N⁺(CH₃)₂—CH₃ | 3 | 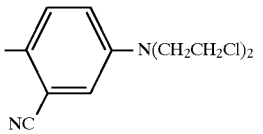 4-N(CH₂CH₂Cl)₂, 3-CN phenyl | 1 |
| 1193 | H₃C—N⁺(CH₃)₂—CH₃ | 3 | 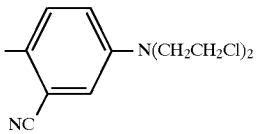 4-N(CH₂CH₂Cl)₂, 3-CN phenyl | 2 |
| 1194 | H₃C—N⁺(CH₃)₂—CH₃ | 3 | 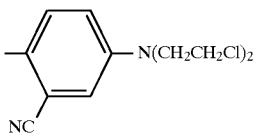 4-N(CH₂CH₂Cl)₂, 3-CN phenyl | 3 |

TABLE 2-continued

| Compd. No. | R$_1$ | m | R$_2$ | n |
|---|---|---|---|---|
| 1195 | H$_3$C—N$^+$(CH$_3$)$_2$—CH$_3$ | 3 | 4-[N(CH$_2$CH$_2$Cl)$_2$]-3-Cl-phenyl | 0 |
| 1196 | H$_3$C—N$^+$(CH$_3$)$_2$—CH$_3$ | 3 | 4-[N(CH$_2$CH$_2$Cl)$_2$]-3-Cl-phenyl | 1 |
| 1197 | H$_3$C—N$^+$(CH$_3$)$_2$—CH$_3$ | 3 | 4-[N(CH$_2$CH$_2$Cl)$_2$]-3-Cl-phenyl | 2 |
| 1198 | H$_3$C—N$^+$(CH$_3$)$_2$—CH$_3$ | 3 | 4-[N(CH$_2$CH$_2$Cl)$_2$]-3-Cl-phenyl | 3 |
| 1199 | H$_3$C—N$^+$(CH$_3$)$_2$—CH$_3$ | 3 | 4-[N(CH$_2$CH$_2$Cl)$_2$]-3-F-phenyl | 0 |
| 1200 | H$_3$C—N$^+$(CH$_3$)$_2$—CH$_3$ | 3 | 4-[N(CH$_2$CH$_2$Cl)$_2$]-3-CF$_3$-phenyl | 0 |
| 1201 | H$_3$C—N$^+$(CH$_3$)$_2$—CH$_3$ | 3 | 4-[N(CH$_2$CH$_2$Cl)$_2$]-3-CONH(CH$_2$)$_2$N(CH$_3$)$_2$-phenyl | 0 |
| 1202 | H$_3$C—N$^+$(CH$_3$)$_2$—CH$_3$ | 3 | 4-[N(CH$_2$CH$_2$Cl)$_2$]-2,3-diCl-phenyl | 0 |
| 1203 | H$_3$C—N$^+$(CH$_3$)$_2$—CH$_3$ | 3 | —O—C$_6$H$_4$—N(CH$_2$CH$_2$Cl)$_2$ | 1 |
| 1204 | H$_3$C—N$^+$(CH$_3$)$_2$—CH$_3$ | 3 | —O—C$_6$H$_4$—N(CH$_2$CH$_2$Cl)$_2$ | 2 |
| 1205 | H$_3$C—N$^+$(CH$_3$)$_2$—CH$_3$ | 3 | —C$_6$H$_4$—CH$_2$N(CH$_2$CH$_2$Cl)$_2$ | 0 |

TABLE 2-continued

| Compd. No. | R₁ | m | R₂ | n |
|---|---|---|---|---|
| 1206 | (CH₃)₃N⁺— | 3 | —C₆H₄—N(CH₂CH₂Cl)₂ (meta) | 0 |
| 1207 | (CH₃)₃N⁺— | 3 | —C₆H₄—N(CH₂CH₃)(CH₂CH₂Cl) (para) | 0 |
| 1208 | CH₃—N(piperazine)N— | 1 | —C₆H₄—N(CH₂CH₂Cl)₂ (para) | 0 |
| 1209 | CH₃—N(piperazine)N— | 1 | —C₆H₄—N(CH₂CH₂Cl)₂ (para) | 3 |
| 1210 | CH₃—N(piperazine)N— | 1 | —C₆H₃(CH₃)—N(CH₂CH₂Cl)₂ | 0 |
| 1211 | CH₃—N(piperazine)N— | 1 | —C₆H₃(Cl)—N(CH₂CH₂Cl)₂ | 0 |
| 1212 | CH₃—N(piperazine)N— | 1 | —C₆H₃(CH₃)—N(CH₂CH₂Cl)₂ | 0 |
| 1213 | CH₃—N(piperazine)N— | 1 | —C₆H₃(CF₃)—N(CH₂CH₂Cl)₂ | 0 |
| 1214 | CH₃—N(piperazine)N— | 1 | —C₆H₃(Cl)—N(CH₂CH₂Cl)₂ | 0 |
| 1215 | CH₃—N(piperazine)N— | 1 | —C₆H₃(CN)—N(CH₂CH₂Cl)₂ | 0 |
| 1216 | CH₃—N(piperazine)N— | 2 | —C₆H₄—N(CH₂CH₂Cl)₂ (para) | 0 |
| 1217 | CH₃—N(piperazine)N— | 2 | —C₆H₄—N(CH₂CH₂Cl)₂ (para) | 3 |

TABLE 2-continued

| Compd. No. | R₁ | m | R₂ | n |
|---|---|---|---|---|
| 1218 | CH₃—N(piperazine)N— | 2 | 4-N(CH₂CH₂Cl)₂-3-CH₃-phenyl | 0 |
| 1219 | CH₃—N(piperazine)N— | 2 | 4-N(CH₂CH₂Cl)₂-3-Cl-phenyl | 0 |
| 1220 | CH₃—N(piperazine)N— | 2 | 4-N(CH₂CH₂Cl)₂-2-CH₃-phenyl | 0 |
| 1221 | CH₃—N(piperazine)N— | 2 | 4-N(CH₂CH₂Cl)₂-2-CF₃-phenyl | 0 |
| 1222 | CH₃—N(piperazine)N— | 2 | 4-N(CH₂CH₂Cl)₂-2-Cl-phenyl | 0 |
| 1223 | CH₃—N(piperazine)N— | 2 | 4-N(CH₂CH₂Cl)₂-2-CN-phenyl | 0 |
| 1224 | CH₃—N(piperazine)N— | 3 | 4-N(CH₂CH₂Cl)₂-phenyl | 0 |
| 1225 | CH₃—N(piperazine)N— | 3 | 4-N(CH₂CH₂Cl)₂-phenyl | 3 |
| 1226 | CH₃—N(piperazine)N— | 3 | 4-N(CH₂CH₂Cl)₂-3-CH₃-phenyl | 0 |
| 1227 | CH₃—N(piperazine)N— | 3 | 4-N(CH₂CH₂Cl)₂-3-Cl-phenyl | 0 |
| 1228 | CH₃—N(piperazine)N— | 3 | 4-N(CH₂CH₂Cl)₂-2-CH₃-phenyl | 0 |

TABLE 2-continued

| Compd. No. | R₁ | m | R₂ | n |
|---|---|---|---|---|
| 1229 | CH₃—N(piperazine)N— | 3 | -C₆H₃(CF₃)-N(CH₂CH₂Cl)₂ | 0 |
| 1230 | CH₃—N(piperazine)N— | 3 | -C₆H₃(Cl)-N(CH₂CH₂Cl)₂ | 0 |
| 1231 | CH₃—N(piperazine)N— | 3 | -C₆H₃(CN)-N(CH₂CH₂Cl)₂ | 0 |
| 1232 | (CH₃)₂—⁺N(piperazine)N— | 1 | -C₆H₄-N(CH₂CH₂Cl)₂ | 0 |
| 1233 | (CH₃)₂—⁺N(piperazine)N— | 1 | -C₆H₄-N(CH₂CH₂Cl)₂ | 3 |
| 1234 | (CH₃)₂—⁺N(piperazine)N— | 1 | -C₆H₃(CH₃)-N(CH₂CH₂Cl)₂ | 0 |
| 1235 | (CH₃)₂—⁺N(piperazine)N— | 1 | -C₆H₃(Cl)-N(CH₂CH₂Cl)₂ | 0 |
| 1236 | (CH₃)₂—⁺N(piperazine)N— | 1 | -C₆H₃(CH₃)-N(CH₂CH₂Cl)₂ | 0 |
| 1237 | (CH₃)₂—⁺N(piperazine)N— | 1 | -C₆H₃(CF₃)-N(CH₂CH₂Cl)₂ | 0 |
| 1238 | (CH₃)₂—⁺N(piperazine)N— | 1 | -C₆H₃(Cl)-N(CH₂CH₂Cl)₂ | 0 |
| 1239 | (CH₃)₂—⁺N(piperazine)N— | 1 | -C₆H₃(CN)-N(CH₂CH₂Cl)₂ | 0 |

TABLE 2-continued

| Compd. No. | R₁ | m | R₂ | n |
|---|---|---|---|---|
| 1240 | CH₃—⁺N(CH₃)(piperazine)N— | 2 | —C₆H₄—N(CH₂CH₂Cl)₂ | 0 |
| 1241 | CH₃—⁺N(CH₃)(piperazine)N— | 2 | —C₆H₄—N(CH₂CH₂Cl)₂ | 3 |
| 1242 | CH₃—⁺N(CH₃)(piperazine)N— | 2 | —C₆H₃(CH₃)—N(CH₂CH₂Cl)₂ | 0 |
| 1243 | CH₃—⁺N(CH₃)(piperazine)N— | 2 | —C₆H₃(Cl)—N(CH₂CH₂Cl)₂ | 0 |
| 1244 | CH₃—⁺N(CH₃)(piperazine)N— | 2 | —C₆H₃(CH₃)—N(CH₂CH₂Cl)₂ | 0 |
| 1245 | CH₃—⁺N(CH₃)(piperazine)N— | 2 | —C₆H₃(CF₃)—N(CH₂CH₂Cl)₂ | 0 |
| 1246 | CH₃—⁺N(CH₃)(piperazine)N— | 2 | —C₆H₃(Cl)—N(CH₂CH₂Cl)₂ | 0 |
| 1247 | CH₃—⁺N(CH₃)(piperazine)N— | 2 | —C₆H₃(CN)—N(CH₂CH₂Cl)₂ | 0 |
| 1248 | CH₃—⁺N(CH₃)(piperazine)N— | 3 | —C₆H₄—N(CH₂CH₂Cl)₂ | 0 |
| 1249 | CH₃—⁺N(CH₃)(piperazine)N— | 3 | —C₆H₄—N(CH₂CH₂Cl)₂ | 3 |
| 1250 | CH₃—⁺N(CH₃)(piperazine)N— | 3 | —C₆H₃(CH₃)—N(CH₂CH₂Cl)₂ | 0 |
| 1251 | CH₃—⁺N(CH₃)(piperazine)N— | 3 | —C₆H₃(Cl)—N(CH₂CH₂Cl)₂ | 0 |

TABLE 2-continued

| Compd. No. | R₁ | m | R₂ | n |
|---|---|---|---|---|
| 1252 | CH₃—⁺N(CH₃)(piperazine)N— | 3 | 4-[N(CH₂CH₂Cl)₂]-3-CH₃-phenyl | 0 |
| 1253 | CH₃—⁺N(CH₃)(piperazine)N— | 3 | 4-[N(CH₂CH₂Cl)₂]-3-CF₃-phenyl | 0 |
| 1254 | CH₃—⁺N(CH₃)(piperazine)N— | 3 | 4-[N(CH₂CH₂Cl)₂]-3-Cl-phenyl | 0 |
| 1255 | CH₃—⁺N(CH₃)(piperazine)N— | 3 | 4-[N(CH₂CH₂Cl)₂]-3-CN-phenyl | 0 |
| 1256 | H₃C—N(CH₃)(CH₃)— | 3 | 4-[N(CH₂CH₂Cl)₂]-phenyl | 0 |
| 1257 | H₃C—N(CH₃)(CH₃)— | 3 | 4-[N(CH₂CH₂Cl)₂]-phenyl | 1 |
| 1258 | H₃C—N(CH₃)(CH₃)— | 3 | 4-[N(CH₂CH₂Cl)₂]-phenyl | 2 |
| 1259 | H₃C—N(CH₃)(CH₃)— | 3 | 4-[N(CH₂CH₂Cl)₂]-phenyl | 3 |
| 1260 | H₃C—N(CH₃)(CH₃)— | 3 | 4-[N(CH₂CH₂Cl)₂]-3-CH₃-phenyl | 0 |
| 1261 | H₃C—N(CH₃)(CH₃)— | 3 | 4-[N(CH₂CH₂Cl)₂]-3-CH₃-phenyl | 1 |
| 1262 | H₃C—N(CH₃)(CH₃)— | 3 | 4-[N(CH₂CH₂Cl)₂]-3-CH₃-phenyl | 2 |
| 1263 | H₃C—N(CH₃)(CH₃)— | 3 | 4-[N(CH₂CH₂Cl)₂]-3-CH₃-phenyl | 3 |

TABLE 2-continued

| Compd. No. | R₁ | m | R₂ | n |
|---|---|---|---|---|
| 1264 | H₃C—N(CH₃)— | 3 | —C₆H₃(OCH₃)(N(CH₂CH₂Cl)₂) | 0 |
| 1265 | H₃C—N(CH₃)— | 3 | —C₆H₃(OCH₃)(N(CH₂CH₂Cl)₂) | 1 |
| 1266 | H₃C—N(CH₃)— | 3 | —C₆H₃(OCH₃)(N(CH₂CH₂Cl)₂) | 2 |
| 1267 | H₃C—N(CH₃)— | 3 | —C₆H₃(OCH₃)(N(CH₂CH₂Cl)₂) | 3 |
| 1268 | H₃C—N(CH₃)— | 3 | —C₆H₃(CN)(N(CH₂CH₂Cl)₂) | 0 |
| 1269 | H₃C—N(CH₃)— | 3 | —C₆H₃(CN)(N(CH₂CH₂Cl)₂) | 1 |
| 1270 | H₃C—N(CH₃)— | 3 | —C₆H₃(CN)(N(CH₂CH₂Cl)₂) | 2 |
| 1271 | H₃C—N(CH₃)— | 3 | —C₆H₃(CN)(N(CH₂CH₂Cl)₂) | 3 |
| 1272 | H₃C—N(CH₃)— | 3 | —C₆H₃(Cl)(N(CH₂CH₂Cl)₂) | 0 |
| 1273 | H₃C—N(CH₃)— | 3 | —C₆H₃(Cl)(N(CH₂CH₂Cl)₂) | 1 |
| 1274 | H₃C—N(CH₃)— | 3 | —C₆H₃(Cl)(N(CH₂CH₂Cl)₂) | 2 |

TABLE 2-continued

| Compd. No. | R₁ | m | R₂ | n |
|---|---|---|---|---|
| 1275 | H₃C—N—CH₃ | 3 |  4-N(CH₂CH₂Cl)₂, 2-Cl phenyl | 3 |
| 1276 | H₃C—N—CH₃ | 3 |  4-N(CH₂CH₂Cl)₂, 2-F phenyl | 0 |
| 1277 | H₃C—N—CH₃ | 3 |  4-N(CH₂CH₂Cl)₂, 2-CF₃ phenyl | 0 |
| 1278 | H₃C—N—CH₃ | 3 |  4-N(CH₂CH₂Cl)₂, 2-CONH(CH₂)₂N(CH₃)₂ phenyl | 0 |
| 1279 | H₃C—N—CH₃ | 3 |  3-N(CH₂CH₂Cl)₂, 5-CH₃ phenyl | 0 |
| 1280 | H₃C—N—CH₃ | 3 | 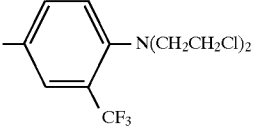 3-N(CH₂CH₂Cl)₂, 5-CH₃ phenyl | 1 |
| 1281 | H₃C—N—CH₃ | 3 |  3-N(CH₂CH₂Cl)₂, 5-CH₃ phenyl | 2 |
| 1282 | H₃C—N—CH₃ | 3 | 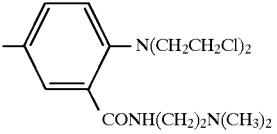 3-N(CH₂CH₂Cl)₂, 5-CH₃ phenyl | 3 |
| 1283 | H₃C—N—CH₃ | 3 |  3-N(CH₂CH₂Cl)₂, 5-OCH₃ phenyl | 0 |
| 1284 | H₃C—N—CH₃ | 3 | 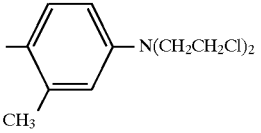 3-N(CH₂CH₂Cl)₂, 5-OCH₃ phenyl | 1 |
| 1285 | H₃C—N—CH₃ | 3 |  3-N(CH₂CH₂Cl)₂, 5-OCH₃ phenyl | 2 |

TABLE 2-continued

| Compd. No. | R₁ | m | R₂ | n |
|---|---|---|---|---|
| 1286 | (CH₃)₂N— | 3 | 4-N(CH₂CH₂Cl)₂-3-OCH₃-phenyl | 3 |
| 1287 | (CH₃)₂N— | 3 | 4-N(CH₂CH₂Cl)₂-3-CN-phenyl | 0 |
| 1288 | (CH₃)₂N— | 3 | 4-N(CH₂CH₂Cl)₂-3-CN-phenyl | 1 |
| 1289 | (CH₃)₂N— | 3 | 4-N(CH₂CH₂Cl)₂-3-CN-phenyl | 2 |
| 1290 | (CH₃)₂N— | 3 | 4-N(CH₂CH₂Cl)₂-3-CN-phenyl | 3 |
| 1291 | (CH₃)₂N— | 3 | 4-N(CH₂CH₂Cl)₂-3-Cl-phenyl | 0 |
| 1292 | (CH₃)₂N— | 3 | 4-N(CH₂CH₂Cl)₂-3-Cl-phenyl | 1 |
| 1293 | (CH₃)₂N— | 3 | 4-N(CH₂CH₂Cl)₂-3-Cl-phenyl | 2 |
| 1294 | (CH₃)₂N— | 3 | 4-N(CH₂CH₂Cl)₂-3-Cl-phenyl | 3 |
| 1295 | (CH₃)₂N— | 3 | 4-N(CH₂CH₂Cl)₂-3-F-phenyl | 0 |
| 1296 | (CH₃)₂N— | 3 | 4-N(CH₂CH₂Cl)₂-3-CF₃-phenyl | 0 |

TABLE 2-continued

| Compd. No. | R₁ | m | R₂ | n |
|---|---|---|---|---|
| 1297 | H₃C—N(CH₃)— | 3 | phenyl with N(CH₂CH₂Cl)₂ and CONH(CH₂)₂N(CH₃)₂ substituents | 0 |
| 1298 | H₃C—N(CH₃)— | 3 | phenyl with N(CH₂CH₂Cl)₂ and two Cl substituents | 0 |
| 1299 | H₃C—N(CH₃)— | 3 | —O—C₆H₄—N(CH₂CH₂Cl)₂ | 1 |
| 1300 | H₃C—N(CH₃)— | 3 | —O—C₆H₄—N(CH₂CH₂Cl)₂ | 2 |
| 1301 | H₃C—N(CH₃)— | 3 | —C₆H₄—CH₂N(CH₂CH₂Cl)₂ | 0 |
| 1302 | H₃C—N(CH₃)— | 3 | meta-substituted phenyl with N(CH₂CH₂Cl)₂ | 0 |
| 1303 | H₃C—N(CH₃)— | 3 | —C₆H₄—N(CH₂CH₃)(CH₂CH₂Cl) | 0 |
| 1304 | H₂N—C(=NH)—NH— | 2 | —C₆H₄—N(CH₂CH₂Cl)₂ | 0 |
| 1305 | H₂N—C(=NH)—NH— | 2 | —C₆H₄—N(CH₂CH₂Cl)₂ | 1 |
| 1306 | H₂N—C(=NH)—NH— | 2 | —C₆H₄—N(CH₂CH₂Cl)₂ | 2 |
| 1307 | H₂N—C(=NH)—NH— | 2 | —C₆H₄—N(CH₂CH₂Cl)₂ | 3 |
| 1308 | H₂N—C(=NH)—NH— | 2 | —C₆H₄—N(CH₂CH₂Cl)₂ with CH₃ substituent | 0 |

TABLE 2-continued

| Compd. No. | R₁ | m | R₂ | n |
|---|---|---|---|---|
| 1309 | H₂N–C(=NH)–NH– | 2 | 4-N(CH₂CH₂Cl)₂-3-OCH₃-phenyl | 0 |
| 1310 | H₂N–C(=NH)–NH– | 2 | 4-N(CH₂CH₂Cl)₂-3-CN-phenyl | 0 |
| 1311 | H₂N–C(=NH)–NH– | 2 | 4-N(CH₂CH₂Cl)₂-3-Cl-phenyl | 0 |
| 1312 | H₂N–C(=NH)–NH– | 2 | 4-N(CH₂CH₂Cl)₂-3-F-phenyl | 0 |
| 1313 | H₂N–C(=NH)–NH– | 2 | 4-N(CH₂CH₂Cl)₂-3-CF₃-phenyl | 0 |
| 1314 | H₂N–C(=NH)–NH– | 2 | 3-N(CH₂CH₂Cl)₂-5-CH₃-phenyl | 0 |
| 1315 | H₂N–C(=NH)–NH– | 2 | 3-N(CH₂CH₂Cl)₂-5-OCH₃-phenyl | 0 |
| 1316 | H₂N–C(=NH)–NH– | 2 | 3-N(CH₂CH₂Cl)₂-5-CN-phenyl | 0 |
| 1317 | H₂N–C(=NH)–NH– | 2 | 3-N(CH₂CH₂Cl)₂-5-Cl-phenyl | 0 |
| 1318 | H₂N–C(=NH)–NH– | 2 | 3-N(CH₂CH₂Cl)₂-5-F-phenyl | 0 |
| 1319 | H₂N–C(=NH)–NH– | 2 | 3-N(CH₂CH₂Cl)₂-5-CF₃-phenyl | 0 |

TABLE 2-continued

| Compd. No. | R₁ | m | R₂ | n |
|---|---|---|---|---|
| 1320 | H₂N−C(=NH)−NH− | 3 | −C₆H₄−N(CH₂CH₂Cl)₂ (para) | 0 |
| 1321 | H₂N−C(=NH)−NH− | 3 | −C₆H₄−N(CH₂CH₂Cl)₂ (para) | 1 |
| 1322 | H₂N−C(=NH)−NH− | 3 | −C₆H₄−N(CH₂CH₂Cl)₂ (para) | 2 |
| 1323 | H₂N−C(=NH)−NH− | 3 | −C₆H₄−N(CH₂CH₂Cl)₂ (para) | 3 |
| 1324 | H₂N−C(=NH)−NH− | 3 | −C₆H₃(CH₃)−N(CH₂CH₂Cl)₂ | 0 |
| 1325 | H₂N−C(=NH)−NH− | 3 | −C₆H₃(OCH₃)−N(CH₂CH₂Cl)₂ | 0 |
| 1326 | H₂N−C(=NH)−NH− | 3 | −C₆H₃(CN)−N(CH₂CH₂Cl)₂ | 0 |
| 1327 | H₂N−C(=NH)−NH− | 3 | −C₆H₃(Cl)−N(CH₂CH₂Cl)₂ | 0 |
| 1328 | H₂N−C(=NH)−NH− | 3 | −C₆H₃(F)−N(CH₂CH₂Cl)₂ | 0 |
| 1329 | H₂N−C(=NH)−NH− | 3 | −C₆H₃(CF₃)−N(CH₂CH₂Cl)₂ | 0 |
| 1330 | H₂N−C(=NH)−NH− | 3 | −C₆H₃(CH₃)−N(CH₂CH₂Cl)₂ | 0 |
| 1331 | H₂N−C(=NH)−NH− | 3 | −C₆H₃(OCH₃)−N(CH₂CH₂Cl)₂ | 0 |

TABLE 2-continued

| Compd. No. | R₁ | m | R₂ | n |
|---|---|---|---|---|
| 1332 | H₂N−C(=NH)−NH− | 3 | 4-[N(CH₂CH₂Cl)₂]-3-CN-phenyl | 0 |
| 1333 | H₂N−C(=NH)−NH− | 3 | 4-[N(CH₂CH₂Cl)₂]-2-Cl-phenyl | 0 |
| 1334 | H₂N−C(=NH)−NH− | 3 | 4-[N(CH₂CH₂Cl)₂]-2-F-phenyl | 0 |
| 1335 | H₂N−C(=NH)−NH− | 3 | 4-[N(CH₂CH₂Cl)₂]-2-CF₃-phenyl | 0 |
| 1336 | (CH₃)₂S⁺− | 1 | 4-[N(CH₂CH₂Cl)₂]-phenyl | 0 |
| 1337 | (CH₃)₂S⁺− | 1 | 4-[N(CH₂CH₂Cl)₂]-phenyl | 1 |
| 1338 | (CH₃)₂S⁺− | 1 | 4-[N(CH₂CH₂Cl)₂]-phenyl | 2 |
| 1339 | (CH₃)₂S⁺− | 1 | 4-[N(CH₂CH₂Cl)₂]-phenyl | 3 |
| 1340 | (CH₃)₂S⁺− | 1 | 4-[N(CH₂CH₂Cl)₂]-3-CH₃-phenyl | 0 |
| 1341 | (CH₃)₂S⁺− | 1 | 4-[N(CH₂CH₂Cl)₂]-3-OCH₃-phenyl | 0 |
| 1342 | (CH₃)₂S⁺− | 1 | 4-[N(CH₂CH₂Cl)₂]-3-CN-phenyl | 0 |
| 1343 | (CH₃)₂S⁺− | 1 | 4-[N(CH₂CH₂Cl)₂]-2-Cl-phenyl | 0 |

TABLE 2-continued

| Compd. No. | R₁ | m | R₂ | n |
|---|---|---|---|---|
| 1344 | H₃C—S⁺— with CH₃ | 1 | 4-N(CH₂CH₂Cl)₂, 3-F phenyl | 0 |
| 1345 | H₃C—S⁺— with CH₃ | 1 | 4-N(CH₂CH₂Cl)₂, 3-CF₃ phenyl | 0 |
| 1346 | H₃C—S⁺— with CH₃ | 1 | 4-N(CH₂CH₂Cl)₂, 3-CH₃ phenyl | 0 |
| 1347 | H₃C—S⁺— with CH₃ | 1 | 4-N(CH₂CH₂Cl)₂, 3-OCH₃ phenyl | 0 |
| 1348 | H₃C—S⁺— with CH₃ | 1 | 4-N(CH₂CH₂Cl)₂, 3-CN phenyl | 0 |
| 1349 | H₃C—S⁺— with CH₃ | 1 | 4-N(CH₂CH₂Cl)₂, 2-Cl phenyl | 0 |
| 1350 | H₃C—S⁺— with CH₃ | 1 | 4-N(CH₂CH₂Cl)₂, 2-F phenyl | 0 |
| 1351 | H₃C—S⁺— with CH₃ | 1 | 4-N(CH₂CH₂Cl)₂, 2-CF₃ phenyl | 0 |
| 1352 | H₃C—S⁺— with CH₃ | 3 | 4-N(CH₂CH₂Cl)₂ phenyl | 0 |
| 1353 | H₃C—S⁺— with CH₃ | 3 | 4-N(CH₂CH₂Cl)₂ phenyl | 1 |
| 1354 | H₃C—S⁺— with CH₃ | 3 | 4-N(CH₂CH₂Cl)₂ phenyl | 2 |
| 1355 | H₃C—S⁺— with CH₃ | 3 | 4-N(CH₂CH₂Cl)₂ phenyl | 3 |

TABLE 2-continued

| Compd. No. | R$_1$ | m | R$_2$ | n |
|---|---|---|---|---|
| 1356 | H$_3$C—S$^+$—(CH$_3$) | 3 | 4-[N(CH$_2$CH$_2$Cl)$_2$]-3-methylphenyl | 0 |
| 1357 | H$_3$C—S$^+$—(CH$_3$) | 3 | 4-[N(CH$_2$CH$_2$Cl)$_2$]-3-methoxyphenyl | 0 |
| 1358 | H$_3$C—S$^+$—(CH$_3$) | 3 | 4-[N(CH$_2$CH$_2$Cl)$_2$]-3-cyanophenyl | 0 |
| 1359 | H$_3$C—S$^+$—(CH$_3$) | 3 | 4-[N(CH$_2$CH$_2$Cl)$_2$]-3-chlorophenyl | 0 |
| 1360 | H$_3$C—S$^+$—(CH$_3$) | 3 | 4-[N(CH$_2$CH$_2$Cl)$_2$]-3-fluorophenyl | 0 |
| 1361 | H$_3$C—S$^+$—(CH$_3$) | 3 | 4-[N(CH$_2$CH$_2$Cl)$_2$]-3-trifluoromethylphenyl | 0 |
| 1362 | H$_3$C—S$^+$—(CH$_3$) | 3 | 3-[N(CH$_2$CH$_2$Cl)$_2$]-5-methylphenyl | 0 |
| 1363 | H$_3$C—S$^+$—(CH$_3$) | 3 | 3-[N(CH$_2$CH$_2$Cl)$_2$]-5-methoxyphenyl | 0 |
| 1364 | H$_3$C—S$^+$—(CH$_3$) | 3 | 3-[N(CH$_2$CH$_2$Cl)$_2$]-5-cyanophenyl | 0 |
| 1365 | H$_3$C—S$^+$—(CH$_3$) | 3 | 3-[N(CH$_2$CH$_2$Cl)$_2$]-5-chlorophenyl | 0 |
| 1366 | H$_3$C—S$^+$—(CH$_3$) | 3 | 3-[N(CH$_2$CH$_2$Cl)$_2$]-5-fluorophenyl | 0 |

TABLE 2-continued

| Compd. No. | R₁ | m | R₂ | n |
|---|---|---|---|---|
| 1367 | H₃C—S⁺— with CH₃ | 3 | 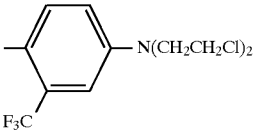 4-N(CH₂CH₂Cl)₂, 3-CF₃ phenyl | 0 |
| 1368 | H₃C—S⁺— with CH₃ | 4 | 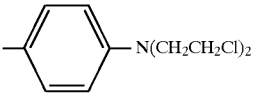 4-N(CH₂CH₂Cl)₂ phenyl | 0 |
| 1369 | H₃C—S⁺— with CH₃ | 4 | 4-N(CH₂CH₂Cl)₂ phenyl | 1 |
| 1370 | H₃C—S⁺— with CH₃ | 4 | 4-N(CH₂CH₂Cl)₂ phenyl | 2 |
| 1371 | H₃C—S⁺— with CH₃ | 4 | 4-N(CH₂CH₂Cl)₂ phenyl | 3 |
| 1372 | H₃C—S⁺— with CH₃ | 4 | 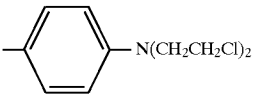 4-N(CH₂CH₂Cl)₂, 3-CH₃ phenyl | 0 |
| 1373 | H₃C—S⁺— with CH₃ | 4 | 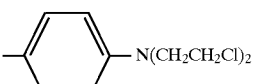 4-N(CH₂CH₂Cl)₂, 3-OCH₃ phenyl | 0 |
| 1374 | H₃C—S⁺— with CH₃ | 4 | 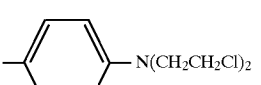 4-N(CH₂CH₂Cl)₂, 3-CN phenyl | 0 |
| 1375 | H₃C—S⁺— with CH₃ | 4 | 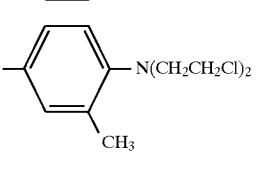 4-N(CH₂CH₂Cl)₂, 3-Cl phenyl | 0 |
| 1376 | H₃C—S⁺— with CH₃ | 4 | 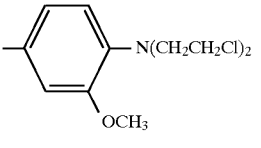 4-N(CH₂CH₂Cl)₂, 3-F phenyl | 0 |
| 1377 | H₃C—S⁺— with CH₃ | 4 | 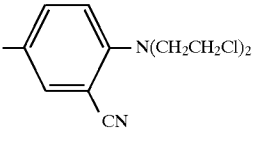 4-N(CH₂CH₂Cl)₂, 3-CF₃ phenyl | 0 |
| 1378 | H₃C—S⁺— with CH₃ | 4 | 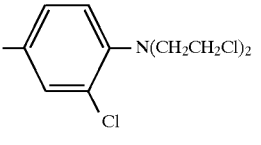 4-N(CH₂CH₂Cl)₂, 3-CH₃ phenyl | 0 |

TABLE 2-continued
| Compd. No. | R₁ | m | R₂ | n |
|---|---|---|---|---|
| 1379 |  | 4 | 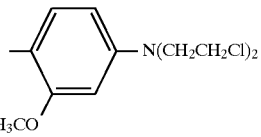 | 0 |
| 1380 |  | 4 | 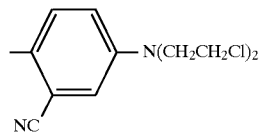 | 0 |
| 1381 |  | 4 | 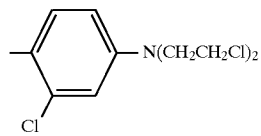 | 0 |
| 1382 |  | 4 | 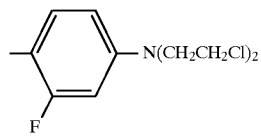 | 0 |
| 1383 |  | 4 | 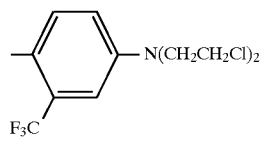 | 0 |
| 1384 | 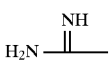 | 1 | 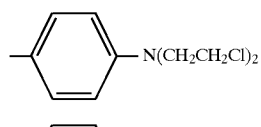 | 0 |
| 1385 | 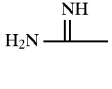 | 1 | 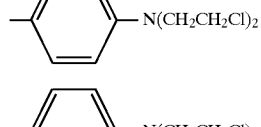 | 1 |
| 1386 |  | 1 | 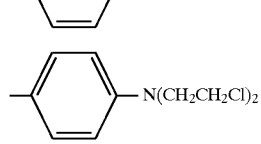 | 2 |
| 1387 | 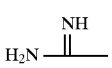 | 1 | 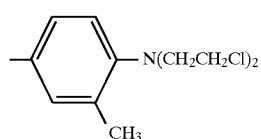 | 3 |
| 1388 | 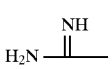 | 1 | 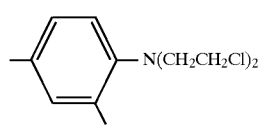 | 0 |
| 1389 | 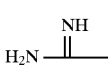 | 1 | 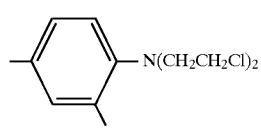 | 0 |
| 1390 |  | 1 |  | 0 |

TABLE 2-continued

| Compd. No. | R₁ | m | R₂ | n |
|---|---|---|---|---|
| 1391 | H₂N-C(=NH)- | 1 | 4-[N(CH₂CH₂Cl)₂]-2-Cl-phenyl | 0 |
| 1392 | H₂N-C(=NH)- | 1 | 4-[N(CH₂CH₂Cl)₂]-2-F-phenyl | 0 |
| 1393 | H₂N-C(=NH)- | 1 | 4-[N(CH₂CH₂Cl)₂]-2-CF₃-phenyl | 0 |
| 1394 | H₂N-C(=NH)- | 1 | 3-[N(CH₂CH₂Cl)₂]-6-CH₃... | 0 |
| 1395 | H₂N-C(=NH)- | 1 | 4-[N(CH₂CH₂Cl)₂]-3-OCH₃-phenyl | 0 |
| 1396 | H₂N-C(=NH)- | 1 | 4-[N(CH₂CH₂Cl)₂]-2-CN-phenyl | 0 |
| 1397 | H₂N-C(=NH)- | 1 | 4-[N(CH₂CH₂Cl)₂]-3-Cl-phenyl | 0 |
| 1398 | H₂N-C(=NH)- | 1 | 4-[N(CH₂CH₂Cl)₂]-3-F-phenyl | 0 |
| 1399 | H₂N-C(=NH)- | 1 | 4-[N(CH₂CH₂Cl)₂]-3-CF₃-phenyl | 0 |
| 1400 | H₂N-C(=NH)- | 3 | 4-[N(CH₂CH₂Cl)₂]-phenyl | 0 |
| 1401 | H₂N-C(=NH)- | 3 | 4-[N(CH₂CH₂Cl)₂]-phenyl | 1 |

TABLE 2-continued
| Compd. No. | R₁ | m | R₂ | n |
|---|---|---|---|---|
| 1402 | 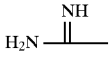 | 3 | 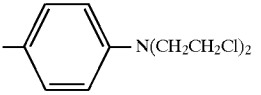 | 2 |
| 1403 |  | 3 | 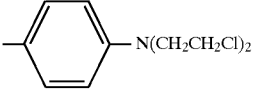 | 3 |
| 1404 | 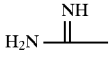 | 3 | 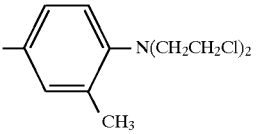 | 0 |
| 1405 | 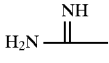 | 3 | 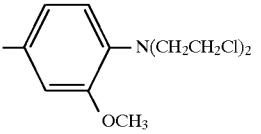 | 0 |
| 1406 | 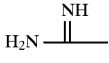 | 3 | 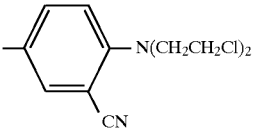 | 0 |
| 1407 | 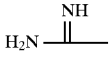 | 3 | 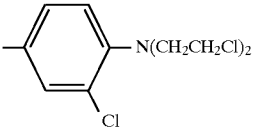 | 0 |
| 1408 | 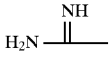 | 3 | 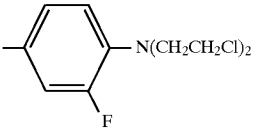 | 0 |
| 1409 | 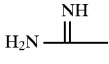 | 3 | 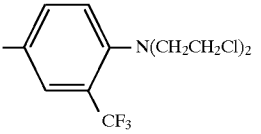 | 0 |
| 1410 | 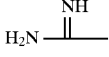 | 3 | 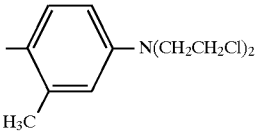 | 0 |
| 1411 |  | 3 | 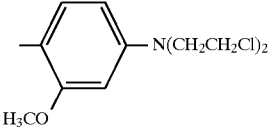 | 0 |
| 1412 | 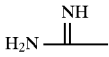 | 3 | 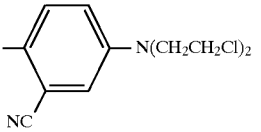 | 0 |

TABLE 2-continued

| Compd. No. | R₁ | m | R₂ | n |
|---|---|---|---|---|
| 1413 | H₂N-C(=NH)- | 3 | 4-[N(CH₂CH₂Cl)₂]-3-Cl-phenyl | 0 |
| 1414 | H₂N-C(=NH)- | 3 | 4-[N(CH₂CH₂Cl)₂]-3-F-phenyl | 0 |
| 1415 | H₂N-C(=NH)- | 3 | 4-[N(CH₂CH₂Cl)₂]-3-CF₃-phenyl | 0 |
| 1416 | 3-pyridyl | 0 | 4-[N(CH₂CH₂Cl)₂]-phenyl | 0 |
| 1417 | 3-pyridyl | 0 | 4-[N(CH₂CH₂Cl)₂]-phenyl | 3 |
| 1418 | 3-pyridyl | 0 | 4-[N(CH₂CH₂Cl)₂]-3-CH₃-phenyl | 0 |
| 1419 | 3-pyridyl | 0 | 4-[N(CH₂CH₂Cl)₂]-3-Cl-phenyl | 0 |
| 1420 | 3-pyridyl | 0 | 4-[N(CH₂CH₂Cl)₂]-2-CH₃-phenyl | 0 |
| 1421 | 3-pyridyl | 0 | 4-[N(CH₂CH₂Cl)₂]-2-CF₃-phenyl | 0 |
| 1422 | 3-pyridyl | 0 | 4-[N(CH₂CH₂Cl)₂]-2-CN-phenyl | 0 |
| 1423 | 3-pyridyl | 0 | 4-[N(CH₂CH₂Cl)₂]-2-Cl-phenyl | 0 |

TABLE 2-continued

| Compd. No. | R₁ | m | R₂ | n |
|---|---|---|---|---|
| 1424 | 3-pyridyl | 1 | 4-[N(CH₂CH₂Cl)₂]phenyl | 0 |
| 1425 | 3-pyridyl | 1 | 4-[N(CH₂CH₂Cl)₂]phenyl | 0 |
| 1426 | 3-pyridyl | 1 | 4-[N(CH₂CH₂Cl)₂]-3-CH₃-phenyl | 0 |
| 1427 | 3-pyridyl | 1 | 4-[N(CH₂CH₂Cl)₂]-3-Cl-phenyl | 0 |
| 1428 | 3-pyridyl | 1 | 4-[N(CH₂CH₂Cl)₂]-2-CH₃-phenyl | 0 |
| 1429 | 3-pyridyl | 1 | 4-[N(CH₂CH₂Cl)₂]-2-CF₃-phenyl | 0 |
| 1430 | 3-pyridyl | 1 | 4-[N(CH₂CH₂Cl)₂]-2-CN-phenyl | 0 |
| 1431 | 3-pyridyl | 1 | 4-[N(CH₂CH₂Cl)₂]-2-Cl-phenyl | 0 |
| 1432 | N-methyl-3-pyridinium | 0 | 4-[N(CH₂CH₂Cl)₂]phenyl | 0 |
| 1433 | N-methyl-3-pyridinium | 0 | 4-[N(CH₂CH₂Cl)₂]phenyl | 3 |
| 1434 | N-methyl-3-pyridinium | 0 | 4-[N(CH₂CH₂Cl)₂]-3-CH₃-phenyl | 0 |

TABLE 2-continued
| Compd. No. | R₁ | m | R₂ | n |
|---|---|---|---|---|
| 1435 | 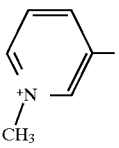 | 0 | 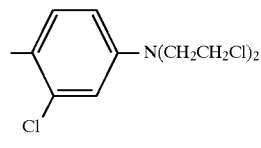 | 0 |
| 1436 | 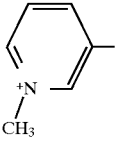 | 0 |  | 0 |
| 1437 | 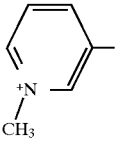 | 0 | 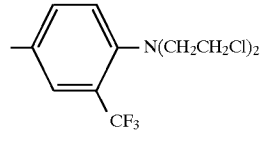 | 0 |
| 1438 | 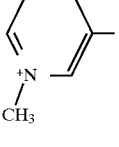 | 0 | 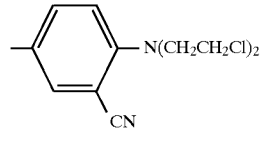 | 0 |
| 1439 | 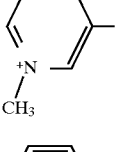 | 0 | 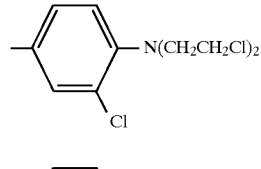 | 0 |
| 1440 | 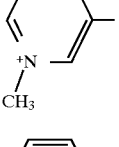 | 1 | 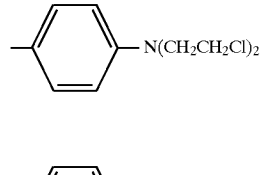 | 0 |
| 1441 | 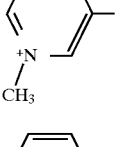 | 1 | 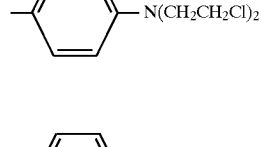 | 3 |
| 1442 | 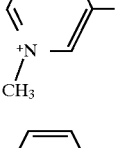 | 1 | 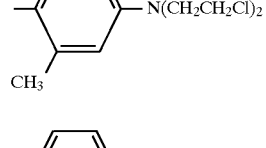 | 0 |
| 1443 | 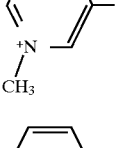 | 1 | 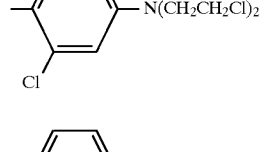 | 0 |
| 1444 | 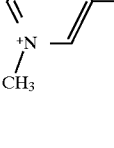 | 1 | 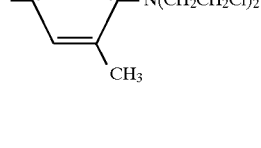 | 0 |

TABLE 2-continued
| Compd. No. | R₁ | m | R₂ | n |
|---|---|---|---|---|
| 1445 | 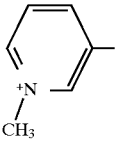 | 1 | 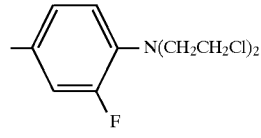 | 0 |
| 1446 | 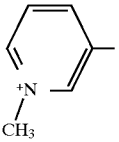 | 1 | 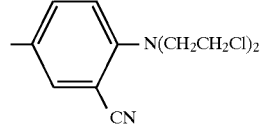 | 0 |
| 1447 | 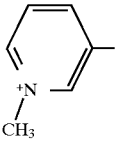 | 1 | 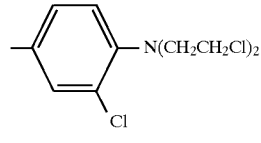 | 0 |
| 1448 | 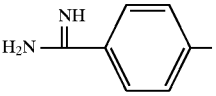 | 0 | 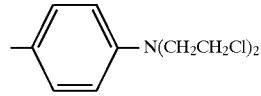 | 0 |
| 1449 | 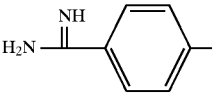 | 0 | 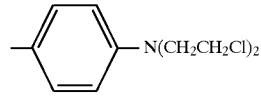 | 1 |
| 1450 | 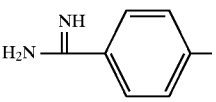 | 0 | 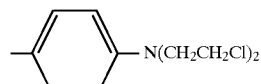 | 2 |
| 1451 | 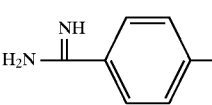 | 0 | 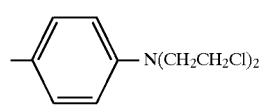 | 3 |
| 1452 | 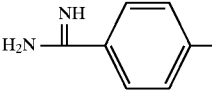 | 0 | 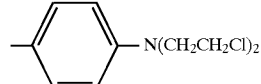 | 0 |
| 1453 | 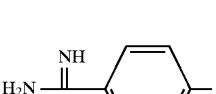 | 0 | 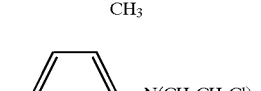 | 0 |
| 1454 | 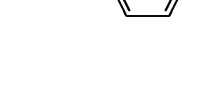 | 0 | 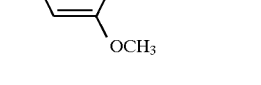 | 0 |
| 1455 | 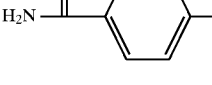 | 0 | 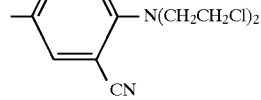 | 0 |

TABLE 2-continued
| Compd. No. | R₁ | m | R₂ | n |
|---|---|---|---|---|
| 1456 | 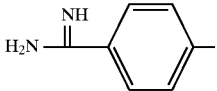 | 0 |  | 0 |
| 1457 | 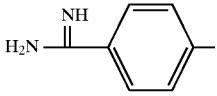 | 0 | 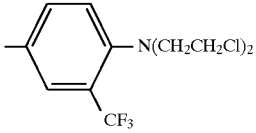 | 0 |
| 1458 | 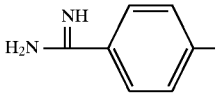 | 0 | 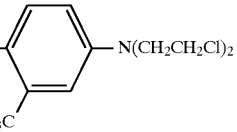 | 0 |
| 1459 | 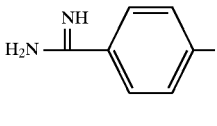 | 0 | 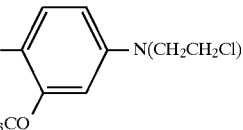 | 0 |
| 1460 | 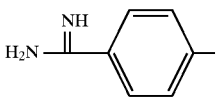 | 0 | 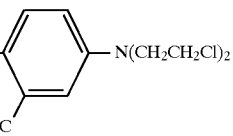 | 0 |
| 1461 | 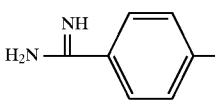 | 0 | 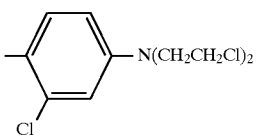 | 0 |
| 1462 | 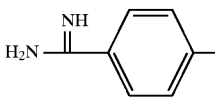 | 0 | 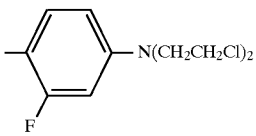 | 0 |
| 1463 | 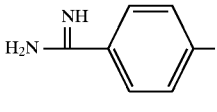 | 0 | 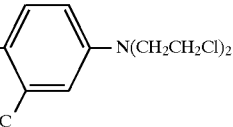 | 0 |
| 1464 |  | 0 | 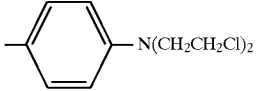 | 0 |
| 1465 |  | 0 | 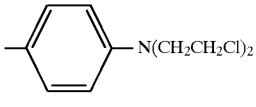 | 1 |
| 1466 |  | 0 | 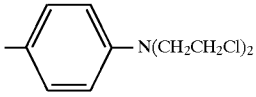 | 2 |

TABLE 2-continued

| Compd. No. | R₁ | m | R₂ | n |
|---|---|---|---|---|
| 1467 | furan-2-yl | 0 | —C₆H₄—N(CH₂CH₂Cl)₂ (para) | 3 |
| 1468 | furan-2-yl | 0 | 4-[N(CH₂CH₂Cl)₂]-3-CH₃-C₆H₃— | 0 |
| 1469 | furan-2-yl | 0 | 4-[N(CH₂CH₂Cl)₂]-3-OCH₃-C₆H₃— | 0 |
| 1470 | furan-2-yl | 0 | 4-[N(CH₂CH₂Cl)₂]-3-CN-C₆H₃— | 0 |
| 1471 | furan-2-yl | 0 | 4-[N(CH₂CH₂Cl)₂]-3-Cl-C₆H₃— | 0 |
| 1472 | furan-2-yl | 0 | 4-[N(CH₂CH₂Cl)₂]-3-F-C₆H₃— | 0 |
| 1473 | furan-2-yl | 0 | 4-[N(CH₂CH₂Cl)₂]-3-CF₃-C₆H₃— | 0 |
| 1474 | furan-2-yl | 0 | 3-[N(CH₂CH₂Cl)₂]-5-CH₃-C₆H₃— | 0 |
| 1475 | furan-2-yl | 0 | 3-[N(CH₂CH₂Cl)₂]-5-OCH₃-C₆H₃— | 0 |
| 1476 | furan-2-yl | 0 | 3-[N(CH₂CH₂Cl)₂]-5-CN-C₆H₃— | 0 |
| 1477 | furan-2-yl | 0 | 3-[N(CH₂CH₂Cl)₂]-5-Cl-C₆H₃— | 0 |

TABLE 2-continued

| Compd. No. | R₁ | m | R₂ | n |
|---|---|---|---|---|
| 1478 | furan-2-yl (O) | 0 | 4-[N(CH₂CH₂Cl)₂]-3-F-phenyl | 0 |
| 1479 | furan-2-yl (O) | 0 | 4-[N(CH₂CH₂Cl)₂]-3-CF₃-phenyl | 0 |
| 1480 | pyrrol-2-yl (NH) | 0 | 4-[N(CH₂CH₂Cl)₂]-phenyl | 0 |
| 1481 | pyrrol-2-yl (NH) | 0 | 4-[N(CH₂CH₂Cl)₂]-phenyl | 1 |
| 1482 | pyrrol-2-yl (NH) | 0 | 4-[N(CH₂CH₂Cl)₂]-phenyl | 2 |
| 1483 | pyrrol-2-yl (NH) | 0 | 4-[N(CH₂CH₂Cl)₂]-phenyl | 3 |
| 1484 | pyrrol-2-yl (NH) | 0 | 4-[N(CH₂CH₂Cl)₂]-3-CH₃-phenyl | 0 |
| 1485 | pyrrol-2-yl (NH) | 0 | 4-[N(CH₂CH₂Cl)₂]-3-OCH₃-phenyl | 0 |
| 1486 | pyrrol-2-yl (NH) | 0 | 4-[N(CH₂CH₂Cl)₂]-3-CN-phenyl | 0 |
| 1487 | pyrrol-2-yl (NH) | 0 | 4-[N(CH₂CH₂Cl)₂]-3-Cl-phenyl | 0 |
| 1488 | H₂N— | 3 | 4-[N(CH₂CH₂Cl)₂]-phenyl | 0 |

TABLE 2-continued

| Compd. No. | R₁ | m | R₂ | n |
|---|---|---|---|---|
| 1489 | H₂N— | 3 | —C₆H₄—N(CH₂CH₂Cl)₂ (para) | 1 |
| 1490 | H₂N— | 3 | —C₆H₄—N(CH₂CH₂Cl)₂ (para) | 2 |
| 1491 | H₂N— | 3 | —C₆H₄—N(CH₂CH₂Cl)₂ (para) | 3 |
| 1492 | H₂N— | 3 | —C₆H₃(CH₃)—N(CH₂CH₂Cl)₂ | 0 |
| 1493 | H₂N— | 3 | —C₆H₃(OCH₃)—N(CH₂CH₂Cl)₂ | 0 |
| 1494 | H₂N— | 3 | —C₆H₃(CN)—N(CH₂CH₂Cl)₂ | 0 |
| 1495 | H₂N— | 3 | —C₆H₃(Cl)—N(CH₂CH₂Cl)₂ | 0 |
| 1496 | H₂N— | 3 | —C₆H₃(F)—N(CH₂CH₂Cl)₂ | 0 |
| 1497 | H₂N— | 3 | —C₆H₃(CF₃)—N(CH₂CH₂Cl)₂ | 0 |
| 1498 | H₂N— | 3 | —C₆H₃(CH₃)—N(CH₂CH₂Cl)₂ | 0 |
| 1499 | H₂N— | 3 | —C₆H₃(OCH₃)—N(CH₂CH₂Cl)₂ | 0 |

TABLE 2-continued
| Compd. No. | R₁ | m | R₂ | n |
|---|---|---|---|---|
| 1500 | H₂N— | 3 | 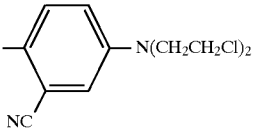 | 0 |
| 1501 | H₂N— | 3 | 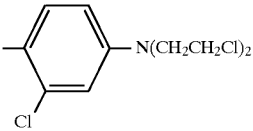 | 0 |
| 1502 | H₂N— | 3 | 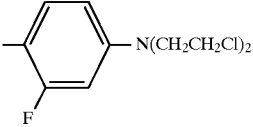 | 0 |
| 1503 | H₂N— | 3 | 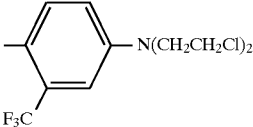 | 0 |
| 1504 | HO— | 2 | 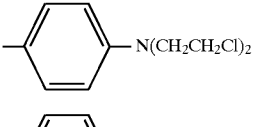 | 0 |
| 1505 | HO— | 2 | 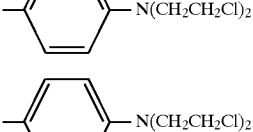 | 1 |
| 1506 | HO— | 2 | 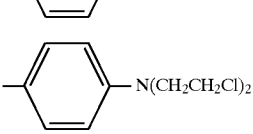 | 2 |
| 1507 | HO— | 2 | 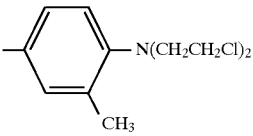 | 3 |
| 1508 | HO— | 2 | 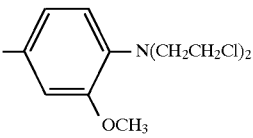 | 0 |
| 1509 | HO— | 2 | 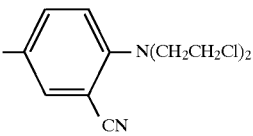 | 0 |
| 1510 | HO— | 2 | 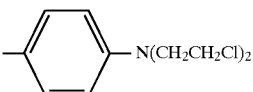 | 0 |
| 1511 | HO— | 2 |  | 0 |

TABLE 2-continued
| Compd. No. | R₁ | m | R₂ | n |
|---|---|---|---|---|
| 1512 | HO— | 2 | 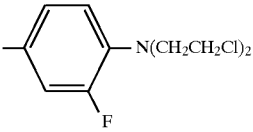 | 0 |
| 1513 | HO— | 2 | 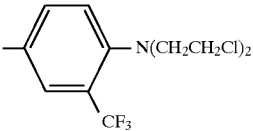 | 0 |
| 1514 | HO— | 2 | 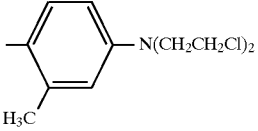 | 0 |
| 1515 | HO— | 2 | 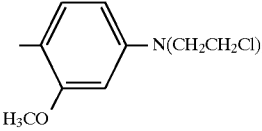 | 0 |
| 1516 | HO— | 2 | 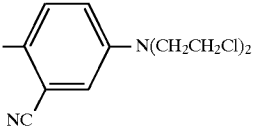 | 0 |
| 1517 | HO— | 2 | 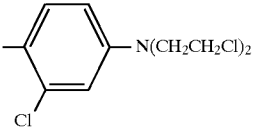 | 0 |
| 1518 | HO— | 2 | 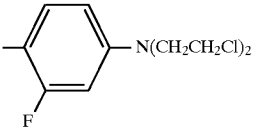 | 0 |
| 1519 | HO— | 2 | 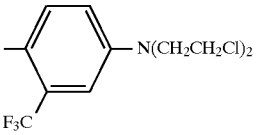 | 0 |
| 1520 | CH₃—S— | 2 | 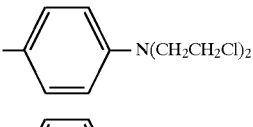 | 0 |
| 1521 | CH₃—S— | 2 | 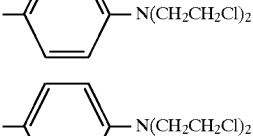 | 1 |
| 1522 | CH₃—S— | 2 |  | 2 |
| 1523 | CH₃—S— | 2 | 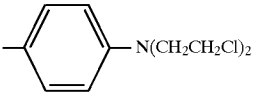 | 3 |

TABLE 2-continued

| Compd. No. | R₁ | m | R₂ | n |
|---|---|---|---|---|
| 1524 | CH₃—S— | 2 | 4-methyl-2-methylphenyl-N(CH₂CH₂Cl)₂ | 0 |
| 1525 | CH₃—S— | 2 | 4-methyl-2-methoxyphenyl-N(CH₂CH₂Cl)₂ | 0 |
| 1526 | CH₃—S— | 2 | 4-methyl-2-cyanophenyl-N(CH₂CH₂Cl)₂ | 0 |
| 1527 | CH₃—S— | 2 | 4-methyl-2-chlorophenyl-N(CH₂CH₂Cl)₂ | 0 |
| 1528 | CH₃—S— | 2 | 4-methyl-2-fluorophenyl-N(CH₂CH₂Cl)₂ | 0 |
| 1529 | CH₃—S— | 2 | 4-methyl-2-trifluoromethylphenyl-N(CH₂CH₂Cl)₂ | 0 |
| 1530 | CH₃—S— | 2 | 4-methyl-3-methylphenyl-N(CH₂CH₂Cl)₂ | 0 |
| 1531 | CH₃—S— | 2 | 4-methyl-3-methoxyphenyl-N(CH₂CH₂Cl)₂ | 0 |
| 1532 | CH₃—S— | 2 | 4-methyl-3-cyanophenyl-N(CH₂CH₂Cl)₂ | 0 |
| 1533 | CH₃—S— | 2 | 4-methyl-3-chlorophenyl-N(CH₂CH₂Cl)₂ | 0 |
| 1534 | CH₃—S— | 2 | 4-methyl-3-fluorophenyl-N(CH₂CH₂Cl)₂ | 0 |

TABLE 2-continued

| Compd. No. | R₁ | m | R₂ | n |
|---|---|---|---|---|
| 1535 | CH₃—S— | 2 | 4-[N(CH₂CH₂Cl)₂]-3-(CF₃)-phenyl, methyl at position 1 | 0 |
| 1536 | morpholino (O N—) | 0 | 4-[N(CH₂CH₂Cl)₂]phenyl | 0 |
| 1537 | morpholino (O N—) | 0 | 4-[N(CH₂CH₂Cl)₂]phenyl | 1 |
| 1538 | morpholino (O N—) | 0 | 4-[N(CH₂CH₂Cl)₂]phenyl | 2 |
| 1539 | morpholino (O N—) | 0 | 4-[N(CH₂CH₂Cl)₂]phenyl | 3 |
| 1540 | morpholino (O N—) | 0 | 4-[N(CH₂CH₂Cl)₂]-3-CH₃-phenyl | 0 |
| 1541 | morpholino (O N—) | 0 | 4-[N(CH₂CH₂Cl)₂]-3-OCH₃-phenyl | 0 |
| 1542 | morpholino (O N—) | 0 | 4-[N(CH₂CH₂Cl)₂]-3-CN-phenyl | 0 |
| 1543 | morpholino (O N—) | 0 | 4-[N(CH₂CH₂Cl)₂]-3-Cl-phenyl | 0 |
| 1544 | morpholino (O N—) | 0 | 4-[N(CH₂CH₂Cl)₂]-3-F-phenyl | 0 |
| 1545 | morpholino (O N—) | 0 | 4-[N(CH₂CH₂Cl)₂]-3-CF₃-phenyl | 0 |
| 1546 | morpholino (O N—) | 0 | 4-[N(CH₂CH₂Cl)₂]-3-CH₃-phenyl (H₃C at meta) | 0 |

TABLE 2-continued

| Compd. No. | R₁ | m | R₂ | n |
|---|---|---|---|---|
| 1547 | morpholino (O-N) | 0 | 4-N(CH₂CH₂Cl)₂, 2-OCH₃ phenyl | 0 |
| 1548 | morpholino (O-N) | 0 | 4-N(CH₂CH₂Cl)₂, 2-CN phenyl | 0 |
| 1549 | morpholino (O-N) | 0 | 4-N(CH₂CH₂Cl)₂, 3-Cl phenyl | 0 |
| 1550 | morpholino (O-N) | 0 | 4-N(CH₂CH₂Cl)₂, 3-F phenyl | 0 |
| 1551 | morpholino (O-N) | 0 | 4-N(CH₂CH₂Cl)₂, 3-CF₃ phenyl | 0 |
| 1552 | thiomorpholino (S-N) | 0 | 4-N(CH₂CH₂Cl)₂ phenyl | 0 |
| 1553 | thiomorpholino (S-N) | 0 | 4-N(CH₂CH₂Cl)₂ phenyl | 3 |
| 1554 | thiomorpholino (S-N) | 0 | 4-N(CH₂CH₂Cl)₂, 3-CH₃ phenyl | 0 |
| 1555 | thiomorpholino (S-N) | 0 | 4-N(CH₂CH₂Cl)₂, 3-Cl phenyl | 0 |
| 1556 | thiomorpholino (S-N) | 0 | 2-N(CH₂CH₂Cl)₂, 3-CH₃ phenyl | 0 |
| 1557 | thiomorpholino (S-N) | 0 | 2-N(CH₂CH₂Cl)₂, 4-OCH₃ phenyl | 0 |

TABLE 2-continued

| Compd. No. | R₁ | m | R₂ | n |
|---|---|---|---|---|
| 1558 | S⟨⟩N— | 0 | 4-N(CH₂CH₂Cl)₂, 2-CN-phenyl | 0 |
| 1559 | S⟨⟩N— | 0 | 4-N(CH₂CH₂Cl)₂, 2-Cl-phenyl | 0 |
| 1560 | CH₃—⁺S⟨⟩N— | 0 | 4-N(CH₂CH₂Cl)₂-phenyl | 0 |
| 1561 | CH₃—⁺S⟨⟩N— | 0 | 4-N(CH₂CH₂Cl)₂-phenyl | 3 |
| 1562 | CH₃—⁺S⟨⟩N— | 0 | 4-N(CH₂CH₂Cl)₂, 3-CH₃-phenyl | 0 |
| 1563 | CH₃—⁺S⟨⟩N— | 0 | 4-N(CH₂CH₂Cl)₂, 2-Cl-phenyl | 0 |
| 1564 | CH₃—⁺S⟨⟩N— | 0 | 4-N(CH₂CH₂Cl)₂, 2-CH₃-phenyl | 0 |
| 1565 | CH₃—⁺S⟨⟩N— | 0 | 4-N(CH₂CH₂Cl)₂, 2-OCH₃-phenyl | 0 |
| 1566 | CH₃—⁺S⟨⟩N— | 0 | 4-N(CH₂CH₂Cl)₂, 2-CN-phenyl | 0 |
| 1567 | CH₃—⁺S⟨⟩N— | 0 | 4-N(CH₂CH₂Cl)₂, 2-Cl-phenyl | 0 |
| 1568 | O⟨⟩N⁺(CH₃)— | 3 | 4-N(CH₂CH₂Cl)₂-phenyl | 0 |
| 1569 | O⟨⟩N⁺(CH₃)— | 3 | 4-N(CH₂CH₂Cl)₂-phenyl | 3 |

TABLE 2-continued

| Compd. No. | R₁ | m | R₂ | n |
|---|---|---|---|---|
| 1570 | N-methylmorpholinium | 3 | 4-N(CH₂CH₂Cl)₂-3-CH₃-phenyl | 0 |
| 1571 | N-methylmorpholinium | 3 | 4-N(CH₂CH₂Cl)₂-3-Cl-phenyl | 0 |
| 1572 | N-methylmorpholinium | 3 | 4-N(CH₂CH₂Cl)₂-2-CH₃-phenyl | 0 |
| 1573 | N-methylmorpholinium | 3 | 4-N(CH₂CH₂Cl)₂-2-OCH₃-phenyl | 0 |
| 1574 | N-methylmorpholinium | 3 | 4-N(CH₂CH₂Cl)₂-2-CN-phenyl | 0 |
| 1575 | N-methylmorpholinium | 3 | 4-N(CH₂CH₂Cl)₂-2-Cl-phenyl | 0 |
| 1576 | piperazin-1-yl | 1 | 4-N(CH₂CH₂Cl)₂-phenyl | 0 |
| 1577 | piperazin-1-yl | 1 | 4-N(CH₂CH₂Cl)₂-phenyl | 3 |
| 1578 | piperazin-1-yl | 1 | 4-N(CH₂CH₂Cl)₂-3-CH₃-phenyl | 0 |
| 1579 | piperazin-1-yl | 1 | 4-N(CH₂CH₂Cl)₂-3-Cl-phenyl | 0 |
| 1580 | piperazin-1-yl | 1 | 4-N(CH₂CH₂Cl)₂-2-CH₃-phenyl | 0 |

TABLE 2-continued

| Compd. No. | R₁ | m | R₂ | n |
|---|---|---|---|---|
| 1581 | HN(piperazine)N— | 1 | 4-N(CH₂CH₂Cl)₂, 3-OCH₃ phenyl | 0 |
| 1582 | HN(piperazine)N— | 1 | 4-N(CH₂CH₂Cl)₂, 3-CN phenyl | 0 |
| 1583 | HN(piperazine)N— | 1 | 4-N(CH₂CH₂Cl)₂, 3-Cl phenyl | 0 |
| 1584 | H₂N-C(=NH)-NH-CH₂CH₂-CH(NH₂)-CH₃ | 0 | 4-N(CH₂CH₂Cl)₂ phenyl | 0 |
| 1585 | benzyl-piperazine-N— | 1 | 4-N(CH₂CH₂Cl)₂ phenyl | 0 |
| 1586 | benzyl-piperazine-N— | 1 | 4-N(CH₂CH₂Cl)₂, 3-CH₃ phenyl | 0 |
| 1587 | benzyl-piperazine-N— | 1 | 4-N(CH₂CH₂Cl)₂, 3-Cl phenyl | 0 |
| 1588 | HOOC-C₆H₄— | 2 | 4-N(CH₂CH₂Cl)₂ phenyl | 0 |
| 1589 | imidazol-1-yl | 2 | 4-N(CH₂CH₂Cl)₂ phenyl | 0 |
| 1590 | 2-(1H-imidazolyl) | 0 | 4-N(CH₂CH₂Cl)₂ phenyl | 0 |
| 1591 | 2-(1-methylimidazolyl) | 0 | 4-N(CH₂CH₂Cl)₂ phenyl | 0 |
| 1592 | H₂N-C(=NH)-NH— | 1 | —CONH-C₆H₄-N(CH₂CH₂Cl)₂ | 3 |

TABLE 2-continued

| Compd. No. | R₁ | m | R₂ | n |
|---|---|---|---|---|
| 1593 | H₂N−C(=NH)− | 1 | −CONH−C₆H₄−N(CH₂CH₂Cl)₂ | 3 |
| 1594 | (CH₃)₃S⁺− | 2 | −CONH−C₆H₄−N(CH₂CH₂Cl)₂ | 3 |
| 1595 | (CH₃)₃N⁺− | 1 | −CONH−C₆H₄−N(CH₂CH₂Cl)₂ | 3 |
| 1596 | H₂N−C(=NH)−NH− | 1 | phenyl with −N(CH₂CH₂Cl)₂ and −CO−N(morpholino) | 0 |
| 1597 | H₂N−C(=NH)− | 1 | phenyl with −N(CH₂CH₂Cl)₂ and −CO−N(morpholino) | 0 |
| 1598 | (CH₃)₃S⁺− | 2 | phenyl with −N(CH₂CH₂Cl)₂ and −CO−N(morpholino) | 0 |
| 1599 | (CH₃)₃N⁺− | 1 | phenyl with −N(CH₂CH₂Cl)₂ and −CO−N(morpholino) | 0 |
| 1600 | H₂N−C(=NH)−NH− | 1 | benzofurazan with −N(CH₂CH₂Cl)₂ | 0 |
| 1601 | H₃C−S− | 2 | benzofurazan with −N(CH₂CH₂Cl)₂ | 0 |
| 1602 | (CH₃)₂S⁺− | 2 | benzofurazan with −N(CH₂CH₂Cl)₂ | 0 |

TABLE 2-continued

| Compd. No. | R₁ | m | R₂ | n |
|---|---|---|---|---|
| 1603 | (CH₃)₃N⁺— | 1 | benzofurazan with N(CH₂CH₂Cl)₂ | 0 |
| 1604 | 2-furyl | 0 | phenyl with CH(CH₂CH₃)NCH₂CH₂Cl (meta) | 0 |
| 1605 | 2-pyrrolyl (NH) | 0 | phenyl with CH(CH₂CH₃)NCH₂CH₂Cl (meta) | 0 |
| 1606 | 2-imidazolyl (NH) | 0 | phenyl with CH(CH₂CH₃)NCH₂CH₂Cl (meta) | 0 |
| 1607 | 3-pyridyl | 1 | phenyl with CH(CH₂CH₃)NCH₂CH₂Cl (meta) | 0 |

R₁(CH₂)ₘCONH— [N-methyl benzimidazole core] —CONH(CH₂)ₙR₂

| Compd. No. | R₁ | m | R₂ | n |
|---|---|---|---|---|
| 1608 | H₂N–C(=NH)–NH— | 1 | 4-[N(CH₂CH₂Cl)₂]phenyl | 0 |
| 1609 | H₂N–C(=NH)–NH— | 1 | 4-[N(CH₂CH₂Cl)₂]phenyl | 1 |
| 1610 | H₂N–C(=NH)–NH— | 1 | 4-[N(CH₂CH₂Cl)₂]phenyl | 2 |
| 1611 | H₂N–C(=NH)–NH— | 1 | 4-[N(CH₂CH₂Cl)₂]phenyl | 3 |
| 1612 | H₂N–C(=NH)–NH— | 1 | 4-[N(CH₂CH₂Cl)₂]-3-methylphenyl | 0 |

TABLE 2-continued

| Compd. No. | R₁ | m | R₂ | n |
|---|---|---|---|---|
| 1613 | H₂N-C(=NH)-NH— | 1 | -C₆H₃(2-OCH₃)-N(CH₂CH₂Cl)₂ | 0 |
| 1614 | H₂N-C(=NH)-NH— | 1 | -C₆H₃(2-Cl)-N(CH₂CH₂Cl)₂ | 0 |
| 1615 | H₂N-C(=NH)-NH— | 1 | -C₆H₃(3-CH₃)-N(CH₂CH₂Cl)₂ | 0 |
| 1616 | H₂N-C(=NH)-NH— | 1 | -C₆H₃(3-Cl)-N(CH₂CH₂Cl)₂ | 0 |

R₁(CH₂)ₘCONH—[thiophene]—[benzimidazole(NH)]—CONH(CH₂)ₙR₂

| Compd. No. | R₁ | m | R₂ | n |
|---|---|---|---|---|
| 1617 | H₂N-C(=NH)-NH— | 1 | -C₆H₄-N(CH₂CH₂Cl)₂ | 0 |
| 1618 | H₂N-C(=NH)-NH— | 1 | -C₆H₄-N(CH₂CH₂Cl)₂ | 1 |
| 1619 | H₂N-C(=NH)-NH— | 1 | -C₆H₄-N(CH₂CH₂Cl)₂ | 2 |
| 1620 | H₂N-C(=NH)-NH— | 1 | -C₆H₄-N(CH₂CH₂Cl)₂ | 3 |
| 1621 | H₂N-C(=NH)-NH— | 1 | -C₆H₃(3-CH₃)-N(CH₂CH₂Cl)₂ | 0 |
| 1622 | H₂N-C(=NH)-NH— | 1 | -C₆H₃(2-OCH₃)-N(CH₂CH₂Cl)₂ | 0 |
| 1623 | H₂N-C(=NH)-NH— | 1 | -C₆H₃(3-Cl)-N(CH₂CH₂Cl)₂ | 0 |

TABLE 2-continued

| Compd. No. | R₁ | m | R₂ | n |
|---|---|---|---|---|
| 1624 | H₂N−C(=NH)−NH− | 1 | 4-[N(CH₂CH₂Cl)₂]-3-methylphenyl | 0 |
| 1625 | H₂N−C(=NH)−NH− | 1 | 4-[N(CH₂CH₂Cl)₂]-3-chlorophenyl | 0 |

$$R_1(CH_2)_mCONH\text{-thiophene-benzimidazole-}CONH(CH_2)_nR_2$$

| Compd. No. | R₁ | m | R₂ | n |
|---|---|---|---|---|
| 1626 | H₂N−C(=NH)−NH− | 1 | 4-[N(CH₂CH₂Cl)₂]phenyl | 0 |
| 1627 | H₂N−C(=NH)−NH− | 1 | 4-[N(CH₂CH₂Cl)₂]phenyl | 1 |
| 1628 | H₂N−C(=NH)−NH− | 1 | 4-[N(CH₂CH₂Cl)₂]phenyl | 2 |
| 1629 | H₂N−C(=NH)−NH− | 1 | 4-[N(CH₂CH₂Cl)₂]phenyl | 3 |
| 1630 | H₂N−C(=NH)−NH− | 1 | 4-[N(CH₂CH₂Cl)₂]-3-methylphenyl | 0 |
| 1631 | H₂N−C(=NH)−NH− | 1 | 4-[N(CH₂CH₂Cl)₂]-3-methoxyphenyl | 0 |
| 1632 | H₂N−C(=NH)−NH− | 1 | 4-[N(CH₂CH₂Cl)₂]-3-chlorophenyl | 0 |
| 1633 | H₂N−C(=NH)−NH− | 1 | 3-[N(CH₂CH₂Cl)₂]-4-methylphenyl | 0 |
| 1634 | H₂N−C(=NH)−NH− | 1 | 3-[N(CH₂CH₂Cl)₂]-4-chlorophenyl | 0 |

TABLE 2-continued

| Compd. No. | R₁ | m | R₂ | n |
|---|---|---|---|---|

Header structure (first structure):

R₁(CH₂)ₘCONH—[furan]—[benzimidazole-NH]—CONH(CH₂)ₙR₂

| Compd. No. | R₁ | m | R₂ | n |
|---|---|---|---|---|
| 1635 | H₂N–C(=NH)–NH– | 1 | –C₆H₄–N(CH₂CH₂Cl)₂ | 0 |
| 1636 | H₂N–C(=NH)–NH– | 1 | –C₆H₄–N(CH₂CH₂Cl)₂ | 1 |
| 1637 | H₂N–C(=NH)–NH– | 1 | –C₆H₄–N(CH₂CH₂Cl)₂ | 2 |
| 1638 | H₂N–C(=NH)–NH– | 1 | –C₆H₄–N(CH₂CH₂Cl)₂ | 3 |
| 1639 | H₂N–C(=NH)–NH– | 1 | –C₆H₃(CH₃)–N(CH₂CH₂Cl)₂ | 0 |
| 1640 | H₂N–C(=NH)–NH– | 1 | –C₆H₃(OCH₃)–N(CH₂CH₂Cl)₂ | 0 |
| 1641 | H₂N–C(=NH)–NH– | 1 | –C₆H₃(Cl)–N(CH₂CH₂Cl)₂ | 0 |
| 1642 | H₂N–C(=NH)–NH– | 1 | –C₆H₃(CH₃)–N(CH₂CH₂Cl)₂ | 0 |
| 1643 | H₂N–C(=NH)–NH– | 1 | –C₆H₃(Cl)–N(CH₂CH₂Cl)₂ | 0 |

Header structure (second structure):

R₁(CH₂)ₘCONH—[N-methyl-imidazole]—[benzimidazole-NH]—CONH(CH₂)ₙR₂

| Compd. No. | R₁ | m | R₂ | n |
|---|---|---|---|---|
| 1644 | H₂N–C(=NH)– | 2 | –C₆H₄–N(CH₂CH₂Cl)₂ | 0 |

TABLE 2-continued

| Compd. No. | R₁ | m | R₂ | n |
|---|---|---|---|---|
| 1645 | H₂N-C(=NH)- | 2 | -C₆H₄-N(CH₂CH₂Cl)₂ | 1 |
| 1646 | H₂N-C(=NH)- | 2 | -C₆H₄-N(CH₂CH₂Cl)₂ | 2 |
| 1647 | H₂N-C(=NH)- | 2 | -C₆H₄-N(CH₂CH₂Cl)₂ | 3 |
| 1648 | H₂N-C(=NH)- | 2 | -C₆H₃(CH₃)-N(CH₂CH₂Cl)₂ | 0 |
| 1649 | H₂N-C(=NH)- | 2 | -C₆H₃(OCH₃)-N(CH₂CH₂Cl)₂ | 0 |
| 1650 | H₂N-C(=NH)- | 2 | -C₆H₃(Cl)-N(CH₂CH₂Cl)₂ | 0 |
| 1651 | H₂N-C(=NH)- | 2 | -C₆H₃(CH₃)-N(CH₂CH₂Cl)₂ | 0 |
| 1652 | H₂N-C(=NH)- | 2 | -C₆H₃(Cl)-N(CH₂CH₂Cl)₂ | 0 |

R₁(CH₂)ₘCONH-[thiophene]-[benzimidazole]-CONH(CH₂)ₙR₂

| Compd. No. | R₁ | m | R₂ | n |
|---|---|---|---|---|
| 1653 | H₂N-C(=NH)- | 2 | -C₆H₄-N(CH₂CH₂Cl)₂ | 0 |
| 1654 | H₂N-C(=NH)- | 2 | -C₆H₄-N(CH₂CH₂Cl)₂ | 1 |
| 1655 | H₂N-C(=NH)- | 2 | -C₆H₄-N(CH₂CH₂Cl)₂ | 2 |
| 1656 | H₂N-C(=NH)- | 2 | -C₆H₄-N(CH₂CH₂Cl)₂ | 3 |

TABLE 2-continued

| Compd. No. | R₁ | m | R₂ | n |
|---|---|---|---|---|
| 1657 | H₂N-C(=NH)- | 2 | -C₆H₃(CH₃)-N(CH₂CH₂Cl)₂ (2-CH₃) | 0 |
| 1658 | H₂N-C(=NH)- | 2 | -C₆H₃(OCH₃)-N(CH₂CH₂Cl)₂ (2-OCH₃) | 0 |
| 1659 | H₂N-C(=NH)- | 2 | -C₆H₃(Cl)-N(CH₂CH₂Cl)₂ (2-Cl) | 0 |
| 1660 | H₂N-C(=NH)- | 2 | -C₆H₃(CH₃)-N(CH₂CH₂Cl)₂ (3-CH₃) | 0 |
| 1661 | H₂N-C(=NH)- | 2 | -C₆H₃(Cl)-N(CH₂CH₂Cl)₂ (3-Cl) | 0 |

R₁(CH₂)ₘCONH—[thiophene]—[benzimidazole]—CONH(CH₂)ₙR₂

| 1662 | H₂N-C(=NH)- | 2 | -C₆H₄-N(CH₂CH₂Cl)₂ | 0 |
| 1663 | H₂N-C(=NH)- | 2 | -C₆H₄-N(CH₂CH₂Cl)₂ | 1 |
| 1664 | H₂N-C(=NH)- | 2 | -C₆H₄-N(CH₂CH₂Cl)₂ | 2 |
| 1665 | H₂N-C(=NH)- | 2 | -C₆H₄-N(CH₂CH₂Cl)₂ | 3 |
| 1666 | H₂N-C(=NH)- | 2 | -C₆H₃(CH₃)-N(CH₂CH₂Cl)₂ (2-CH₃) | 0 |
| 1667 | H₂N-C(=NH)- | 2 | -C₆H₃(OCH₃)-N(CH₂CH₂Cl)₂ (2-OCH₃) | 0 |

TABLE 2-continued

| Compd. No. | R₁ | m | R₂ | n |
|---|---|---|---|---|
| 1668 | H₂N-C(=NH)- | 2 | 4-N(CH₂CH₂Cl)₂-3-Cl-phenyl | 0 |
| 1669 | H₂N-C(=NH)- | 2 | 4-N(CH₂CH₂Cl)₂-3-CH₃-phenyl | 0 |
| 1670 | H₂N-C(=NH)- | 2 | 3-N(CH₂CH₂Cl)₂-4-Cl-phenyl (with Cl on ring) | 0 |

Core structure: R₁(CH₂)ₘCONH—[furan]—[benzimidazole]—CONH(CH₂)ₙR₂

| Compd. No. | R₁ | m | R₂ | n |
|---|---|---|---|---|
| 1671 | H₂N-C(=NH)- | 2 | 4-N(CH₂CH₂Cl)₂-phenyl | 0 |
| 1672 | H₂N-C(=NH)- | 2 | 4-N(CH₂CH₂Cl)₂-phenyl | 1 |
| 1673 | H₂N-C(=NH)- | 2 | 4-N(CH₂CH₂Cl)₂-phenyl | 2 |
| 1674 | H₂N-C(=NH)- | 2 | 4-N(CH₂CH₂Cl)₂-phenyl | 3 |
| 1675 | H₂N-C(=NH)- | 2 | 4-N(CH₂CH₂Cl)₂-3-CH₃-phenyl | 0 |
| 1676 | H₂N-C(=NH)- | 2 | 4-N(CH₂CH₂Cl)₂-3-OCH₃-phenyl | 0 |
| 1677 | H₂N-C(=NH)- | 2 | 4-N(CH₂CH₂Cl)₂-3-Cl-phenyl | 0 |
| 1678 | H₂N-C(=NH)- | 2 | 4-N(CH₂CH₂Cl)₂-3-CH₃-phenyl | 0 |

TABLE 2-continued

| Compd. No. | R₁ | m | R₂ | n |
|---|---|---|---|---|
| 1679 | 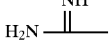 H₂N-C(=NH)- | 2 | 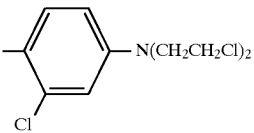 4-[N(CH₂CH₂Cl)₂]-3-Cl-C₆H₃- | 0 |

R₁(CH₂)ₘCONH— (1-methylimidazole)—benzimidazole—CONH(CH₂)ₙR₂

| 1680 | H₃C—S⁺(CH₃)— | 2 | 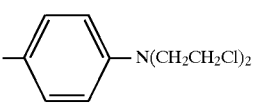 4-[N(CH₂CH₂Cl)₂]-C₆H₄- | 0 |
| 1681 | H₃C—S⁺(CH₃)— | 2 |  4-[N(CH₂CH₂Cl)₂]-C₆H₄- | 1 |
| 1682 | H₃C—S⁺(CH₃)— | 2 | 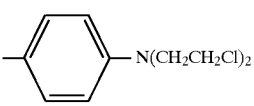 4-[N(CH₂CH₂Cl)₂]-C₆H₄- | 2 |
| 1683 | H₃C—S⁺(CH₃)— | 2 |  4-[N(CH₂CH₂Cl)₂]-C₆H₄- | 3 |
| 1684 | H₃C—S⁺(CH₃)— | 2 | 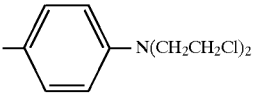 4-[N(CH₂CH₂Cl)₂]-3-CH₃-C₆H₃- | 0 |
| 1685 | H₃C—S⁺(CH₃)— | 2 |  4-[N(CH₂CH₂Cl)₂]-3-OCH₃-C₆H₃- | 0 |
| 1686 | H₃C—S⁺(CH₃)— | 2 | 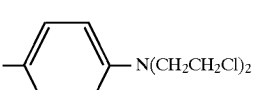 4-[N(CH₂CH₂Cl)₂]-2-Cl-C₆H₃- | 0 |
| 1687 | H₃C—S⁺(CH₃)— | 2 |  4-[N(CH₂CH₂Cl)₂]-2-CH₃-C₆H₃- | 0 |
| 1688 | H₃C—S⁺(CH₃)— | 2 | 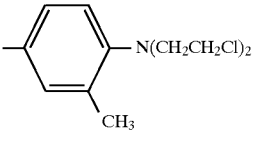 4-[N(CH₂CH₂Cl)₂]-3-Cl-C₆H₃- | 0 |

R₁(CH₂)ₘCONH—(thiophene)—benzimidazole—CONH(CH₂)ₙR₂

TABLE 2-continued

| Compd. No. | R₁ | m | R₂ | n |
|---|---|---|---|---|
| 1689 | H₃C—S⁺— (CH₃)₂ | 2 | —C₆H₄—N(CH₂CH₂Cl)₂ | 0 |
| 1690 | H₃C—S⁺— (CH₃)₂ | 2 | —C₆H₄—N(CH₂CH₂Cl)₂ | 1 |
| 1691 | H₃C—S⁺— (CH₃)₂ | 2 | —C₆H₄—N(CH₂CH₂Cl)₂ | 2 |
| 1692 | H₃C—S⁺— (CH₃)₂ | 2 | —C₆H₄—N(CH₂CH₂Cl)₂ | 3 |
| 1693 | H₃C—S⁺— (CH₃)₂ | 2 | —C₆H₃(CH₃)—N(CH₂CH₂Cl)₂ | 0 |
| 1694 | H₃C—S⁺— (CH₃)₂ | 2 | —C₆H₃(OCH₃)—N(CH₂CH₂Cl)₂ | 0 |
| 1695 | H₃C—S⁺— (CH₃)₂ | 2 | —C₆H₃(Cl)—N(CH₂CH₂Cl)₂ | 0 |
| 1696 | H₃C—S⁺— (CH₃)₂ | 2 | —C₆H₃(CH₃)—N(CH₂CH₂Cl)₂ | 0 |
| 1697 | H₃C—S⁺— (CH₃)₂ | 2 | —C₆H₃(Cl)—N(CH₂CH₂Cl)₂ | 0 |

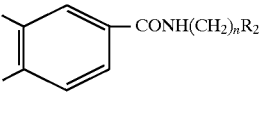

R₁(CH₂)ₘCONH—[thiophene]—[benzimidazole]—CONH(CH₂)ₙR₂

| 1698 | H₃C—S⁺— (CH₃)₂ | 2 | —C₆H₄—N(CH₂CH₂Cl)₂ | 0 |
| 1699 | H₃C—S⁺— (CH₃)₂ | 2 | —C₆H₄—N(CH₂CH₂Cl)₂ | 1 |

TABLE 2-continued

| Compd. No. | R₁ | m | R₂ | n |
|---|---|---|---|---|
| 1700 | H₃C—S⁺— (CH₃) | 2 |  —C₆H₄—N(CH₂CH₂Cl)₂ | 2 |
| 1701 | H₃C—S⁺— (CH₃) | 2 | 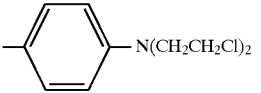 —C₆H₄—N(CH₂CH₂Cl)₂ | 3 |
| 1702 | H₃C—S⁺— (CH₃) | 2 |  —C₆H₃(CH₃)—N(CH₂CH₂Cl)₂ | 0 |
| 1703 | H₃C—S⁺— (CH₃) | 2 | 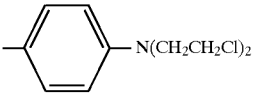 —C₆H₃(OCH₃)—N(CH₂CH₂Cl)₂ | 0 |
| 1704 | H₃C—S⁺— (CH₃) | 2 |  —C₆H₃(Cl)—N(CH₂CH₂Cl)₂ | 0 |
| 1705 | H₃C—S⁺— (CH₃) | 2 | 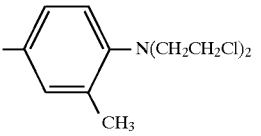 —C₆H₃(CH₃)—N(CH₂CH₂Cl)₂ | 0 |
| 1706 | H₃C—S⁺— (CH₃) | 2 |  —C₆H₃(Cl)—N(CH₂CH₂Cl)₂ | 0 |

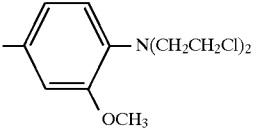

R₁(CH₂)ₘCONH—[furan]—[benzimidazole]—CONH(CH₂)ₙR₂

| Compd. No. | R₁ | m | R₂ | n |
|---|---|---|---|---|
| 1707 | H₃C—S⁺— (CH₃) | 2 |  —C₆H₄—N(CH₂CH₂Cl)₂ | 0 |
| 1708 | H₃C—S⁺— (CH₃) | 2 |  —C₆H₄—N(CH₂CH₂Cl)₂ | 1 |
| 1709 | H₃C—S⁺— (CH₃) | 2 |  —C₆H₄—N(CH₂CH₂Cl)₂ | 2 |
| 1710 | H₃C—S⁺— (CH₃) | 2 | 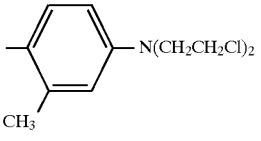 —C₆H₄—N(CH₂CH₂Cl)₂ | 3 |

TABLE 2-continued
| Compd. No. | R₁ | m | R₂ | n |
|---|---|---|---|---|
| 1711 |  | 2 | 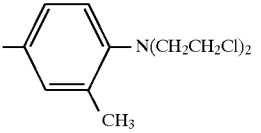 | 0 |
| 1712 |  | 2 | 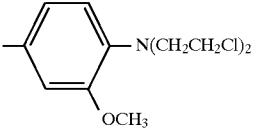 | 0 |
| 1713 |  | 2 | 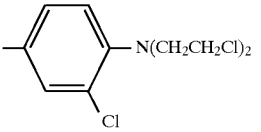 | 0 |
| 1714 |  | 2 | 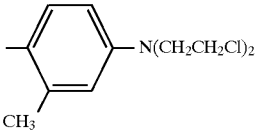 | 0 |
| 1715 |  | 2 | 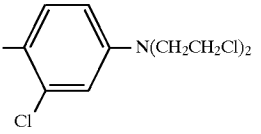 | 0 |
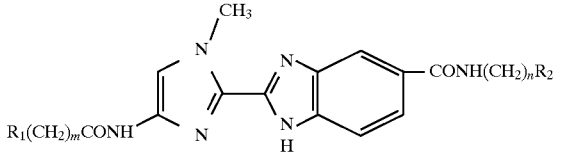
| 1716 | 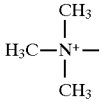 | 2 | 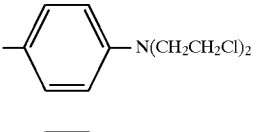 | 0 |
| 1717 | 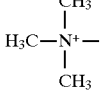 | 2 | 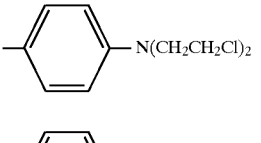 | 1 |
| 1718 | 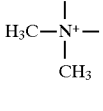 | 2 | 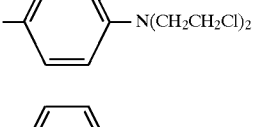 | 2 |
| 1719 | 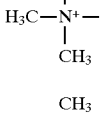 | 2 | 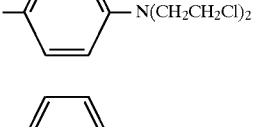 | 3 |
| 1720 | 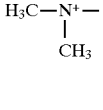 | 2 | 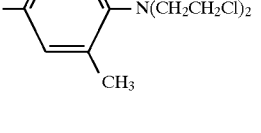 | 0 |

TABLE 2-continued

| Compd. No. | R₁ | m | R₂ | n |
|---|---|---|---|---|
| 1721 | H₃C—N⁺(CH₃)₂—CH₃ | 2 | 4-[N(CH₂CH₂Cl)₂]-3-OCH₃-phenyl | 0 |
| 1722 | H₃C—N⁺(CH₃)₂—CH₃ | 2 | 4-[N(CH₂CH₂Cl)₂]-3-Cl-phenyl | 0 |
| 1723 | H₃C—N⁺(CH₃)₂—CH₃ | 2 | 3-[N(CH₂CH₂Cl)₂]-4-CH₃-phenyl | 0 |
| 1724 | H₃C—N⁺(CH₃)₂—CH₃ | 2 | 3-[N(CH₂CH₂Cl)₂]-4-Cl-phenyl | 0 |

R₁(CH₂)ₘCONH—[thiophene]—[benzimidazole(NH)]—CONH(CH₂)ₙR₂

| Compd. No. | R₁ | m | R₂ | n |
|---|---|---|---|---|
| 1725 | H₃C—N⁺(CH₃)₂—CH₃ | 2 | 4-[N(CH₂CH₂Cl)₂]-phenyl | 0 |
| 1726 | H₃C—N⁺(CH₃)₂—CH₃ | 2 | 4-[N(CH₂CH₂Cl)₂]-phenyl | 1 |
| 1727 | H₃C—N⁺(CH₃)₂—CH₃ | 2 | 4-[N(CH₂CH₂Cl)₂]-phenyl | 2 |
| 1728 | H₃C—N⁺(CH₃)₂—CH₃ | 2 | 4-[N(CH₂CH₂Cl)₂]-phenyl | 3 |
| 1729 | H₃C—N⁺(CH₃)₂—CH₃ | 2 | 4-[N(CH₂CH₂Cl)₂]-3-CH₃-phenyl | 0 |
| 1730 | H₃C—N⁺(CH₃)₂—CH₃ | 2 | 4-[N(CH₂CH₂Cl)₂]-3-OCH₃-phenyl | 0 |
| 1731 | H₃C—N⁺(CH₃)₂—CH₃ | 2 | 4-[N(CH₂CH₂Cl)₂]-3-Cl-phenyl | 0 |

TABLE 2-continued

| Compd. No. | R₁ | m | R₂ | n |
|---|---|---|---|---|
| 1732 | (CH₃)₃N⁺— | 2 | 4-[N(CH₂CH₂Cl)₂]-3-methylphenyl | 0 |
| 1733 | (CH₃)₃N⁺— | 2 | 4-[N(CH₂CH₂Cl)₂]-3-chlorophenyl | 0 |

$$R_1(CH_2)_m CONH-\text{[thiophene]}-\text{[benzimidazole]}-CONH(CH_2)_n R_2$$

| Compd. No. | R₁ | m | R₂ | n |
|---|---|---|---|---|
| 1734 | (CH₃)₃N⁺— | 2 | 4-[N(CH₂CH₂Cl)₂]phenyl | 0 |
| 1735 | (CH₃)₃N⁺— | 2 | 4-[N(CH₂CH₂Cl)₂]phenyl | 1 |
| 1736 | (CH₃)₃N⁺— | 2 | 4-[N(CH₂CH₂Cl)₂]phenyl | 2 |
| 1737 | (CH₃)₃N⁺— | 2 | 4-[N(CH₂CH₂Cl)₂]phenyl | 3 |
| 1738 | (CH₃)₃N⁺— | 2 | 4-[N(CH₂CH₂Cl)₂]-3-methylphenyl | 0 |
| 1739 | (CH₃)₃N⁺— | 2 | 4-[N(CH₂CH₂Cl)₂]-3-methoxyphenyl | 0 |
| 1740 | (CH₃)₃N⁺— | 2 | 4-[N(CH₂CH₂Cl)₂]-3-chlorophenyl | 0 |
| 1741 | (CH₃)₃N⁺— | 2 | 4-[N(CH₂CH₂Cl)₂]-2-methylphenyl | 0 |

TABLE 2-continued

General structure:

R₁(CH₂)ₘCONH—[furan]—[benzimidazole(NH)]—CONH(CH₂)ₙR₂

| Compd. No. | R₁ | m | R₂ | n |
|---|---|---|---|---|
| 1742 | (CH₃)₃N⁺— | 2 | 4-[N(CH₂CH₂Cl)₂]-3-Cl-phenyl | 0 |
| 1743 | (CH₃)₃N⁺— | 2 | 4-[N(CH₂CH₂Cl)₂]-phenyl | 0 |
| 1744 | (CH₃)₃N⁺— | 2 | 4-[N(CH₂CH₂Cl)₂]-phenyl | 1 |
| 1745 | (CH₃)₃N⁺— | 2 | 4-[N(CH₂CH₂Cl)₂]-phenyl | 2 |
| 1746 | (CH₃)₃N⁺— | 2 | 4-[N(CH₂CH₂Cl)₂]-phenyl | 3 |
| 1747 | (CH₃)₃N⁺— | 2 | 4-[N(CH₂CH₂Cl)₂]-3-CH₃-phenyl | 0 |
| 1748 | (CH₃)₃N⁺— | 2 | 4-[N(CH₂CH₂Cl)₂]-3-OCH₃-phenyl | 0 |
| 1749 | (CH₃)₃N⁺— | 2 | 4-[N(CH₂CH₂Cl)₂]-2-Cl-phenyl | 0 |
| 1750 | (CH₃)₃N⁺— | 2 | 4-[N(CH₂CH₂Cl)₂]-2-CH₃-phenyl | 0 |
| 1751 | (CH₃)₃N⁺— | 2 | 3-[N(CH₂CH₂Cl)₂]-4-Cl-phenyl | 0 |

TABLE 2-continued

| Compd. No. | R₁ | m | R₂ | n |
|---|---|---|---|---|

Core structure (header):

R₁(CH₂)ₘCONH— [pyrrole with N-CH₃] —[benzimidazole, NH]— CONH(CH₂)ₙR₂

| Compd. No. | R₁ | m | R₂ | n |
|---|---|---|---|---|
| 1752 | CH₃CH₂CH₂CONH—C(=NH)—NH— | 2 | —C₆H₄—N(CH₂CH₂Cl)₂ (para) | 0 |
| 1753 | CH₃CH₂CH₂CONH—C(=NH)—NH— | 2 | —C₆H₄—N(CH₂CH₂Cl)₂ (para) | 3 |
| 1754 | CH₃CH₂CH₂CONH—C(=NH)—NH— | 2 | —C₆H₃(CH₃)—N(CH₂CH₂Cl)₂ | 0 |
| 1755 | CH₃CH₂CH₂CONH—C(=NH)—NH— | 2 | —C₆H₃(Cl)—N(CH₂CH₂Cl)₂ | 0 |
| 1756 | CH₃CH₂CH₂CONH—C(=NH)—NH— | 2 | —C₆H₃(OCH₃)—N(CH₂CH₂Cl)₂ | 0 |
| 1757 | CH₃CH₂CH₂CONH—C(=NH)—NH— | 2 | —C₆H₃(CF₃)—N(CH₂CH₂Cl)₂ | 0 |
| 1758 | CH₃CH₂CH₂CONH—C(=NH)—NH— | 2 | —C₆H₃(CH₃)—N(CH₂CH₂Cl)₂ (meta-CH₃) | 0 |
| 1759 | CH₃CH₂CH₂CONH—C(=NH)—NH— | 2 | —C₆H₃(Cl)—N(CH₂CH₂Cl)₂ (meta-Cl) | 0 |
| 1760 | CH₃CONH—C(=NH)—NH— | 2 | —C₆H₄—N(CH₂CH₂Cl)₂ | 0 |
| 1761 | CH₃CONH—C(=NH)—NH— | 2 | —C₆H₄—N(CH₂CH₂Cl)₂ | 3 |

TABLE 2-continued

| Compd. No. | R₁ | m | R₂ | n |
|---|---|---|---|---|
| 1762 | CH₃CONH-C(=NH)-N(H)- | 2 | 4-[N(CH₂CH₂Cl)₂]-2-CH₃-phenyl | 0 |
| 1763 | CH₃CONH-C(=NH)-N(H)- | 2 | 4-[N(CH₂CH₂Cl)₂]-2-Cl-phenyl | 0 |
| 1764 | CH₃CONH-C(=NH)-N(H)- | 2 | 4-[N(CH₂CH₂Cl)₂]-3-OCH₃-phenyl | 0 |
| 1765 | CH₃CONH-C(=NH)-N(H)- | 2 | 4-[N(CH₂CH₂Cl)₂]-3-CF₃-phenyl | 0 |
| 1766 | CH₃CONH-C(=NH)-N(H)- | 2 | 3-CH₃-4-[N(CH₂CH₂Cl)₂]-phenyl | 0 |
| 1767 | CH₃CONH-C(=NH)-N(H)- | 2 | 3-Cl-4-[N(CH₂CH₂Cl)₂]-phenyl | 0 |
| 1768 | CH₃NH-C(=NH)- | 3 | 4-[N(CH₂CH₂Cl)₂]-phenyl | 0 |
| 1769 | CH₃NH-C(=NH)- | 3 | 4-[N(CH₂CH₂Cl)₂]-phenyl | 3 |
| 1770 | CH₃NH-C(=NH)- | 3 | 4-[N(CH₂CH₂Cl)₂]-2-CH₃-phenyl | 0 |
| 1771 | CH₃NH-C(=NH)- | 3 | 4-[N(CH₂CH₂Cl)₂]-2-Cl-phenyl | 0 |
| 1772 | CH₃NH-C(=NH)- | 3 | 4-[N(CH₂CH₂Cl)₂]-2-CF₃-phenyl | 0 |

TABLE 2-continued

| Compd. No. | R₁ | m | R₂ | n |
|---|---|---|---|---|
| 1773 | CH₃NH−C(=NH)− | 3 | 4-N(CH₂CH₂Cl)₂, 2-CN phenyl | 0 |
| 1774 | CH₃NH−C(=NH)− | 3 | 4-N(CH₂CH₂Cl)₂, 3-CH₃ phenyl | 0 |
| 1775 | CH₃NH−C(=NH)− | 3 | 4-N(CH₂CH₂Cl)₂, 3-Cl phenyl | 0 |
| 1776 | piperazin-1-yl (HN-piperazine) | 2 | 4-N(CH₂CH₂Cl)₂ phenyl | 0 |
| 1777 | piperazin-1-yl | 2 | 4-N(CH₂CH₂Cl)₂ phenyl | 3 |
| 1778 | piperazin-1-yl | 2 | 4-N(CH₂CH₂Cl)₂, 3-CH₃ phenyl | 0 |
| 1779 | piperazin-1-yl | 2 | 4-N(CH₂CH₂Cl)₂, 3-Cl phenyl | 0 |
| 1780 | piperazin-1-yl | 2 | 4-N(CH₂CH₂Cl)₂, 2-CH₃ phenyl | 0 |
| 1781 | piperazin-1-yl | 2 | 4-N(CH₂CH₂Cl)₂, 2-CF₃ phenyl | 0 |
| 1782 | piperazin-1-yl | 2 | 4-N(CH₂CH₂Cl)₂, 2-CN phenyl | 0 |
| 1783 | piperazin-1-yl | 2 | 4-N(CH₂CH₂Cl)₂, 2-Cl phenyl | 0 |

TABLE 2-continued

| Compd. No. | R₁ | m | R₂ | n |
|---|---|---|---|---|
| 1784 | HN⟨piperazine⟩N— | 3 | —C₆H₄—N(CH₂CH₂Cl)₂ | 0 |
| 1785 | HN⟨piperazine⟩N— | 3 | —C₆H₄—N(CH₂CH₂Cl)₂ | 3 |
| 1786 | HN⟨piperazine⟩N— | 3 | —C₆H₃(CH₃)—N(CH₂CH₂Cl)₂ | 0 |
| 1787 | HN⟨piperazine⟩N— | 3 | —C₆H₃(Cl)—N(CH₂CH₂Cl)₂ | 0 |
| 1788 | HN⟨piperazine⟩N— | 3 | —C₆H₃(CH₃)—N(CH₂CH₂Cl)₂ | 0 |
| 1789 | HN⟨piperazine⟩N— | 3 | —C₆H₃(CF₃)—N(CH₂CH₂Cl)₂ | 0 |
| 1790 | HN⟨piperazine⟩N— | 3 | —C₆H₃(CN)—N(CH₂CH₂Cl)₂ | 0 |
| 1791 | HN⟨piperazine⟩N— | 3 | —C₆H₃(Cl)—N(CH₂CH₂Cl)₂ | 0 |
| 1792 | ⟨piperidine⟩N— | 1 | —C₆H₄—N(CH₂CH₂Cl)₂ | 0 |
| 1793 | ⟨piperidine⟩N— | 1 | —C₆H₄—N(CH₂CH₂Cl)₂ | 3 |
| 1794 | ⟨piperidine⟩N— | 1 | —C₆H₃(CH₃)—N(CH₂CH₂Cl)₂ | 0 |
| 1795 | ⟨piperidine⟩N— | 1 | —C₆H₃(Cl)—N(CH₂CH₂Cl)₂ | 0 |

TABLE 2-continued

| Compd. No. | R₁ | m | R₂ | n |
|---|---|---|---|---|
| 1796 | piperidin-1-yl | 1 | 4-N(CH₂CH₂Cl)₂-2-CH₃-phenyl | 0 |
| 1797 | piperidin-1-yl | 1 | 4-N(CH₂CH₂Cl)₂-2-CF₃-phenyl | 0 |
| 1798 | piperidin-1-yl | 1 | 4-N(CH₂CH₂Cl)₂-2-CN-phenyl | 0 |
| 1799 | piperidin-1-yl | 1 | 4-N(CH₂CH₂Cl)₂-2-Cl-phenyl | 0 |
| 1800 | piperidin-1-yl | 2 | 4-N(CH₂CH₂Cl)₂-phenyl | 0 |
| 1801 | piperidin-1-yl | 2 | 4-N(CH₂CH₂Cl)₂-phenyl | 3 |
| 1802 | piperidin-1-yl | 2 | 3-N(CH₂CH₂Cl)₂-5-CH₃-phenyl | 0 |
| 1803 | piperidin-1-yl | 2 | 3-N(CH₂CH₂Cl)₂-5-Cl-phenyl | 0 |
| 1804 | piperidin-1-yl | 2 | 4-N(CH₂CH₂Cl)₂-2-CH₃-phenyl | 0 |
| 1805 | piperidin-1-yl | 2 | 4-N(CH₂CH₂Cl)₂-2-CF₃-phenyl | 0 |
| 1806 | piperidin-1-yl | 2 | 4-N(CH₂CH₂Cl)₂-2-CN-phenyl | 0 |

TABLE 2-continued

| Compd. No. | R₁ | m | R₂ | n |
|---|---|---|---|---|
| 1807 | piperidin-N-yl | 2 | 4-[N(CH₂CH₂Cl)₂]-2-Cl-phenyl | 0 |
| 1808 | piperidin-N-yl | 3 | 4-[N(CH₂CH₂Cl)₂]-phenyl | 0 |
| 1809 | piperidin-N-yl | 3 | 4-[N(CH₂CH₂Cl)₂]-phenyl | 3 |
| 1810 | piperidin-N-yl | 3 | 4-[N(CH₂CH₂Cl)₂]-3-CH₃-phenyl | 0 |
| 1811 | piperidin-N-yl | 3 | 4-[N(CH₂CH₂Cl)₂]-2-Cl-phenyl | 0 |
| 1812 | piperidin-N-yl | 3 | 4-[N(CH₂CH₂Cl)₂]-2-CH₃-phenyl | 0 |
| 1813 | piperidin-N-yl | 3 | 4-[N(CH₂CH₂Cl)₂]-2-CF₃-phenyl | 0 |
| 1814 | piperidin-N-yl | 3 | 4-[N(CH₂CH₂Cl)₂]-2-CN-phenyl | 0 |
| 1815 | piperidin-N-yl | 3 | 4-[N(CH₂CH₂Cl)₂]-2-Cl-phenyl | 0 |
| 1816 | piperidin-4-yl (HN) | 1 | 4-[N(CH₂CH₂Cl)₂]-phenyl | 0 |
| 1817 | piperidin-4-yl (HN) | 1 | 4-[N(CH₂CH₂Cl)₂]-phenyl | 3 |
| 1818 | piperidin-4-yl (HN) | 1 | 4-[N(CH₂CH₂Cl)₂]-3-CH₃-phenyl | 0 |

TABLE 2-continued
| Compd. No. | R₁ | m | R₂ | n |
|---|---|---|---|---|
| 1819 |  | 1 | 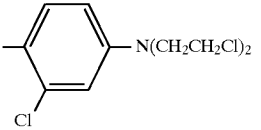 | 0 |
| 1820 |  | 1 | 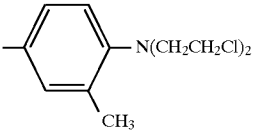 | 0 |
| 1821 |  | 1 | 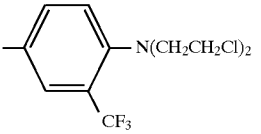 | 0 |
| 1822 |  | 1 | 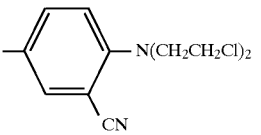 | 0 |
| 1823 | 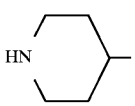 | 1 | 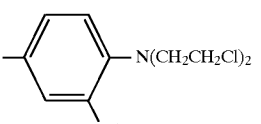 | 0 |
| 1824 | 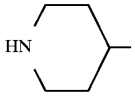 | 2 | 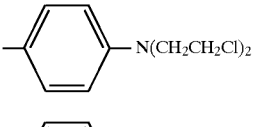 | 0 |
| 1825 | 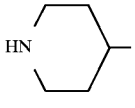 | 2 | 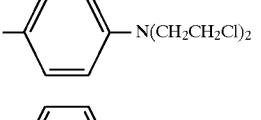 | 3 |
| 1826 |  | 2 | 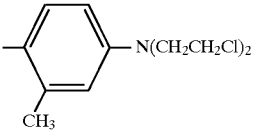 | 0 |
| 1827 |  | 2 | 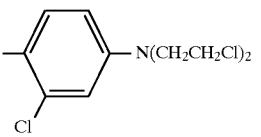 | 0 |
| 1828 | 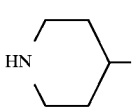 | 2 | 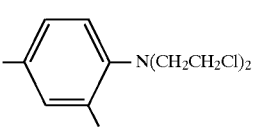 | 0 |
| 1829 | 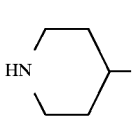 | 2 | 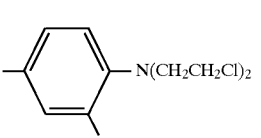 | 0 |

TABLE 2-continued
| Compd. No. | R₁ | m | R₂ | n |
|---|---|---|---|---|
| 1830 | 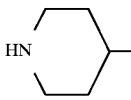 | 2 | 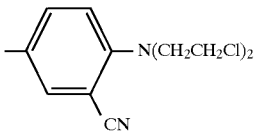 | 0 |
| 1831 | 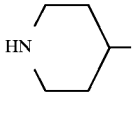 | 2 | 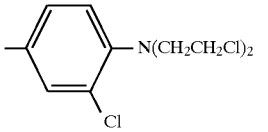 | 0 |
| 1832 |  | 3 | 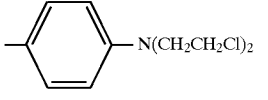 | 0 |
| 1833 | 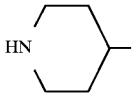 | 3 | 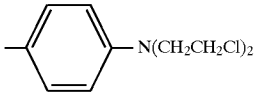 | 3 |
| 1834 | 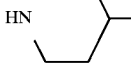 | 3 | 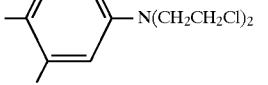 | 0 |
| 1835 |  | 3 | 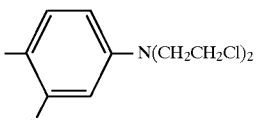 | 0 |
| 1836 | 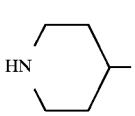 | 3 | 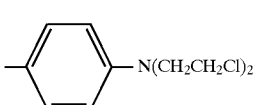 | 0 |
| 1837 | 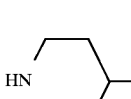 | 3 | 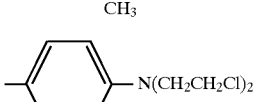 | 0 |
| 1838 | 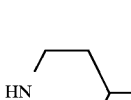 | 3 | 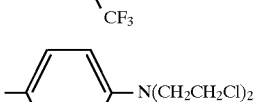 | 0 |
| 1839 | 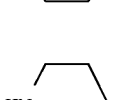 | 3 | 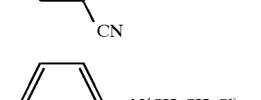 | 0 |
| 1840 | 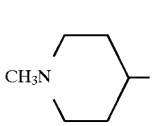 | 1 | 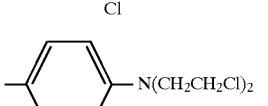 | 0 |
| 1841 | 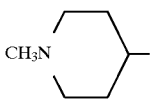 | 1 | 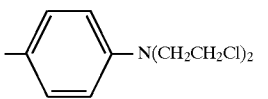 | 3 |

TABLE 2-continued

| Compd. No. | R₁ | m | R₂ | n |
|---|---|---|---|---|
| 1842 | CH₃N-piperidinyl | 1 | 4-N(CH₂CH₂Cl)₂-3-CH₃-phenyl | 0 |
| 1843 | CH₃N-piperidinyl | 1 | 4-N(CH₂CH₂Cl)₂-2-Cl-phenyl | 0 |
| 1844 | CH₃N-piperidinyl | 1 | 4-N(CH₂CH₂Cl)₂-3-CH₃-phenyl | 0 |
| 1845 | CH₃N-piperidinyl | 1 | 4-N(CH₂CH₂Cl)₂-3-CF₃-phenyl | 0 |
| 1846 | CH₃N-piperidinyl | 1 | 4-N(CH₂CH₂Cl)₂-3-CN-phenyl | 0 |
| 1847 | CH₃N-piperidinyl | 1 | 4-N(CH₂CH₂Cl)₂-3-Cl-phenyl | 0 |
| 1848 | CH₃N-piperidinyl | 2 | 4-N(CH₂CH₂Cl)₂-phenyl | 0 |
| 1849 | CH₃N-piperidinyl | 2 | 4-N(CH₂CH₂Cl)₂-phenyl | 3 |
| 1850 | CH₃N-piperidinyl | 2 | 4-N(CH₂CH₂Cl)₂-3-CH₃-phenyl | 0 |
| 1851 | CH₃N-piperidinyl | 2 | 4-N(CH₂CH₂Cl)₂-2-Cl-phenyl | 0 |
| 1852 | CH₃N-piperidinyl | 2 | 4-N(CH₂CH₂Cl)₂-3-CH₃-phenyl | 0 |

TABLE 2-continued

| Compd. No. | R₁ | m | R₂ | n |
|---|---|---|---|---|
| 1853 | CH₃N-piperidinyl | 2 | phenyl-N(CH₂CH₂Cl)₂, CF₃ | 0 |
| 1854 | CH₃N-piperidinyl | 2 | phenyl-N(CH₂CH₂Cl)₂, CN | 0 |
| 1855 | CH₃N-piperidinyl | 2 | phenyl-N(CH₂CH₂Cl)₂, Cl | 0 |
| 1856 | CH₃N-piperidinyl | 3 | phenyl-N(CH₂CH₂Cl)₂ | 0 |
| 1857 | CH₃N-piperidinyl | 3 | phenyl-N(CH₂CH₂Cl)₂ | 3 |
| 1858 | CH₃N-piperidinyl | 3 | phenyl-N(CH₂CH₂Cl)₂, CH₃ | 0 |
| 1859 | CH₃N-piperidinyl | 3 | phenyl-N(CH₂CH₂Cl)₂, Cl | 0 |
| 1860 | CH₃N-piperidinyl | 3 | phenyl-N(CH₂CH₂Cl)₂, CH₃ | 0 |
| 1861 | CH₃N-piperidinyl | 3 | phenyl-N(CH₂CH₂Cl)₂, CF₃ | 0 |
| 1862 | CH₃N-piperidinyl | 3 | phenyl-N(CH₂CH₂Cl)₂, CN | 0 |
| 1863 | CH₃N-piperidinyl | 3 | phenyl-N(CH₂CH₂Cl)₂, Cl | 0 |

TABLE 2-continued
| Compd. No. | R₁ | m | R₂ | n |
|---|---|---|---|---|
| 1864 | 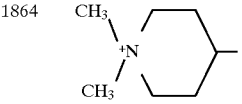 | 1 | 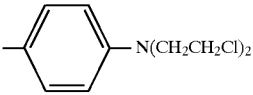 | 0 |
| 1865 | 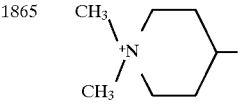 | 1 | 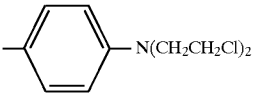 | 3 |
| 1866 | 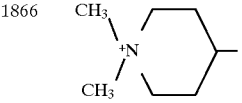 | 1 | 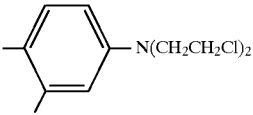 | 0 |
| 1867 | 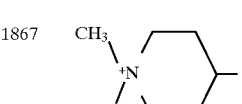 | 1 | 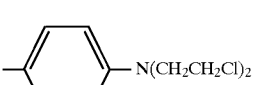 | 0 |
| 1868 | 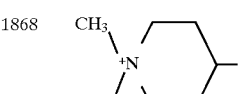 | 1 | 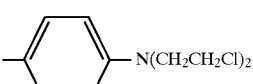 | 0 |
| 1869 | 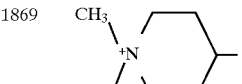 | 1 | 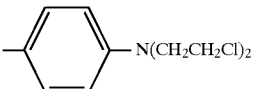 | 0 |
| 1870 | 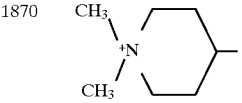 | 1 | 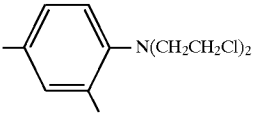 | 0 |
| 1871 | 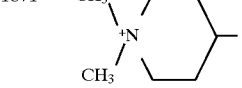 | 1 | 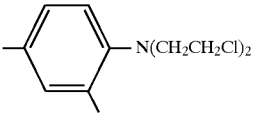 | 0 |
| 1872 | 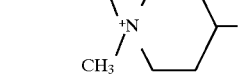 | 2 | 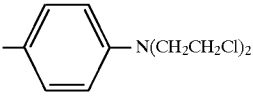 | 0 |
| 1873 | 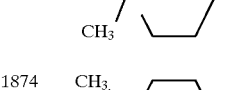 | 2 | 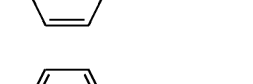 | 3 |
| 1874 | 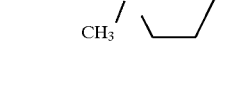 | 2 | 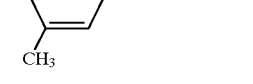 | 0 |

TABLE 2-continued
| Compd. No. | R₁ | m | R₂ | n |
|---|---|---|---|---|
| 1875 | 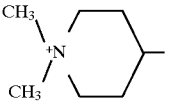 | 2 | 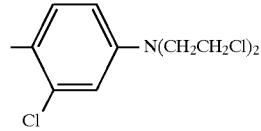 | 0 |
| 1876 | 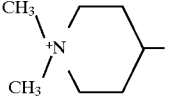 | 2 | 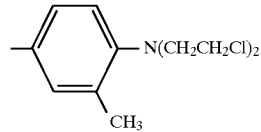 | 0 |
| 1877 | 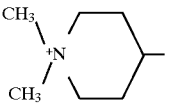 | 2 | 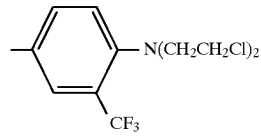 | 0 |
| 1878 | 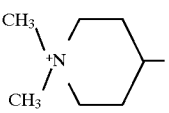 | 2 | 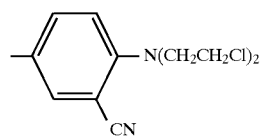 | 0 |
| 1879 | 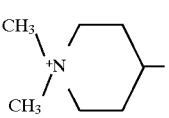 | 2 | 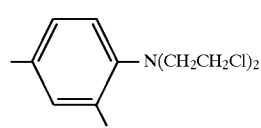 | 0 |
| 1880 | 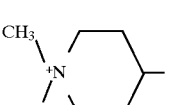 | 3 | 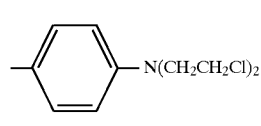 | 0 |
| 1881 | 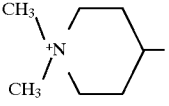 | 3 | 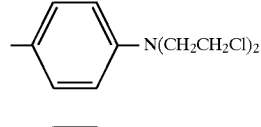 | 3 |
| 1882 | 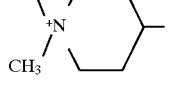 | 3 | 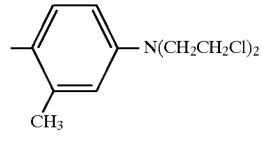 | 0 |
| 1883 | 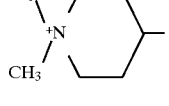 | 3 | 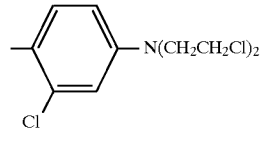 | 0 |
| 1884 | 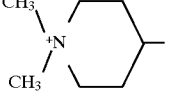 | 3 | 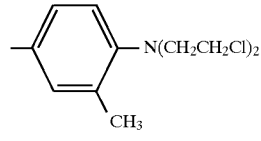 | 0 |
| 1885 | 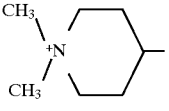 | 3 | 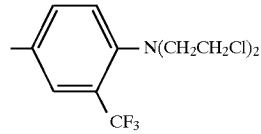 | 0 |

TABLE 2-continued
| Compd. No. | R₁ | m | R₂ | n |
|---|---|---|---|---|
| 1886 | 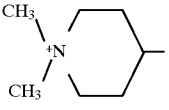 | 3 | 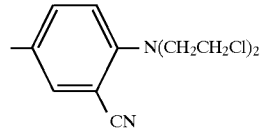 | 0 |
| 1887 | 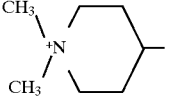 | 3 | 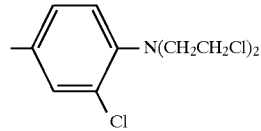 | 0 |
| 1888 | CH₃—S— | 3 | 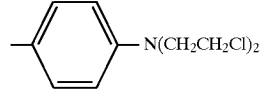 | 0 |
| 1889 | CH₃—S— | 3 | 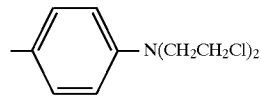 | 3 |
| 1890 | CH₃—S— | 3 | 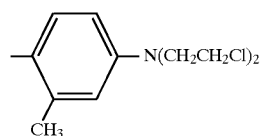 | 0 |
| 1891 | CH₃—S— | 3 | 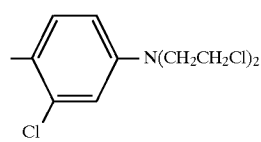 | 0 |
| 1892 | CH₃—S— | 3 | 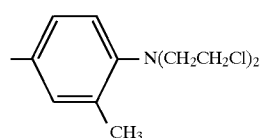 | 0 |
| 1893 | CH₃—S— | 3 | 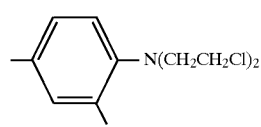 | 0 |
| 1894 | CH₃—S— | 3 | 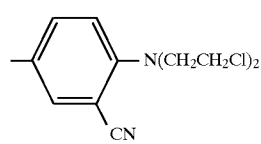 | 0 |
| 1895 | CH₃—S— | 3 | 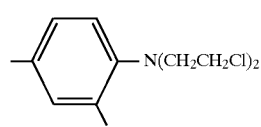 | 0 |
| 1896 | CH₃—S— | 4 | 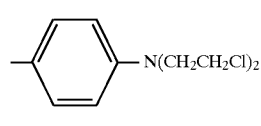 | 0 |
| 1897 | CH₃—S— | 4 | 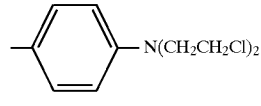 | 3 |

TABLE 2-continued

| Compd. No. | R₁ | m | R₂ | n |
|---|---|---|---|---|
| 1898 | CH₃—S— | 4 | 4-N(CH₂CH₂Cl)₂, 3-CH₃-phenyl | 0 |
| 1899 | CH₃—S— | 4 | 4-N(CH₂CH₂Cl)₂, 2-Cl-phenyl | 0 |
| 1900 | CH₃—S— | 4 | 3-N(CH₂CH₂Cl)₂, 2-CH₃-phenyl | 0 |
| 1901 | CH₃—S— | 4 | 3-N(CH₂CH₂Cl)₂, 2-CF₃-phenyl | 0 |
| 1902 | CH₃—S— | 4 | 3-N(CH₂CH₂Cl)₂, 2-CN-phenyl | 0 |
| 1903 | CH₃—S— | 4 | 3-N(CH₂CH₂Cl)₂, 2-Cl-phenyl | 0 |
| 1904 | CH₃—S— | 1 | 4-N(CH₂CH₂Cl)₂-phenyl | 0 |
| 1905 | CH₃—S— | 1 | 4-N(CH₂CH₂Cl)₂-phenyl | 3 |
| 1906 | CH₃—S— | 1 | 4-N(CH₂CH₂Cl)₂, 3-CH₃-phenyl | 0 |
| 1907 | CH₃—S— | 1 | 4-N(CH₂CH₂Cl)₂, 2-Cl-phenyl | 0 |
| 1908 | CH₃—S— | 1 | 3-N(CH₂CH₂Cl)₂, 2-CH₃-phenyl | 0 |

TABLE 2-continued

| Compd. No. | R₁ | m | R₂ | n |
|---|---|---|---|---|
| 1909 | CH₃—S— | 1 | -C₆H₃(CF₃)-N(CH₂CH₂Cl)₂ (2-CF₃) | 0 |
| 1910 | CH₃—S— | 1 | -C₆H₃(CN)-N(CH₂CH₂Cl)₂ (2-CN) | 0 |
| 1911 | CH₃—S— | 1 | -C₆H₃(Cl)-N(CH₂CH₂Cl)₂ (2-Cl) | 0 |
| 1912 | (CH₃)₂S⁺— | 4 | -C₆H₄-N(CH₂CH₂Cl)₂ | 0 |
| 1913 | (CH₃)₂S⁺— | 4 | -C₆H₄-N(CH₂CH₂Cl)₂ | 3 |
| 1914 | (CH₃)₂S⁺— | 4 | -C₆H₃(CH₃)-N(CH₂CH₂Cl)₂ (3-CH₃) | 0 |
| 1915 | (CH₃)₂S⁺— | 4 | -C₆H₃(Cl)-N(CH₂CH₂Cl)₂ (3-Cl) | 0 |
| 1916 | (CH₃)₂S⁺— | 4 | -C₆H₃(CH₃)-N(CH₂CH₂Cl)₂ (2-CH₃) | 0 |
| 1917 | (CH₃)₂S⁺— | 4 | -C₆H₃(CF₃)-N(CH₂CH₂Cl)₂ (2-CF₃) | 0 |
| 1918 | (CH₃)₂S⁺— | 4 | -C₆H₃(CN)-N(CH₂CH₂Cl)₂ (2-CN) | 0 |
| 1919 | (CH₃)₂S⁺— | 4 | -C₆H₃(Cl)-N(CH₂CH₂Cl)₂ (2-Cl) | 0 |

TABLE 2-continued

| Compd. No. | R₁ | m | R₂ | n |
|---|---|---|---|---|
| 1920 | CH₃CH₂—S⁺(CH₃)— | 2 | —C₆H₄—N(CH₂CH₂Cl)₂ | 0 |
| 1921 | CH₃CH₂—S⁺(CH₃)— | 2 | —C₆H₄—N(CH₂CH₂Cl)₂ | 3 |
| 1922 | CH₃CH₂—S⁺(CH₃)— | 2 | —C₆H₃(CH₃)—N(CH₂CH₂Cl)₂ | 0 |
| 1923 | CH₃CH₂—S⁺(CH₃)— | 2 | —C₆H₃(Cl)—N(CH₂CH₂Cl)₂ | 0 |
| 1924 | CH₃CH₂—S⁺(CH₃)— | 2 | —C₆H₃(CH₃)—N(CH₂CH₂Cl)₂ | 0 |
| 1925 | CH₃CH₂—S⁺(CH₃)— | 2 | —C₆H₃(CF₃)—N(CH₂CH₂Cl)₂ | 0 |
| 1926 | CH₃CH₂—S⁺(CH₃)— | 2 | —C₆H₃(CN)—N(CH₂CH₂Cl)₂ | 0 |
| 1927 | CH₃CH₂—S⁺(CH₃)— | 2 | —C₆H₃(Cl)—N(CH₂CH₂Cl)₂ | 0 |

R₁(CH₂)ₘCONH—[pyrrole]—[benzimidazole]—CONH(CH₂)ₙR₂

| 1928 | CH₃—S⁺(CH₃)— | 2 | —C₆H₄—N(CH₂CH₂Cl)₂ | 0 |
| 1929 | CH₃—S⁺(CH₃)— | 2 | —C₆H₄—N(CH₂CH₂Cl)₂ | 3 |
| 1930 | CH₃—S⁺(CH₃)— | 2 | —C₆H₃(CH₃)—N(CH₂CH₂Cl)₂ | 0 |

TABLE 2-continued
| Compd. No. | R₁ | m | R₂ | n |
|---|---|---|---|---|
| 1931 |  | 2 | 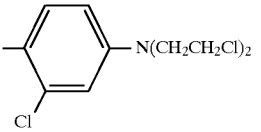 | 0 |
| 1932 |  | 2 | 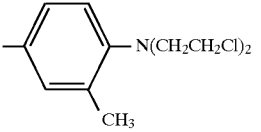 | 0 |
| 1933 |  | 2 | 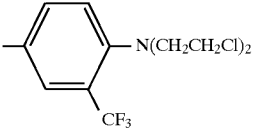 | 0 |
| 1934 |  | 2 | 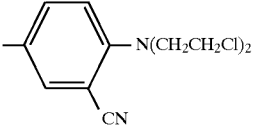 | 0 |
| 1935 |  | 2 | 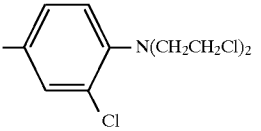 | 0 |
| 1936 | 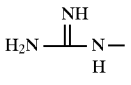 | 1 | 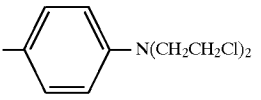 | 0 |
| 1937 | 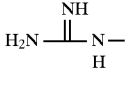 | 1 | 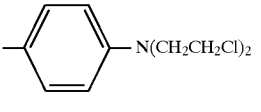 | 3 |
| 1938 | 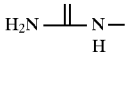 | 1 | 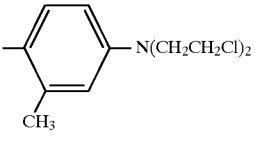 | 0 |
| 1939 | 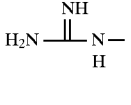 | 1 | 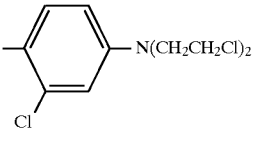 | 0 |
| 1940 | 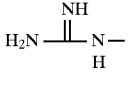 | 1 | 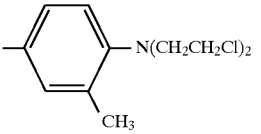 | 0 |
| 1941 | 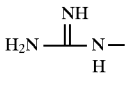 | 1 | 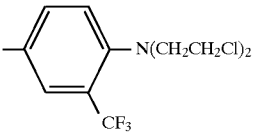 | 0 |

TABLE 2-continued

| Compd. No. | R₁ | m | R₂ | n |
|---|---|---|---|---|
| 1942 | H₂N-C(=NH)-N(H)- | 1 | -C₆H₃(CN)-N(CH₂CH₂Cl)₂ | 0 |
| 1943 | H₂N-C(=NH)-N(H)- | 1 | -C₆H₃(Cl)-N(CH₂CH₂Cl)₂ | 0 |

R₁(CH₂)ₘCONH—[1-methyl-pyrrole]—[2-(1H-benzimidazol-2-yl)]—CONH(CH₂)ₙR₂

| Compd. No. | R₁ | m | R₂ | n |
|---|---|---|---|---|
| 1944 | 2-pyridyl | 1 | -C₆H₄-N(CH₂CH₂Cl)₂ | 0 |
| 1945 | 2-pyridyl | 1 | -C₆H₄-N(CH₂CH₂Cl)₂ | 3 |
| 1946 | 2-pyridyl | 1 | -C₆H₃(CH₃)-N(CH₂CH₂Cl)₂ | 0 |
| 1947 | 2-pyridyl | 1 | -C₆H₃(Cl)-N(CH₂CH₂Cl)₂ | 0 |
| 1948 | 2-pyridyl | 1 | -C₆H₃(CH₃)-N(CH₂CH₂Cl)₂ | 0 |
| 1949 | 2-pyridyl | 1 | -C₆H₃(CF₃)-N(CH₂CH₂Cl)₂ | 0 |
| 1950 | 2-pyridyl | 1 | -C₆H₃(CN)-N(CH₂CH₂Cl)₂ | 0 |
| 1951 | 2-pyridyl | 1 | -C₆H₃(Cl)-N(CH₂CH₂Cl)₂ | 0 |

TABLE 2-continued
| Compd. No. | R₁ | m | R₂ | n |
|---|---|---|---|---|
| 1952 | 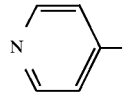 | 1 | 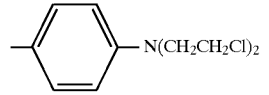 —N(CH₂CH₂Cl)₂ | 0 |
| 1953 | 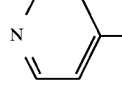 | 1 | 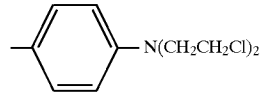 —N(CH₂CH₂Cl)₂ | 3 |
| 1954 | 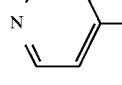 | 1 | 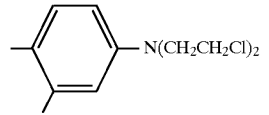 —N(CH₂CH₂Cl)₂, CH₃ | 0 |
| 1955 | 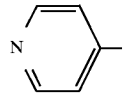 | 1 | 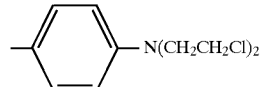 —N(CH₂CH₂Cl)₂, Cl | 0 |
| 1956 | 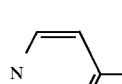 | 1 | 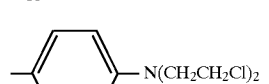 —N(CH₂CH₂Cl)₂, CH₃ | 0 |
| 1957 |  | 1 | 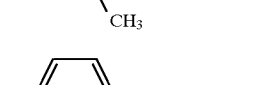 —N(CH₂CH₂Cl)₂, CF₃ | 0 |
| 1958 | 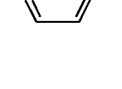 | 1 | 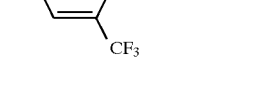 —N(CH₂CH₂Cl)₂, CN | 0 |
| 1959 | 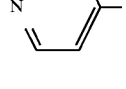 | 1 | 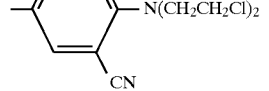 —N(CH₂CH₂Cl)₂, Cl | 0 |
| 1960 | 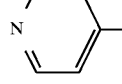 | 1 | 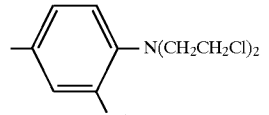 —N(CH₂CH₂Cl)₂ | 0 |
| 1961 | 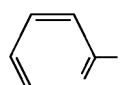 | 1 | 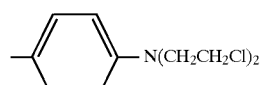 —N(CH₂CH₂Cl)₂ | 3 |
| 1962 | 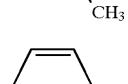 | 1 | 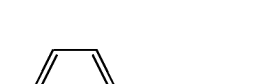 —N(CH₂CH₂Cl)₂, CH₃ | 0 |

TABLE 2-continued
| Compd. No. | R₁ | m | R₂ | n |
|---|---|---|---|---|
| 1963 | 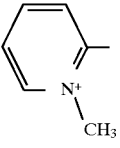 | 1 | 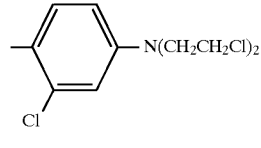 | 0 |
| 1964 | 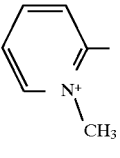 | 1 | 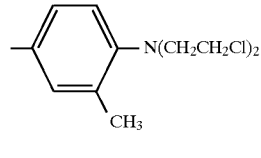 | 0 |
| 1965 | 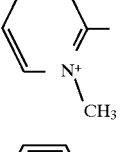 | 1 | 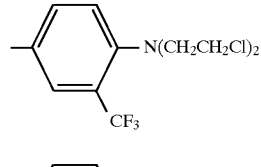 | 0 |
| 1966 | 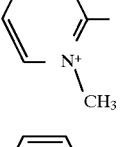 | 1 | 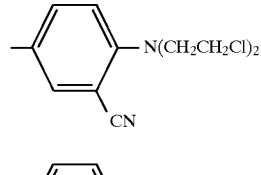 | 0 |
| 1967 | 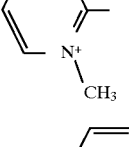 | 1 | 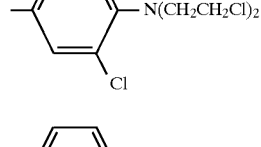 | 0 |
| 1968 | 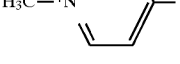 | 1 | 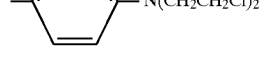 | 0 |
| 1969 | 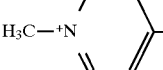 | 1 | 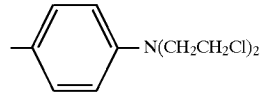 | 3 |
| 1970 | 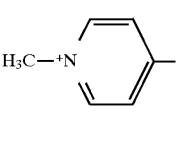 | 1 | 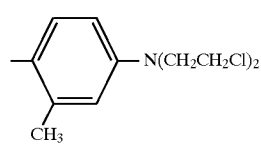 | 0 |
| 1971 | 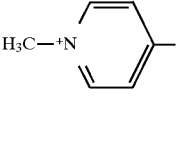 | 1 | 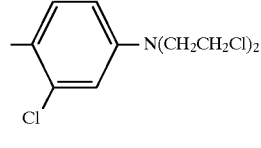 | 0 |
| 1972 | 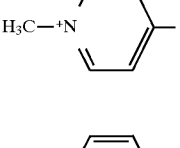 | 1 | 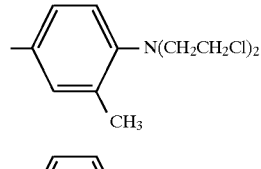 | 0 |
| 1973 | 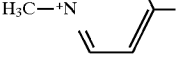 | 1 | 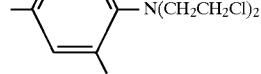 | 0 |

TABLE 2-continued

| Compd. No. | R₁ | m | R₂ | n |
|---|---|---|---|---|
| 1974 | H₃C—⁺N-pyridyl | 1 | 4-N(CH₂CH₂Cl)₂, 2-CN phenyl | 0 |
| 1975 | H₃C—⁺N-pyridyl | 1 | 4-N(CH₂CH₂Cl)₂, 2-Cl phenyl | 0 |
| 1976 | morpholino | 3 | 4-N(CH₂CH₂Cl)₂ phenyl | 0 |
| 1977 | morpholino | 3 | 4-N(CH₂CH₂Cl)₂ phenyl | 3 |
| 1978 | morpholino | 3 | 4-N(CH₂CH₂Cl)₂, 3-CH₃ phenyl | 0 |
| 1979 | morpholino | 3 | 3-N(CH₂CH₂Cl)₂, 4-Cl phenyl | 0 |
| 1980 | morpholino | 3 | 4-N(CH₂CH₂Cl)₂, 2-CH₃ phenyl | 0 |
| 1981 | morpholino | 3 | 4-N(CH₂CH₂Cl)₂, 2-CF₃ phenyl | 0 |
| 1982 | morpholino | 3 | 4-N(CH₂CH₂Cl)₂, 2-CN phenyl | 0 |
| 1983 | morpholino | 3 | 4-N(CH₂CH₂Cl)₂, 2-Cl phenyl | 0 |
| 1984 | morpholino | 2 | 4-N(CH₂CH₂Cl)₂ phenyl | 0 |
| 1985 | morpholino | 2 | 4-N(CH₂CH₂Cl)₂ phenyl | 3 |

TABLE 2-continued

| Compd. No. | R₁ | m | R₂ | n |
|---|---|---|---|---|
| 1986 | O(CH₂CH₂)₂N— (morpholino) | 2 | 4-[N(CH₂CH₂Cl)₂]-3-CH₃-C₆H₃— | 0 |
| 1987 | O(CH₂CH₂)₂N— | 2 | 4-[N(CH₂CH₂Cl)₂]-3-Cl-C₆H₃— | 0 |
| 1988 | O(CH₂CH₂)₂N⁺(CH₃)— | 2 | 4-[N(CH₂CH₂Cl)₂]-C₆H₄— | 0 |
| 1989 | O(CH₂CH₂)₂N⁺(CH₃)— | 2 | 4-[N(CH₂CH₂Cl)₂]-C₆H₄— | 3 |
| 1990 | O(CH₂CH₂)₂N⁺(CH₃)— | 2 | 4-[N(CH₂CH₂Cl)₂]-3-CH₃-C₆H₃— | 0 |
| 1991 | O(CH₂CH₂)₂N⁺(CH₃)— | 2 | 4-[N(CH₂CH₂Cl)₂]-3-Cl-C₆H₃— | 0 |
| 1992 | S(CH₂CH₂)₂N— | 2 | 4-[N(CH₂CH₂Cl)₂]-C₆H₄— | 0 |
| 1993 | S(CH₂CH₂)₂N— | 2 | 4-[N(CH₂CH₂Cl)₂]-C₆H₄— | 3 |
| 1994 | S(CH₂CH₂)₂N— | 2 | 4-[N(CH₂CH₂Cl)₂]-3-CH₃-C₆H₃— | 0 |
| 1995 | S(CH₂CH₂)₂N— | 2 | 4-[N(CH₂CH₂Cl)₂]-3-Cl-C₆H₃— | 0 |
| 1996 | H₃C—S⁺(CH₂CH₂)₂N— | 2 | 4-[N(CH₂CH₂Cl)₂]-C₆H₄— | 0 |
| 1997 | H₃C—S⁺(CH₂CH₂)₂N— | 2 | 4-[N(CH₂CH₂Cl)₂]-C₆H₄— | 3 |

TABLE 2-continued
| Compd. No. | R₁ | m | R₂ | n |
|---|---|---|---|---|
| 1998 | 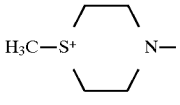 | 2 | 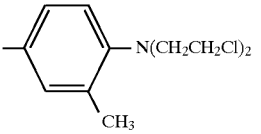 | 0 |
| 1999 | 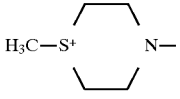 | 2 | 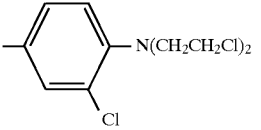 | 0 |
TABLE 3
| Compd. No. | R₁ | m | R₂ | n |
|---|---|---|---|---|
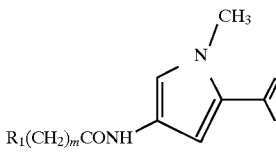
| | | | | |
|---|---|---|---|---|
| 2001 | 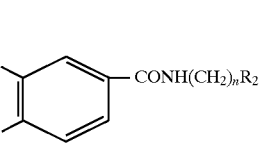 | 0 | 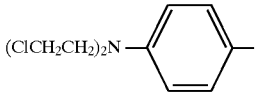 | 0 |
| 2002 | 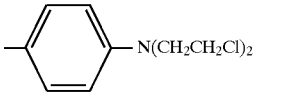 | 0 | 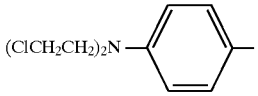 | 1 |
| 2003 | 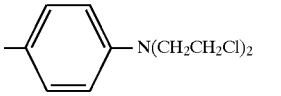 | 0 | 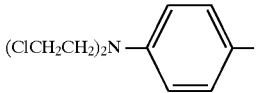 | 2 |
| 2004 | 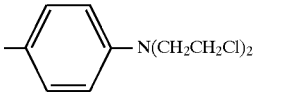 | 0 | 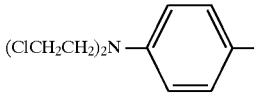 | 3 |
| 2005 | 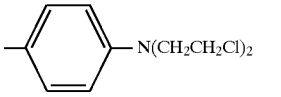 | 0 | 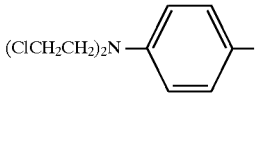 | 0 |
| 2006 | 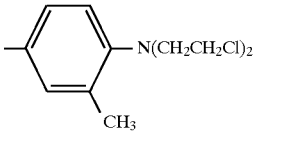 | 0 | 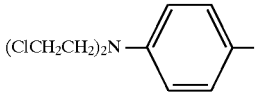 | 0 |
| 2007 | 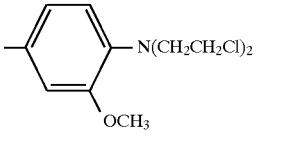 | 0 | 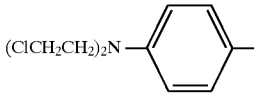 | 0 |
| 2008 | 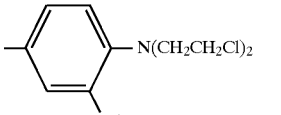 | 0 | 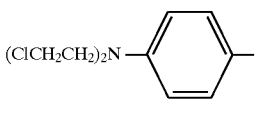 | 0 |

TABLE 3-continued

| Compd. No. | R₁ | m | R₂ | n |
|---|---|---|---|---|
| 2009 | (ClCH₂CH₂)₂N—⟨C₆H₄⟩— | 0 | —⟨C₆H₃⟩(N(CH₂CH₂Cl)₂)(CH₃) | 0 |
| 2010 | (ClCH₂CH₂)₂N—⟨C₆H₄⟩— | 0 | —⟨C₆H₃⟩(N(CH₂CH₂Cl)₂)(OCH₃) | 0 |
| 2011 | (ClCH₂CH₂)₂N—⟨C₆H₄⟩— | 0 | —⟨C₆H₃⟩(N(CH₂CH₂Cl)₂)(Cl) | 0 |
| 2012 | (ClCH₂CH₂)₂N—⟨C₆H₄⟩— | 0 | —⟨C₆H₃⟩(N(CH₂CH₂Cl)₂)(CN) | 0 |
| 2013 | (ClCH₂CH₂)₂N—⟨C₆H₄⟩— | 0 | —⟨C₆H₄⟩—N(CH₂CH₂Cl)₂ | 0 |
| 2014 | (ClCH₂CH₂)₂N—⟨C₆H₄⟩— | 0 | —⟨C₆H₄⟩—N(CH₂CH₃)(CH₂CH₂Cl) | 0 |
| 2015 | (ClCH₂CH₂)₂N—⟨C₆H₄⟩— | 0 | —⟨C₆H₄⟩—N(CH₂CH₃)(CH₂CH₂Cl) | 0 |
| 2016 | (ClCH₂CH₂)₂N—⟨C₆H₄⟩— | 1 | —⟨C₆H₄⟩—N(CH₂CH₂Cl)₂ | 0 |
| 2017 | (ClCH₂CH₂)₂N—⟨C₆H₄⟩— | 1 | —⟨C₆H₄⟩—N(CH₂CH₂Cl)₂ | 1 |
| 2018 | (ClCH₂CH₂)₂N—⟨C₆H₄⟩— | 1 | —⟨C₆H₄⟩—N(CH₂CH₂Cl)₂ | 2 |
| 2019 | (ClCH₂CH₂)₂N—⟨C₆H₄⟩— | 1 | —⟨C₆H₄⟩—N(CH₂CH₂Cl)₂ | 3 |
| 2020 | (ClCH₂CH₂)₂N—⟨C₆H₄⟩— | 1 | —⟨C₆H₃⟩(N(CH₂CH₂Cl)₂)(CH₃) | 0 |

TABLE 3-continued

| Compd. No. | R₁ | m | R₂ | n |
|---|---|---|---|---|
| 2021 | (ClCH₂CH₂)₂N—⟨C₆H₄⟩— | 1 | —⟨C₆H₃(OCH₃)⟩—N(CH₂CH₂Cl)₂ | 0 |
| 2022 | (ClCH₂CH₂)₂N—⟨C₆H₄⟩— | 1 | —⟨C₆H₃(Cl)⟩—N(CH₂CH₂Cl)₂ | 0 |
| 2023 | (ClCH₂CH₂)₂N—⟨C₆H₄⟩— | 1 | —⟨C₆H₃(CN)⟩—N(CH₂CH₂Cl)₂ | 0 |
| 2024 | (ClCH₂CH₂)₂N—⟨C₆H₄⟩— | 1 | —⟨C₆H₃(CH₃)⟩—N(CH₂CH₂Cl)₂ | 0 |
| 2025 | (ClCH₂CH₂)₂N—⟨C₆H₄⟩— | 1 | —⟨C₆H₃(OCH₃)⟩—N(CH₂CH₂Cl)₂ | 0 |
| 2026 | (ClCH₂CH₂)₂N—⟨C₆H₄⟩— | 1 | —⟨C₆H₃(Cl)⟩—N(CH₂CH₂Cl)₂ | 0 |
| 2027 | (ClCH₂CH₂)₂N—⟨C₆H₄⟩— | 1 | —⟨C₆H₃(CN)⟩—N(CH₂CH₂Cl)₂ | 0 |
| 2028 | (ClCH₂CH₂)₂N—⟨C₆H₄⟩— | 1 | —⟨C₆H₄⟩—N(CH₂CH₂Cl)₂ | 0 |
| 2029 | (ClCH₂CH₂)₂N—⟨C₆H₄⟩— | 1 | —⟨C₆H₄⟩—N(CH₂CH₃)(CH₂CH₂Cl) | 0 |
| 2030 | (ClCH₂CH₂)₂N—⟨C₆H₄⟩— | 1 | —⟨C₆H₄⟩—N(CH₂CH₃)(CH₂CH₂Cl) | 0 |
| 2031 | (ClCH₂CH₂)₂N—⟨C₆H₄⟩— | 2 | —⟨C₆H₄⟩—N(CH₂CH₂Cl)₂ | 0 |
| 2032 | (ClCH₂CH₂)₂N—⟨C₆H₄⟩— | 2 | —⟨C₆H₄⟩—N(CH₂CH₂Cl)₂ | 1 |

TABLE 3-continued

| Compd. No. | R$_1$ | m | R$_2$ | n |
|---|---|---|---|---|
| 2033 | (ClCH$_2$CH$_2$)$_2$N—⟨C$_6$H$_4$⟩— | 2 | —⟨C$_6$H$_4$⟩—N(CH$_2$CH$_2$Cl)$_2$ | 2 |
| 2034 | (ClCH$_2$CH$_2$)$_2$N—⟨C$_6$H$_4$⟩— | 2 | —⟨C$_6$H$_4$⟩—N(CH$_2$CH$_2$Cl)$_2$ | 3 |
| 2035 | (ClCH$_2$CH$_2$)$_2$N—⟨C$_6$H$_4$⟩— | 2 | —⟨C$_6$H$_3$(CH$_3$)⟩—N(CH$_2$CH$_2$Cl)$_2$ | 0 |
| 2036 | (ClCH$_2$CH$_2$)$_2$N—⟨C$_6$H$_4$⟩— | 2 | —⟨C$_6$H$_3$(OCH$_3$)⟩—N(CH$_2$CH$_2$Cl)$_2$ | 0 |
| 2037 | (ClCH$_2$CH$_2$)$_2$N—⟨C$_6$H$_4$⟩— | 2 | —⟨C$_6$H$_3$(Cl)⟩—N(CH$_2$CH$_2$Cl)$_2$ | 0 |
| 2038 | (ClCH$_2$CH$_2$)$_2$N—⟨C$_6$H$_4$⟩— | 2 | —⟨C$_6$H$_3$(CN)⟩—N(CH$_2$CH$_2$Cl)$_2$ | 0 |
| 2039 | (ClCH$_2$CH$_2$)$_2$N—⟨C$_6$H$_4$⟩— | 2 | —⟨C$_6$H$_3$(CH$_3$)⟩—N(CH$_2$CH$_2$Cl)$_2$ | 0 |
| 2040 | (ClCH$_2$CH$_2$)$_2$N—⟨C$_6$H$_4$⟩— | 2 | —⟨C$_6$H$_3$(OCH$_3$)⟩—N(CH$_2$CH$_2$Cl)$_2$ | 0 |
| 2041 | (ClCH$_2$CH$_2$)$_2$N—⟨C$_6$H$_4$⟩— | 2 | —⟨C$_6$H$_3$(Cl)⟩—N(CH$_2$CH$_2$Cl)$_2$ | 0 |
| 2042 | (ClCH$_2$CH$_2$)$_2$N—⟨C$_6$H$_4$⟩— | 2 | —⟨C$_6$H$_3$(CN)⟩—N(CH$_2$CH$_2$Cl)$_2$ | 0 |
| 2043 | (ClCH$_2$CH$_2$)$_2$N—⟨C$_6$H$_4$⟩— | 2 | —⟨C$_6$H$_4$⟩—N(CH$_2$CH$_2$Cl)$_2$ | 0 |

TABLE 3-continued

| Compd. No. | R₁ | m | R₂ | n |
|---|---|---|---|---|
| 2044 | (ClCH₂CH₂)₂N—⟨C₆H₄⟩— | 2 | —⟨C₆H₄⟩—N(CH₂CH₃)(CH₂CH₂Cl) | 0 |
| 2045 | (ClCH₂CH₂)₂N—⟨C₆H₄⟩— | 2 | —⟨C₆H₄⟩—N(CH₂CH₃)(CH₂CH₂Cl) (meta) | 0 |
| 2046 | (ClCH₂CH₂)₂N—⟨C₆H₄⟩— | 3 | —⟨C₆H₄⟩—N(CH₂CH₂Cl)₂ | 0 |
| 2047 | (ClCH₂CH₂)₂N—⟨C₆H₄⟩— | 3 | —⟨C₆H₄⟩—N(CH₂CH₂Cl)₂ | 1 |
| 2048 | (ClCH₂CH₂)₂N—⟨C₆H₄⟩— | 3 | —⟨C₆H₄⟩—N(CH₂CH₂Cl)₂ | 2 |
| 2049 | (ClCH₂CH₂)₂N—⟨C₆H₄⟩— | 3 | —⟨C₆H₄⟩—N(CH₂CH₂Cl)₂ | 3 |
| 2050 | (ClCH₂CH₂)₂N—⟨C₆H₄⟩— | 3 | —⟨C₆H₃(CH₃)⟩—N(CH₂CH₂Cl)₂ | 0 |
| 2051 | (ClCH₂CH₂)₂N—⟨C₆H₄⟩— | 3 | —⟨C₆H₃(OCH₃)⟩—N(CH₂CH₂Cl)₂ | 0 |
| 2052 | (ClCH₂CH₂)₂N—⟨C₆H₄⟩— | 3 | —⟨C₆H₃(Cl)⟩—N(CH₂CH₂Cl)₂ | 0 |
| 2053 | (ClCH₂CH₂)₂N—⟨C₆H₄⟩— | 3 | —⟨C₆H₃(CN)⟩—N(CH₂CH₂Cl)₂ | 0 |
| 2054 | (ClCH₂CH₂)₂N—⟨C₆H₄⟩— | 3 | —⟨C₆H₃(CH₃)⟩—N(CH₂CH₂Cl)₂ | 0 |
| 2055 | (ClCH₂CH₂)₂N—⟨C₆H₄⟩— | 3 | —⟨C₆H₃(OCH₃)⟩—N(CH₂CH₂Cl)₂ | 0 |

TABLE 3-continued

| Compd. No. | R₁ | m | R₂ | n |
|---|---|---|---|---|
| 2056 | (ClCH₂CH₂)₂N—C₆H₄— | 3 | —C₆H₃(Cl)—N(CH₂CH₂Cl)₂ | 0 |
| 2057 | (ClCH₂CH₂)₂N—C₆H₄— | 3 | —C₆H₃(CN)—N(CH₂CH₂Cl)₂ | 0 |
| 2058 | (ClCH₂CH₂)₂N—C₆H₄— | 3 | —C₆H₄—N(CH₂CH₂Cl)₂ (meta) | 0 |
| 2059 | (ClCH₂CH₂)₂N—C₆H₄— | 3 | —C₆H₄—N(CH₂CH₃)(CH₂CH₂Cl) | 0 |
| 2060 | (ClCH₂CH₂)₂N—C₆H₄— | 3 | —C₆H₄—N(CH₂CH₃)(CH₂CH₂Cl) (meta) | 0 |
| 2061 | (ClCH₂CH₂)₂N—C₆H₄— | 0 | —C₆H₄—N(CH₂CH₂Cl)₂ | 0 |
| 2062 | (ClCH₂CH₂)₂N—C₆H₄— | 0 | —C₆H₄—N(CH₂CH₂Cl)₂ | 1 |
| 2063 | (ClCH₂CH₂)₂N—C₆H₄— | 0 | —C₆H₄—N(CH₂CH₂Cl)₂ | 2 |
| 2064 | (ClCH₂CH₂)₂N—C₆H₄— | 0 | —C₆H₄—N(CH₂CH₂Cl)₂ | 3 |
| 2065 | (ClCH₂CH₂)₂N—C₆H₄— | 0 | —C₆H₃(CH₃)—N(CH₂CH₂Cl)₂ | 0 |
| 2066 | (ClCH₂CH₂)₂N—C₆H₄— | 0 | —C₆H₃(OCH₃)—N(CH₂CH₂Cl)₂ | 0 |
| 2067 | (ClCH₂CH₂)₂N—C₆H₄— | 0 | —C₆H₃(Cl)—N(CH₂CH₂Cl)₂ | 0 |

TABLE 3-continued

| Compd. No. | R₁ | m | R₂ | n |
|---|---|---|---|---|
| 2068 | (ClCH₂CH₂)₂N—C₆H₄— | 0 | —C₆H₃(CN)—N(CH₂CH₂Cl)₂ | 0 |
| 2069 | (ClCH₂CH₂)₂N—C₆H₄— | 0 | —C₆H₃(CH₃)—N(CH₂CH₂Cl)₂ | 0 |
| 2070 | (ClCH₂CH₂)₂N—C₆H₄— | 0 | —C₆H₃(OCH₃)—N(CH₂CH₂Cl)₂ | 0 |
| 2071 | (ClCH₂CH₂)₂N—C₆H₄— | 0 | —C₆H₃(Cl)—N(CH₂CH₂Cl)₂ | 0 |
| 2072 | (ClCH₂CH₂)₂N—C₆H₄— | 0 | —C₆H₃(CN)—N(CH₂CH₂Cl)₂ | 0 |
| 2073 | (ClCH₂CH₂)₂N—C₆H₄— | 0 | —C₆H₄—N(CH₂CH₂Cl)₂ | 0 |
| 2074 | (ClCH₂CH₂)₂N—C₆H₄— | 0 | —C₆H₄—N(CH₂CH₃)(CH₂CH₂Cl) | 0 |
| 2075 | (ClCH₂CH₂)₂N—C₆H₄— | 0 | —C₆H₄—N(CH₂CH₃)(CH₂CH₂Cl) | 0 |
| 2076 | ClCH₂CH₂—N(CH₂CH₃)—C₆H₄— | 0 | —C₆H₄—N(CH₂CH₂Cl)₂ | 0 |
| 2077 | ClCH₂CH₂—N(CH₂CH₃)—C₆H₄— | 0 | —C₆H₄—N(CH₂CH₂Cl)₂ | 1 |
| 2078 | ClCH₂CH₂—N(CH₂CH₃)—C₆H₄— | 0 | —C₆H₄—N(CH₂CH₂Cl)₂ | 2 |
| 2079 | ClCH₂CH₂—N(CH₂CH₃)—C₆H₄— | 0 | —C₆H₄—N(CH₂CH₂Cl)₂ | 3 |

TABLE 3-continued
| Compd. No. | R₁ | m | R₂ | n |
|---|---|---|---|---|
| 2080 | 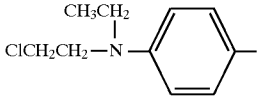 | 0 | 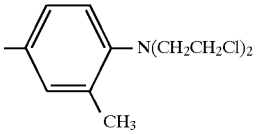 | 0 |
| 2081 | 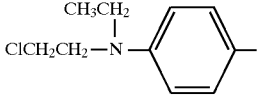 | 0 | 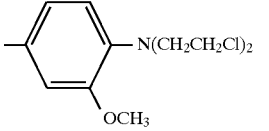 | 0 |
| 2082 | 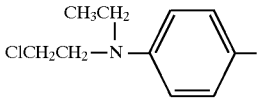 | 0 | 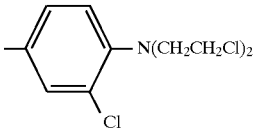 | 0 |
| 2083 | 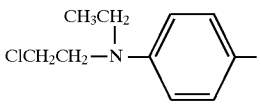 | 0 | 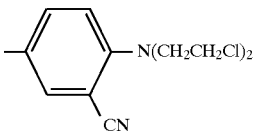 | 0 |
| 2084 | 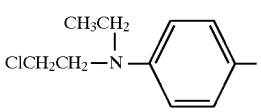 | 0 | 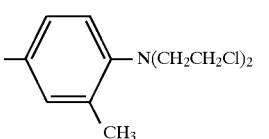 | 0 |
| 2085 | 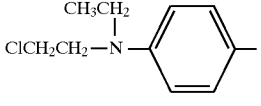 | 0 | 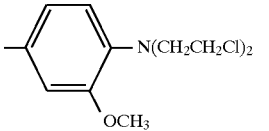 | 0 |
| 2086 | 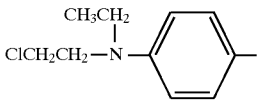 | 0 | 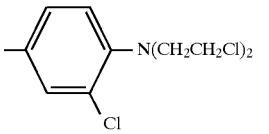 | 0 |
| 2087 | 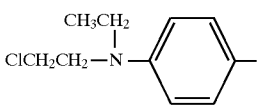 | 0 | 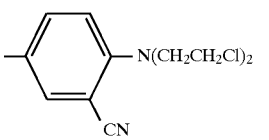 | 0 |
| 2088 | 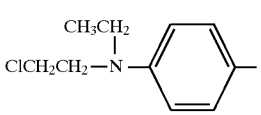 | 0 | 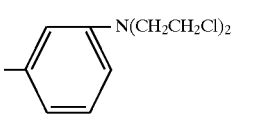 | 0 |
| 2089 | 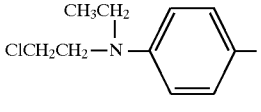 | 0 | 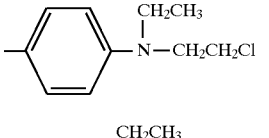 | 0 |
| 2090 | 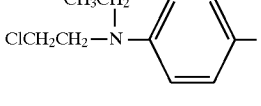 | 0 | 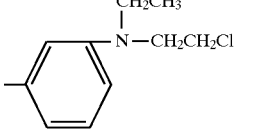 | 0 |

TABLE 3-continued

| Compd. No. | R$_1$ | m | R$_2$ | n |
|---|---|---|---|---|
| 2091 | ClCH$_2$CH$_2$—N(CH$_3$CH$_2$)—C$_6$H$_4$— | 0 | —C$_6$H$_4$—N(CH$_2$CH$_2$Cl)$_2$ | 0 |
| 2092 | ClCH$_2$CH$_2$—N(CH$_3$CH$_2$)—C$_6$H$_4$— | 0 | —C$_6$H$_4$—N(CH$_2$CH$_2$Cl)$_2$ | 1 |
| 2093 | ClCH$_2$CH$_2$—N(CH$_3$CH$_2$)—C$_6$H$_4$— | 0 | —C$_6$H$_4$—N(CH$_2$CH$_2$Cl)$_2$ | 2 |
| 2094 | ClCH$_2$CH$_2$—N(CH$_3$CH$_2$)—C$_6$H$_4$— | 0 | —C$_6$H$_4$—N(CH$_2$CH$_2$Cl)$_2$ | 3 |
| 2095 | ClCH$_2$CH$_2$—N(CH$_3$CH$_2$)—C$_6$H$_4$— | 0 | —C$_6$H$_3$(CH$_3$)—N(CH$_2$CH$_2$Cl)$_2$ | 0 |
| 2096 | ClCH$_2$CH$_2$—N(CH$_3$CH$_2$)—C$_6$H$_4$— | 0 | —C$_6$H$_3$(OCH$_3$)—N(CH$_2$CH$_2$Cl)$_2$ | 0 |
| 2097 | ClCH$_2$CH$_2$—N(CH$_3$CH$_2$)—C$_6$H$_4$— | 0 | —C$_6$H$_3$(Cl)—N(CH$_2$CH$_2$Cl)$_2$ | 0 |
| 2098 | ClCH$_2$CH$_2$—N(CH$_3$CH$_2$)—C$_6$H$_4$— | 0 | —C$_6$H$_3$(CN)—N(CH$_2$CH$_2$Cl)$_2$ | 0 |
| 2099 | ClCH$_2$CH$_2$—N(CH$_3$CH$_2$)—C$_6$H$_4$— | 0 | —C$_6$H$_3$(CH$_3$)—N(CH$_2$CH$_2$Cl)$_2$ | 0 |
| 2100 | ClCH$_2$CH$_2$—N(CH$_3$CH$_2$)—C$_6$H$_4$— | 0 | —C$_6$H$_3$(OCH$_3$)—N(CH$_2$CH$_2$Cl)$_2$ | 0 |
| 2101 | ClCH$_2$CH$_2$—N(CH$_3$CH$_2$)—C$_6$H$_4$— | 0 | —C$_6$H$_3$(Cl)—N(CH$_2$CH$_2$Cl)$_2$ | 0 |

TABLE 3-continued
| Compd. No. | R₁ | m | R₂ | n |
|---|---|---|---|---|
| 2102 | 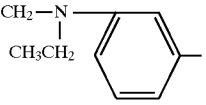 | 0 | 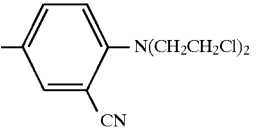 | 0 |
| 2103 | 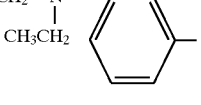 | 0 | 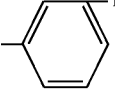 | 0 |
| 2104 | 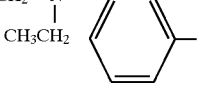 | 0 | 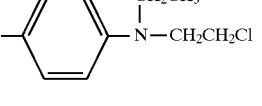 | 0 |
| 2105 | 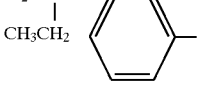 | 0 | 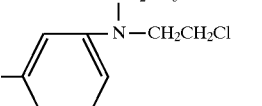 | 0 |
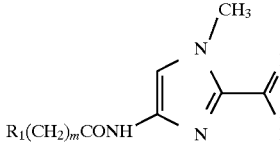
| | | | | |
|---|---|---|---|---|
| 2106 | 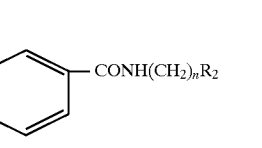 | 0 | 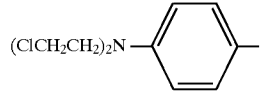 | 0 |
| 2107 | 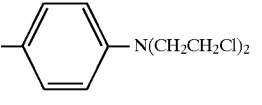 | 0 | 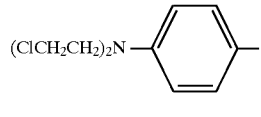 | 0 |
| 2108 | 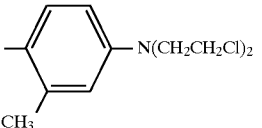 | 0 | 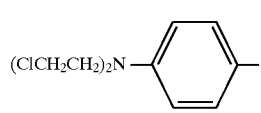 | 0 |
| 2109 | 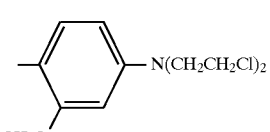 | 0 | 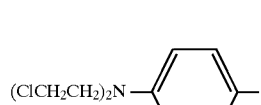 | 0 |
| 2110 | 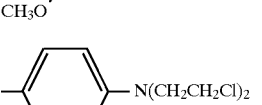 | 0 | 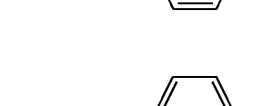 | 0 |
| 2111 |  | 0 | 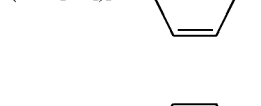 | 0 |

TABLE 3-continued

| Compd. No. | R₁ | m | R₂ | n |
|---|---|---|---|---|
| 2112 | (ClCH₂CH₂)₂N—⟨C₆H₄⟩— | 0 | —⟨C₆H₃(Cl)⟩—N(CH₂CH₂Cl)₂ | 0 |
| 2113 | (ClCH₂CH₂)₂N—⟨C₆H₄⟩— | 0 | —⟨C₆H₃(CF₃)⟩—N(CH₂CH₂Cl)₂ | 0 |
| 2114 | (ClCH₂CH₂)₂N—⟨C₆H₄⟩— | 3 | —⟨C₆H₄⟩—N(CH₂CH₂Cl)₂ | 0 |
| 2115 | (ClCH₂CH₂)₂N—⟨C₆H₄⟩— | 3 | —⟨C₆H₃(CH₃)⟩—N(CH₂CH₂Cl)₂ | 0 |
| 2116 | (ClCH₂CH₂)₂N—⟨C₆H₄⟩— | 3 | —⟨C₆H₃(OCH₃)⟩—N(CH₂CH₂Cl)₂ | 0 |
| 2117 | (ClCH₂CH₂)₂N—⟨C₆H₄⟩— | 3 | —⟨C₆H₃(Cl)⟩—N(CH₂CH₂Cl)₂ | 0 |
| 2118 | (ClCH₂CH₂)₂N—⟨C₆H₄⟩— | 3 | —⟨C₆H₃(CH₃)⟩—N(CH₂CH₂Cl)₂ | 0 |
| 2119 | (ClCH₂CH₂)₂N—⟨C₆H₄⟩— | 3 | —⟨C₆H₃(OCH₃)⟩—N(CH₂CH₂Cl)₂ | 0 |
| 2120 | (ClCH₂CH₂)₂N—⟨C₆H₄⟩— | 3 | —⟨C₆H₃(Cl)⟩—N(CH₂CH₂Cl)₂ | 0 |
| 2121 | (ClCH₂CH₂)₂N—⟨C₆H₄⟩— | 3 | —⟨C₆H₃(CF₃)⟩—N(CH₂CH₂Cl)₂ | 0 |

R₁(CH₂)ₘCONH—[thiophene]—[benzimidazole]—CONH(CH₂)ₙR₂

TABLE 3-continued

| Compd. No. | R₁ | m | R₂ | n |
|---|---|---|---|---|
| 2122 | (ClCH₂CH₂)₂N—C₆H₄— | 0 | —C₆H₄—N(CH₂CH₂Cl)₂ | 0 |
| 2123 | (ClCH₂CH₂)₂N—C₆H₄— | 0 | —C₆H₃(CH₃)—N(CH₂CH₂Cl)₂ | 0 |
| 2124 | (ClCH₂CH₂)₂N—C₆H₄— | 0 | —C₆H₃(OCH₃)—N(CH₂CH₂Cl)₂ | 0 |
| 2125 | (ClCH₂CH₂)₂N—C₆H₄— | 0 | —C₆H₃(Cl)—N(CH₂CH₂Cl)₂ | 0 |
| 2126 | (ClCH₂CH₂)₂N—C₆H₄— | 0 | —C₆H₃(CH₃)—N(CH₂CH₂Cl)₂ | 0 |
| 2127 | (ClCH₂CH₂)₂N—C₆H₄— | 0 | —C₆H₃(OCH₃)—N(CH₂CH₂Cl)₂ | 0 |
| 2128 | (ClCH₂CH₂)₂N—C₆H₄— | 0 | —C₆H₃(Cl)—N(CH₂CH₂Cl)₂ | 0 |
| 2129 | (ClCH₂CH₂)₂N—C₆H₄— | 0 | —C₆H₃(CF₃)—N(CH₂CH₂Cl)₂ | 0 |
| 2130 | (ClCH₂CH₂)₂N—C₆H₄— | 3 | —C₆H₄—N(CH₂CH₂Cl)₂ | 0 |
| 2131 | (ClCH₂CH₂)₂N—C₆H₄— | 3 | —C₆H₃(CH₃)—N(CH₂CH₂Cl)₂ | 0 |
| 2132 | (ClCH₂CH₂)₂N—C₆H₄— | 3 | —C₆H₃(OCH₃)—N(CH₂CH₂Cl)₂ | 0 |

TABLE 3-continued

| Compd. No. | R₁ | m | R₂ | n |
|---|---|---|---|---|
| 2133 | (ClCH₂CH₂)₂N—⟨C₆H₄⟩— | 3 | —⟨C₆H₃(Cl)⟩—N(CH₂CH₂Cl)₂ | 0 |
| 2134 | (ClCH₂CH₂)₂N—⟨C₆H₄⟩— | 3 | —⟨C₆H₃(CH₃)⟩—N(CH₂CH₂Cl)₂ | 0 |
| 2135 | (ClCH₂CH₂)₂N—⟨C₆H₄⟩— | 3 | —⟨C₆H₃(OCH₃)⟩—N(CH₂CH₂Cl)₂ | 0 |
| 2136 | (ClCH₂CH₂)₂N—⟨C₆H₄⟩— | 3 | —⟨C₆H₃(Cl)⟩—N(CH₂CH₂Cl)₂ | 0 |
| 2137 | (ClCH₂CH₂)₂N—⟨C₆H₄⟩— | 3 | —⟨C₆H₃(CF₃)⟩—N(CH₂CH₂Cl)₂ | 0 |

R₁(CH₂)ₘCONH—⟨thiophene⟩—⟨benzimidazole⟩—CONH(CH₂)ₙR₂

| Compd. No. | R₁ | m | R₂ | n |
|---|---|---|---|---|
| 2138 | (ClCH₂CH₂)₂N—⟨C₆H₄⟩— | 0 | —⟨C₆H₄⟩—N(CH₂CH₂Cl)₂ | 0 |
| 2139 | (ClCH₂CH₂)₂N—⟨C₆H₄⟩— | 0 | —⟨C₆H₃(CH₃)⟩—N(CH₂CH₂Cl)₂ | 0 |
| 2140 | (ClCH₂CH₂)₂N—⟨C₆H₄⟩— | 0 | —⟨C₆H₃(CH₃O)⟩—N(CH₂CH₂Cl)₂ | 0 |
| 2141 | (ClCH₂CH₂)₂N—⟨C₆H₄⟩— | 0 | —⟨C₆H₃(Cl)⟩—N(CH₂CH₂Cl)₂ | 0 |
| 2142 | (ClCH₂CH₂)₂N—⟨C₆H₄⟩— | 0 | —⟨C₆H₃(CH₃)⟩—N(CH₂CH₂Cl)₂ | 0 |

TABLE 3-continued

| Compd. No. | R$_1$ | m | R$_2$ | n |
|---|---|---|---|---|
| 2143 | (ClCH$_2$CH$_2$)$_2$N—⌬— | 0 | —⌬(N(CH$_2$CH$_2$Cl)$_2$)(OCH$_3$) | 0 |
| 2144 | (ClCH$_2$CH$_2$)$_2$N—⌬— | 0 | —⌬(N(CH$_2$CH$_2$Cl)$_2$)(Cl) | 0 |
| 2145 | (ClCH$_2$CH$_2$)$_2$N—⌬— | 0 | —⌬(N(CH$_2$CH$_2$Cl)$_2$)(CF$_3$) | 0 |
| 2146 | (ClCH$_2$CH$_2$)$_2$N—⌬— | 3 | —⌬—N(CH$_2$CH$_2$Cl)$_2$ | 0 |
| 2147 | (ClCH$_2$CH$_2$)$_2$N—⌬— | 3 | —⌬(N(CH$_2$CH$_2$Cl)$_2$)(CH$_3$) | 0 |
| 2148 | (ClCH$_2$CH$_2$)$_2$N—⌬— | 3 | —⌬(N(CH$_2$CH$_2$Cl)$_2$)(CH$_3$O) | 0 |
| 2149 | (ClCH$_2$CH$_2$)$_2$N—⌬— | 3 | —⌬(N(CH$_2$CH$_2$Cl)$_2$)(Cl) | 0 |
| 2150 | (ClCH$_2$CH$_2$)$_2$N—⌬— | 3 | —⌬(N(CH$_2$CH$_2$Cl)$_2$)(CH$_3$) | 0 |
| 2151 | (ClCH$_2$CH$_2$)$_2$N—⌬— | 3 | —⌬(N(CH$_2$CH$_2$Cl)$_2$)(OCH$_3$) | 0 |
| 2152 | (ClCH$_2$CH$_2$)$_2$N—⌬— | 3 | —⌬(N(CH$_2$CH$_2$Cl)$_2$)(Cl) | 0 |
| 2153 | (ClCH$_2$CH$_2$)$_2$N—⌬— | 3 | —⌬(N(CH$_2$CH$_2$Cl)$_2$)(CF$_3$) | 0 |

TABLE 3-continued

| Compd. No. | R₁ | m | R₂ | n |
|---|---|---|---|---|

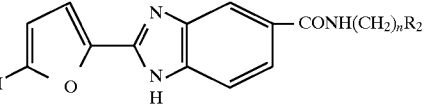

| 2154 | (ClCH₂CH₂)₂N—C₆H₄— | 0 | —C₆H₄—N(CH₂CH₂Cl)₂ | 0 |
| 2155 | (ClCH₂CH₂)₂N—C₆H₄— | 0 | —C₆H₃(CH₃)—N(CH₂CH₂Cl)₂ | 0 |
| 2156 | (ClCH₂CH₂)₂N—C₆H₄— | 0 | —C₆H₃(OCH₃)—N(CH₂CH₂Cl)₂ | 0 |
| 2157 | (ClCH₂CH₂)₂N—C₆H₄— | 0 | —C₆H₃(Cl)—N(CH₂CH₂Cl)₂ | 0 |
| 2158 | (ClCH₂CH₂)₂N—C₆H₄— | 0 | —C₆H₃(CH₃)—N(CH₂CH₂Cl)₂ | 0 |
| 2159 | (ClCH₂CH₂)₂N—C₆H₄— | 0 | —C₆H₃(OCH₃)—N(CH₂CH₂Cl)₂ | 0 |
| 2160 | (ClCH₂CH₂)₂N—C₆H₄— | 0 | —C₆H₃(Cl)—N(CH₂CH₂Cl)₂ | 0 |
| 2161 | (ClCH₂CH₂)₂N—C₆H₄— | 0 | —C₆H₃(CF₃)—N(CH₂CH₂Cl)₂ | 0 |
| 2162 | (ClCH₂CH₂)₂N—C₆H₄— | 3 | —C₆H₄—N(CH₂CH₂Cl)₂ | 0 |
| 2163 | (ClCH₂CH₂)₂N—C₆H₄— | 3 | —C₆H₃(CH₃)—N(CH₂CH₂Cl)₂ | 0 |

TABLE 3-continued
| Compd. No. | R$_1$ | m | R$_2$ | n |
|---|---|---|---|---|
| 2164 | (ClCH$_2$CH$_2$)$_2$N—C$_6$H$_4$— | 3 | —C$_6$H$_3$(OCH$_3$)—N(CH$_2$CH$_2$Cl)$_2$ | 0 |
| 2165 | (ClCH$_2$CH$_2$)$_2$N—C$_6$H$_4$— | 3 | —C$_6$H$_3$(Cl)—N(CH$_2$CH$_2$Cl)$_2$ | 0 |
| 2166 | (ClCH$_2$CH$_2$)$_2$N—C$_6$H$_4$— | 3 | —C$_6$H$_3$(CH$_3$)—N(CH$_2$CH$_2$Cl)$_2$ | 0 |
| 2167 | (ClCH$_2$CH$_2$)$_2$N—C$_6$H$_4$— | 3 | —C$_6$H$_3$(OCH$_3$)—N(CH$_2$CH$_2$Cl)$_2$ | 0 |
| 2168 | (ClCH$_2$CH$_2$)$_2$N—C$_6$H$_4$— | 3 | —C$_6$H$_3$(Cl)—N(CH$_2$CH$_2$Cl)$_2$ | 0 |
| 2169 | (ClCH$_2$CH$_2$)$_2$N—C$_6$H$_4$— | 3 | —C$_6$H$_3$(CF$_3$)—N(CH$_2$CH$_2$Cl)$_2$ | 0 |
TABLE 4
| Compd. No. | |
|---|---|
| 3001 | 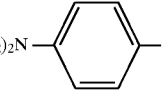 |
| 3002 | 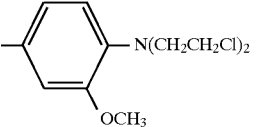 |
| 3003 | 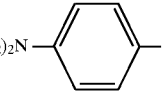 |
| 3004 | 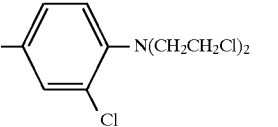 |
| 3005 | 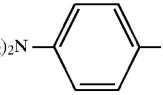 |
| 3006 | 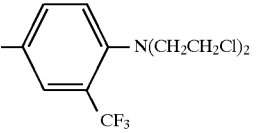 |
| 3007 | 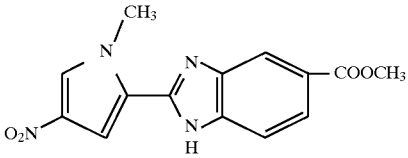 |

TABLE 4-continued

| Compd. No. | Structure |
|---|---|
| 3008 | (5-nitrofuran-2-yl)–benzimidazole-COOCH₃ |
| 3009 | (N-methyl-4-nitropyrrol-2-yl)–benzimidazole-COCH₂CH₃ |
| 3010 | (4-nitropyrrol-2-yl)–benzimidazole-COCH₂CH₃ |
| 3011 | (5-nitropyrrol-2-yl)–benzimidazole-COCH₂CH₃ |
| 3012 | (3-nitro-enamine)–benzimidazole-COCH₂CH₃ |
| 3013 | (N-methyl-nitro-enamine)–benzimidazole-COCH₂CH₃ |
| 3014 | (5-nitrothien-3-yl)–benzimidazole-COCH₂CH₃ |
| 3015 | (5-nitrothien-2-yl)–benzimidazole-COCH₂CH₃ |
| 3016 | (5-nitrofuran-2-yl)–benzimidazole-COCH₂CH₃ |
| 3017 | (N-methyl-4-nitropyrrol-2-yl)–benzimidazole-COOH |
| 3018 | (4-nitropyrrol-2-yl)–benzimidazole-COOH |
| 3019 | (5-nitropyrrol-2-yl)–benzimidazole-COOH |
| 3020 | (3-nitro-enamine)–benzimidazole-COOH |
| 3021 | (N-methyl-nitro-enamine)–benzimidazole-COOH |
| 3022 | (5-nitrothien-3-yl)–benzimidazole-COOH |
| 3023 | (5-nitrothien-2-yl)–benzimidazole-COOH |
| 3024 | (5-nitrofuran-2-yl)–benzimidazole-COOH |
| 3025 | (N-methyl-4-aminopyrrol-2-yl)–benzimidazole-COOCH₃ |
| 3026 | (4-aminopyrrol-2-yl)–benzimidazole-COOCH₃ |
| 3027 | (5-aminopyrrol-2-yl)–benzimidazole-COOCH₃ |
| 3028 | (3-amino-enamine)–benzimidazole-COOCH₃ |

TABLE 4-continued

| Compd. No. | Structure |
|---|---|
| 3029 | (structure) |
| 3030 | (structure) |
| 3031 | (structure) |
| 3032 | (structure) |
| 3033 | (structure) |
| 3034 | (structure) |
| 3035 | (structure) |
| 3036 | (structure) |
| 3037 | (structure) |
| 3038 | (structure) |
| 3039 | (structure) |
| 3040 | (structure) |
| 3041 | (structure) |
| 3042 | (structure) |
| 3043 | (structure) |
| 3044 | (structure) |
| 3045 | (structure) |
| 3046 | (structure) |
| 3047 | (structure) |
| 3048 | (structure) |

NMR DATA OF EXAMPLES

EXAMPLE 1

(Reaction1)

NMR(DMSO-$d_6$) δ: 9.64(s, 1H), 8.33(s, 1H), 7.65(s, 1H), 3.95(s, 1H)

EXAMPLE 1

(Reaction2)

NMR(DMSO-$d_6$) δ: 8.28(d, 1H), 8.17(s, 1H), 7.86(d, 1H), 7.67(d, 1H), 7.56(d, 1H), 4.19(s, 3H), 3.88(s, 3H)

EXAMPLE 1

(Reaction3)

NMR(DMSO-d$_6$) δ: 8.30(d, 1H), 8.17(s, 1H), 7.85(d, 1H), 7.65(d, 1H), 7.59(d, 1H), 4.20(s, 3H)

EXAMPLE 2

(Reaction2)

NMR(DMSO-d$_6$) δ: 9. 09(s, 2H), 8.85(bs, 0.5H), 8.74(bs, 0.5), 8.71(s, 2H), 8.29(s, 1H), 8.07(s, 0.5H), 7.83–7.54(m, 3.5H), 4.20(s, 3H), 3.63(q, 2H), 2.71(t, 2H)

EXAMPLE 2

(Reaction3)

NMR(DMSO-d$_6$) δ: 9.91(1H, s), 9.03(2H, bs), 8.70(1H, br), 8.62(2H, bs), 8.20–7.90(1H, m), 7.70(1H, m), 7.65–7.4 (1H, m), 7.09(1H, s), 7.05(2H, d), 6.91(1H, br), 6.68 (2H, d), 4.06(3H, s), 3.70(8H,m), 3.62(2H, m), 2.69(2H, m), 2.49 (2H, m), 1.83(2H, m)

EXAMPLE 3

NMR9.92(1H, s), 9.06(2H, bs), 8.73(1H, br), 8.66(2H, bs), 8.20–7.90(1H, m), 7.71(1H, m), 7.65–7.40(1H, m), 7.27(1H, s), 7.05(2H, d), 6.90(1H, br), 6.67(2H, d), 4.06(3H, s), 3.70(8H, m), 3.63(2H, m), 2.70(2H, m), 2.50(2H, m), 2.27(2H, m), 1.83(2H, m),

EXAMPLE 4

NMR (DMSO-d$_6$) δ: 9.90(s, 1H), 8.94(bs, 2H), 8.59(bs, 2H), 8.49(bs, 1H), 8.16(bs, 1H, 7.88(d, 1H)), 7.73(d, 1H), 7.52(bs, 1H), 7.36(d, 1H), 7.13(s, 1H), 6.85(d, 2H), 4.11(s, 3H), 3.80(m, 8H), 3.67(q, 2H), 2.76(t, 2H)

EXAMPLE 5

NMR (DMSO-d$_6$) δ: 10.24(s, 1H), 8.98(bs, 2H), 8.66(bs, 2H), 8.52(bs, 1H), 7.96(s, 1H), 7.92(s, 1H), 7.74(d, 1H), 7.56–7.44(m, 5H), 7.40(d, 1H), 7.16(bs, 1H), 4.12(s, 3H), 3.64(bs, 2H), 2.70(t, 2H)

EXAMPLE 6

NMR(DMSO-d$_6$) δ: 10.5(1H, s), 9.20(2H, bs), 8.85(2H, s), 8.80(1H, br), 8.14(1H, br), 7.77(1H, m), 7.63–7.35(4H, m), 7.33(1H, s), 7.04(1H, s), 4.08(3H, s), 4.07(2H, m), 2.74(2H, m)

EXAMPLE 7

(Reaction1)

NMR(DMSO-d$_6$) δ: 8.55(1H, br), 8.26(1H, s), 8.12(1H, br), 7.75(1H, d), 7.63(1H, br), 7.55(1H, s), 3.60–3.30(2H, m), 2.37(2H, t), 2.22(6H, s), 1.71(2H, q)

EXAMPLE 7

(Reaction2)

NMR(DMSO-d$_6$) δ: 10.4(1H, s), 8.65(1H, br), 8.1(1H, m), 7.80–7.50(2H, m), 7.31(1H, s), 6.99(1H, s), 4.08(3H, s), 4.04(2H, m), 3.4(2H, m), 3.10(2H, m), 2.77(6H, s), 1.93(2H, m)

EXAMPLE 8

NMR(CDCl$_3$+DMSO-d$_6$) δ: 9.39(1H, br), 8.40(1H, br), 8.20(1H, s), 8.09(1H, s), 7.50(2H, br), 7.20(1H, br), 6.86 (1H,s), 5.52(2H, m), 3.99(3H, s), 2.48(2H, t), 6H, s), 1.78 (2H, q)

EXAMPLE 9

NMR(DMSO-d$_6$) δ: 9.80(1H, s), 8.06(1H, s), 7.74(2H, m), 7.25(2H, m), 7.02(2H, d), 7.0 (1H, m), 6.66(2H, d), 3.86(3H, s), 3.38(8H, m), 2.77(4H, m), 2.54(2H , m), 2.48(2H, m), 2.21(2H,m), 1.80(2H, m)

EXAMPLE 10

(Reaction2)

NMR(DMSO-d$_6$) δ: 10.15(1H, s), 8.15(1H, s), 8.14(1H, s), 7.83(2H, m), 7.30(1H, s), 7.25(1H, s), 7.02(1H, s), 3.89(3H, s), 3.78(6H, s), 3.65(3H, s)

EXAMPLE 11

(Reaction1)

NMR(CDCl$_3$+DMSO-d$_6$) δ: 8.10(bs, 1H), 8.02(s, 1H), 7.68(m, 3H), 7.57(s, 1H), 4.26(s, 3H), 34.6(q, 2H), 1.65(m, 2H), 1.25(s, 30H), 0.88(t, 3H)

EXAMPLE 11

(Reaction2)

NMR(DMSO-d$_6$) δ10.04(s, 1H), 8.35–8.29(m, 1H), 8.09 (s, 0.5H), 7.86(s, 0.5H), 7.80(d, 2H, J=8.8), 7.66–7.58(d, 1H), 7.53(d, 0.5H), 7.37(d, 0.5H), 7.34(s, 1H), 7.05 (s, 0.5H), 7.01(s, 0.5H), 6.77(d, 2H), 4.02(s, 3H), 3.73(m, 8H), 3.21(m, 2H)

EXAMPLE 12

NMR(DMSO-d$_6$) δ: 10.08(s, 1H), 8.32(m, 1H), 8.09(s, 1H+0.5H), 7.88(s, 0.5H), 7.66–7.58(d, 1H), 7.54(d, 0.5H), 7.36(d, 0.5H), 7.21(s, 1H), 6.95(s, 1H), 4.00(s, 3H), 3.19(m, 2H), 1.46(m, 2H), 1.15(s, 30H), 0.78(t, 3H)

EXAMPLE 13

(Reaction1)

NMR(CDCl$_3$) δ: 8.04(d, 2H), 7.46(d, 2H), 4.62(s, 2H), 3.92(s, 3H)

EXAMPLE 13

(Reaction2)

NMR(CDCl$_3$) δ: 8.00(d,J=7.8,2H), 7.41(d,J=8.6,2H), 3.92(s, 3H), 3.77(s, 2H), 3.64(t,J=5.1,4H), 2.73(t,J=5.1,4H)

EXAMPLE 13

(Reaction4)

NMR(DMSO-d$_6$) δ: 7.99(d, 2H), 7.74(d, 2H), 4.42(bs, 2H), 3.99(bs, 4H), 3.37(bs, 4H)

EXAMPLE 13

(Reaction6)

NMR(DMSO-d$_6$) δ: 10.44(s, 1H), 9.05(s, 2H), 8.64(s, 2H), 8.18(bs, 1H), 8.01(bs, 1H), 7.75(s, 1H), 7.49(d, 2H), 7.46(d, 2H), 7.17(s, 1H), 4.21(s, 3H), 3.83(s, 2H), 3.66(m, 6H), 2.89(t, 4H), 2.71(t, 2H)

EXAMPLE 14

(Reaction1)

NMR(DMSO-d$_6$) δ: 8.50(t, 0.5H), 8.42(t, 0.5H), 8.29(d, 1H), 8.24(s, 0.5H), 8.00(s, 0.5H), 7.81–7.57(m, 2H), 7.57(s, 1H), 4.19(s, 3H), 3.28(q, 2H), 1.54m, 2H), 1.35(m, 2H), 0.92(t, 3H)

EXAMPLE 14

(Reaction2)

NMR(DMSO-d$_6$, 80° C.) δ: 8.09(bs, 1H), 7.66(bd, 1H), 7.56–7.43(bm, 1H), 7.20(s, 1H), 6.92(s, 1H), 4.07(s, 3H), 3.28(m, 2H), 1.52(m, 2H), 1.35(m, 2H), 0.92(t, 3H)

EXAMPLE 15

NMR(DMSO-d$_6$, 80°) δ: 9.85(s, 1H), 8.11(m, 1H), 7.86 (d, 2H), 7.65(d, 1H), 7.55–7.38(m, 2H), 7.33(s, 1H), 7.08(s,

1H), 6.84(d, 2H), 4.09(s, 3H), 3.78(m, 8H)3.29(q, 2H), 1.56(m, 2H), 1.38(m, 2H), 0.93(3H)

EXAMPLE 16
(Reaction1)
NMR(CDCl$_3$) δ: 7.77(dd, 1H), 7.52(dt, 1H), 7.39(d, 1H), 7.21(t, 1H), 4.39(q, 2H), 3.54 (t, 4H), 3.22(t, 4H), 1.40(t, 3H)

EXAMPLE 16
(Reaction2)
NMR(CDCl$_3$) δ: 8.17(dd, 1H), 7.63(t, 1H), 4.52(q, 6H), 3.78(t, 4H), 1.47(t, 3H)

EXAMPLE 16
(Reaction3)
NMR(CDCl$_3$) δ: 7.85(dd, 1H), 7.56(m, 2H), 7.29(dt, 1H), 3.64(t, 4H), 3.50(t, 4H)

EXAMPLE 16
(Reaction4)
NMR(DMSO-d$_6$) δ: 10.67(s, 1H), 8.94(bs, 2H), 8.58(bs, 2H), 8.48(bt, 1H), 8.09(bs, 1H), 7.52(d, 1H), 7.47(d, 1H), 7.39(d, 1H), 7.37(s, 1H), 7.23(t, 1H), 7.07(s, 1H), 3.69(m, 6H), 3.54(t, 4H), 2.74(s, 2H)

EXAMPLE 17
(Reaction1)
NMR(CDCl$_3$) δ: 7.37–7.22(m, 3H), 6.86(d, 1H), 3.87(s, 3H), 3.82(t, 4H), 3.58(t, 4H)

EXAMPLE 17
(Reaction2)
NMR(CDCl$_3$) δ: 7.44(d, 1H), 7.35(s, 1H), 7.29(t, 1H), 6.88(d, 1H), 3.91(s, 3H), 3.79(t, 4H), 3.66(t, 4H)

EXAMPLE 17
(Reaction3)
NMR(CDCl$_3$+DMSO-d$_6$) δ: 7.48–7.29(m, 3H), 6.90(dd, 1H), 3.82–3.77(m, 4H), 3.69–3.64(m, 4H)

EXAMPLE 17
(Reaction4)
NMR(DMSO-d$_6$) δ: 10.38(s, 1H), 9.02(bs, 2H), 8.73(t, 0.5H), 8.67(t, 0.5H), 8.60(bs, 2H), 8.20(s, 0.5H), 7.96(s, 0.5H), 7.73(d, 0.5H), 7.70(d, 0.5H), 7.63(d, 0.5H), 7.47(d, 0.5H), 7.45(s, 1H), 7.35(d, 1H), 7.28(t, 1H), 7.23(s, 1H), 7.18(s, 0.5H), 7.13 (s, 0.5H), 6.96(d, 1H), 4.11(s, 3H), 3.80(s, 8H), 3.63(m, 2H), 2.68(m, 2H)

EXAMPLE 18
(Reaction1)
NMR(CDCl$_3$) δ: 8.22(d, 2H), 6.98(d, 2H), 4.74(s, 2H), 3.83(s, 3H)

EXAMPLE 18
(Reaction4)
NMR(DMSO-d$_6$) δ: 6.83(2H, d), 6.69(2H, d), 4.67(2H, s), 3.75–3.60(11H, m)

EXAMPLE 18
(Reaction5)
NMR(DMSO-d$_6$) δ: 7.68(1H, br, D$_2$O exchangeable), 6.82(2H, d), 6.71(2H, d), 4.55(2H, s), 3.67(8H, bs)

EXAMPLE 18
(Reaction6)
NMR(DMSO-d$_6$) δ: 10.2(1H, s), 9.03(2H, br), 8.80–8.63 (1H, m), 8.61(2H, br), 8.19(0.6H, m), 7.96(0.4H, m), 7.28–7.76(3H, m), 7.06(1H, m), 6.93(2H, d), 6.73(2H, d), 4.56(2H, s), 4.07(3H, s), 3.67(8H, m), 3.63(2H, m), 2.69 (2H, t)

EXAMPLE 19
(Reaction1)
NMR(CDCl$_3$) δ: 6.46(d, 2H), 6.05(t, 1H), 5.15(bs, 4H), 3.75(s, 3H)

EXAMPLE 19
(Reaction5)
NMR(DMSO-d$_6$) δ: 10.3(1H, s), 9.00(2H, bs), 8.72 (0.42H, m), 8.64(0.58H, m), 8.59(2H, bs), 8.20(0.58H, s), 7.95(0.42H, d, J=2.2), 7.4–7.76(3H, m), 7.15(0.42H, d,J= 2.2), 7.10(0.58H, d,J=2.2), 6.61(2H, s), 6.15(1H, s), 4.11 (3H, s), 3.79(16H, bs), 3.63(2H, m), 2.68(2H, m)

EXAMPLE 20
(Reaction1)
NMR(CDCl$_3$) δ: 7.13(d, 2H), 6.65(d, 2H), 3.84(t, 2H), 3.68(s, 3H), 3.56(t, 2H), 3.52(s, 2H)

EXAMPLE 20
(Reaction2)
NMR(CDCl$_3$) δ: 7.17(d, 2H), 6.65(d, 2H), 3.75–3.69(m, 4H), 3.69(s, 3H), 3.65–3.59(m, 4H), 3.54(s, 2H)

EXAMPLE 20
(Reaction3)
NMR(CDCl$_3$) δ: 7.16(d, 2H), 6.65(d, 2H), 3.75–3.69(d, 4H), 3.65–3.59(m, 4H), 3.55(s, 3H)

EXAMPLE 20
(Reaction4)
NMR(DMSD-d$_6$) δ: 10.12(s, 1H), 9.02(bs, 2H), 8.72(t, 0.5H), 8.64(t, 0.5H), 8.61(bs, 2H), 8.18(s, 0.5H), 7.95(s, 0.5H), 7.72(d, 0.5H), 7.70(d, 0.5H), 7.61(d, 0.5H), 7.46(d, 0.5H), 7.24(s, 1H), 7.17(d, 2H), 6.96(s, 0.5H), 6.91(s, 0.5H), 6.70(d, 2H), 4.05(s, 3H), 3.71(s, 8H), 3.62(m, 2H), 3.44(s, 2H), 2.68(m, 2H)

EXAMPLE 21
(Reaction1)
NMR(CDCl$_3$) δ: 7.84(d, 1H), 7.76(d, 1H), 7.68(dd, 1H), 4.02(s, 3H), 3.97(s, 3H)

EXAMPLE 21
(Reaction2)
NMR(CDCl$_3$) δ: 7.55(dd, 1H), 7.45(d, 1H), 6.66(d, 1H), 4.22(bs, 2H), 3.90(s, 3H), 3.86(s, 3H)

EXAMPLE 21
(Reaction3)
NMR(CDCl$_3$) δ: 7.64(dd, 1H), 7.56(d, 1H), 7.10(d, 1H), 3.92(s, 3H), 3.90(s, 3H), 3.66(t, 4H), 3.37(t, 4H), 2.95(bs, 2H)

EXAMPLE 21
(Reaction4)
NMR(CDCl$_3$) δ: 7.96(d, 1H), 7.70(d, 1H), 7.69(s, 1H), 4.04(s, 3H), 3.95(s, 3H), 3.87(t, 4H), 3.72(t, 4H)

EXAMPLE 21
(Reaction5)
NMR(CDCl$_3$) δ: 7.49(dd, 1H), 7.44(d, 1H), 7.01(d, 1H), 3.84(s, 3H), 3.65(m, 8H)

EXAMPLE 21
(Reaction6)

NMR(DMSO-d$_6$) δ: 10.02(s, 1H), 8.92(bs, 2H), 8.53(bs, 2H), 8.46(bs, 1H), 8.17(bs 0.5H), 7.96(bs, 0.5H), 7.72(d, 1H), 7.56(s, 1H), 7.55(d, 1H), 7.36(s, 1H), 7.13(bs, 1H), 7.07(d, 1H), 4.10(s, 3H), 3.90(s, 3H), 3.64(m, 10H), 2.74(t, 2H)

EXAMPLE 22
(Reaction5)
NMR(DMSO-d$_6$) δ: 9.92(s, 1H), 9.02(bs, 2H), 8.63(bm, 1H), 8.57(bs, 2H), 8.18bs, 0.5H), 7.96(bs, 0.5H), 7.71(bd, 1H), 7.61(bs, 0.5H), 7.47(bs, 0.5H), 7.26(s, 1H), 7.08(d, 2H), 6.91(bs, 1H), 6.66(d, 2H), 4.07(s, 3H), 3.69(s, 8H), 3.65(m, 2H), 2.83(t, 2H), 2.69(t, 2H), 2.52(m, 2H)

EXAMPLE 23
(Reaction3)
NMR(DMSO-d$_6$) δ: 9.78(s, 1H), 8.85(bs, 2H), 8.36(1H+2H), 8.07(s, 1H+1H), 7.86(d, 2H), 7.70(d, 1H), 7.53(d, 1H), 7.32(s, 1H), 7.11(s, 1H), 6.83(d, 2H), 4.09(s, 3H), 3.82(m, 1H), 3.64(m, 2H), 2.74(t, 2H)

EXAMPLE 24
(Reaction2)
NMR(DMSO-d$_6$) δ: 10.67(s, 1H), 8.97(t, 1H), 8.28(s, 1H), 8.14(bs, 3H), 8.00(d, 3H), 7.76(d, 1H), 7.70(s, 1H), 7.59–7.50(m, 3H), 7.37(s, 1H), 4.12(s, 3H), 3.58(q, 2H), 3.03(q, 2H)

EXAMPLE 25
(Reaction3)
NMR(DMSO-d$_6$) δ: 10.34(s, 1H), 8.97(t, 1H), 8.27(s, 1H), 8.15(bs, 2H), 7.99(d, 1H), 7.90(d, 2H), 7.76(d, 1H), 7.66(s, 1H), 7.35(s, 1H), 6.85(d, 2H), 4.11(s, 3H), 3.80(m, 8H), 3.58(q, 2H), 3.02(q, 2H)

EXAMPLE 26
(Reaction2)
NMR(DMSO-d$_6$) δ: 10.33(s, 1H), 9.58(t, 1H), 8.94(s, 1H), 8.84(d, 1H), 8.55(d, 1H), 8.27(s, 1H), 8.04(dd, 1H), 7.98(d, 1H), 7.91(d, 2H), 7.76(d, 1H), 7.65(s, 1H), 7.33(s, 1H), 6.86(d, 2H), 4.70(d, 2H), 4.11(s, 3H), 3.80(bs, 8H)

EXAMPLE 27
NMR(DMSO-d$_6$) δ: 10.15(s, 1H), 9.30(bs, 1H), 9.03(s, 1H), 8.89(d, 1H), 8.54(d, 1H), 8.33(s, 0.5H), 8.25(bs, 0.5H), 8.11(dd, 1H), 7.87(d, 2H), 7.77(d, 1H), 7.57(bm, 1H), 7.43 (s, 1H), 7.15(s, 1H), 6.85(d, 2H), 4.67(d, 2H), 4.37(s, 3H), 4.10(s, 3H), 3.79(m, 8H)

EXAMPLE 28
NMR(DMSO-d$_6$) δ: 9.48(s, 1H), 8.82(bs, 2H), 8.38(bs, 2H), 8.32(t, 1H), 8.06s, 1H), 7.70(d, 1H), 7.50(d, 1H), 7.16(s, 1H), 6.92(s, 1H), 4.05(s, 3H), 3.65(q, 2H), 3.61(t, 2H), 2.75(t, 2H), 2.28(t, 2H), 1.76(m, 2H), 1.63(m, 2H), 1.47(m, 2H)

EXAMPLE 29
(Reaction1)
NMR(DMSO-d$_6$) δ: 10.1(3H, br), 7.20(2H), 6.82(2H, d), 3.73(8H, s)

EXAMPLE 29
(Reaction2)
NMR(DMSO-d$_6$): 10.08(s, 0.5H), 10.01(s, 0.5H), 8.40(s, 0.5H), 8.40(s, 0.5H), 8.10(s, 0.5H), 8.31(s, 1H), 7.91–7.83 (m, 1H), 7.75–7.58(m, 4H), 6.76(d, 2H), 4.21(s, 3H), 3.73(s, 8H)

EXAMPLE 29
(Reaction3)
NMR(DMSO-d$_6$) δ: 10.32(s, 1H), 10.04(s, 0.5H), 9.97(s, 0.5H), 8.32(s, 0.5H), 8.03(s, 0.5H), 7.81(d, 1H), 7.67–7.50 (m, 3H), 7.60–7.20(bs, 5H), 7.30(s, 1H), 6.99(s, 0.5H), 6.97(s, 0.5H), 6.75(d, 2H), 4.09(s, 3H), 4.03(d, 2H), 3.73(s, 8H)

EXAMPLE 30
(Reaction4)
NMR(DMSO-d$_6$) δ: 10.32(s, 1H), 10.00(s, 0.5H), 9.94(s, 0.5H), 8.31(s, 0.5H), 8.03(s, 0.5H), 7.82(d, 0.5H), 7.79(d, 0.5H), 7.68–7.53(m, 3H), 7.50–7.17(bs, 4H), 7.30(s, 1H), 6.99(s, 0.5H), 6.97(s, 0.5H), 6.78(d, 2H), 4.16(t, 4H), 4.09(s, 3H), 4.03(d, 2H), 3.59(t, 4H), 2.01(s, 6H)

EXAMPLE 31
(Reaction3)
NMR(DMSO-d$_6$) δ: 10.32(s, 1H), 8.55(t, 0.4H), 8.48(t, 0.6H), 8.15(s, 0.6H), 7.93s, 0.4H), 7.74(d, 0.4H), 7.70(d, 0.6H), 7.62(s, 1H), 7.60(m, 0.6H), 7.46(d, 0.4H), 7.43–7.20 (bs, 4H), 7.10(d, 2H), 6.98(s, 0.4H), 6.95(s, 0.6H), 6.79(d, 2H), 4.08(s, 3H), 4.03(d, 2H), 3.70(s, 8H), 3.43(q, 2H), 2.75(t, 2H)

EXAMPLE 32
(Reaction1)
NMR(DMSO-d$_6$) δ; 7.07(d, 2H), 6.62(d, 2H), 3.73–3.56 (m, 8H), 2.86(bs, 2H), 2.76–2.72(m, 2H), 2.59–2.51(m, 2H), 1.82–1.74(m, 2H)

EXAMPLE 32
(Reaction2)
NMR(DMSO-d$_6$) δ: 8.52(t, 0.5H), 8.44(t, 0.5H), 8.30(s, 1H), 8.25(s, 0.5H), 7.99(s, 0.5H), 7.79(d, 0.5H), 7.76–7.71 (m, 1H), 7.58–7.54(m, 0.5H), 7.07(d, 2H), 6.67(d, 2H), 4.19(s, 3H), 3.70(s, 8H), 3.32(q, 2H), 2.53(t, 2H), 1.80(m, 2H)

EXAMPLE 32
(Reaction3)
NMR(DMSO-d$_6$) δ: 10.34(s, 1H), 8.47(t, 0.5H), 8.41(t, 0.5H), 8.17(s, 0.5H), 7.94(s, 0.5H), 7.74–7.62(m, 2.5H), 7.48–7.29(m, 5.5H), 7.08(d, 2H), 6.98(s, 0.5H), 6.95(s, 0.5H), 6.67(d, 2H), 4.08(s, 3H), 4.04(q, 2H), 3.30(m, 2H), 1.79(m, 2H)

EXAMPLE 33
NMR(DMSO-d$_6$) δ: 10.13(s, 1H), 9.98–10.02(m, 1H), 8.33(s, 0.5H), 8.03(s, 0.5H), 7.88(d, 2H), 7.81(d, 1H), 7.65(d, 2H), 7.52(d,. 1H), 7.43(s, 1H), 7.13(s, 1H), 6.85(d, 2H), 6.76(d, 2H), 4.11(s, 3H), 3.80(s, 8H), 3.73(s, 8H)

EXAMPLE 34
(Reaction1)
NMR(CDCl$_3$) δ: 9.83(s, 1H), 7.28(s, 1H), 7.12(s, 1H), 4.03(s, 3H)

EXAMPLE 34
(Reaction2)
NMR(CDCl$_3$) δ: 9.85(s, 1H), 7.91(s, 1H), 4.13(s, 3H)

EXAMPLE 34
(Reaction3)
NMR(DMSO-d$_6$) δ: 8.71(s, 1H), 8.31(s, 0.5H), 8.15(s, 0.5H), 7.93(d, 0.5H), 7.60(d, 0.5H), 4.28(s, 3H)

EXAMPLE 34
(Reaction4)

NMR(DMSO-d$_6$) δ: 8.88(bs, 1H), 8.71(s, 1H), 8.32(s, 0.5H), 8.08(s, 0.5H), 7.95–7.60(m, 2H), 4.28(s, 3H), 3.53(q, 2H), 2.81(t, 2H)

EXAMPLE 34
(Reaction5)
NMR(DMSO-d$_6$) δ: 9.04(bs, 2H), 8.83(t, 0.5H), 8.75(s, 1H), 8.73(s, 1H), 8.63(bs, 2H), 8.34(s, 0.5H), 8.07(s, 0.5H), 7.87(d, 0.5H), 7.80(bs, 1H), 7.57(d, 0.5H), 4.28(s, 3H), 3.63(q, 2H), 2.69(t, 2H)

EXAMPLE 34
(Reaction6)
NMR(DMSO-d$_6$) δ: 10.41(s, 1H), 9.03(bs, 2H), 8.74(bs, 1H), 8.60(bs, 2H), 8.20(s, 1H), 7.94(d, 2H), 7.80(d, 1H), 7.68(s, 1H), 7.65(d, 1H), 6.82(d, 2H), 4.20(s, 3H), 3.79(m, 8H), 3.64(m, 2H), 2.70(m, 2H)

EXAMPLE 35
NMR(DMSO-d$_6$) δ: 10.22(s, 1H), 9.01(bs, 2H), 8.74(m, 0.5H), 8.68(m, 0.5H), 8.59(bs, 2H), 8.27(s, 0.5H), 8.05(s, 0.5H), 7.81–7.73(m, 2.5H), 7.57(s, 0.5H), 7.54(s, 1H), 7.05 (d, 2H, J=8.1), 6.67(d, 2H, J=8.1), 4.15(s, 3H), 3.70(s, 8H), 3.63(m, 2H), 2.68(m, 2H), 2.37(t, 2H), 1.84(m, 2H)

EXAMPLE 36
NMR(DMSO-d$_6$) δ: 8.79(bs, 1H), 8.24(s, 1H), 8.16(s, 1H), 7.74(d, 1H), 7.62(d, 1H), 7.56(s, 1H), 4.16(s, 3H), 3.59(m, 2H), 2.62(t, 2H)

EXAMPLE 37
(Reaction1)
NMR(DMSO-d$_6$) δ: 10.13(s, 0.4H), 10.04(s, 0.6H), 8.73 (s, 1H), 8.46(s, 0.6H), 8.13(s, 0.4H), 7.95(d, 0.6H), 7.90–7.82(m, 1H), 7.67–7.60(m, 2.6H), 6.77(d, 2H), 4.29(s, 3H), 3.73(s, 8H)

EXAMPLE 37
(Reaction2)
NMR(DMSO-d$_6$) δ: 10.62(s, 1H), 10.10(s, 1H), 8.30(s, 1H), 7.91(d, 1H, J=8.8), 7.71(d, 1H, J=8.8), 7.65(d, 3H), 7.59(s, 1H), 7.70–7.20(bs, 4H), 6.77(d, 2H), 4.18(s, 3H), 4.13(d, 2H), 3.74(s, 3H)

EXAMPLE 38
(Reaction1)
NMR(DMSO-d$_6$) δ: 8.68(s, 2H), 8.26(bs, 1H), 7.87(d, 1H), 7.67(bd, 1H)

EXAMPLE 38
(Reaction2)
NMR(DMSO-d$_6$) δ: 8.85(m, 1H), 8.68(s, 2H), 8.23(s, 0.5H), 8.05(s, 0.5H), 7.82(d, 0.5H), 7.62(d, 0.5H), 7.74(m, 1H), 3.55(q, 2H), 2.81(t, 2H)

EXAMPLE 38
(Reaction3)
NMR(DMSO-d$_6$) δ: 9.12(bs, 2H), 8.88((m, 1H), 8.78(bs, 2H), 8.72(bs, 2H), 8.26(s, 0.5H), 8.14(s, 0.5H), 7.82(d, 1H), 7.70(d, 0.5H), 7.60(d, 0.5H), 3.65(q, 2H), 2.74(t, 2H)

EXAMPLE 38
(Reaction4)
NMR(DNSO-d$_6$, 80° C.) δ: 8.89(bs, 2H), 8.48(bs, 2H), 8.10(s, 1H), 7.83(s, 1H), 7.74(d, 1H), 7.56(d, 1H), 7.54(s, 1H), 7.06(d, 2H), 6.69(d, 2H), 3.69(s, 8H), 2.76–2.37(m, 8H), 1.90(m, 2H)

EXAMPLE 39
NMR(DMSO-d$_6$) δ: 8.11(s, 1H), 8.00(s, 1H), 7.80–7.45 (m, 8H), 3.77(t, 2H), 2.79t, 2H)

EXAMPLE 40
(Reaction1)
NMR(DMSO-d$_6$) δ: 10.08(s, 0.5H), 10.03(s, 0.5H), 8.69 (bs, 2H), 83.5(s, 0.5H) 8.13(s, 0.5H), 7.87–7.70(m, 2H), 7.60(d, 2H), 6.77(d, 2H), 3.73(s, 8H)

EXAMPLE 40
(Reaction2)
NMR(DMSO-d$_6$) δ: 12.25(s, 1H), 10.31(s, 1H), 8.40(s, 1H), 8.33(s, 1H), 8.10(d, 1H, J=8.8), 7.85(d, 1H, J=8.8), 7.69(m, 2H), 7.63(d, 2H, J=8.8), 7.60–7.25(bs, 4H), 6.77 (d, 2H), 4.22(d, 2H), 3.74(s, 8H)

EXAMPLE 41
(Reaction1)
NMR(DMSO-d$_6$) δ: 8.25(m, 2H), 7.90(m, 2H), 7.72(d, 1H), 3.89(s, 3H)

EXAMPLE 41
(Reaction2)
NMR(DMSO-d$_6$) δ: 8.24(d, 1H), 8.21(s, 1H), 7.95(d, 1H), 7.89((d, 1H), 7.71(d, 1H)

EXAMPLE 41
(Reaction3)
NMR(DMSO-d$_6$) δ: 8.92(t, 1H), 8.27(d, 1H), 8.19(s, 1H), 7.90(d, 1H), 7.81(d, 1H) 7.70(d, 1H), 3.53(q, 2H), 2.78(t, 2H)

EXAMPLE 41
(Reaction4)
NMR(DMSO-d$_6$) δ: 9.11(bs, 2H), 8.88(bs, 1H), 8.71(bs, 2H), 8.22(m, 2H), 8.10(s, 1H), 7.86(d, 1H), 7.68(bs, 1H), 3.67(q, 2H), 2.75(t, 2H)

EXAMPLE 41
(Reaction6)
NMR(CD$_3$OD) δ: 8.04(s, 1H), 7.73(d, 1H), 7.55(d, 1H), 7.55(d, 1H), 7.08(d, 2H), 6.72(d, 1H) 6.65(d, 2H), 3.77(t, 2H), 3.68(t, 4H), 3.61(t, 4H), 2.78(t, 2H), 2.61(t, 2H), 2.43(t, 2H), 2.01(m, 2H)

EXAMPLE 42
NMR(DMSO-d$_6$) δ: 9.08(bs, 2H), 8.77(m, 1H), 8.67(bs, 2H), 8.40(s, 1H), 8.07(bs, 0.8H), 8.02(s, 0.2H), 7.76(bs, 1H), 7.70(d, 1H), 7.53(d, 1H), 6.82(d, 1H), 3.63m, 2H), 2.72(m, 2H)

EXAMPLE 43
NMR(DMSO-d$_6$) δ: 8.3–8.15(m, 1H), 7.91(d, 1H), 7.90 (m, 1H), 7.71–7.64m, 1H), 7.57(d, 1H)

EXAMPLE 44
(Reaction1)
NMR(DMSO-d$_6$) δ: 14.2–11.3(1H, br), 7.89(1H, d, J=8.2), 7.71(1H d, J=8.2), 7.30(1H, d, J=4.4), 7.08(1H, d, J=4.4), 5.8–2.5(2H, br)

EXAMPLE 44
(Reaction2)
NMR(DMSO-d$_6$) δ: 8.90(1H, t, J=5.5), 8.16(1H, s), 7.81 (1H, d, J=8.1), 7.69(1H, d J=8.1), 7.30(1H, d,J=3.7), 7.07 (1H, d, J=3.7), 3.54(2H, q, J=5.9), 5.80–3.15(2H, br), 2.82 (2H, t, J=6.6)

EXAMPLE 44
(Reaction3)
NMR(DMSO-d$_6$) δ: 9.06–8.80(2H, br), 8.67–8.45(2H, br), 8.56(1H, m) 7.99(1H, s), 7.64(1H, d, J=8.8), 7.48(1H, d, J=8.8), 7.00(1H, d, J=3.7), 6.80(1H, d, J=3.7), 3.61(2H, m), 2.66(2H, t, J=6.6)

EXAMPLE 44
(Reaction4)
NMR(DMSO-d$_6$) δ: 9.05(2H, bs), 8.63(2H, bs), 8.62–8.75(1H, m), 8.14–7.92(3H, m), 7.4–7.74(5H, m), 6.96–6.87(1H, m), 6.24(1H, bs), 3.56–3.70(2H, m), 2.70 (2H, t, J=5.9)

EXAMPLE 45
NMR(DMSO-d$_6$) δ: 8.25(1H, s), 7.98(1H, bs), 7.69(1H, dd), 7.51(1H, d), 6.88(1H, d), 5.93(1H, d), 3.67(2H, t), 2.57(2H, t)

EXAMPLE 46
NMR(DMSO-d$_6$) δ: 7. ( ), 6.87(1H, d), 6.66(2H, d), 5.82(1H, d), 2.00(2H, q), 3.77(2 H, t), 2.38(2H, t), 2.61(2H, t), 3.4–3.7(8H, m), 2.78(2H, t)

EXAMPLE 47
(Reaction1)
(DMSO-d$_6$) δ: 8.52(m, 0.5H), 8.46(m, 0.5H), 8.29(s, 1H), 8.24(s, 0.5), 8.00(s, 0.5H), 7.78–7.62(m, 1.5H), 7.57(bs, 1.5H), 4.19(s, 3H), 3.30(m, 2H), 2.30(t, 2H), 1.80(m, 2H)

EXAMPLE 47
(Reaction2)
(DMSO-d$_6$) δ: 9.66(s, 1H), 8.56(t, 0.5H), 8.48(t, 0.5H), 8.29(s, 1H), 8.26(s, 0.5H), 8.00(s, 0.5H), 7.82–7.71(m, 1.5H), 7.58–7.54(m, 1.5H), 7.41(d, 2H), 6.68(d, 2H), 4.19(s, 3H), 3.68(s, 8H), 3.33(m, 2H), 2.34(t, 2H), 1.86(m, 2H)

EXAMPLE 47
(Reaction3)
(DMSO-d$_6$) δ: 10.29(s, 1H), 9.69(s, 1H), 8.5–8.4(m, 1H), 8.19(s, 0.5H), 7.95(s, 0.5H), 7.73(d, 0.5H), 7.69(d, 0.5H), 7.59(d, 0.5H), 7.45(d, 0.5H), 7.43(d, 2H), 7.27s, 1H), 7.60–7.20(bs, 5H), 6.95(d, 1H), 6.68(d, 2H), 4.08(s, 3H), 4.02(s, 2H), 3.68(s, 8H), 3.35(m, 2H), 2.34(t, 2H), 1.86(m, 2H)

EXAMPLE 48
(Reaction1)
(CDCl$_3$) δ: 8.26(d, 1H), 8.07(dd, 1H), 7.32(d, 1H), 2.34 (bs, 2H)

EXAMPLE 48
(Reaction2)
(CDCl$_3$) δ: 8.28(d, 1H), 8.10(dd, 1H), 7.24(d, 1H), 3.75(t, 4H), 3.59(t, 4H)

EXAMPLE 48
(Reaction3)
(DMSO-d$_6$) δ: 10.34(s, 1H), 8.41(bs, 1H), 8.32((d, 1H), 8.03(d, 1H), 7.87(d, 1H), 7.87(d, 1H), 7.73(dd, 1H), 7.71(bs, 1H), 7.59(d, 1H), 7.37(d, 1H), 4.21(s, 3H), 3.61(t, 4H), 3.50(t, 4H)

EXAMPLE 48
(Reaction4)
(DMSO-d$_6$) δ: 10.53(s, 2H), 8.30(s, 1H), 8.04(d, 1H), 7.99(d, 1H), 7.77(d, 1H), 7.74(dd, 1H), 7.66(t, 1H), 7.48(s, 1H), 7.37(4H+1H), 7.18(s, 1H), 4.11(s, 3H), 4.06(d, 2H), 3.62(t, 4H), 3.50(t, 4H)

EXAMPLE 49
(DMSO-d$_6$) δ: 10.55(s, 1H), 10.50(s, 1H), 8.30–7.13(m, 12H), 4.11(s, 3H), 4.07(d, 2H), 3.67(t, 4H), 3.56(t, 4H)

EXAMPLE 50
(Reaction1)
(DMSO-d$_6$) δ: 10.45(s, 0.5H), 10.38(s, 0.5H), 8.62–7.10) (8H), 4.2 1(s, 3H), 3.72(s, 8H)

EXAMPLE 50
(Reaction2)
(DMSO-d$_6$) δ: 10.58(s, 1H), 10.50(s, 1H), 8.30(s, 1H), 8.19(d, 1H), 7.98(dd, 1H), 7.75(d, 1H), 7.64(t, 1H), 7.45(s, 1H), 7.35(4H+1H), 7.15(s, 1H), 4.10(s, 3H), 4.07(d, 2H), 3.73(s, 8H)

EXAMPLE 51
(Reaction1)
(CDCl$_3$) δ: 8.17(d, 1H), 7.54(dd, 1H), 7.39(d, 1H), 3.86–3.23(m, 8H)

EXAMPLE 51
(Reaction2)
(DMSO-d$_6$) δ: 8.02(d, 1H), 6.84(dd, 1H), 6.61(d, 1H), 4.86(bs, 2H), 3.67–3.01(m, 14H)

EXAMPLE 51
(Reaction3)
(CDCl$_3$) δ: 8.17(d, 1H), 6.71(dd, 1H), 6.50(d, 1H), 4.11–3.22(m, 16H)

EXAMPLE 51
(Reaction4)
(DMSO-d$_6$) δ: 9.94(d, 1H), 8.30–6.67(m, 8H), 4.20(s, 3H) 3.76(s, 8H), 3.52(s, 6H), 3.31(s, 2H)

EXAMPLE 51
(Reaction5)
(DMSO-d$_6$) δ: 10.36(s, 1H), 9.98(s, 1H), 8.16–6.66(m, 13H), 4.09(s, 3H), 4.03(d, 2H), 3.77–3.35(m, 16H)

EXAMPLE 52
(Reaction1)
(CDCl$_3$) δ: 8.05(d, 1H), 7.68(s, 1H), 7.52(m, 1H), 3.53(q, 2H), 2.54(t, 2H), 2.26(s, 6H)

EXAMPLE 52
(Reaction2)
(DMSO-d$_6$) δ: 8.27(t, 1H), 7.94(d, 1H), 6.80(dd, 1H), 6.58((d, 1H), 4.86(bs, 2H), 3.55(s, 8H), 3.27(q, 2H), 2.38(t, 2H), 2.34(s, 6H)

EXAMPLE 52
(Reaction3)
(DMSO-d$_6$) δ: 8.42(t, 1H), 7.98(d, 1H), 6.95(dd, 1H), 6.77(d, 1H), 4.37(t, 4H), 3.90(t, H), 2.27(s, 6H) (comment: Signals of ethylene in the dimethylaminoethyl residue could not be identified, because they were overlapped by those of solvent.)

EXAMPLE 52
(Reaction4)
(DMSO-d$_6$) δ: 10.25(bs, 1H), 9.17(bt, 1H), 8.36(d, 1H), 8.32(d, 1H), 8.21(s, 0.5H) 8.09(s, 0.5H), 7.88–7.62(3H), 7.14(d, 1H), 7.03(dd, 1H), 4.22(s, 3H), 3.82(s, 8H) 3.69(m, 2H), 3.30(m, 2H), 2.89(s, 6H)

EXAMPLE 52

(Reaction5)

(DMSO-d$_6$) δ: 10.52(s, 2H), 9.25(bt, 1H), 8.64(bs, 1H), 8.35(d, 1H), 8.19(S, 1H), 7.90(d, 1H), 7.78(d, 1H), 7.67(t, 1H), 7.46(s, 1H), 7.39(bs, 4H), 7.17(s, 1H), 7.03(d, 1H), 4.11(s, 3H), 4.06(d, 2H), 4.00–3.40(m, 10H), 3.32(m, 2H), 2.85(d, 6H)

EXAMPLE 53

(Reaction1)

(DMSO-d$_6$) δ: 10.12(s, 1H), 10.04(s, 1H), 9.97(s, 1H), 8.32(s, 0.5H), 8.25(m, 1H), 8.03(s, 0.5H), 7.80–7.50(m, 4H), 7.40–6.85(bs, 4H), 7.29(s, 1H), 6.96(s, 1H), 6.75d, 2H), 4.08(s, 3H), 3.73(s, 8H), 3.34(m, 2H)

EXAMPLE 53

(Reaction2)

(DMSO-d$_6$) δ: 11.10(s, 1H), 10.20(s, 1H), 8.28(bs, 3H+1H), 7.98(d, 1H), 7.89(t, 1H), 7.76(d, 1H), 7.63(d, 2H), 7.54(s, 1H), 7.23(s, 1H), 7.65–6.90(bs, 4H), 6.77(d, 2H) 4.12(s, 3H), 4.05(m, 1H), 3.74(s, 8H), 3.21(m, 2H), 1.85(m, 2H), 1.57(m, 2H)

EXAMPLE 54

(DMSO-d$_6$) δ: 10.02(s, 0.5H), 9.95(s, 0.5H), 9.71(s, 1H), 8.32(s, 0.5H), 8.01s, 0.5H), 7.80(dd, 1H), 7.66(d, 2H), 7.62(d, 0.5H), 7.49(d, 0.5H), 7.33–7.30(m, 6H), 7.03(d, 1H), 6.76(d, 2H), 4.07(s, 3H), 3.73(s, 8H), 3.48(s, 2H), 3.00(s, 2H), 2.50–2.45(bd, 8H)

EXAMPLE 55

(DMSO-d$_6$) δ: 10.05(s, 0.5H), 9.97(s, 0.5H) 9.93(s, 1H), 8.31(s, 0.5H), 8.03(s, 0.5H), 7.82(d, 0.5H), 7.79(d, 0.5H), 7.65(m, 2.5H), 7.51(d, 0.5H), 7.31(s, 1H), 7.07(s, 6.5H), 7.03(s, 6.5H), 6.75(d, 2H), 4.08(s, 3H), 3.73(s, 8H), 3.38(m, 2H), 3.10(m, 4H), 2.73(m, 4H)

EXAMPLE 56

(DMSO-d6) δ: 11.71(s, 1H), 10.20(s, 1H), 8.29(s, 1H), 7.99(d, 1H), 7.77(d, 1H), 7.73(s, 2H), 7.67(s, 1H), 7.65(d, 2H), 7.36(s, 1H), 6.77(d, 2H), 4.15(s, 3H), 3.74(s, 8H)

EXAMPLE 57

(DMSO-d$_6$) δ: 10.05(s, 1H), 10.04(s, 0.6H), 9.96(s, 0.4H), 8.31(s, 0.6H), 8.02(s, 0.4H), 7.80(m, 1H), 7.64(bs, 3.4H), 7.50(d, 0.6H), 7.27(s, 1H), 7.16(s, 1H), 6.88(m, 2H), 6.75(d, 2H), 4.29(t, 2H), 4.08(s, 3H), 3.73(s, 8H), 2.77(t, 2H)

EXAMPLE 58

(Reaction1)

(DMSO-d$_6$) δ: 10.42(bs, 1H), 8.62(t, 1H), 7.89(d, 1H), 7.88(d, 1H), 7.59(t, 1H), 2.10(s, 3H)

EXAMPLE 58

(Reaction2)

(DMSO-d$_6$) δ: 7.30(m, 3H), 6.97(m, 1H), 6.33(bt, 1H), 3.09(m, 2H), 1.18(t, 3H)

EXAMPLE 58

(Reaction3)

(CDCl$_3$) δ: 7.53–7.46(m, 2H), 7.30(t, 1H), 7.00(dd, 1H), 3.84(t, 2H), 3.56–3.45(m, 4H), 1.93(bs, 1H), 1.20(t, 3H)

EXAMPLE 58

(Reaction4)

(CDCl$_3$) δ: 8.21(s, 1H), 8.15–8.03(m, 2H), 7.67(t, 1H), 3.82(s, 4H), 3.63(m, 2H), 1.30(t, 3H)

EXAMPLE 58

(Reaction5)

(CDCl$_3$) δ: 10.32(bs, 2H), 7.25(t, 1H), 6.74–6.67(m, 2H), 6.62(d, 1H), 3.82–3.60(m, 4H), 3.42(q, 2H), 1.09(t, 3H)

EXAMPLE 58

(Reaction6)

(DMSO-d$_6$) δ: 10.10(s, 0.5H), 10.01(s, 0.5H), 8.41–6.44(m, 9H), 4.21(s, 3H), 3.74(t, 2H), 3.61(t, 2H), 3.46–3.38(m, 2H), 1.12(t, 3H)

EXAMPLE 58

(Reaction7)

(DMSO-d$_6$) δ: 10.44(s, 1H), 10.06(s, 0.5H), 9.97(s, 0.5H), 8.35–6.33(m, 12H), 4.12 (s, 3H), 3.75(t, 2H), 3.61(t, 2H), 3.49–3.39(m, 2H), 1.13(t, 3H)

EXAMPLE 59

(DMSO-d$_6$) δ: 10.02(s, 0.5H), 9.96(s, 0.5H), 9.92(s, 1H), 8.33(s, 0.5H), 8.03(s, 0.5H), 7.82(t, 0.5H), 7.79(d, 0.5H), 7.66(d, 2H), 7.63(d, 0.5H), 7.52(d, 05H), 7.36 (s, 1H), 7.07(dd, 0.5H), 6.97–6.93(m, 2H), 6.76(d, 2H), 6.15(dd, 1H), 4.11(s, 3H), 3.73(s, 8H)

EXAMPLE 60

(DMSO-d$_6$) δ: 9.97(s, 2H), 8.19(bs, 1H), 7.80(d, 1H), 7.64(d, 2H), 7.60(m, 1H), 7.28(s, 1H), 6.93(s, 1H), 6.76(d, 2H), 4.08(s, 3H), 3.73(s, 8H), 2.75(t, 2H), 2.56(t, 2H), 2.09(s, 3H)

EXAMPLE 61

(DMSO-d$_6$) δ: 10.33(s, 0.5H), 10.27(s, 0.5H), 9.99(s, 1H), 8.34(bs, 1H), 8.04(bs, 1H), 7.81(d, 1H), 7.73(d, 1H), 7.53(bd, 1H), 7.36(d, 1H), 7.28(s, 1H+1H), 6.93(bs, 1H), 4.08(s, 1H), 3.61(t, 4H), 3.50(t, 4H), 2.75(t, 2H)2.56(t, 2H), 2.09(s, 3H)

EXAMPLE 62

(Reaction1)

(CDCl$_3$) δ: 7.95–7.86(m, 2H), 6.95–6.88(m, 1H), 3.91(bs, 4H), 3.74–3.69(m, 4H), 2.87(bs, 2H)

EXAMPLE 62

(Reaction2)

(CDCl$_3$) δ: 8.01–7.91(m, 2H), 6.88(t, 1H), 3.84(t, 4H), 3.68(t, 4H)

EXAMPLE 62

(Reaction3)

(DMSO-d$_6$) δ: 10.29(bs, 1H), 8.40–7.11(m, 8H), 4.21(s, 3H), 3.66(t, 4H), 3.55(t, 4H)

EXAMPLE 62

(Reaction4)

(DMSO-d$_6$) δ: 10.29(s, 0.5H), 10.22(s, 0.5H), 9.99(s, 1H), 8.33–6.92(m, 12H), 4.08(s, 3H), 3.66(t, 4H), 3.55(t, 4H), 2.75(t, 2H), 2.56(t, 2H), 2.09(s, 3H)

EXAMPLE 63

(DMSO-d$_6$) δ: 9.98(s, 1H), 9.64(s, 0.5H), 9.58(s, 0.5H), 8.30(s, 0.5H), 8.03(s, 0.5H), 7.83–7.78(m, 1H), 76.5(d, 0.5H), 7.50(d, 0.5H), 7.27(s, 1H), 7.15(s, 0.5H), 7.12(s, 0.5H), 6.93(dd, 1H), 6.66(s, 1H), 6.61(d, 1H), 4.08(s, 3H), 3.75(s, 8H), 2.75(t, 2H), 2.56(t, 2H), 2.21(s, 3H), 2.09(s, 3H)

EXAMPLE 64

(DMSO-d$_6$) δ: 9.98(s, 1H), 9.64(s, 0.5H), 9.58(s, 0.5H), 8.61(s, 0.5H), 8.30(s, 0.5H), 8.03(s, 0.5H), 7.96(m1H), 7.65(d, 1H), 7.50(d, 1H), 7.35(dd, 0.5H), 7.27(s, 1H), 6.66(s, 1H), 6.61(d, 1H), 4.08(s, 3H), 3.74(s, 8H), 2.75(t, 2H), 2.56(t, 2H) 2.21(s, 3H), 2.09(s, 3H)

EXAMPLE 65

(Reaction1)
(CDCl$_3$) δ: 8.34(d, 1H), 8.29(dd, 1H), 7.53(d, 1H), 4.69(t, 2H), 3.51(m,4),3.41(m, 4H)

EXAMPLE 65

(Reaction2)
(CDCl$_3$) δ: 8.55(d, 1H), 8.36(dd, 1H), 7.50(d, 1H), 3.61(m, 8H)

EXAMPLE 65

(Reaction3)
(DMSO-d$_6$) δ: 10.58(bs, 1H), 10.51(bs, 1H), 8.45–7.57(8H), 4.21(s, 3H), 3.60(t, 2H), 3.37(t, 4H)

EXAMPLE 65

(Reaction4)
(DMSO-d$_6$) δ: 10.51(s, 0.5H), 10.44(s, 0.5H), 9.99(s, 1H), 8.37–6.93(8H), 4.08(s, 3H), 3.60(t, 4H), 3.37(t, 4H), 2.76(t, 2H), 2.57(t, 2H), 2.10(s, 3H)

EXAMPLE 66

(Reaction1)
(CDCl$_3$) δ: 8.45.(d, 1H), 6.56(d, 1H), 5.02(t, 2H), 4.14(bs, 4H), 3.77(m, 4H)

EXAMPLE 66

(Reaction2)
(CDCl$_3$) δ: 8.49(d, 1H), 6.29(d, 1H), 4.40(t, 4H), 3.87(t, 4H)

EXAMPLE 66

(Reaction3)
(DMSO-d$_6$) δ: 10.46(s, 0.5H), 10.40(s, 0.5H), 8.45–7.51(m, 6H), 6.52(d, 1H), 4.21(s, 3H), 4.13(t, 4H), 3.88(t, 4H)

EXAMPLE 66

(Reaction4)
(DMSO-d$_6$) δ: 10.39(s, 0.5H), 10.35(s, 0.5H), 9.99(s, 1H), 8.36(s, 0.5H), 8.09(s, 0.5H), 7.87–7.82(m, 1H), 7.69(d, 0.5H), 7.55–7.50(m, 1.5H), 7.28(s, 1H), 6.95(dd, 1H), 6.52(d, 1H), 4.13(t, 4H), 4.09(s, 3H), 3.88(t, 4H), 2.76(t, 2H), 2.57(t, 2H), 2.09(s, 3H)

EXAMPLE 67

(DMSO-d$_6$) δ: 10.30(s, 1H), 9.99(s, 1H), 8.19(bs, 1H), 7.82((d, 1H), 7.64(d, 2H, 8.8), 7.58(m, 1H), 7.29(s, 1H), 6.96(s, 1H), 6.76(d, 2H), 4.09(s, 3H), 3.73(s, 8H), 3.54(t, 2H), 2.95(s, 6H), 2.93(m, 2H)

EXAMPLE 68

(DMSO-d$_6$) δ: 10.32(s, 1H), 10.26(bs, 1H), 8.33–6.97(m, 8H), 4.09(s, 3H), 3.66(t, 4H), 3.57–3.51(m, 6H), 2.95–2.90(m, 8H)

EXAMPLE 69

(DMSO-d$_6$) δ: 10.29(s, 1H), 9.61(bs, 1H), 8.23(bs, 1H), 7.58(bs, 1H), 7.52(d, 1H), 7.28(s, 1H), 7.14(d, 1H), 6.95(s, 1H), 6.65(s, 1H), 6.61(d, 1H), 4.10(s, 3H), 3.74(s, 8H), 3.54(t, 2H), 2.95(s, 6H), 2.93(t, 2H), 2.21(s, 3H)

EXAMPLE 70

(DMSO-d$_6$) δ: 10.29(s, 1H), 9.64(s, 0.5H), 9.58(s, 0.5H), 8.30–6.55(8H), 4.09(s, 3H), 3.74(s, 8H), 3.54(t, 2H), 2.95(s, 6H), 2.93(2H), 2.21(s, 3H)

EXAMPLE 71

(DMSO-d$_6$) δ: 10.53(s, 1H), 10.49(s, 1H), 8.28(1H+1H), 8.13(dd, 1H), 7.87(dd, 1H), 7.70(d, 1H), 7.64(d, 1H), 7.34(d, 1H), 7.02(d, 1H), 4.10(s, 3H), 3.60(t, 4H), 3.55(t, 2H), 3.37(t, 4H), 2.96(s, 6H)

EXAMPLE 72

(DMSO-d$_6$) δ: 10.54(s, 1H), 10.43(bs, 1H), 8.26(bs, 1H), 7.90(d, 1H), 7.65(d, 1H), 7.52(d, 1H), 7.34(s, 1H), 7.04(s, 1H), 6.52(d, 1H), 4.13(t, 4), 4.10(s, 3H), 3.88(t, 4H), 3.56(t, 2H), 2.96(6H+2H)

EXAMPLE 73

(DMSO-d$_6$) δ: 10.37(s, 1H), 10.33(bs, 1H), 8.23(bs, 1H), 8.04(d, 1H), 7.85(dd, 1H), 7.73(dd, 1H), 7.63(d, 1H), 7.37(d, 1H), 7.33(d, 1H), 7.00(d, 1H), 4.09(s, 3H), 3.61(t, 4H), 3.60(m, 4H), 3.51(m, 6H), 2.95(s, 6H), 2.94(2H)

EXAMPLE 74

(DMSO-d$_6$) δ: 10.32(s, 1H), 10.26(bs, 1H), 7.83–6.97(m, 8H), 4.09(s, 3H), 3.66(t, 4H), 3.55–3.35(m, 6H), 2.94–2.90(m, 8H)

EXAMPLE 75

(DMSO-d$_6$) δ: 10.56(s, 1H), 9.69(s, 1H), 8.21(s, 1H), 7.87(d, 1H), 7.63(d, 1H), 7.36(s, 1H), 7.14(d, 1H), 6.66(s, 1H), 6.62((d, 1H), 4.09(s, 3H), 3.75(s, 8H), 3.56(t, 2H), 2.96(2H), 2.21(s, 3H)

EXAMPLE 76

(DMSO-d$_6$) δ: 10.50(s, 1H), 9.66(s, 0.5H), 9.59(s, 0.5H), 8.30(s, 0.5H), 8.05(s, 0.5H), 7.83–7.80(m, 1H), 7.65(d, 0.5H), 7.49(d, 0.5H), 7.23(s, 1H), 7.13(d, (d, 1H), 6.99(d, 1H), 6.61(d, 1H), 4.09(s, 3H), 3.74(s, 8H), 3.55(t, 2H), 2.96(s, 6H), 2.96(2H), 2.21(s, 3H)

EXAMPLE 77

NMR(DMSO-d$_6$) δ: 10.07(s, 1H), 9.98(bs, 1H), 8.32–7.63(m, 5H), 7.29(s, 1H), 6.95(s, 1H), 6.72(d, 2H), 4.08(s, 3H), 3.73(s, 8H), 3.10(s, 2H), 2.17(s, 3H)

EXAMPLE 78

NMR(DMSO-d$_6$) δ: 10.08(s, 1H), 10.03(s, 0.5H), 9.96(s, 0.5H), 8.33(s, 0.5H), 8.03(s, 0.5H), 7.85–7.79(m, 1H), 7.72–7.51(m, 3H), 7.31(s, 1H), 7.11(d, 1H) 6.78–6.71(m, 2H), 4.58(s, 2H), 4.10(s, 3H), 3.73(s, 8H), 2.97(s, 6H)

EXAMPLE 79

NMR(DMSO-d$_6$) δ: 10.26(s, 1H), 10.02(s, 0.5H), 9.96(s, 0.5H), 8.50(d, 1H), 8.32(s, 0.5H), 8.01(s, 0.5H), 7.83–7.25(m, 8H), 6.95(d, 1H), 6.76(d, 2H), 4.07(s, 3H), 3.80(s, 2H), 3.73(s, 8H)

EXAMPLE 80

NMR(DMSO-d$_6$) δ: 10.27(s, 1H), 10.01(bs, 0.5H), 9.96(bs, 0.5H), 8.52(d, 2H), 8.32(bs, 0.5H), 8.02(bs, 0.5H), 7.81(bd, 1H), 7.64(bd, 2H+0.5H), 7.51(bd, 0.5H). 7.35(d,

2H), 7.27(s, 1H), 6.94(bs, 1H), 6.76(d, 2H), 4.07(s, 3H), 3.73(s, 8H), 3.66(s, 2H)

EXAMPLE 81

NMR(DMSO-$d_6$) δ: 10.25(s, 1H), 10.02(s, 0.5H), 9.96(s, 0.5H), 8.54(dd, 1H), 8.47(d d, 1H), 8.32(s, 0.5H), 8.02(s, 0.5H), 7.83–7.72(m, 2H) 7.66(d, 2H), 7.63(d, 0.5H), 7.51(d, 0.5H), 7.36, (dd, 1H), 7.27(s, 1H), 6.95(dd, 1H), 6.76(d, 2H), 4.07(s, 3H), 3.73(s, 8H), 3.65(s, 2H)

EXAMPLE 82

NMR(DMSO-$d_6$) δ: 10.66(s, 1H), 10.01(s, 1H), 9.03(s, 1H), 8.93(d, 1H), 8.55(d, 1H), 8.13(s, 0.5H), 8.11(d, 1H). 7.64(d, 2H), 7.63(bs, 1H), 7.30((d, 1H), 7.00(s, 1H), 6.76(d, 2H), 4.37(s, 3H), 4.08(s, 3H), 3.99(s, 2H), 3.73(s, 8H)

EXAMPLE 83

NMR(DMSO-$d_6$) δ: 10.36(s, 1H), 10.08(s, 1H), 8.22(bs, 1H), 7.87(d, 1H), 7.68(d, 2H), 7.65(d, 1H), 7.37(s, 1H), 7.04(s, 1H), 6.76(d, 2H), 4.09(s, 3H), 3.73(s, 8H), 3.45–3.32 (m, 2H), 3.10(s, 9H), 2.40(t, 2H), 2.05(m, 2H)

EXAMPLE 84

NMR(DMSO-$d_6$) δ: 9.97(s, 1H), 8.49(bs, 1H), 8.12–7.93 (m, 1H), 7.71–7.38(m, 2H), 7.26(s, 1H), 7.10(d, 2H,J=8.8), 6.91(s, 1H), 6.69(d, 2H,J=8.8), 4.06(s, 3H), 3.70(s, 8H), 3.42–3.33(m, 4H), 2.75(t, 2H), 2.56(t, 2H), 2.09(s, 3H)

EXAMPLE 85

NMR(DMSO-$d_6$) δ: 10.31(s, 0.7H), 9.98(s, 0.3H), 8.47 (m, 1H), 8.16(s, 0.7H), 7.93(s, 0.3H), 7.73–7.58(m, 1.3H), 7.46(d, 0.7H), 7.27(s, 1H), 7.10(d, 2H), 6.93(d, 1H), 6.69(d, 2H), 4.08(s, 3H), 3.70(s, 8H), 3.53(t, 2H), 3.42(m, 2H), 2.94(s, 8H), 2.75(m, 2H)

EXAMPLE 86

(Reaction1)
NMR(CDCl$_3$) δ: 7.98(d, 1H), 6.66(m, 2H), 4.84(d, 2H), 3.56(s, 8H), 2.55(s, 3H)

EXAMPLE 86

(Reaction2)
NMR(CDCl$_3$) δ: 8.11(d, 1H), 6.55(dd, 1H), 6.47(d, 1H), 3.84(t, 4H), 3.68(t, 4H), 2.66(s, 3H)

EXAMPLE 86

(Reaction3)
NMR(DMSO-$d_6$) δ: 9.92(s, 1H), 8.30(d, 1H), 8.29(s, 1H), 7.91(d, 1H), 7.70(d, 1H), 7.64(d, 1H), 7.14(d, 1H), 6.66(s, 1H), 6.61(d, 1H), 4.21(s, 3H), 3.75(s, 8H), 2.21(s, 3H)

EXAMPLE 86

(Reaction4)
NMR(DMSO-$d_6$) δ: 10.52(s, 1H), 9.82(s, 1H), 8.28(s, 1H), 7.99(d, 1H), 7.75(d,, 1H), 7.64(t, 1H), 7.48(s, 1H), 7.36(bs, 4H), 7.18(s, 1H), 7.14(d, 1H), 6.66(s, 1H), 6.62(d, 1H), 4.10(s, 3H), 4.06((1, 2H), 3.75(s, 8H), 2.21(s, 3H)

EXAMPLE 87

NMR(DMSO-$d_6$) δ: 10.27(s, 1H), 9.78(s, 1H), 8.25(s, 1H), 7.96(d, 1H), 7.71(d, 1H), 7.44(d, 1H), 7.14(d, 1H), 7.10(s, 1H), 6.67(s, 1H), 6.62(d, 1H), 4.08(s, 3H), 3.75(s, 8H), 3.06(m, 2H), 2.75(m, 6H), 2.40(t, 2H), 2.21(s, 3H), 1.97(m, 2H)

EXAMPLE 88

NMR(DMSO-$d_6$) δ: 10.41(s, 1H), 10.01(s, 0.5H), 9.95(s, 0.5H), 8.33(s, 1H), 8.03(s, 1H), 7.90(d, 1H), 7.80(t, 1), 7.67–7.61(m, 3H), 7.38(s, 1H), 7.24(d, 1H), 7.14–7.11(m, 1H), 6.76(d, 2H), 6.68(dd, 1H), 3.4.11(s, 3H), 3.73(s, 8H)

EXAMPLE 89

(Reaction1)
NMR(DMSO-$d_6$) δ: 8.02(d, 2H), 6.79(d, 2H), 4.86(t, 1H), 3.58(t, 2H), 3.51(m, 4H), 1.13(t, 3H)

EXAMPLE 89

(Reaction3)
NMR(DMSO-$d_6$) δ: 7.24(d, 2H), 6.89(d, 2H), 3.79(m, 4H), 3.42(q, 2H), 1.07(t, 3H)

EXAMPLE 89

(Reaction4)
NMR(DMSO-$d_6$) δ: 10.03(s, 0.5H), 9.96(s, 0.5H), 8.60–7.58(7H), 6.71(d, 2H), 4.21(s, 3H), 3.72(bm, 2H), 3.61(bm, 2H), 3.43(q, 2H), 1.10(t, 3H)

EXAMPLE 89

(Reaction6)
NMR(CDCl$_3$) δ: 7.47(d, 2H), 6.65(d, 2H), 3.63(m, 4H), 3.48(q, 2H), 1.21(t, 3H)

EXAMPLE 89

(Reaction7)
NMR(CDCl$_3$) δ: 7.97(d, 2H), 6.67(d, 2H), 3.63(m, 4H), 3.51(q, 2H), 1.22(t, 3H)

EXAMPLE 89

(Reaction8)
NMR(DMSO-$d_6$) δ: 10.02(s, 0.5H), 9.96(s, 0.5H), 9.92(s, 1H), 8.83(s, 0.5H), 8.03(s, 0.5H), 7.81(t, 1H), 7.64(t, 2H), 7.52(d, 0.5H), 7.36(s, 1H), 7.07(d, 0.5H), 6.95(d, 1H), 6.76(d, 1H), 6.15(dd, 1H), 4.11(s, 3H), 3.73(s, 8H)

EXAMPLE 90

NMR(DMSO-$d_6$) δ: 10.56(s, 1H), 10.39(bs, 1H), 8.31(s, 1H), 8.03(d, 1H), 7.79(d, 3H), 7.67(t, 1H), 7.52(s, 1H), 7.38(bs, 4H), 7.22(s, 1H), 7.10(bd, 2H), 4.11(s, 3H), 4.07(d, 2H), 3.73(s, 4H), 3.49(bm, 2H), 1.08(t, 3H)

EXAMPLE 91

NMR(DMSO-$d_6$) δ: 10.37(s, 1H), 10.02(s, 1H), 7.83–6.43(m, 14H), 4.09(s, 3H), 4.04(d, 2H), 3.74(t, 2H), 3.61(t, 2H), 1.12(t, 3H)

EXAMPLE 92

(Reaction1)
NMR(CDCl$_3$) δ: 7.86(dd, 1H), 7.67(d, 1H), 7.00(d, 1H), 3.93(s, 3H), 3.80–3.54(m, 8H)

EXAMPLE 92

(Reaction2)
NMR(CDCl$_3$) δ: 7.85(dd, 1H), 7.74(d, 1H), 6.90(d, 1H), 4.03(s, 3H), 3.73(m, 4H), 3.62(m, 4H)

EXAMPLE 92

(Reaction3)
NMR(DMSO-$d_6$) δ: 10.19(s, 1H), 8.31(s, 2H), 7.88(d, 1H), 7.69(d, 1H), 7.59(s, 2H), 7.38(dd, 1H), 7.03(d, 1H), 4.21(s, 3H), 3.82(s, 3H), 3.58(t, 4H), 3.45(t, 4H)

EXAMPLE 92

(Reaction4)
NMR(DMSO-$d_6$) δ: 10.54(s, 1H), 10.38(s, 1H), 8.31(s, 1H), 8.03(d, 1H), 7.79(d, 1H), 7.64(t, 1H), 7.60(d, 1H), 7.51(s, 1H), 7.39(dd, 1H), 7.37(bs, 4H), 7.21(s, 1H), 7.05(d, 1H), 4.11(s, 3H), 4.06(d, 2H), 3.83(s, 3H), 3.59(t, 4H), 3.47(t, 4H)

EXAMPLE 93
(Reaction1)

NMR(DMSO-$d_6$) δ: 7.98(d, 1H), 6.68(m, 2H), 4.84(t, 2H), 3.56(m, 8H), 2.55(s, 3H)

EXAMPLE 93
(Reaction2)

NMR(CDCl$_3$) δ: 8.11(d, 1H), 6.55(dd, 1H), 6.47(d, 1H), 3.84(t, 4H), 3.68(t, 4H), 1.58(s, 3H)

EXAMPLE 93
(Reaction3)

NMR(DMSO-$d_6$) δ: 9.71(s, 0.5H), 9.64(s, 0.5H), 8.38(s, 0.5H), 8.31(d, 1H), 8.11(s, 0.5H), 7.91–7.57(3H), 7.14(d, 1H), 6.67(d, 1H), 6.61(d, 1H), 4.21(s, 3H), 3.75(s, 8H), 2.21(s, 3H)

EXAMPLE 93
(Reaction4)

NMR(DMSO-$d_6$) δ: 10.58(s, 1H), 9.89(s, 1H), 8.31(s, 1H), 8.05(d, 1H), 7.79(d,, 1H), 7.67(t, 1H), 7.54(d, 1H), 7.38(bs, 4H), 7.23(d, 1H), 7.14(d, 1H), 6.67(s, 1H), 6.62(d, 1H), 4.11(s, 3H), 3.75(s, 8H), 2.21(s, 3H)

EXAMPLE 94

NMR(DMSO-$d_6$) δ:10.23(s, 1H), 10.06(s, 0.4H), 9.98(s, 0.6H), 8.31(s, 0.6H), 8.04(s, 0.4H), 7.81(m, 1H), 7.65(m, 2.4H), 7.51(d, 0.6H), 7.30(s, 1H), 6.99(s, 0.4H), 6.96(s, 0.6H), 6.75(d, 2H), 4.08(s, 3H), 3.73(s, 8H), 3.05(m, 2H), 2.74(s, 6H), 2.40(t, 2H), 1.99(m, 2H)

EXAMPLE 95
(Reaction1)

NMR(DMSO-$d_6$) δ: 10.02(s, 0.5H), 9.95(s, 0.5H), 9.90(s, 1H), 8.31(s, 0.5H), 8.01(s, 0.5H), 7.80(t, 1H), 7.65(d, 2H), 7.62(d, 0.5H), 7.50(d, 0.5H), 7.40–7.28(m, 7H), 7.27(s, 1H), 6.95(s, 0.5H), 6.90(s, 0.5H), 6.75(d, 2H), 5.02(s, 2H), 4.07 (s, 3H), 3.73(s, 8H), 3.04(q, 2H), 2.28(t, 2H), 1.72(m, 2H)

EXAMPLE 95
(Reaction2)

NMR(DMSO-$d_6$) δ: 10.33(s, 1H), 10.22(s, 1H), 8.28(s, 1H), 8.02–7.96(m, 4H), 7.76(d, 1H), 7.64(d, 2H), 7.50(s, 1H), 7.16(s, 1H), 6.77(d, 2H), 4.08(s, 3H), 3.74(s, 8H), 2.84(q, 2H), 2.42(t, 2H), 1.88(m, 2H)

EXAMPLE 96

NMR(DMSO-$d_6$) δ: 9.96(bs, 1H), 8.56(s, 1H), 8.30(bs, 0.5H), 7.98(bs, 0.5H), 7.79(d, 1H), 7.63(d, 2H), 7.49(m, 1H), 7.09(s, 1H), 6.92(s, 1H), 6.76(d, 2H), 4.57(s, 3H), 3.73(s, 8H), 3.60(m, 4H), 3.40(m, 4H)

EXAMPLE 97
(Reaction1)

NMR(DMSO-$d_6$) δ: 10.30–9.80(bs, 3H), 7.27(t, 1H), 6.76(d, 1H), 6.73(s, 1H), 6.63(d, 1H), 3.74(s, 8H)

EXAMPLE 97
(Reaction2)

NMR(DMSO-$d_6$) δ: 10.15(s, 0.3H), 10.05(s, 0.7H), 8.41 (s, 0.7H), 8.31(s, 1H), 8.09(s, 0.3H), 7.91–7.79(m, 1H), 7.64–7.59(m, 2H), 7.35–7.14(m, 3H), 6.49(d, 1H), 4.21(s, 3H), 3.75(bs, 8H)

EXAMPLE 97
(Reaction3)

NMR(DMSO-$d_6$) δ: 10.48(s, 1H), 10.22(s, 1H), 8.26(s, 1H), 7.95(d, 1H), 7.73(d, 1H), 7.64(t, 1H), 7.45(s, 1H), 7.50–7.14(m, 4H), 7.30(d, 1H), 7.23(s, 1H), 7.17(t, 1H), 7.14(s, 1H), 6.51(d, 1H), 4.10(s, 3H), 4.02(d, 2H), 3.76(m, 8H)

EXAMPLE 98

NMR(DMSO-$d_6$) δ: 10.60(s, 1H), 10.10(s, 1H), 8.22(s, 1H), 7.87(d, 1H), 7.65(d, 2H), 7.63(s, 1H), 7.35(s, 1H), 7.04(s, 1H), 6.76(d, 2H), 4.09(s, 3H), 3.73(s, 8H), 3.56(t, 2H), 2.96(s+t, 8H)

The present invention will hereinafter be described by the following examples. It is however borne in mind that the present invention is not limited to or by the following examples. Each Compound No. indicated in parentheses after Example No. corresponds to Compound No. shown in Tables 1–4.

Referential Preparation 1

Methyl 3,4-diaminobenzoate 3,4-Diaminobenzoic acid (3.0 g) was suspended in methanol, followed by the dropwise addition of 1.86 ml of thionyl chloride. Thionyl chloride was added twice, in an amount of 0.5 ml each time, and the resulting mixture was heated under reflux for 10 hours and 40 minutes. The thionyl chloride and methanol were distilled out, followed by the dissolution of the residue in methylene chloride. The solution so formed was washed with a 0.5N aqueous solution of sodium hydroxide and then with a saturated aqueous solution of sodium chloride, and was dried over sodium sulfate. The solvent was distilled out. The residue was washed with n-hexane and then dried, whereby 3.04 g of the target compound were obtained (yield: 93%).

Referential Preparation 2
(Reaction 1)

3-[N,N-Bis(2-hydroxyethyl)amino]nitrobenzene

3-Aminobenzene (5.0 g; 36.2 mmol) was dissolved in 36 ml of 30% acetic acid, followed by the addition of 22.9 ml of ethylene oxide under ice cooling. The resulting mixture was stirred overnight at room temperature. The reaction mixture was extracted with ethyl acetate. The ethyl acetate solution was dried over sodium sulfate and then concentrated. The residue was washed with ethyl ether, whereby 5.21 g (23.0 mmol) of the title compound were obtained as yellow crystals (yield: 63.6%).

m.p. 98.5°–100° C.

(Reaction 2)

3-[N,N-Bis(2-chloroethyl)amino]nitrobenzene

3-[N,N-Bis(2-hydroxyethyl)amino]nitrobenzene (2.5 g; 11.0 mmol) was suspended in 25 ml of toluene, followed by the addition of 10.2 g (85.7 mmol; 7.8 equivalents) of thionyl chloride under ice cooling. The resultant mixture was heated for 5 hours over an oil bath controlled at 70° C. The reaction mixture was concentrated under reduced pressure. Ethyl acetate and water were added to the residue so that the residue was dissolved. The resulting mixture was allowed to separate into two layers. The ethyl acetate layer, that is, the ethyl acetate extract was dried over sodium sulfate and then concentrated under reduced pressure. The residue was washed with ethyl ether, whereby 2.67 g (10.1 mmol) of the title compound were obtained as yellow crystals (yield: 92.2%).

m.p. 112°–113° C.
(Reaction 3)

N,N-Bis(2-chloroethyl)-1,3-phenylenediamine hydrochloride

3-[N,N-Bis(2-chloroethyl)amino]nitrobenzene (2.0 g; 7.6 mmol) was dissolved in 35 ml of concentrated hydrochloric acid, followed by the addition of 6.9 g (30.6 mmol; 4.0 equivalents) of tin(II) chloride dihydrate. The resultant mixture was stirred under heating for 1 hour over an oil bath controlled at 100° C. The reaction mixture was allowed to cool down to room temperature and then diluted with water. The resulting mixture was basified with concentrated aqueous ammonia and then extracted twice with ethyl acetate. The extracts were combined, dried over sodium sulfate and then concentrated under reduced pressure. The residue was added with 4N hydrochloric acid/dioxane, followed by concentration. The residue was crystallized from a mixed solvent of a small amount of methanol and ethyl ether, whereby 1.97 g (7.3 mmol) of the title compound were obtained as yellow crystals (yield: 96.1%).
m.p. 195°–201° C.

EXAMPLE 1
(Compound No. 3017)

1H-2-(1-Methyl-4-nitropyrrol-2-yl)benzimidazole-5-carboxylic acid
(Reaction 1)

1-Methyl-4-nitropyrrol-2-carboxyaldehyde

A solution of 25 g (0.23 mol) of 1-methylpyrrole-2-carboxyaldehyde in 200 ml of acetic anhydride was cooled to −40° C. Fuming nitric acid (17.6 g) was added dropwise to the solution over 30 minutes, followed by stirring at −40° C. for 1 hour and at −10° C. for additional 2 hours. The reaction mixture was added with ice and allowed to stand over night. The reaction mixture was extracted with ethyl acetate and then neutralized with sodium hydrogencarbonate. The solvent was then distilled out under reduced pressure. The residue was purified by chromatography on a silica gel column (ethyl acetate/n-hexane =1/2) and then crystallized from a 5:1 mixture of ethanol and water, whereby 5.67 g of the title compound were obtained as brown crystals (yield: 16%).
(Reaction 2)

Methyl 1H-2-(1-methyl-4-nitropyrrol-2-yl) benzimidazole-5-carboxylate

A solution of 3.0 g (19.5 mmol) of 1-methyl-4-nitropyrrole-2-carboxyaldehyde and 3.4 g (20.5 mmol) of methyl 3,4-diaminobenzoate in 300 ml of nitrobenzene was heated under reflux at 150°–160° C. for 32 hours. After completion of the reaction, the precipitated particles were collected by filtration and then washed with 100 ml of IPA, whereby 4.79 g of the title compound were obtained as yellow powder (yield: 81.9%).
IR(KBr)cm$^{-1}$: 3246, 1691, 1628, 1300, 751.
(Reaction 3)

1H-2-(1-Methyl-4-nitropyrrol-2-yl)benzimidazole-5-carboxylic acid

A solution of 4.4 g of potassium hydroxide in 30 ml of water was added to a solution of 4.7 g (15.6 mmol) of methyl 1H-2-(1-methyl-4-nitropyrrol-2-yl)benzimidazole-5-carboxylate in 30 ml of ethanol, followed by stirring at 85° C. for 2.5 hours. After completion of the reaction, the reaction mixture was acidified with concentrated hydrochloric acid while the mixture was still warm. The resultant mixture was allowed to cool down to room temperature. The precipitated particles were then collected by filtration. The precipitated particles were washed with water and then with ethanol, and thereafter dried, whereby 4.1 g of the title compound were obtained as pale yellow powder (yield: 92.4%).
IR(KBr)cm$^{-1}$: 3133, 1655, 1625, 1310, 1120.

EXAMPLE 2
(Compound No. 318)

1H-2-(4-Formylamino-1-methylpyrrol-2-yl) benzimidazole-5-[N-(2-amidinoethyl)]carboxamide hydrochloride
(Reaction 1)

1H-2-(1-Methyl-4-nitropyrrol-2-yl)benzimidazole-5-[N-(2-cyanoethyl)]carboxamide

CDI (448 mg; 2.76 mmol) was added to a solution of 608 mg (2.13 mmol) of 1H-2-(1-methyl-4-nitropyrrol-2-yl) benzimidazole-5-carboxylic acid in 18 ml of DMF, followed by stirring at room temperature for 30 minutes. 2-Aminopropionitrile (446 mg; 6.38 mmol) was added dropwise, followed by stirring at room temperature for 30 minutes. The reaction mixture was concentrated, followed by the addition of ethanol. The precipitated crystals were collected by filtration, whereby 360 mg of the title compound were obtained as pale yellow crystals (yield: 50%).
(Reaction 2)

1H-2-(1-Methyl-4-nitropyrrol-2-yl)benzimidazole-5-[N-(2-amidinoethyl)]carboxamide hydrochloride 1H-2-(1-Methyl-4-nitropyrrol-2-yl)benzimidazole-5-[N-(2-cyanoethyl)]carboxamide (1.8 g; 5.32 mmol) was suspended in 100 ml of ethanol. Hydrogen chloride gas was bubbled at 0° C. through the suspension under stirring for 30 minutes. After the resultant mixture was stirred further at room temperature for 1 hour with hydrogen chloride gas bubbled therethrough, nitrogen gas was bubbled to purge excess hydrogen chloride gas. The reaction mixture was concentrated under reduced pressure and the residue was washed with ethyl ether. The residue was again suspended in 60 ml of a 1:1 mixed solvent of ethanol and methanol, followed by stirring with ammonia gas bubbled therethrough. After completion of the reaction, nitrogen gas was bubbled to purge excess ammonia gas and the resulting mixture was evaporated to dryness under reduced pressure. The residue was added with IPA and an insoluble matter was collected by filtration, whereby 2.0 g of yellow powder were obtained (yield: 95.9%).
(Reaction 3)

1H-2-(4-Formylamino-1-methylpyrrol-2-yl) benzimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide hydrochloride (200 mg; 0.51 mmol) was dissolved in 12 ml of a 1:1 mixed solvent of DMF and methanol in a reactor, followed by the addition of 0.7 ml of 1N hydrochloric acid and 180 mg of 5% Pd/C. The reactor was purged with nitrogen gas. The resulting mixture was stirred under a hydrogen gas atmosphere at room temperature for 2 hours. After completion of the reaction, the reactor was purged again with nitrogen gas. The 5% Pd/C was filtered off and the methanol was distilled out under reduced pressure. The resulting solution was cooled to 0° C., to which 0.17 ml of triethylamine was added under a nitrogen gas atmosphere. The solution so obtained was added with a solution of N-formylimidazole (5 equivalents) in 5 ml of tetrahydrofuran, which had been prepared right before [by adding 410 mg (2.53 mmol) of CDI to a solution of 0.1 ml (2.53 mmol) of formic acid in 5 ml of tetrahydrofuran and then stirring the resultant mixture at room temperature for 15 minutes]. The thus-obtained solution was stirred, as was, for 30 minutes. The solvent was distilled out under reduced pressure and the residue was purified by chromatography on a silica gel column (ethyl acetate/IPA/water=5/2/1), whereby 187 mg of white powder were obtained (yield: 94%).

IR(KBr)cm$^{-1}$: 3276, 2938, 2363, 1636, 1542, 1519, 1473, 1312.

Elemental analysis for $C_{30}H_{36}N_8O_2Cl_2.HCl.0.5H_2O$: Calculated: C, 54.84; H, 5.83; N, 17.05 Found: C, 55.07; H, 6.14; N, 16.98

EXAMPLE 3
(Compound No. 4)

1H-2-[4-[4-[4-[N,N-bis(2-chloroethyl)amino]phenyl]butylylamino]-1-methylpyrrol-2-yl]benzimidazole-5-[N-(2-amidinoethyl)]carboxamide hydrochloride Triethylamine (164 mg; 1.62 mmol) was added to a solution of 645 mg (1.62 mmol) of 1H-2-(4-amino-1-methyl-2-pyrrole)benzimidazole-5-[N-(2-amidinoethyl)]carboxamide dihydrochloride, 739 mg (2.43 mmol) of chlorambucil, 601 mg (2.91 mmol) of DCC and a catalytic amount of DMAP in 19 ml of DMF, followed by stirring at room temperature for 3 hours. After completion of the reaction, the precipitated crystals were filtered off and the filtrate was concentrated. The residue was subjected to flush column chromatography (ethyl acetate/IPA/water=6/2/1), whereby 170 mg of the title compound were obtained as pale red crystals.

m.p.≧289° C. (dec.).

IR(KBr)cm$^{-1}$: 3276, 2939, 2363, 1637, 1542, 1519, 1474.

Elemental analysis for $C_{30}H_{36}N_8O_2Cl_2HCl$ Calculated: C, 55.60; H, 5.75; N, 17.29 Found: C, 55.27; H, 6.14; N, 16.98

EXAMPLE 4
(Compound No. 1)

1H-2-[4-[4-[N,N-bis(2-chloroethyl)amino]benzoylamino]-1-methylpyrrol-2-yl]benzimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide hydrochloride (500 mg; 1.28 mmol; see Reaction 2 in Example 2) was dissolved in a 1:1 mixed solvent of DMF and methanol in a reactor, followed by the addition of 250 mg of 5% Pd/C. The reactor was purged with nitrogen gas. The resulting mixture was stirred under a hydrogen gas atmosphere at room temperature for 2 hours and then at 40° C. for additional 1 hour. After completion of the reaction, the reactor was purged again with nitrogen gas. The Pd/C was filtered off and the methanol was distilled out under reduced pressure. The resulting solution was cooled to −40° C. Under a nitrogen gas atmosphere, the solution so obtained was added dropwise with a solution of 4-[N,N-bis(2-chloroethyl)amino]benzoyl chloride (1.1 equivalents) in 5 ml of methylene chloride, said solution having been prepared right before. The thus-obtained solution was stirred for 30 minutes and was then allowed to stand overnight. The solvent was distilled out under reduced pressure and the residue was purified by chromatography on a silica gel column (ethyl acetate/IPA/water=6/2/1), whereby 91 mg of white powder were obtained.

IR(KBr)cm$^{-1}$: 3329, 2361, 1692, 1607, 1545, 1281, 759.

Elemental analysis for $C_{27}H_{31}N_8O_2Cl_3.2H_2O$: Calculated: C, 50.51; H, 5.50; N, 17.45 Found: C, 50.37; H, 5.39; N, 17.20

EXAMPLE 5
(Compound No. 326)

1H-2-(4-Benzoylamino-1-methylpyrrol-2-yl)benzimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide hydrochloride (216 mg; 5.51 mmol) was dissolved in 20 ml of a 1:1 mixed solvent of DMF and methanol in a reactor, followed by the addition of 200 mg of 5% Pd/C. Under a hydrogen gas atmosphere, the resulting mixture was stirred at room temperature for 3 hours. After completion of the reaction, the reactor was purged again with nitrogen gas, the Pd/C was filtered off, and the methanol was distilled out under reduced pressure. The solution was cooled to 0° C. and under a nitrogen gas atmosphere, a solution of benzoyl chloride (1.1 equivalents) in 5 ml of methylene chloride was added dropwise. The solution was stirred for 30 minute and was then allowed to stand overnight. After the solvent was distilled out under reduced pressure, the residue was purified by chromatography on a silica gel column (ethyl acetate/IPA/water=6/2/1), whereby 50 mg of white powder were obtained (yield: 19.5%).

IR(KBr)cm$^{-1}$: 3294, 1690, 1638, 1552, 1309, 708.

EXAMPLE 6
(Compound No. 341)

1H-2-(4-(Guanidinoacetylamino)-1-methylpyrrol-2-yl]benzimidazole-5-[N-(2-amidinoethyl)]dicarboxamide hydrochloride 1H-2-(1-Methyl-4-nitropyrrol-2-yl)benzimidazole-5-[N-(2-amidinoethyl)]carboxamide hydrochloride (33.1 mg; 0.0842 mmol) was dissolved in 8.3 ml of a 1:1 mixed solvent of methanol and DMF. Using 16.0 mg of 10% Pd/C, the reactant was hydrogenated at room temperature so that it was converted to its corresponding amino derivative. Then, 38.9 mg (0.253 mmol) of guanidinoacetic acid hydrochloride and 53.9 mg (0.261 mmol) of DCC were added. The resulting mixture was stirred at room temperature for one day and then concentrated. The residue was purified by flush column chromatography (ODS, methanol-water), whereby 19.5 mg of the title compound were obtained as colorless crystals (yield: 47%).

m.p. 180°–187° C. (dec.).

IR(KBr)cm$^{-1}$: 3398, 1648, 1561, 1399, 1320, 1236.

Elemental analysis for $C_{19}H_{24}N_{10}O_2 2HCl$ Calculated: C, 45.88; H, 5.27; N, 28.16 Found: C, 45.83; H, 5.00; N, 28.02

EXAMPLE 7
(Compound No. 340)

1H-2-(4-Guanidinoacetylamino-1-methylpyrrol-2-yl)
benzimidazole-5-(N-(3-dimethylaminopropyl)]
carboxamide hydrochloride (Reaction 1)

1H-2-(1-Methyl-4-nitropyrrol-2-yl)benzimidazole-5-
[N-(3-dimethylaminopropyl)]carboxamide CDI (30.3 mg; 0.187 mmol) was added to a solution of 44.5 mg (0.155 mmol) of 1H-2-(1-methyl-4-nitropyrrol-2-yl)benzimidazole-5-carboxylic acid in 1.3 ml of DMF, followed by stirring at room temperature for 30 minutes. The resultant mixture was concentrated, to which ethanol was added. The precipitated crystals were collected by filtration, whereby 43.8 mg of the title compound were obtained as pale yellow crystals (yield: 76%).

m.p. 244°–246° C.

(Reaction 2)

1H-2-(4-Guanidinoacetylamino-1-methylpyrrol-2-yl)
benzimidazole-5-[N-(3-dimethylaminopropyl)]
carboxamide hydrochloride 10% Pd/C (6.8 mg) was added to a solution of 13.2 mg (0.0356 mmol) of 1H-2-(1-methyl-4-nitropyrrol-2-yl)benzimidazole-5-[N-(3-dimethylaminopropyl)]carboxamide in 1.4 ml of a 1:1 mixed solvent of methanol and DMF, followed by hydrogenation at room temperature. The Pd/C was filtered off and the filtrate was washed with DMF. Under a nitrogen gas atmosphere, 16.4 mg of guanidine acetate hydrochloride and 22.8 mg (0.110 mmol) of DCC were added to the filtrate. The resulting mixture was stirred under shading at room temperature for 30 minutes and was then concentrated. The residue was subjected to flush column chromatography (ODS:methanol/water=0/1→1/10). Relevant fractions were concentrated to obtain crystals. The crystals were dissolved in methanol and, after an insoluble matter was filtered off, the filtrate was concentrated again, whereby 9.5 mg of the title compound were obtained as colorless crystals (yield: 56%).

m.p. 190°–195° C. (dec.).

EXAMPLE 8
(Compound No. 321)

1H-2-(4-Formylamino-1-methylpyrrol-2-yl)
benzimidazole-5-[N-(3-dimethylaminopropyl)]
carboxamide hydrochloride Formic acid (186 mg; 4.03 mmol) was added dropwise to a THF solution of 653 mg (4.03 mmol) of CDI, followed by stirring for 15 minutes. The resultant mixture was added dropwise at −40° C. to a solution of 0.805 mmol of 1H-2-(1-methyl-4-aminopyrrol-2-yl)benzimidazole- 5-[N-(3-dimethylaminopropyl)]carboxamide in a mixed solvent of methanol and DMF. The thus-obtained mixture was stirred at room temperature for 15 minutes and then concentrated. The concentrate was fractionated by chromatography on a silica gel column (methanol/chloroform/aqueous ammonia). An oil so obtained was treated with IPA and ethyl acetate and further with 4N hydrochloric acid, whereby 240 mg of the title compound were obtained as colorless crystals (yield: 74%).

m.p. 123°–128° C. (dec.).

EXAMPLE 9
(Compound No. 84)

1H-2-[4-[4-[N,N-Bis(2-chloroethyl)amino]
phenylbutyrylamino]-1-methylpyrrol-2-yl]
benzimidazole-5-[N-(3-dimethylaminopropyl)]
carboxamide hydrochloride Following the procedures of Example 3, 1H-2-(4-amino-1-methylpyrrol-2-yl)benzimidazole-5-[N-(3-dimethylaminopropyl))carboxamide hydrochloride and chlorambucil were bonded together to obtain the title compound.

m.p. 134°–140° C.

IR(KBr)cm$^{-1}$: 3424, 3282, 2955, 1655, 1648, 1579, 1519, 1460.

EXAMPLE 10
(Compound No. 320)

1H-2-(4-Formylamino-1-methylpyrrol-2-yl)
benzimidazole-5-[N-(3,4,5-trimethoxyphenyl)]
carboxamide (Reaction 1)

1H-2-(1-Methyl-4-nitropyrrol-2-yl)benzimidazole-5-
[N-(3,4,5-trimethoxyphenyl)]carboxamide In 40 ml of DMF, 233 mg (0.814 mmol) of 1H-2-(1-methyl-4-nitropyrrol-2-yl)benzimidazole-5-carboxylic acid, 218 mg (1.06 mmol) of DCC and 132 mg (0.977 mmol) of HOBt were stirred for 1 hour at room temperature. The reaction mixture was concentrated, followed by the addition of methanol. The precipitated crystals were collected by filtration, whereby 360 mg of the title compound were obtained as pale yellow crystals (yield: 50%).

(Reaction 2)

1H-2-(4-Formylamino-1-methylpyrrol-2-yl)
benzimidazole-5-[N-(3,4,5-trimethoxyphenyl)]
carboxamide 10% Pd/C was added to a solution of 1H-2-(1-methyl-4-nitropyrrol-2-yl)benzimidazole-5-[N-(3,4,5-trimethoxyphenyl)]carboxamide in 30 ml of a 1:1 mixed solvent of DMF and methanol, followed by stirring at room temperature for 3 hours. The corresponding amino derivative was obtained and following the procedures of Example 8, was then formylated, whereby 100 mg of the title compound were obtained as colorless crystals (yield: 41%).

m.p. 177°–182° C.

IR(KBr)cm$^{-1}$: 3449, 3309, 1655, 1610, 1509, 1466, 1409, 1315.

EXAMPLE 11
(Compound No. 339)

1H-2-[4-[4-[N,N-Bis(2-chloroethyl)amino]
benzoylamino]-1-methylpyrrol-2-yl]benzimidazole-
5-(N-stearyl)carboxamide (Reaction 1)

1H-2-(1-Methyl-4-nitropyrrol-2-yl)benzimidazole-5-
(N-stearyl)carboxamide 1H-2-(1-Methyl-4-nitropyrrol-2-yl)benzimidazole-5-carboxylic acid (0.20 g; 0.68 mmol) was dissolved in 5 ml of DMF, followed by the addition of 0.12 g (0.74 mmol; 1.1 equivalents) of CDI. The thus-obtained mixture was stirred under a nitrogen gas atmosphere at room temperature for 2 hours. The reaction mixture was ice-cooled, followed by the addition of 0.20 g (0.74 mmol; 1.1 equivalents) of stearylamine. The temperature of the resultant mixture was allowed to rise back to room temperature, at which the mixture was stirred for 3.5 hours and was then allowed to stand overnight. DMF (5 ml) was added further, followed by stirring for 10 hours. The resulting solid was collected by filtration and then washed with methanol, whereby 0.23 g (0.45 mmol) of the title compound was obtained as yellow crystals (yield: 65.8%).

m.p. 142°–144° C.
(Reaction 2)

1H-2-[4-[4-[N,N-Bis(2-chloroethyl)amino] benzoylamino]-1-methylpyrrol-2-yl)benzimidazole-5-(N-stearyl)carboxamide 1H-2-(1-Methyl-4-nitropyrrol-2-yl)benzimidazole-5-(N-stearyl)carboxamide (0.22 g; 0.43 mmol) was suspended in a mixed solvent of 5 ml of DMF and 5 ml of methanol, followed by the addition of 0.5 ml of 1N hydrochloric acid. Using 10% Pd/C as a catalyst, hydrogenation was conducted under normal pressure so that the reactant was converted to its corresponding amino derivative. A solution of half the amino derivative in DMF was stirred under a nitrogen gas atmosphere and ice cooling, to which 68 μl (0.49 mmol; 2.0 equivalents) of triethylamine were added. To the thus-obtained mixture, a solution of 4-[N,N-bis(2-chloroethyl)amino]benzolyl chloride, which had been synthesized from 0.07 g (0.27 mmol) of 4-[N,N-bis(2-chloroethyl)amino] benzoic acid, in 2 ml of dichloromethane was added dropwise. The temperature of the resultant mixture was allowed to rise back to room temperature, at which the mixture was stirred for 3.5 hours and was then allowed to stand overnight. The mixture was concentrated under reduced pressure. The residue was purified by chromatography on a silica gel column (eluted with methylene chloride/2–4% methanol) and then crystallized from methylene chloride-water, whereby 36 mg (0.048 mmol) of the title compound were obtained as light brown crystals (yield: 22.3%).

m.p. 173°–177° C.

IR(KBr)cm$^{-1}$: 3422, 2923, 1636, 1541, 1473.

Elemental analysis for $C_{42}H_{60}N_6O_2Cl_2 \cdot H_2O$: Calculated: C, 65.52; H, 8.12; N, 10.92; Cl, 9.21 Found: C, 65.87; H, 8.24; N, 10.53; Cl, 9.21

EXAMPLE 12

(Compound No. 337)

1H-2-(4-Formylamino-1-methylpyrrol-2-yl)benzimidazole-5-(N-stearyl)carboxamide 1H-2-(1-Methyl-4-nitropyrrol-2-yl)benzimidazole-5-(N-stearyl)carboxamide (0.22 g; 0.43 mmol) was suspended in a mixed solvent of 5 ml of DMF and 5 ml of methanol, followed by the addition of 0.5 ml of 1N hydrochloric acid. Using 10% Pd/C as a catalyst, hydrogenation was conducted under normal pressure so that the reactant was converted to its corresponding amino derivative. Half of the DMF solution of the amino derivatives was stirred under a nitrogen gas atmosphere and ice cooling, to which 68 μl (0.49 mmol; 2.0 equivalents) of triethylamine were added. To the thus-obtained mixture, a solution of 1-formylimidazole, which had been prepared from 0.17 g (1.05 mmol; 5.0 equivalents) of CDI and 40 μl (1.06 mmol; 5.0 equivalents) of formic acid, in THF was added dropwise. The temperature of the resultant mixture was allowed to rise back to room temperature, at which the mixture was stirred for 5 hours and was then allowed to stand overnight. The mixture was concentrated under reduced pressure. The residue was purified by chromatography on a silica gel column (eluted with methylene chloride/4–8% methanol) and then crystallized from ethyl ether-water, whereby 57 mg (0.11 mmol) of the title compound were obtained as light brown crystals (yield: 48.4%).

m.p. 160°–163° C.

IR(KBr)cm$^{-1}$: 3368, 2918, 1654, 1541, 1472.

Elemental analysis for $C_{32}H_{49}N_5O_2 \cdot 1.5H_2O$: Calculated: C, 68.29; H, 9.31; N, 12.44 Found: C, 68.18; H, 9.03; N, 12.38

EXAMPLE 13

(Compound No. 14)

1H-2-[4-[4-[N,N-Bis(2-chloroethyl)aminomethyl] benzoylamino]-1-methylpyrrol-2-yl]benzimidazole-5-(N-(2-amidinoethyl)]carboxamide hydrochloride (Reaction 1)

Methyl 4-chloromethylbenzoate

A solution of 2.0 g (12 mmol) of 4-chloromethylbenzoic acid in 50 ml of methanol was added with 5 droplets of concentrated sulfuric acid, followed by stirring under heat and reflux for 4 days. After neutralization with a 5% aqueous solution of sodium carbonate, the resultant mixture was extracted with chloroform. The chloroform extract was dried over magnesium sulfate and then concentrated under reduced pressure, whereby 1.7 g of a colorless liquid were obtained.

IR(KBr)cm$^{-1}$: 2953, 1720, 1281, 1106, 713.

(Reaction 2)

Methyl 4-[N,N-bis(2-hydroxyethyl)aminomethyl] benzoate

A solution of 1.7 g (9.2 mmol) of methyl 4-chloromethylbenzoate in 25 ml of chloroform was added with 10 g (95 mmol) of diethanolamine, followed by heating under reflux for 10 hours. The resulting solution was washed with water and then dried over magnesium sulfate. The solvent was distilled off under reduced pressure. The residue was purified by chromatography on a silica gel column (chloroform), whereby 1.5 g of a colorless oil were obtained.

IR(KBr)cm$^{-1}$: 3384, 2952, 1721, 1283, 754.

(Reaction 3)

Methyl 4-[N,N-bis(2-chloroethyl)aminomethyl] benzoate

Thionyl chloride (5 ml) was added to 1.5 g (5.9 mmol) of methyl 4-[N,N-bis(2-hydroxyethyl)aminomethyl]benzoate, followed by stirring at 50° C. for 2 hours. After excess thionyl chloride was distilled out under reduced pressure, methylene chloride was added again. Distillation was repeated twice under reduced pressure, whereby 9.5 g of a colorless oil were obtained.

(Reaction 4)

4-[N,N-Bis(2-chloroethyl)aminomethyl]benzoic acid

Concentrated hydrochloric acid (50 ml) was added to 9.5 g (32.7 mmol) of methyl 4-[N,N-bis(2-chloroethyl) aminomethyl]benzoate, followed by stirring under heating and reflux for 2 hours. After the solvent was distilled out under reduced pressure, the residue was washed with acetone, whereby 8.5 g of white powder were obtained.

IR(KBr)cm$^{-1}$: 3409, 2917, 1713, 1220, 1108, 752.

(Reaction 5)

4-[N,N-Bis(2-chloroethyl)aminomethyl]benzoyl chloride

Thionyl chloride (1 ml) was added to a solution of 320 mg (1.0 mmol) of 4-[N,N-bis(2-chloroethyl)aminomethyl] benzoic acid in 2 ml of benzene, followed by stirring under heating at 80° C. for 2 hours. After the solvent was distilled out under reduced pressure, the residue was dried up under reduced pressure so that a white solid was obtained.

(Reaction 6)

1H-2-[4-[4-[N,N-Bis(2-chloroethyl)aminomethyl]
benzoylamino]-1-methylpyrrol-2-yl]benzimidazole-
5-[N-(2-amidinoethyl)]carboxamide hydrochloride 1H-2-(1-Methyl-4-nitropyrrol-2-yl)benzimidazole-5-[N-(2-aminodiethyl)]carboxamide hydrochloride was dissolved in 20 ml of a 1:1 mixed solvent of DMF and methanol in a reactor, followed by the addition of 1 ml of 1N hydrochloric acid and 250 mg of 5% Pd/C. The reactor was purged with nitrogen gas. Under a hydrogen gas atmosphere, the reaction mixture was stirred at room temperature for 2 hours. After completion of the reaction, the reactor was purged again with nitrogen gas. The Pd/C was filtered off and the methanol was distilled out under reduced pressure. The resultant solution was cooled to 0° C. and, after 350 µl of triethylamine were added under a nitrogen gas atmosphere, a solution of 4-[N,N-bis(2-chloroethyl)aminomethyl]benzoyl chloride (1.1 equivalents) in 5 ml of DMF was added dropwise. After the resultant solution was stirred, as was, for 3 hours, methanol was added, followed by further stirring for 30 minutes. After the solvent was distilled out under reduced pressure, the residue was purified by chromatography on a silica gel column (ethyl acetate/IPA/water/acetic acid=5/2/1/1), whereby 110 mg of white powder were obtained.

IR(KBr)cm$^{-1}$: 3328, 1688, 1560, 1404, 1027, 674.

EXAMPLE 14
(Compound No. 334)

1H-2-(4-Formylamino-1-methylpyrrol-2-yl)
benzimidazole-5-(N-butyl)carboxamide
(Reaction 1)

1H-2-(1-Methyl-4-nitropyrrol-2-yl)benzimidazole-5-
(N-butyl)carboxamide 1H-2-(1-Methyl-4-nitropyrrol-2-yl)benzimidazole-5-carboxylic acid (0.30 g; 1.05 mmol) was dissolved in 10 ml of DMF, followed by the addition of 0.20 g (1.23 mmol; 1.2 eq.)) of CDI. The thus-obtained mixture was stirred under a nitrogen gas atmosphere at room temperature for 2 hours. The mixture was ice-cooled, to which 0.11 ml (1.11 mmol; 1.1 equivalents) of butylamine was added. The temperature of the thus-obtained mixture was allowed to rise back to room temperature, at which the mixture was stirred for 3 hours and then allowed to stand overnight. The reaction mixture was concentrated under reduced pressure and the residue was washed with IPA, whereby 0.26 g (0.76 mmol) of the title compound was obtained as yellow crystals (yield: 72.8%).

m.p. 229°–230° C.
(Reaction 2)

1H-2-(4-Formylamino-1-methylpyrrol-2-yl)
benzimidazole-5-(N-butyl)carboxamide 1H-2-(1-Methyl-4-nitropyrrol-2-yl)benzimidazole-5-(N-butyl)carboxamide (0.24 g; 0.71 mmol) was suspended in a mixed solvent of 5 ml of DMF and 5 ml of methanol, followed by the addition of 0.7 ml of 1N hydrochloric acid. Using 10% Pd/C as a catalyst, hydrogenation was conducted under normal pressure so that the reactant was converted to its corresponding amino derivative. Half of the DMF solution of the amino derivative was stirred under a nitrogen gas atmosphere and ice cooling, to which 49 µl (0.35 mmol; 1.0 equivalent) of triethylamine were added. To the thus-obtained mixture, a solution of 1-formylimidazole, which had been prepared from 0.28 g (1.73 mmol; 5.0 equivalents) of CDI and 66 µl (1.75 mmol; 5.0 equivalents) of formic acid, in THF was added dropwise. The temperature of the resultant mixture was allowed to rise back to room temperature, at which the mixture was stirred for 4 hours and was then allowed to stand overnight. The mixture was concentrated under reduced pressure. The residue was purified by chromatography on a silica gel column (methylene chloride/5–8% methanol) and then crystallized from ethyl ether, whereby 78 mg (0.23 mmol) of the title compound were obtained as white purple crystals (yield: 65.7%).

m.p. 228°–230° C.

IR(KBr)cm$^{-1}$: 3277, 2960, 1677, 1610, 1560, 1290, 1128.

Elemental analysis for $C_{18}H_{21}N_5O_2 \cdot 0.2H_2O$:

Calculated: C, 63.03; H, 6.29; N, 20.42 Found: C, 62.71; H, 6.07; N, 20.20

EXAMPLE 15
(Compound No. 336)

1H-2-[4-[4-[N,N-Bis(2-chloroethyl)amino]
benzoylamino]-1-methylpyrrol-2-yl]benzimidazole-
5-(N-butyl)carboxamide 1H-2-(1-Methyl-4-nitropyrrol-2-yl)benzimidazole-5-(N-butyl)carboxamide (0.24 g; 0.71 mmol) was suspended in a mixed solvent of 5 ml of DMF and 5 ml of methanol, followed by the addition of 0.7 ml of 1N hydrochloric acid. Using 10% Pd/C as a catalyst, hydrogenation was conducted under normal pressure so that the reactant was converted to its corresponding amino derivative. Half of the DMF solution of the amino derivative was added with 49 µl (0.35 mmol 1.0 equivalent) of triethylamine, 0.10 g (0.38 mmol; 1,1 equivalents) of 4-[N,N-bis(2-chloroethyl)amino]benzoic acid and 52 mg (0.38 mmol; 1.1 equivalents) of HOBt. The resultant mixture was ice-cooled under a nitrogen gas atmosphere, followed by the addition of 79 mg (0.38 mmol; 1.1 equivalents) of DCC. The temperature of the resultant mixture was allowed to rise back to room temperature, at which the mixture was stirred for 4 hours and was then allowed to stand overnight. The mixture was concentrated under reduced pressure. The residue was purified by chromatography on a silica gel column (methylene chloride/4% methanol) and then crystallized from ethyl ether, whereby 90 mg (0.16 mmol) of the title compound were obtained as pale yellow crystals (yield: 42.6%).

m.p. 190°–192° C.

IR(KBr)cm$^{-1}$: 3390, 2925, 1655, 1518, 1458, 1328, 815.

Elemental analysis for $C_{26}H_{29}N_9O_2Cl_2 \cdot HCl \cdot 2H_2O$: Calculated: C, 48.57; H, 5.33; N, 19.61; Cl, 16.54 Found: C, 48.38; H, 5.22; N, 19.26; Cl, 16.36

EXAMPLE 16
(Compound No. 305)

1H-2-[4-[2-[N,N-Bis(2-chloroethyl)amino]
benzoylamino]-1-methylpyrrol-2-yl)benzimidazole-
5-[N-(2-amidinoethyl)]carboxamide hydrochloride
(Reaction 1)

Ethyl 2-[N,N-bis(2-hydroxyethyl)amino]benzoate

Ethylene oxide (12 ml; 242 mmol) was added dropwise under ice cooling to a solution of 4.1 g (25 mmol) of ethyl 2-aminobenzoate in 25 ml of a 30% suspension of acetic acid, followed by stirring for 1 hour. After the resultant mixture was stirred at room temperature for 2 nights, the mixture was stirred for 2 hours while bubbling nitrogen gas therethrough. Sodium hydrogencarbonate was added to the mixture to neutralized the same. Sodium chloride was then added until saturation, followed by extraction with ethyl acetate. The extract was dried over magnesium sulfate and the solvent was distilled out under reduced pressure. The residue was purified by chromatography on a silica gel column (n-hexane/ethyl acetate=1:1→0:1), whereby 3.4 g of a pale yellow oil were obtained (yield: 53%).

IR(KBr)cm$^{-1}$: 3421, 2957, 1699, 1252, 1078, 764.
(Reaction 2)

Ethyl 2-[N,N-bis(2-chloroethyl)amino]benzoate

Thionyl chloride (0.8 ml; 11.0 mmol) was added to a solution of 1.0 g (4.0 mmol) of ethyl 2-[N,N-bis(2-hydroxyethyl)amino]benzoate in 5 ml of methylene chloride, followed by stirring at room temperature for 1 hour. After the solvent was distilled out under reduced pressure, methylene chloride was added again in a small amount and was then distilled out under reduced pressure. This procedure was repeated twice. The resultant mixture was concentrated under reduced pressure, whereby 950 mg of a brown oil were obtained (yield: 83%).
(Reaction 3)

2-[N,N-Bis(2-chloroethyl)amino]benzoic acid

Ethyl 2-[N,N-bis(2-chloroethyl)amino]benzoate (950 mg; 3.3 mmol) was added to 15 ml of concentrated hydrochloric acid, followed by stirring for 8 hours under heating and reflux. The solvent was distilled out under reduced pressure and the residue was purified by chromatography on a silica gel column (methylene chloride→acetone), whereby 520 mg of white powder were obtained (yield: 61%).

IR(KBr)cm$^{-1}$: 3433, 1695, 1467, 1131, 776.
(Reaction 4)

1H-2-[4-[2-[N,N-Bis(2-chloroethyl)amino]benzoylamino]-1-methylpyrrol-2-yl]benzimidazole-5-[N-(2-amidinoethyl)]carboxamide hydrochloride 1H-2-(1-Methyl-4-nitropyrrol-2-yl)benzimidazole-5-[(N-(2-amidinoethyl)]carboxamide hydrochloride (300 mg; 0.77 mmol) was dissolved in 25 ml of a 1:1 mixed solvent of DMF and methanol in a reactor, followed by the addition of 850 μl of 1N hydrochloric acid and 250 mg of 5% Pd/C. The reactor was purged with nitrogen gas. The resulting mixture was stirred under a hydrogen gas atmosphere at room temperature for 2 hours. After completion of the reaction, the reactor was purged again with nitrogen gas. The 5% Pd/C was filtered off and the methanol was distilled out under reduced pressure. The resulting solution was cooled to −40° C., to which 250 μl of triethylamine were added under a nitrogen gas atmosphere. To the solution so obtained, 5 ml of a methylene chloride solution of 2-[N,N-bis(2-chloroethyl)amino]benzoyl chloride (1.1 equivalents), which had been prepared right before from 2-[N,N-bis(2-chloroethyl)amino]benzoic acid, were added dropwise. The thus-obtained solution was stirred, as was, for 30 minutes. Methanol was added, followed by further stirring for 10 minutes. The solvent was distilled out under reduced pressure and the residue was purified by chromatography on a silica gel column (ethyl acetate/IPA/water=5/2/1), whereby 291 mg of white powder were obtained (yield: 61%).

Elemental analysis for $C_{27}H_{31}N_8O_2Cl_3 \cdot 2H_2O$: Calculated: C, 50.51; H, 5.50; N, 17.45 Found: C, 50.17; H, 5.36; N, 16.92

EXAMPLE 17
(Compound No. 15)

1H-2-[4-[3-[N,N-bis(2-chloroethyl)amino]benzoylamino]-1-methylpyrrol-2-yl]benzimidazole-5-[N-(2-amidinoethyl)]carboxamide hydrochloride
(Reaction 1)

Methyl 3-[N,N-bis(2-hydroxyethyl)amino]benzoate

Methyl 3-aminobenzoate (3.8 g; 25 mmol) was reacted with 11 g (250 mmol; 10 equivalents) of ethylene oxide in 25 ml of 30% acetic acid, followed by post treatments. The crude product so obtained was purified by chromatography on a silica gel column (eluted with methylene chloride/2–4% methanol), whereby 5.95 g (24.9 mmol) of the title compound were obtained as a yellow oil (yield: quantitative).
(Reaction 2)

Methyl 3-[N,N-bis(2-chloroethyl)amino]benzoate

Methyl 3-[N,N-bis(2-hydroxyethyl)amino]benzoate (3.0 g; 12.5 mmol) was dissolved in 50 ml of benzene, to which 7.5 ml (103 mmol; 8.3 equivalents) of thionyl chloride were added dropwise under ice cooling. The resulting mixture was stirred under heating for 1.5 hours over an oil bath which was controlled at 80° C. The mixture was concentrated under reduced pressure and ethyl acetate was added to the residue. The ethyl acetate solution was washed twice with a saturated aqueous solution of sodium hydrogencarbonate and then with a saturated aqueous solution of sodium chloride. The solution was dried over sodium sulfate and then concentrated under reduced pressure. The resulting concentrate was purified by chromatography on a silica gel column (eluted with n-hexane/ethyl acetate=5/1) and then washed with n-hexane, whereby 2.44 g (8.83 mmol) of the title compound were obtained as white crystals (yield: 70.7%).

m.p. 60.5°–61.5° C.
(Reaction 3)

3-[N,N-Bis(2-chloroethyl)amino]benzoic acid

Concentrated hydrochloric acid (40 ml) was added to 2.0 g (7.44 mmol) of methyl 3-[N,N-bis(2-chloroethyl)amino]benzoate, followed by stirring under heating for 3 hours over an oil bath which was controlled at 90° C. The reaction mixture was diluted with water. The resulting crystals were collected by filtration and then washed with 50% ethanol, whereby 1.95 g (7.44 mmol) of the title compound were obtained as white crystals (yield: quantitative).

m.p. 179°–180° C.
(Reaction 4)

1H-2-[4-[3-[N,N-Bis(2-chloroethyl)amino]benzoylamino]-1-methylpyrrol-2-yl]benzimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide (0.80 g; 2.0 mmol) was suspended in a mixed solvent of 15 ml of DMF and 10 ml of methanol, followed by the addition of 0.18 ml (2.16 mmol; 1.1 equivalents) of concentrated hydrochloric acid. Using 0.38 g of 10% Pd/C, hydrogenation was conducted under normal pressure so that the reactant was converted to its corresponding amino derivative. A solution of half the amino derivative in DMF was stirred under a nitrogen gas atmosphere and ice cooling, to which 0.30 ml (2.15 mmol; 1.1 equivalents) of triethylamine were added. To the thus-obtained mixture, a solution of 3-[N,N-bis(2-chloroethyl)amino]benzoyl chloride, which had been synthesized from 3-[N,N-bis(2-chloroethyl)amino]benzoic acid while using thionyl chloride, in 5 ml of benzene was added dropwise over 7 minutes. The temperature of the resultant mixture was allowed to rise back to room temperature, at which the mixture was stirred for 3 hours. The resulting white crystals were filtered off and the filtrate was concentrated under reduced pressure. The residue was purified by chromatography on a silica gel column (ethyl acetate/IPA/water=6/2/1) and then crystallized from ethanol-ethyl ether, whereby 0.39 g (0.64 mmol) of the title compound was obtained as pale yellow white crystals (yield: 64.0%).

m.p.>275° C.

IR(KBr)cm$^{-1}$: 3257, 1637, 1551, 1350, 1308, 747.

Elemental analysis for $C_{27}H_{30}N_8O_2Cl_2 \cdot HCl \cdot 1.8H_2O$: Calculated: C, 50.80; H, 5.46; N, 17.55; Cl, 16.66 Found: C, 51.09; H, 5.54; N, 17.15; Cl, 16.57

EXAMPLE 18
(Compound No. 13)

1H-2-[4-[4-[N,N-Bis(2-chloroethyl)amino] phenoxyacetylamino]-1-methylpyrrol-2-yl] benzimidazole-5-[N-(2-amidinoethyl)]carboxamide hydrochloride (Reaction 1)

Methyl 4-nitrophenoxyacetate

Thionyl chloride (2.3 ml) was added dropwise under ice cooling to a solution of 5.0 g (25 mmol) of 4-nitrophenoxyacetic acid in 250 ml of methanol, followed by stirring at room temperature for 1 hour. After the solvent was distilled out under reduced pressure, the residue was dissolved in 50 ml of methylene chloride, followed by neutralization with an aqueous solution of sodium hydrogencarbonate. The organic layer was washed with a saturated aqueous solution of sodium chloride and then dried over sodium sulfate. The solvent was thereafter distilled out under reduced pressure, whereby 5.2 g of pale yellow powder were obtained (yield: 96%).

IR(KBr)cm$^{-1}$: 2446, 1753, 1594, 1340, 1221, 856.

(Reaction 2)

Methyl 4-aminophenoxyacetate

Methyl 4-nitrophenoxyacetate (5.0 g; 24 mmol) was dissolved in 150 ml of methanol in a reactor, followed by the addition of 480 mg of 5% Pd/C. The reactor was purged with nitrogen gas. Under a hydrogen gas atmosphere, the resultant mixture was stirred at room temperature for 2 hours. After completion of the reaction, the reactor was purged again with nitrogen gas. The Pd/C was filtered off and the solvent was then distilled out under reduced pressure, whereby 4.1 g of a brown oil were obtained (yield: 92%).

(Reaction 3)

Methyl 4-[N,N-bis(2-hydroxyethyl)amino] phenoxyacetate

Ethylene oxide (10 g; 227 mmol) was added under ice cooling to a solution of 4.0 g (22 mmol) of methyl 4-aminophenoxyacetate in 22 ml of 30% acetic acid. After the resultant mixture was stirred overnight at room temperature, nitrogen gas was bubbled to eliminate excess ethylene oxide. Subsequent to neutralization with sodium hydrogencarbonate, sodium chloride was added, followed by extraction with n-butanol. The extract was dried over magnesium sulfate and the solvent was distilled out. The residue was purified by chromatography on a silica gel column (chloroform/methanol=20/1), whereby 5.29 g of the title compound were obtained as a colorless oil (yield: 89%).

(Reaction 4)

Methyl 4-[N,N-bis(2-chloroethyl)amino] phenoxyacetate

Thionyl chloride (3.17 g; 26.6 mmol) was added dropwise under ice cooling to a solution of 2.39 g (8.87 mmol) of methyl 4-[N,N-bis(2-hydroxyethyl)amino]phenoxyacetate in 72 ml of 1,2-dichloroethane. The thus-obtained mixture was stirred at room temperature for 4 hours and then concentrated. The resulting residue was purified by flush chromatography (chloroform/methanol=200/3), whereby 2.0 g of the title compound were obtained as brown crystals (yield: 74%).

m.p. 69°–70° C.

IR(KBr)cm$^{-1}$: 3449, 2956, 1759, 1516, 1440, 1257, 1220, 1092, 829.

(Reaction 5)

4-[N,N-Bis(2-chloroethyl)amino]phenoxyacetic acid

A suspension of 1.99 g (6.50 mmol) of methyl 4-[N,N-bis(2-chloroethyl)amino]phenoxyacetate in 60 ml of concentrated hydrochloric acid was heated at 50° C. for 30 minutes. The suspension was washed with methylene chloride, neutralized with sodium hydrogencarbonate, and then extracted with methylene chloride. The extract was washed with a saturated aqueous solution of sodium chloride, dried over magnesium sulfate and then concentrated, whereby 1.23 g of the title compound were obtained as colorless crystals (yield: 65%).

m.p. 112°–113° C.

IR(KBr)cm$^{-1}$: 3436, 2968, 1743, 1514, 1433, 1235, 1201, 1099, 817.

(Reaction 6)

1H-2-[4-[4-[N,N-Bis(2-chloroethyl)amino] phenoxyacetylamino]-1-methylpyrrol-2-yl] benzimidazole-5-[N-(2-amidinoethyl)]carboxamide hydrochloride A solution of 302 mg (0.77 mmol) of 1H-2-(1-methyl-4-nitropyrrol-2-yl)benzimidazole-5-[N-(2-amidinoethyl)] carboxamide hydrochloride in 35 ml of methanol-DMF was subjected at room temperature to catalytic reduction in the presence of 10% Pd/C as a catalyst, whereby the corresponding amino derivative was obtained. The amino derivative was added with triethylamine and also with 4-[N,N-bis(2-chloroethyl)amino]phenoxyacetyl chloride which had been prepared from 4-[N,N-bis(2-chloroethyl)amino] phenoxyacetic acid and oxalyl chloride. The resultant mixture was stirred for 30 minute and then concentrated. The residue was purified by flush column chromatography (ethyl acetate/IPA/water=6/2/1), whereby 218 mg of the title compound were obtained (yield: 44%).

m.p. 270°–290° C. (dec.).

IR(KBr)cm$^{-1}$: 3271, 1687, 1639, 1561, 1511, 1238, 1069, 816, 746.

EXAMPLE 19
(Compound No. 310)

1H-2-[4-[3,5-Bis[N,N-bis(2-chloroethyl)amino] benzoylamino]-1-methylpyrrol-2-yl]benzimidazole-5-[N-(2-amidinoethyl)]carboxamide hydrochloride (Reaction 1)

Methyl 3,5-diaminobenzoate

Thionyl chloride (3.7 g) was added dropwise under ice cooling to a solution of 5.0 g (33 mmol) of 3,5-diaminobenzoic acid in 250 ml of methanol, followed by stirring at room temperature for 2 hours and then stirring under heating and reflux for additional 6 hours. After the solvent was distilled out under reduced pressure, the residue was neutralized with aqueous ammonia and then extracted with methylene chloride. The extract was dried over sodium sulfate and then dried up under reduced pressure, whereby 3.3 g of white powder were obtained (yield: 60%).

IR(KBr)cm$^{-1}$: 3389, 3314, 3219, 1705, 1602, 771.

(Reaction 2)

Methyl 3,5-bis[N,N-bis(2-hydroxyethyl)amino] benzoate

Ethylene oxide (15 g; 341 mmol) was added under ice cooling to a solution of 2.8 g (17 mmol) of methyl 3,5-diaminobenzoate in 17 ml of 30% acetic acid. After the resultant mixture was stirred overnight at room temperature, nitrogen gas was bubbled to eliminate excess ethylene oxide. Subsequent to neutralization of the resultant mixture with sodium hydrogencarbonate, the mixture was extracted with n-butanol while salting it out with sodium chloride. The extract was dried over magnesium sulfate. After the solvent was distilled out, the residue so obtained was purified by chromatography on a column (methanol/chloroform=1/10), whereby 1.94 g of the title compound were obtained as colorless crystals.

(Reaction 3)

Methyl 3,5-bis[N,N-bis(2-chloroethyl)amino]benzoate

Mixed were 1.94 g (5.67 mmol) of methyl 3,5-bis[N,N-bis(2-hydroxyethyl)amino]benzoate and 19 ml of phosphorus oxychloride, followed by heating at 90° C. for 1 hour (the benzoate dissolved in several minutes after the initiation of the heating). After completion of the reaction, the reaction mixture was concentrated. The residue so obtained was carefully added to an ice-cooled aqueous solution of sodium hydrogencarbonate, followed by extraction with ethyl acetate. The extract was washed with a saturated aqueous solution of sodium chloride, dried over magnesium sulfate and then concentrated. The concentrate was purified by flush chromatography (methanol/chloroform=3/200), whereby 1.74 g of the title compound were obtained as brown crystals.

(Reaction 4)

3,5-Bis[N,N-bis(2-chloroethyl)amino]benzoic acid

A suspension of 1.59 g (3.82 mmol) of methyl 3,5-bis[N,N-bis(2-chloroethyl)amino]benzoate in 48 ml of concentrated hydrochloric acid was heated at 50° C. for 5 hours. After completion of the reaction, the suspension was extracted with methylene chloride. The extract was washed with an aqueous solution of sodium hydrogencarbonate and then with a saturated aqueous solution of sodium chloride, dried over magnesium sulfate, and was then concentrated. The resultant residue was purified by flush chromatography (methanol/chloroform=1/20), whereby 1.01 g of the title compound were obtained as colorless crystals.

(Reaction 5)

1H-2-[4-[3,5-Bis[N,N-bis(2-chloroethyl)amino] benzoylamino]-1-methylpyrrol-2-yl]benzimidazole-5-[N-(2-amidinoethyl)]carboxamide hydrochloride After purging a reactor with nitrogen gas, a solution of 300 mg (0.766 mmol) of 1H-2-(1-methyl-4-nitropyrrol-2-yl)benzimidazole-5-[N-(2-amidinoethyl)]carboxamide hydrochloride and 0.84 ml of 1N hydrochloric acid in 30 ml of methanol-DMF was ice-cooled and then added with 145 mg of 10% Pd/C. Thereafter, the resultant mixture was stirred under a hydrogen gas atmosphere at room temperature for 45 minutes. After completion of the reaction, Pd/C was filtered off under a nitrogen gas stream. The filtrate was washed with degasified DMF. The thus-obtained filtrate was thoroughly concentrated. To the concentrate, 186 mg (1.84 mmol) of triethylamine and 5.0 ml of 3,5-bis[N,N-bis(2-chloroethyl)amino]benzoyl chloride—0.193 M/1,2-dichloroethane solution; prepared by adding 368 mg (2.9 mmol) of oxalyl chloride dropwise at −20° C. to a solution of 389 mg (0.967 mmol) of 3,5-bis[N,N-bis(2-chloroethyl)amino]benzoic acid in 12 ml of 1,2-dichloroethane, stirring the resultant mixture overnight at room temperature, concentrating the mixture to dryness, and then dissolving the thus-obtained oil in 5.0 ml of 1,2-dichloroethane—were added dropwise at −78° C. under a nitrogen gas atmosphere, followed by stirring for 30 minutes. After completion of the reaction, the reaction mixture was concentrated and the residue was subjected to flush column chromatography (ethyl acetate/IPA/water=6/2/1), whereby 76.5 mg of the title compound were obtained as an amorphous substance (yield: 13%).

IR(KBr)cm$^{-1}$: 3396, 1638, 1591, 1552, 1476, 1409, 1358, 1306, 746.

Elemental analysis for $C_{31}H_{37}N_9O_2Cl_4 \cdot HCl \cdot 1.5H_2O$: Calculated: C, 48.17; H, 5.35; N, 16.31 Found: C, 48.09; H, 5.60; N, 16.02

EXAMPLE 20
(Compound No. 2)

1H-2-[4-[2-[4-[N,N-Bis(2-chloroethyl)amino] phenyl]acetylamino]-1-methylpyrrol-2-yl] benzimidazole-5-[N-(2-amidinoethyl)]carboxamide hydrochloride (Reaction 1)

Methyl 4-[N,N-bis(2-hydroxyethyl)amino] phenylacetate

Methyl 4-aminophenylacetate (5.5 g; 33 mmol) was reacted with 45 g (341 mmol, 10 equivalents) of ethylene oxide in 33 ml of 30% acetic acid, followed by post treatments. The crude product so obtained was purified by chromatography on a silica gel column (n-hexane/ethyl acetate=1/2→1/4) and washed with n-hexane, whereby 6.07 g (24.0 mmol) of the title compound were obtained as white crystals (yield: 72.6%).

(Reaction 2)

Methyl 4-[N,N-bis(2-chloroethyl)amino] phenylacetate

Methyl 4-[N,N-bis(2-hydroxyethyl)amino]phenylacetate (3.0 g; 11.8 mmol) was dissolved in 8 ml of benzene, followed by the dropwise addition of 3 ml (32.2 mmol; 2.7 equivalents) of phosphorus oxychloride under ice cooling. The resultant mixture was stirred under heat for 1.5 hours over an oil bath which was controlled at 80° C. The reaction mixture was added dropwise to water to hydrolyze any unreacted phosphorus oxychloride. The reaction mixture was then extracted with ethyl acetate. The extract was washed with a saturated aqueous solution of sodium chloride, dried over sodium sulfate, and then concentrated under reduced pressure. The residue was purified by chromatography on a silica gel column (n-hexane/ethyl acetate= 4/1), whereby 2.97 g (10.2 mmol) of the title compound were obtained as a yellow oil (yield: 81.0%).
(Reaction 3)

4-[N,N-Bis(2-chloroethyl)amino]phenylacetic acid

Concentrated hydrochloric acid (10 ml) was added to 2.0 g (6.9 mmol) of methyl 4-[N,N-bis(2-chloroethyl)amino] phenylacetate, followed by stirring under heat for 1 hour over an oil bath controlled at 90° C. The reaction mixture was diluted with water and was then extracted three times with methylene chloride. As the raw material still remained, the reaction product was extracted with a 1N aqueous solution of sodium hydroxide. The water layer was acidified with hydrochloric acid and then extracted again with methylene chloride. The extract was dried and concentrated under reduced pressure. The residue so obtained was washed with n-hexane, whereby 1.61 g (5.83 mmol) of the title compound were obtained as white crystals (yield: 84.5%).

m.p. 102.5°–104° C.
(Reaction 4)

1H-2-[4-[2-[4-[N,N-Bis(2-chloroethyl)amino] phenylacetylamino]-1-methylpyrrol-2-yl] benimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide hydrochloride (0.80 g; 2.0 mmol) was suspended (practically undissolved) in a mixed solvent of 15 ml of DMF and 10 ml of methanol, followed by the addition of 0.18 ml (2.16 mmol; 1.1 equivalents) of concentrated hydrochloric acid. Using 0.38 g of 10% Pd/C as a catalyst, hydrogenation was conducted under normal pressure so that the reactant was converted to its corresponding amino derivative. Half the amount of the amino derivative was dissolved in DMF. The solution so obtained was stirred under a nitrogen gas atmosphere and ice cooling, to which 0.30 ml (2.15 mmol; 1.1 equivalents) of triethylamine was added. A solution of 1.12 mmol of 4-[N,N-bis(2-chloroethyl)amino]phenylacetyl chloride in 5 ml of methylene chloride was added dropwise over 7 minutes. The temperature of the thus-obtained mixture was allowed to rise again to room temperature, at which the mixture was stirred for 1.5 hours. The resulting white crystals were filtered off, followed by concentration under reduced pressure. The residue was purified by chromatography on a silica gel column (ethyl acetate/IPA/water=6/2/1) and then crystallized from ethanol-ethyl ether, whereby 0.33 g (0.53 mmol) of the title compound was obtained as pale yellow white amorphous powder (yield: 53.2%).

IR(KBr)cm$^{-1}$: 3409, 1637, 1519, 1308

EXAMPLE 21
(Compound No. 6)

1H-2-[4-[3-Methoxy-4-[N,N-bis(2-chloroethyl) amino]benzoylamino]-1-methylpyrrol-2-yl] benzimidazole-5-[N-(2-amidinoethyl)]carboxamide hydrochloride (Reaction 1)

Methyl 3-methoxy-4-nitrobenzoate

Thionyl chloride (3.7 g) was added dropwise under ice cooling to a solution of 4.7 g (24 mmol) of 3-methoxy-4-nitrobenzoic acid in 250 ml of methanol. The thus-obtained mixture was stirred at room temperature for 2 hours and then stirred under heating and reflux for 3 hours. After the solvent was distilled out under reduced pressure, the residue was neutralized with aqueous ammonia and then extracted with methylene chloride. The extract was dried over sodium sulfate and then dried up under reduced pressure, whereby 4.9 g of white powder were obtained (yield: 97%).

IR(KBr)cm$^{-1}$: 1732, 1614, 1529, 1306, 1249, 745.
(Reaction 2)

Methyl 3-methoxy-4-aminobenzoate

Methyl 3-methoxy-4-nitrobenzoate (4.8 g; 23 mmol) was dissolved in 150 ml of a 2:1 mixed solvent of methanol and tetrahydrofuran, followed by addition of 480 mg of 5% Pd/C. The resulting mixture was stirred for 2 hours under a hydrogen gas atmosphere at room temperature. After completion of the reaction, the Pd/C was filtered off and the solvent was distilled out under reduced pressure, whereby 3.9 g of white crystals were obtained (yield: 54%).

IR(KBr)cm$^{-1}$: 3482, 3362, 1680, 1311, 1231, 765
(Reaction 3)

Methyl 3-methoxy-4-[N,N-bis(2-hydroxyethyl) amino]benzoate

Ethylene oxide (16.5 ml; 333 mmol) was added dropwise under ice cooling to a solution of 3.9 g (22 mmol) of methyl 3-methoxy-4-aminobenzoate in 33 ml of a 30% acetic acid suspension. The thus-obtained was stirred for 1 hour and then stirred at room temperature for 2 nights. The mixture was then stirred for 2 hours while bubbling nitrogen gas therethrough. Sodium hydrogencarbonate was added to the mixture to neutralized the same. Sodium chloride was then added until saturation, followed by extraction with ethyl acetate. The extract was dried over magnesium sulfate and the solvent was distilled out under reduced pressure. The residue was purified by chromatography on a silica gel column (methylene chloride/ethyl acetate=1:1→0:1), whereby 3.1 g of a pale yellow oil were obtained (yield: 54%).

IR(KBr)cm$^{-1}$: 3421, 2951, 1716, 1268, 1033, 766.
(Reaction 4)

Methyl 3-methoxy-4-[N,N-bis(2-chloroethyl)amino] benzoate

Thionyl chloride (0.7 ml; 9.6 mmol) was added to a solution of 1.0 g (3.7 mmol) of methyl 3-methoxy-4-[bis(2-hydroxyethyl)amino]benzoate in 20 ml of methylene chloride, followed by stirring at room temperature for 3 hours. After the solvent was distilled out under reduced pressure, methylene chloride was added again in a small amount and was then distilled out under reduced pressure. This procedure was repeated twice. The resultant mixture was evaporated to dryness under reduced pressure, whereby 1.0 g of a brown oil was obtained (yield: 88%).
(Reaction 5)

3-Methoxy-4-[N,N-bis(2-chloroethyl)amino]benzoic acid

Methyl 3-methoxy-4-[bis(2-chloroethyl)amino]benzoate (1.0 g; 3.3 mmol) was added to 20 ml of concentrated hydrochloric acid, followed by stirring for 30 minutes under heating and reflux. The solvent was distilled out under reduced pressure, whereby 707 mg of white powder were obtained (yield: 74%).

IR(KBr)cm$^-$: 3435, 1674, 1600, 1279, 751.
(Reaction 6)

1H-2-[4-[3-Methoxy-4-[N,N-bis(2-chloroethyl) amino]benzoylamino]-1-methylpyrrol-2-yl] benzimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide hydrochloride (300 mg; 0.77 mmol) was dissolved in 25 ml of a 1:1 mixed solvent of DMF and methanol in a reactor, followed by the addition of 850 µl of 1N hydrochloric acid and 250 mg of 5% Pd/C. The reactor was purged with nitrogen gas. The resulting mixture was stirred under a hydrogen gas atmosphere at room temperature for 2 hours. After completion of the reaction, the reactor was purged again with nitrogen gas. The Pd/C was filtered off and the methanol was distilled out under reduced pressure. The resulting solution was cooled to −40° C., to which 250 µl of triethylamine were added under a nitrogen gas atmosphere. To the solution so obtained, 5 ml of a methylene chloride solution of 3-methoxy-4-[N,N-bis(2-chloroethyl)amino]benzoyl chloride (1.1 equivalents), which had been prepared right before, were added dropwise. The thus-obtained solution was stirred, as was, for 30 minutes. Methanol was added, followed by further stirring for 10 minutes. The solvent was distilled out under reduced pressure and the residue was purified by chromatography on a silica gel column (ethyl acetate/IPA/water=5/2/1), whereby 241 mg of white powder were obtained (yield: 49%).

IR(KBr)cm$^{-1}$: 3422, 2312, 1685, 1541, 1313, 756.

EXAMPLE 22
(Compound No. 3)

1H-2-[4-[3-[4-[N,N-Bis(2-chloroethyl)amino] phenyl]propionylamino]-1-methylpyrrol-2-yl] benzimidazole-5-[N-(2-amidinoethyl)]carboxamide hydrochloride (Reaction 1)

Methyl 4-[N,N-bis(2-hydroxyethyl)amino] phenylpropionate

Methyl 3-(4-aminophenyl)propionate (4.3 g; 24 mmol) was reacted with 11 g (250 mmol, 10 equivalents) of ethylene oxide in 24 ml of 30% acetic acid in a similar manner to Reaction 3 in Example 21. The reaction mixture was worked up. The crude product so obtained was purified by chromatography on a silica gel column (methylene chloride/2–4% methanol) and then crystallized from n-hexane-ethyl ether, whereby 5.04 g (18.9 mmol) of the title compound were obtained as white crystals (yield: 78.6%).

(Reaction 2)

Methyl 3-[4-[N,N-bis(2-chloroethyl)amino]phenyl] propionate

Methyl 3-[4-[N,N-[bis(2-hydroxyethyl)]amino]phenyl] propionate (2.0 g; 7.48 mmol) was dissolved in 5 ml of benzene, followed by the dropwise addition of 2 ml (21.5 mmol; 2.9 equivalents) of phosphorus oxychloride under ice cooling. The resultant mixture was stirred under heat for 1.5 hours over an oil bath which was controlled at 80° C. The reaction mixture was added dropwise to water to hydrolyze any unreacted phosphorus oxychloride. The reaction mixture was then extracted with ethyl acetate. The extract was washed with a saturated aqueous solution of sodium chloride, dried over sodium sulfate, and then concentrated under reduced pressure. The residue was purified by chromatography on a silica gel column (n-hexane/ethyl acetate=4/1), whereby 1.87 g (6.15 mmol) of the title compound were obtained as a yellow oil (yield: 82.2%).

(Reaction 3)

3-[4-[N,N-Bis(2-chloroethyl)amino]phenyl] propionic acid

Concentrated hydrochloric acid (10 ml) was added to 1.5 g (4.93 mmol) of methyl 3-[4-[N,N-bis(2-chloroethyl) amino]phenyl]propionate, followed by stirring under heat for 2.5 hours over an oil bath controlled at 90° C. The reaction mixture was diluted with water and was then adjusted to about pH 2 or so with a 5N aqueous solution of sodium hydroxide. The resultant crystals were collected by filtration, whereby 1.21 g (4.17 mmol) of the title compound were obtained as white crystals (yield: 84.6%).

(Reaction 4)

3-[4-[N,N-Bis(2-chloroethyl)amino]phenyl] propionyl chloride

3-[4-[N,N-Bis(2-chloroethyl)amino]phenyl]propionic acid (0.24 g; 0.83 mmol) was dissolved in 5 ml of 1,2-dichloroethane, followed by the dropwise addition of 0.22 ml (2.58 mmol; 3.1 equivalents) of oxalyl chloride (with ice-cooling from an intermediary time point due to violent exotherm). After completion of the dropwise addition, the temperature of the resultant mixture was allowed to rise again to room temperature, at which the mixture was stirred for 3 hours and then allowed to stand overnight. The mixture was thereafter concentrated under reduced pressure, whereby the title compound was obtained in a crude form. The crude compound was provided for use in the next reaction without purification.

(Reaction 5)

1H-2-[4-[3-[4-[N,N-Bis(2-chloroethyl)amino] phenyl]propionylamino]-1-methylpyrrol-2-yl] benzimidazole-5-[N-(2-amidinoethyl)]carboxamide hydrochloride 1H-2-(1-Methyl-4-nitropyrrol-2-yl)benzimidazole-5-[N-(2-amidinoethyl)]carboxamide hydrochloride (0.30 g; 0.77 mmol) was suspended in a mixed solvent of 10 ml of DMF and 6.5 ml of methanol, followed by the addition of 65 µl (0.78 mmol; 1.0 equivalent) of concentrated hydrochloric acid. Using 0.12 g of 10% Pd/C as a catalyst, hydrogenation was conducted under normal pressure so that the reactant was converted to its corresponding amino derivative. The amino derivative was dissolved in DMF. The solution so obtained was stirred under a nitrogen gas atmosphere and ice cooling, to which 0.21 ml (1.5 mmol; 1.9 equivalents) of triethylamine was added. A solution of 0.83 mmol of 3-[4-[N,N-bis(2-chloroethyl)amino]phenyl]propionyl chloride in 2 ml of methylene chloride was added dropwise over 7 minutes. The temperature of the thus-obtained mixture was allowed to rise again to room temperature, at which the mixture was stirred for 4.5 hours. The resulting white crystals were filtered off, followed by concentration under reduced pressure. The residue was purified by chromatography on a silica gel column (ethyl acetate/IPA/water=6/2/1) and then crystallized from ethanol-ethyl ether, whereby 0.25 g (0.37 mmol) of the title compound was obtained as a pale yellow white amorphous substance (yield: 47.6%).

m.p.: No distinct melting point was observed.

IR(KBr)cm$^{-1}$: 3267, 1638, 1546, 1519, 1350, 1308, 812, 747.

Elemental analysis for $C_{29}H_{34}N_8O_2Cl_2 \cdot HCl \cdot 2H_2O$: Calculated: C, 51.98; H, 5.87; N, 16.72; Cl, 15.87 Found: C, 51.68; H, 5.83; N, 16.45 Cl, 16.26

EXAMPLE 23
(Compound No. 260)

1H-2-[4-[4-[N,N-Bis(2-bromoethyl)amino]
benzoylamino]-1-methylpyrrol-2-yl]benzimidazole-
5-[N-(2-amidinoethyl)]carboxamide hydrochloride (Reaction 1)

Ethyl 4-[N,N-bis(2-bromoethyl)amino]benzoate

Phosphorus tribromide (1.1 ml; 11.3 mmol) was added under ice-cooling to a solution of 2.0 g (7.9 mmol) of ethyl 4-[N,N-bis(2-hydroxyethyl)amino]benzoate in 50 ml of methylene chloride. The resulting mixture was stirred, as was, for 2 hours, followed by further stirring at room temperature for 12 hours. After the solvent was distilled out under reduced pressure, the residue was dissolved in ethanol and the insoluble matter was eliminated. The product was purified by chromatography on a silica gel column (ethyl acetate/n-hexane=3/1), whereby 1.0 g of white powder was obtained (yield: 34%).

(Reaction 2)

4-[N,N-Bis(2-bromoethyl)amino]benzoic acid

Ethyl 4-[N,N-bis(2-bromoethyl)amino]benzoate (1.0 g; 2.6 mmol) was added to 10 ml of a 47% aqueous solution of hydrobromic acid, followed by stirring for 30 minutes under heating and reflux. The solvent was distilled out under reduced pressure, whereby 650 mg of white powder were obtained (yield: 70%).

(Reaction 3)

1H-2-[4-[4-[N,N-Bis(2-bromoethyl)amino]
benzoylamino]-1-methylpyrrol-2-yl]benzimidazole-
5-[N-(2-amidinoethyl)]carboxamide hydrochloride 1H-2-(1-Methyl-4-nitropyrrol-2-yl)benzimidazole-5-[N-(2-amidinoethyl)]carboxamide (200 mg; 0.51 mmol) was dissolved in 20 ml of a 1:1 mixed solvent of DMF and methanol in a reactor, followed by the addition of 200 mg of 5% Pd/C and 0.7 ml of 1N hydrochloric acid. The reactor was purged with nitrogen gas. The resulting mixture was stirred under a hydrogen gas atmosphere at room temperature for 2 hours. After completion of the reaction, the reactor was purged again with nitrogen gas. The 5% Pd/C was filtered off and the methanol was distilled out under reduced pressure. The resulting solution was cooled to 0° C., to which 0.17 ml of triethylamine and a solution of 4-[N,N-bis(2-bromoethyl)amino]benzoyl chloride (1.1 equivalents), which had been prepared right before, in 5 ml of DMF were added dropwise under a nitrogen gas atmosphere. The resultant mixture was stirred, as was, for 30 minutes. Methanol was added, followed by further stirring for 5 minutes. The solvent was distilled out under reduced pressure and the residue was purified by chromatography on a silica gel column (ethyl acetate/IPA/water=5/2/1), whereby 193 mg of white powder were obtained (yield: 55%).

m.p.>270° C.

IR(KBr)cm$^{-1}$: 3292, 2367, 1690, 1606, 1543, 1350, 1204.

Elemental analysis for $C_{27}H_{31}N_8O_2Cl_1Br_2.5H_2O$: Calculated: C, 41.17; H, 4.43; N, 14.00 Found: C, 41.32; H, 4.43; N, 14.28

EXAMPLE 24
(Compound No. 332)

1H-2-(4-Benzoylamino-1-methylpyrrol-2-yl)
benzimidazole- 5-[N-(2-aminoethyl)]carboxamide
hydrochloride (Reaction 1)

1H-2-(4-Benzoylamino-1-methylpyrrol-2-yl)
benzimidazole-5-[N-[2-(t-butoxycarbonylamino)
ethyl]]-carboxamide 1H-2-(1-Methyl-4-nitropyrrol-2-yl)benzimidazole-5-[N-[2-(t-butoxycarbonylamino)ethyl]]carboxamide (0.11 g; 0.26 mmol) was suspended in a mixed solvent of 3 ml of DMF and 2 ml of methanol. Using 0.10 g of 10% Pd/C as a catalyst, hydrogenation was conducted under normal pressure so that the reactant was converted to its corresponding amino derivative. A DMF solution of the amino derivative was stirred under a nitrogen gas atmosphere and ice cooling, to which 45 µl (0.32 mmol; 1.2 equivalents) of triethylamine was added, followed by the dropwise addition of 36 µl (0.31 mmol; 1.2 equivalents) of benzoyl chloride. The resultant mixture was stirred, as was, for 4 hours and was then allowed to stand overnight. The mixture was concentrated under reduced pressure. The residue was purified by chromatography on a silica gel column (chloroform/8% methanol).Relevant fractions were concentrated, whereby 103 mg (0.20 mmol) of the title compound were obtained as amorphous powder (yield: 82.0%).

(Reaction 2)

1H-2-(4-Benzoylamino-1-methylpyrrol-2-yl)
benzimidazole-5-[N-(2-aminoethyl)]carboxamide
hydrochloride 1H-2-(4-Benzoylamino-1-methylpyrrol-2-yl) benzimidazole-5-[N-[2-(t-butoxycarbonylamino)ethyl]]carboxamide (0.10 g; 0.20 mmol) was dissolved in 2 ml of trifluoroacetic acid, followed by stirring at room temperature for 1 hour. The resultant mixture was concentrated under reduced pressure. After evaporated with toluene, 2 ml of 4N HCl/dioxane was added. The thus-obtained mixture was stirred for 1 hour, followed by concentration under reduced pressure. The residue was crystallized from ethyl ether, whereby 84 mg (0.18 mmol) of the title compound were obtained as pale yellow white crystals (yield: 88.8%).

m.p. 252°–260° C.

IR(KBr)cm$^{-1}$: 3400, 3044, 1647, 1560, 1395, 1321, 823, 705.

Elemental analysis for $C_{22}H_{22}N_6O_2.2HCl.1.5H_2O$: Calculated: C, 52.60; H, 5.42; N, 16.73 Cl, 14.11 Found: C, 52.73; H, 5.47; N, 16.46; Cl, 13.95

EXAMPLE 25
(Compound No. 129)

1H-2-[4-[4-[N,N-Bis(2-chloroethyl)amino]
benzoylamino]-1-methylpyrrol-2-yl]benzimidazole-
5-[N-(2-aminoethyl)]carboxamide hydrochloride (Reaction 1)

1H-2-(1-Methyl-4-nitropyrrol-2-yl)benzimidazole-5-
[N-[2-(t-butoxycarbonylamino)ethyl]]carboxamide 1H-2-(1-Methyl-4-nitropyrrol-2-yl)benzimidazole-5-carboxylic acid (0.10 g; 0.35 mmol) was dissolved in 5 ml of DMF, followed by the addition of 0.07 g (0.43 mmol; 1.2 equivalents) of CDI. The resultant mixture was stirred under a nitrogen gas atmosphere at room temperature for 2.5 hours and was then ice-cooled, to which a solution of 0.07 g (0.44 mmol; 1.2 equivalents) of N-t-butoxycarbonyl-1,2-ethanediamine in 2 ml of DMF was added. The temperature of the thus-obtained mixture was allowed to rise again to room temperature, at which the mixture was stirred for 4 hours and then allowed to stand overnight. The mixture was then concentrated under reduced pressure. The residue was washed with methanol, whereby 0.11 g (0.26 mmol) of the title compound was obtained as yellow crystals (yield: 73.3%).
(Reaction 2)

1H-2-[4-[4-[N,N-Bis(2-chloroethyl)amino]
benzoylamino]-1-methylpyrrol-2-yl]benzimidazole-
5-[N-[2-(t-butoxycarbonylamino)ethyl]]carboxamide 1H-2-(1-Methyl-4-nitropyrrol-2-yl)benzimidazole-5-[N-[2-(t-butoxycarbonylamino)ethyl]]carboxamide (0.11 g; 0.26 mmol) was suspended in a mixed solvent of 3 ml of DMF and 2 ml of methanol. Using 0.10 g of 10% Pd/C as a catalyst, hydrogenation was conducted under normal pressure so that the reactant was converted to its corresponding amino derivative. A DMF solution of the amino derivative was stirred under a nitrogen gas atmosphere and ice cooling, to which 0.45 µl (0.32 mmol; 1.2 equivalents) of triethylamine was added. A solution of 4-[N,N-bis(2-chloroethyl) amino]benzoyl chloride, which had been synthesized from 0.09 g (0.34 mmol) of 4-[N,N-bis(2-chloroethyl)amino] benzoic acid, in 2 ml of benzene was added dropwise. The temperature of the thus-obtained mixture was allowed to rise again to room temperature, at which the mixture was stirred for 4 hours and was then allowed to stand overnight. The mixture was then concentrated under reduced pressure. The residue was purified by chromatography on a silica gel column (chloroform/5% methanol). Relevant fractions were concentrated, whereby 133 mg (0.21 mmol) of the title compound were obtained as amorphous powder (yield: 81.0%).
(Reaction 3)

1H-2-[4-[4-[N,N-Bis(2-chloroethyl)amino]
benzoylamino]-1-methylpyrrol-2-yl]benzimidazole-
5-[N-(2-aminoethyl)]carboxamide hydrochloride 1H-2-[4-[4-[N,N-Bis(2-chloroethyl)amino] benzoylamino]-1-methylpyrrol-2-yl]benzimidazole-5-[N-[2-(t-butoxycarbonylamino)ethyl]]carboxamide (0.13 g; 0.20 mmol) was dissolved in 2 ml of trifluoroacetic acid, followed by stirring at room temperature for 30 minutes. The resultant mixture was concentrated under reduced pressure. After evaporated with toluene, 4N hydrochloric acid in dioxane was added, followed by concentration. This procedure was repeated three times. The residue was crystallized from ethanol, whereby 98 mg (0.16 mmol) of the title compound were obtained as pale yellow white crystals (yield: 79.6%).

m.p.>275° C.

IR(KBr)cm$^{-1}$: 3423, 2959, 1605, 1560, 1389, 1059, 828.

Elemental analysis for $C_{26}H_{29}N_7O_2Cl_2 \cdot 2HCl \cdot 2H_2O$: Calculated: C, 47.94; H, 5.42; N, 15.05 Cl, 21.77 Found: C, 48.16; H, 5.34; N, 14.75; Cl, 21.43

EXAMPLE 26
(Compound No. 223)

1H-2-[4-[4-[N,N-Bis(2-chloroethyl)amino]
benzoylamino]-1-methylpyrrol-2-yl]benzimidazole-
5-[N-(3-picolyl)]carboxamide hydrochloride
(Reaction 1)

1H-2-(1-Methyl-4-nitropyrrol-2-yl)benzimidazole-5-[N-(3-picolyl)]carboxamide 1H-2-(1-Methyl-4-nitropyrrol-2-yl)benzimidazole-5-carboxylic acid (0.20 g; 0.70 mmol) was dissolved in 5 ml of DMF, followed by the addition of 0.17 g (1.05 mmol; 1.5 equivalents) of CDI. The resultant mixture was stirred under a nitrogen gas atmosphere at room temperature for 1.5 hours and was then ice-cooled, to which 0.12 ml (1.18 mmol; 1.7 equivalents) of 3-picolylamine was added. The temperature of the thus-obtained mixture was allowed to rise again to room temperature, at which the mixture was stirred for 4 hours and then allowed to stand overnight. The mixture was then concentrated under reduced pressure. The residue was washed with methanol, whereby 0.25 g (0.66 mmol) of the title compound was obtained as yellow crystals (yield: 93.8%).
(Reaction 2)

1H-2-[4-[4-[N,N-Bis(2-chloroethyl)amino]
benzoylamino]-1-methylpyrrol-2-yl]benzimidazole-
5-[N-(3-picolyl)]carboxamide hydrochloride 1H-2-(1-Methyl-4-nitropyrrol-2-yl)benzimidazole-5-[N-(3-picolyl)]carboxamide (0.24 g; 0.64 mmol) was suspended in a mixed solvent of 8 ml of DMF and 5 ml of methanol, followed by the addition of 2 equivalents of concentrated hydrochloric acid. Using 0.09 g of 10% Pd/C as a catalyst, hydrogenation was conducted under normal pressure so that the reactant was converted to its corresponding amino derivative. A DMF solution of the amino derivative was stirred under a nitrogen gas atmosphere and ice cooling, to which 0.2 ml (1.43 mmol; 2.2 equivalents) of triethylamine was added. A solution of 4-[N,N-bis(2-chloroethyl)amino] benzoyl chloride, which had been synthesized from 0.18 g (0.69 mmol) of 4-[N,N-bis(2-chloroethyl)amino]benzoic acid, in 5 ml of benzene was added dropwise. The temperature of the thus-obtained mixture was allowed to rise again to room temperature, at which the mixture was stirred for 4 hours and was then allowed to stand overnight. The mixture was then concentrated under reduced pressure. The residue was purified by chromatography on a silica gel column (chloroform/10% methanol). Relevant fractions were suspended in water and the resulting precipitate was collected by filtration, whereby 0.12 g (0.20 mmol) of the title compound was obtained as white crystals (yield: 31.2%). Of the reaction product, 52 mg (0.078 mmol) were suspended in 2 ml of ethanol, to which 4N hydrochloric acid in dioxane was added. The resulting mixture was concentrated to obtain crystals. The crystals were washed with ethyl ether, so that the reaction product was converted to its hydrochloride.

m.p.>275° C.

IR(KBr)cm$^{-1}$: 3369, 1655, 1604, 1546, 1277.

Elemental analysis for $C_{30}H_{29}N_7O_2Cl_2 \cdot 2HCl \cdot 2.5H_2O$: Calculated: C, 50.86; H, 5.12; N, 13.84 Cl, 20.02 Found: C, 50.67; H, 4.86; N, 13.68; Cl, 20.34

EXAMPLE 27
(Compound No. 247)

3-[[1H-2-[4-[4-[N,N-Bis(2-chloroethyl)amino]-
benzoylamino]-1-methylpyrrol-2-yl]benzimidazole-
5-carboxamido]methyl]-1-methylpyridinium
chloride 1H-2-[4-[4-[N,N-Bis(2-chloroethyl)amino] benzoylamino]-1-methylpyrrol-2-yl]benzimidazole-5-[N-(3-picolyl)]carboxamide (84 mg; 0.13 mmol) was dissolved in 2 ml of DMF, followed by the addition of 40 µl (0.642 mmol; 5.1 equivalents) of methyl iodide. The resulting mixture was stirred at room temperature for 6 hours and was then allowed to stand overnight. The thus-obtained mixture was concentrated under reduced pressure and the residue was subjected to chromatography on an ion-exchange column ("DOWEX" 1×8, 200–400 mesh, Cl⁻ type). Relevant fractions were combined and concentrated. The residue was crystallized from ethyl ether and then washed with chloroform, whereby 46 mg (0.072 mmol) of the title compound were obtained as white crystals (yield: 56.5%).

m.p. 189°–193° C. (dec.).

IR(KBr)cm$^{-1}$: 3420, 1637, 1605, 1541.

Elemental analysis for $C_{31}H_{32}N_7O_2Cl_3 \cdot 0.25CHCl_3 \cdot 2H_2O$: Calculated: C, 53.10; H, 5.17; N, 13.87 Cl, 18.81 Found: C, 52.96; H, 5.01; N, 13.50; Cl, 18.53

EXAMPLE 28
(Compound No. 16)

1H-2-[4-(6-Bromohexylamino)-1-methylpyrrol-2-yl]benzimidazole-5-[N-(2-amidinoethyl)]carboxamide hydrochloride 1H-2-[1-methyl-4-nitropyrrol-2-yl]benzimidazole-5-[N-(2-amidinoethyl)]carboxamide hydrochloride (200 mg; 0.51 mmol) was dissolved in 12 ml of a 1:1 mixed solvent of DMF and methanol in a reactor, followed by the addition of 200 mg of 5% Pd/C and 0.7 ml of 1N hydrochloric acid. The reactor was purged with nitrogen gas. The resultant mixture was stirred under a hydrogen gas atmosphere at room temperature for 2 hours. After completion of the reaction, the reactor was purged again with nitrogen gas. The 5% Pd/C was filtered off and the methanol was distilled out under reduced pressure. The resulting solution was cooled to 0° C., to which 0.17 ml of triethylamine and 1.1 equivalents of 6-bromohexanoic chloride were added under a nitrogen gas atmosphere. The thus-obtained mixture was stirred, as was, for 30 minutes. Methanol was added, followed by further stirring for 5 minutes. After the solvent was distilled out under reduced pressure, the residue was purified by chromatography on a silica gel column (ethyl acetate/IPA/water=5/2/1), whereby 200 mg of white powder were obtained (yield: 73%).

IR(KBr)cm$^{-1}$: 3272, 2362, 1690, 1637, 1542, 1311, 958.

EXAMPLE 29
(Compound No. 1001)

1H-2-[1-Methyl-4-(2-guanidinoacetylamino)pyrrol-2-yl]benzimidazole-5-[N-[4-[N,N-bis(2-chloroethyl)amino]phenyl]]carboxamide hydrochloride (Reaction 1)

N,N-Bis(2-chloroethyl)-1,4-phenylenediamine hydrochloride

4-Nitro-[N,N-bis(2-chloroethyl)]aniline (5.0 g; 19.0 mmol) was dissolved in a mixed solvent of 50 ml of ethyl acetate and 25 ml of methanol, followed by the addition of 5.0 ml of 4N hydrochloric acid. Using 10% Pd/C, the reactant was subjected to hydrogenation under normal pressure at room temperature. The Pd/C was filtered off and the solvent was distilled out. The residue was crystallized from ethanol-ethyl ether, whereby 4.1 g (15.2 mmol) of the title compound was obtained (yield: 80%).

m.p. 230°–233° C.

(Reaction 2)

1H-2-(1-Methyl-4-nitropyrrol-2-yl)benzimidazole-5-[N-[4-[N,N-bis(2-chloroethyl)amino]phenyl]]carboxamide 1H-2-(1-Methyl-4-nitropyrrol-2-yl)benzimidazole-5-carboxylic acid (0.3 g; 1.05 mmol) was dissolved in 6 ml of DMF, to which a solution of 0.3 g (1.1 mmol; 1.05 equivalents) of N,N-bis(2-chloroethyl)-1,4-phenylenediamine hydrochloride and 0.15 ml (1.82 mmol; 3.1 equivalents) of triethylamine in 8 ml of DMF was added dropwise. Added next was 0.16 g (1.18 mmol; 1.1 equivalents) of HOBt. The resulting mixture was ice-cooled under a nitrogen gas atmosphere, followed by the addition of 0.24 g (1.16 mmol; 1.1 equivalents) of DCC. The temperature of the resulting mixture was allowed to rise again to room temperature, at which the mixture was stirred for 3 hours and was then allowed to stand overnight. The resulting solid was filtered off and the filtrate was concentrated under reduced pressure. The residue was purified by chromatography on a silica gel column (methylene chloride/2% methanol). The reaction product was washed with methanol, whereby 0.38 g (0.76 mmol) of the title compound was obtained as yellow crystals (yield: 72.2%).

m.p. 144°–148° C.

(Reaction 3)

1H-2-[1-Methyl-4-(2-guanidinoacetylamino)pyrrol-2-yl]benzimidazole-5-[N-[4-[N,N-bis(2-chloroethyl)amino]phenyl]]carboxamide hydrochloride 1H-2-(1-Methyl-4-nitropyrrol-2-yl)benzimidazole-5-[N-[4-[N,N-bis(2-chloroethyl)amino]phenyl]]carboxamide (0.30 g; 0.60 mmol) was dissolved in a mixed solvent of 3 ml of DMF and 3 ml of methanol. Using 0.12 g of Pd/C as a catalyst, the reactant was hydrogenated under normal pressure so that it was converted to the corresponding amino derivative. A DMF solution of the amino derivative was stirred under a nitrogen gas stream and ice-cooling, to which 0.17 ml (1.22 mmol; 2.0 equivalents) of triethylamine and 0.37 g (1.79 mmol; 3.0 equivalents) of DCC were successively added. The thus-obtained mixture was stirred, as was, for 1 hour and was then allowed to stand overnight. The mixture was concentrated under reduced pressure and the residue was purified by chromatography on a silica gel column (methylene chloride/12% methanol; repeated twice). From IPA, 78 mg (0.13 mmol) of the title compound were obtained as light yellow powder (yield: 21.5%).

IR(KBr)cm$^{-1}$: 3390, 2925, 1655, 1518, 1458

EXAMPLE 30
(Compound No. 1054)

1H-2-[4-(2-Guanidinoacetylamino)-1-methylpyrrol-2-yl]benzimidazole-5-[N-[4-[N,N-bis(2-acetoxyethyl)amino]phenyl]]carboxamide hydrochloride (Reaction 1)

4-Nitro-[N,N-bis(2-acetoxyethyl)]aniline

4-Nitro-[N,N-bis(2-hydroxyethyl)]aniline (1.0 g; 4.42 mmol) was dissolved in 20 ml of pyridine, followed by the addition of 0.80 ml (11.3 mmol; 2.5 equivalents) of acetyl chloride under ice-cooling. The temperature of the resulting mixture was allowed to rise again to room temperature, at which the mixture was stirred for 2 hours. The mixture was concentrated under reduced pressure. The residue was added with 0.4 N hydrochloric acid and reacted with ethyl acetate. This extraction was repeated twice. The extract was washed with an aqueous solution of hydrochloric acid, dried over sodium sulfate, and then concentrated. The residue was washed with ethyl ether/methanol, whereby 1.03 g (3.32 mmol) of the title compound were obtained as yellow white crystals (yield: 75.1%).

(Reaction 2)

4-[N,N-Bis(2-acetoxyethyl)amino]aniline
hydrochloride

4-Nitro-[N,N-Bis(2-acetoxyethyl)]aniline (0.30 g; 0.97 mmol) was dissolved in a mixed solvent of 5 ml of methanol and 3 ml of ethyl acetate. Using 10% Pd/C as a catalyst, hydrogenation was conducted under normal pressure. The catalyst was filtered off and the filtrate was concentrated under reduced pressure. The residue was dissolved in dioxane, followed by the addition of 4N hydrochloric acid/dioxane. The thus-obtained mixture was concentrated. The residue was crystallized from ethyl ether/n-hexane/acetone, whereby 0.36 g (1.12 mmol) of the title compound was obtained as white crystals (yield: quantitative).
(Reaction 3)

1H-2-(1-Methyl-4-nitropyrrol-2-yl)benzimidazole-5-
[N-[4-[N,N-bis(2-acetoxyethyl)]amino]phenyl]]
carboxamide 1H-2-(1-Methyl-4-nitropyrrol-2-yl)benzimidazole-5-carboxylic acid (0.25 g; 0.88 mmol) was dissolved in 4 ml of DMF, followed by the addition of 0.13 g (0.96 mmol; 1.1 equivalents) of HOBt. Further, a solution of 0.34 g (1.1 mmol; 1.2 equivalents) of 4-[N,N-bis(2-acetoxyethyl)amino]aniline hydrochloride and 0.15 ml (1.82 mmol; 2 equivalents) of triethylamine in 6 ml of DMF was added dropwise. The thus-obtained mixture was ice-cooled under a nitrogen gas atmosphere, to which 0.20 g (0.97 mmol; 1.1 equivalents) of DCC was added. The temperature of the resulting mixture was allowed to rise again to room temperature, at which the mixture was stirred for 6 hours and was then allowed to stand overnight. The resulting solid was filtered off and the filtrate was concentrated under reduced pressure. The residue was purified by chromatography on a silica gel column (eluted with chloroform/2–4% methanol). The reaction product was then washed with methanol, whereby 0.28 g (0.51 mmol) of the title compound was obtained as yellow crystals (yield: 58.0%).
(Reaction 4)

1H-2-[4-(2-guanidinoacetylamino)-1-methylpyrrol-
2-yl]benzimidazole-5-[N-[4-[N,N-bis(2-acetoxy-
ethyl]amino]phenyl]]carboxamide hydrochloride 1H-2-(1-Methyl-4-nitropyrrol-2-yl)benzimidazol5-[N-[4-[N,N-bis(2-acetoxyethyl)amino]phenyl]]carboxamide (0.27 g; 0.49 mmol) was dissolved in a mixed solvent of 2 ml of DMF and 2 ml of methanol, followed by the addition of 0.12 ml of 4N hydrochloric acid. Using 0.12 g of Pd/C as a catalyst, the reactant was hydrogenated under normal pressure so that it was converted to the corresponding amino derivative. A DMF solution of the amino derivative was stirred under a nitrogen gas stream and ice-cooling, to which 70 µl (0.50 mmol; 1.0 equivalent) of triethylamine, 0.23 g (1.45 mmol; 3.0 equivalents) of 2-guanidine acetate hydrochloride and 0.23 g (1.50 mmol; 3.0 equivalents) of DCC were successively added. The thus-obtained mixture was stirred, as was, for 2 hours and then allowed to stand overnight. The mixture was concentrated under reduced pressure and the residue was purified by chromatography on a silica gel column (the first chromatography: chloroform/16–20% methanol; the second chromatography: ethyl acetate/IPA/water=7/2/1→5/2/1). The reaction product was washed with ethyl acetate, whereby 0.12 g (0.18 mmol) of the title compound was obtained as a white amorphous substance (yield: 37.4%).

m.p.: No distinct melting point was observed.
IR(KBr)cm$^{-1}$: 3385, 3178, 1735, 1655, 1520, 1231.

EXAMPLE 31
(Compound No. 1003)

1H-2-[4-(2-Guanidinoacetylamino)-1-methylpyrrol-
2-yl]benzimidazole-5-[N-[2-[4-[N,N-bis(2-
chloroethyl)amino]phenyl]ethyl]]carboxamide
hydrochloride (Reaction 1)

2-[4-[N,N-Bis(2-chloroethyl)amino]phenyl]
ethylamine

3-[4-[N,N-Bis(2-chloroethyl)amino]phenyl]propionic acid (0.20 g; 0.69 mmol) was suspended in 1 ml of acetone and the resulting mixture was stirred under a nitrogen gas atmosphere and ice-cooling. Triethylamine (115 µl; 0.82 mmol; 1.2 equivalents) and ethyl chloroformate (79 µl; 0.82 mmol; 1.2 equivalents) were added successively. Fifteen minutes later, a solution of 90 mg (1.38 mmol; 2.0 equivalents) of sodium azide in 1 ml of water was added dropwise. The resulting mixture was stirred, as was, for 30 minutes, to which ice was added to terminate the reaction. The thus-obtained mixture was extracted three times with 15 ml portions of benzene. The benzene layers were combined, dried over sodium sulfate and then heated under reflux for 1 hour. The reaction mixture was concentrated under reduced pressure. The residue was added with 7.5 ml of 8N hydrochloric acid, followed by heating for 15 minutes at 100° C. The resulting mixture was concentrated under reduced pressure and the residue was diluted with water. The thus-obtained mixture was adjusted to pH 12 with concentrated aqueous ammonia, followed by extraction with ethyl acetate. The extract was dried and concentrated, whereby 0.15 g of the title compound was obtained as a brown oil. This reaction product was provided for use in the next reaction without purification.
(Reaction 2)

1H-2-(1-Methyl-4-nitropyrrol-2-yl)benzimidazole-5-
[N-[2-[4-[N,N-bis(2-chloroethyl)amino]phenyl]
ethyl]]carboxamide 1H-2-(1-Methyl-4-nitropyrrol-2-yl)benzimidazole-5-carboxylic acid (0.1 g; 0.35 mmol) was dissolved in 3 ml of DMF, followed by the addition of 68 mg (0.42 mmol; 1.2 equivalents) of CDI. The resulting mixture was stirred for 1 hour under a nitrogen gas stream at room temperature. The thus-obtained mixture was ice-cooled, to which a solution of 0.15 g (1.1 mmol; 1.05 equivalents: crude) of 2-[4-[N,N-bis(2-chloroethyl)amino]phenyl]ethylamine in 2 ml of DMF was added dropwise. The ice bath was removed. The mixture was stirred for 7 hours and was then allowed to stand overnight. The thus-obtained mixture was concentrated under reduced pressure and methanol was added to the residue. The precipitated crystals were collected by filtration, whereby 0.14 g (0.26 mmol) of the title compound was obtained as light yellow crystals (yield: 75.6%).
(Reaction 3)

1H-2-[4-(2-guanidinoacetylamino)-1-methylpyrrol-
2-yl]benzimidazole-5-[N-[2-[4-[N,N-bis(2-chloro-
ethyl)amino]phenyl]ethyl]]carboxamide
hydrochloride 1H-2-(1-Methyl-4-nitropyrrol-2-yl)benzimidazole-5-[N-[2-[4-[N,N-bis(2-chloroethyl)amino]phenyl]ethyl]]

carboxamide (0.30 g; 0.57 mmol) was dissolved in a mixed solvent of 5 ml of DMF and 5 ml of methanol, followed by the addition of 0.6 ml of 1N hydrochloric acid. Using 0.15 g of 10% Pd/C as a catalyst, the reactant was hydrogenated under normal pressure so that it was converted to the corresponding amino derivative. A DMF solution of the amino derivative was stirred under a nitrogen gas stream and ice-cooling, to which 108 μl (0.78 mmol; 1.4 equivalents) of triethylamine, 0.26 g (1.7 mmol; 3.0 equivalents) of 2-guanidine acetate hydrochloride and 0.36 g (1.7 mmol; 3.0 equivalents) of DCC were successively added. The thus-obtained mixture was stirred, as was, for 1 hour and then allowed to stand overnight. The resulting crystals were filtered off and the residue was purified by chromatography on a silica gel column (the first chromatography: ethyl acetate/IPA/water=7/2/1; the second chromatography: chloroform-12% methanol; the third chromatography: ethyl acetate/IPA/water=7/2/1). The reaction product was crystallized from ethyl ether, whereby 67 mg (0.11 mmol) of the title compound were obtained as white crystals (yield: 18.5%).

m.p. 175°–185° C. (dec.).

EXAMPLE 32
(Compound No. 1004)

1H-2-[4-(2-Guanidinoacetylamino)-1-methylpyrrol-2-yl]benzimidazole-5-[N-[3-[4-[N,N-bis(2-chloroethyl)amino]phenyl]propyl]]carboxamide hydrochloride (Reaction 1)

3-[4-[N,N-Bis(2-chloroethyl)amino]phenyl]propylamine

Chlorambucil (0.30 g; 0.99 mmol) was suspended in 2 ml of acetone. The resultant mixture was stirred under a nitrogen gas atmosphere and ice-cooling, to which 0.17 ml (1.22 mmol; 1.2 equivalents) of triethylamine and 0.11 ml (1.22 mmol; 1.2 equivalents) of ethyl chloroformate were added successively. Twenty minutes later, a solution of 0.13 g (2.0 mmol; 2.0 equivalents) of sodium azide in 2 ml of water was added dropwise. The resulting mixture was stirred, as was, for 1 hour, to which ice was added to terminate the reaction. The thus-obtained mixture was extracted three times with 20 ml portions of benzene. The benzene layers were combined, dried over sodium sulfate and then heated under reflux for 1 hour. The reaction mixture was concentrated under reduced pressure. The residue was added with 9 ml of 8N hydrochloric acid, followed by heating for 15 minutes at 100° C. The resulting mixture was concentrated under reduced pressure and the residue was diluted with water. The thus-obtained mixture was adjusted to pH 12 with concentrated aqueous ammonia, followed by extraction with ethyl acetate. The extract was dried and concentrated, whereby 0.21 g of the title compound was obtained as a crude yellow oil of high viscosity. This reaction product was provided for use in the next reaction without purification.

(Reaction 2)

1H-2-(1-Methyl-4-nitropyrrol-2-yl)benzimidazole-5-[N-[3-[4-[N,N-bis(2-chloroethyl)amino]phenyl] propyl]]carboxamide 1H-2-(1-Methyl-4-nitropyrrol-2-yl)benzimidazole-5-carboxylic acid (0.17 g; 0.59 mmol) was dissolved in 5 ml of DMF, followed by the addition of 0.12 g (0.74 mmol; 1.2 equivalents) of CDI. The resulting mixture was stirred for 1 hour under a nitrogen gas atmosphere at room temperature. The thus-obtained mixture was ice-cooled, to which a solution of 0.24 g (crude) of 3-[4-[N,N-bis(2-chloroethyl)amino] phenyl]propylamine in 2 ml of DMF was added dropwise. The ice bath was removed. The mixture was stirred for 3 hours and was then allowed to stand overnight. The thus-obtained mixture was concentrated under reduced pressure and methanol was added to the residue. The precipitated crystals were collected by filtration, whereby 0.17 g (0.31 mmol) of the title compound was obtained as light yellow crystals (yield: 53.0%).

m.p. 164°–168° C.

(Reaction 3)

1H-2-[4-(2-Guanidinoacetylamino)-1-methylpyrrol-2-yl]benzimidazole-5-[N-[3-[4-[N,N-bis(2-chloroethyl)amino]phenyl]propyl]]carboxamide hydrochloride 1H-2-(1-Methyl-4-nitropyrrol-2-yl)benzimidazole-5-[N-[3-[4-[N,N-bis(2-chloroethyl)amino]phenyl]propyl]]carboxamide (0.26 g; 0.48 mmol) was dissolved in a mixed solvent of 3 ml of DMF and 3 ml of methanol, followed by the addition of 0.12 ml of 4N hydrochloric acid. Using 0.11 g of 10% Pd/C as a catalyst, the reactant was hydrogenated under normal pressure so that it was converted to the corresponding amino derivative. A DMF solution of the amino derivative was stirred under a nitrogen gas stream and ice-cooling, to which 67 μl (0.48 mmol; 1.0 equivalent) of triethylamine, 0.22 g (1.43 mmol; 3.0 equivalents) of 2-guanidinoacetic acid hydrochloride and 0.30 g (1.45 mmol; 3.0 equivalents) of DCC were successively added. The thus-obtained mixture was stirred, as was, for 6 hours and then allowed to stand overnight. The resulting crystals were filtered off and the filtrate was concentrated under reduced pressure. The residue was purified by chromatography on a silica gel column (ethyl acetate/IPA/water=7/2/1; performed twice). The reaction product was crystallized from ethyl ether, whereby 91 mg (0.14 mmol) of the title compound were obtained as white crystals (yield: 29.2%).

m.p. 168°–173° C.

Elemental analysis for $C_{29}H_{35}N_9O_2Cl_2$.2HCl: Calculated: C, 50.81; H, 5.44; N, 18.39, Cl, 20.69 Found: C, 50.90, H, 5.80; N, 18.05, Cl,: 21.06

EXAMPLE 33
(Compound No. 2001)

1H-2-[4-[4-[N,N-Bis(2-chloroethyl)amino] benzoylamino]-1-methylpyrrol-2-yl]benzimidazole-5-[N-[4-[N,N-bis(2-chloroethyl)amino]phenyl]]carboxamide 1H-2-(1-Methyl-4-nitropyrrol-2-yl)benzimidazole-5-[N-[4-[N,N-bis(2-chloroethyl)amino]phenyl]]carboxamide (0.18 g; 0.36 mmol) was suspended in a mixed solvent of 10 ml of DMF and 8 ml of methanol, followed by the addition of 1 equivalent of concentrated hydrochloric acid. Using 0.07 g of 10% Pd/C as a catalyst, the reactant was hydrogenated under normal pressure so that it was converted to the corresponding amino derivative. A DMF solution of the amino derivative was stirred under a nitrogen gas atmosphere and ice-cooling, to which 0.11 ml (0.79 mmol; 2.2 equivalents) of triethylamine was added. Further added dropwise was a solution of 4-[N,N-bis(2-chloroethyl)amino] benzoyl chloride, which had been synthesized from 0.11 g (0.42 mmol) of 4-[N,N-bis-(2-chloroethyl)amino]benzoic acid, in 3 ml of benzene. The temperature of the resulting mixture was allowed to rise back to room temperature, at which the mixture was stirred for 5 hours and then allowed to stand overnight. The thus-obtained mixture was concentrated under reduced pressure and the residue was purified by chromatography on a silica gel column (chloroform/ 2–4% methanol). The reaction product was crystallized from ethanol/ethyl ether, whereby 73 mg (0.10 mmol) of the title compound were obtained as white crystals (yield: 28.3%).

m.p. 168°–174° C.

IR(KBr)cm$^{-1}$: 3414, 1655, 1637, 1606, 1517, 1278.

Elemental analysis for $C_{34}H_{35}N_7O_2Cl_4 \cdot 1.5H_2O$: Calculated: C, 55.00; H, 5.16; N, 13.20; Cl, 19.10 Found: C, 54.79; H, 4.89; N, 12.96; Cl, 18.73

EXAMPLE 34

(Compound No. 342)

1H-2-[1-Methyl-4-[4-[N,N-bis(2-chloroethyl)amino] benzoylamino]imidazol-2-yl]benzimidazole-5-[N-(2-amidinoethyl)]carboxamide hydrochloride (Reaction 1)

2-Formyl-1-methylimidazole

To a solution of 0.5 g (6.1 mmol) of 1-methylimidazole in 15 ml of THF (anhydrous), 4.6 ml of a 1.6M n-hexane solution of n-butyllithium (7.4 mmol; 1.2 equivalents) were added dropwise under a nitrogen gas atmosphere, ice-cooling and stirring. The temperature of the resulting mixture was allowed to rise back to room temperature. 1.5 Hours later, the mixture was ice-cooled again, to which 1.4 ml (18.1 mmol; 3.0 equivalents) of DMF were added dropwise. The thus-obtained mixture was allowed to stand overnight as was. The resulting white solid was filtered off and the filtrate was concentrated under reduced pressure. The residue was dissolved in ethyl acetate. The solution so obtained was washed with water, dried over sodium sulfate and then concentrated. The residue was purified by chromatography on a silica gel column (n-hexane/ethyl acetate=3/1), whereby 0.31 g (2.82 mmol) of the title compound was obtained as a yellow oil (yield: 46.2%).

(Reaction 2)

2-Formyl-1-methyl-4-nitroimidazole

Fuming nitric acid (3 ml) was cooled to −10° C., to which 3 ml of concentrated sulfuric acid were added dropwise. The resulting mixture was added dropwise at an internal temperature of −10° C. or lower to 0.5 g (4.54 mmol) of 2-formyl-1-methylimidazole. The temperature of the thus-obtained was naturally allowed to rise to room temperature, at which the mixture was allowed to stand overnight. The reaction mixture was poured into ice, followed by neutralization with sodium carbonate. The resultant mixture was extracted twice with methylene chloride. The organic layers were washed with a saturated aqueous solution of sodium hydrogencarbonate, dried over sodium sulfate and then concentrated. The residue was crystallized from ethyl ether/ ethanol, whereby 0.21 g (1.35 mmol) of the title compound was obtained as cream-colored crystals (yield: 29.8%).

m.p. 140°–142° C.

(Reaction 3)

1H-2-(1-Methyl-4-nitroimidazol-2-yl) benzimidazole-5-carboxylic acid

Suspended in 75 ml of nitrobenzene were 1.48 g (9.54 mmol) of 2-formyl-1-methyl-4-nitroimidazole and 1.45 g (9.53 mmol; 1.0 equivalent) of 3,4-diaminobenzoic acid. The resulting suspension was stirred for 27 hours under heat over an oil bath which was controlled at 150° C. The reaction mixture was allowed to gradually cool down to room temperature. The resulting crystals were collected by filtration and then washed with IPA, whereby 1.92 g (6.68 mmol) of the title compound were obtained as a brown solid (yield: 70.0%).

(Reaction 4)

1H-2-(1-Methyl-4-nitroimidazol-2-yl) benzimidazole-5-[N-(2-cyanoethyl)]carboxamide Suspended in 50 ml of DMF were 1.44 g (5.01 mmol) of 1H-2-(1-methyl-4-nitroimidazol-2-yl)benzimidazole-5-carboxylic acid, followed by the addition of 0.89 g (5.49 mmol; 1.1 equivalents) of CDI. Under a nitrogen gas atmosphere, the thus-obtained mixture was stirred at room temperature. 2.5 Hours later, the mixture was ice-cooled, followed by the addition of 0.37 ml (5.01 mmol; 1.0 equivalent) of β-aminopropionitrile. The temperature of the resulting mixture was allowed to rise back to room temperature, at which the mixture was stirred for 5.5 hours and then allowed to stand overnight. The resultant mixture was concentrated under reduced pressure and the residue was washed with IPA-methanol, whereby 1.36 g (4.0 mmol) of the title compound were obtained as ocherous crystals (yield: 80.0%).

m.p.>277° C.

(Reaction 5)

1H-2-(1-Methyl-4-nitroimidazol-2-yl) benzimidazole-5-[N-(2-amidinoethyl)]carboxamide hydrochloride Suspended in 45 ml of ethanol were 1.35 g (3.98 mmol) of 1H-2-(1-methyl-4-nitroimidazol-2-yl)benzimidazole-5-[N-(2-cyanoethyl)]carboxamide. Under ice-cooling, hydrogen chloride gas was bubbled (for 30 minutes). After saturation, the temperature of the resultant mixture was allowed to rise back to room temperature, at which the mixture was stirred for additional two hours. After nitrogen gas was bubbled for 10 minutes, the thus-obtained mixture was concentrated under reduced pressure. The residue was washed with ethyl ether and the ethyl ether was then poured out. This procedure was repeated twice. The thus-obtained solid was suspended in 40 ml of ethanol, through which ammonia gas was bubbled under ice-cooling (for 1.5 hours). After saturation, the temperature of the resultant mixture was allowed to rise back to room temperature, at which it was stirred for 3 hours. The thus-obtained mixture was the concentrated under reduced pressure. The residue was washed with ethanol. The resulting solid was dissolved in ethanol/methanol. The solution so obtained was treated with activated carbon and then concentrated. The concentrate was washed with methanol, whereby 1.20 g (3.05 mmol) of the title compound were obtained as yellow crystals (yield: 76.8%).

m.p. 198°–210° C.

(Reaction 6)

1H-2-[1-Methyl-4-[4-[N,N-bis(2-chloroethyl)amino] benzoylamino]imidazol-2-yl]benzimidazole-5-[N-(2-amidinoethyl)]carboxamide hydrochloride Suspended in a mixed solvent of 5 ml of DMF and 3.5 ml of methanol was 0.30 g (0.76 mmol) of 1H-2-(1-methyl-4-nitroimidazol-2-yl)benzimidazole-5-[N-(2-amidinoethyl)] carboxamide hydrochloride. Using 0.12 g of Pd/C as a catalyst, catalytic hydrogenation was conducted to obtain the corresponding amino derivative. The amino derivative was dissolved, as was, in 5 ml of DMF without purification.

To the solution, a solution of 4-[N,N-bis(2-chloroethyl) amino]benzoyl chloride, which had been synthesized by reacting 0.26 g (0.99 mmol) of 4-[N,N-bis(2-chloroethyl) amino]benzoic acid with thionyl chloride, in 2 ml of benzene was added dropwise under a nitrogen gas atmosphere, ice-cooling and stirring. The temperature of the resulting mixture was allowed to rise back to room temperature, followed by stirring for 5 hours. The reaction mixture was concentrated under reduced pressure. The residue was purified by chromatography on a silica gel column (ethyl acetate/IPA/water=6/2/1) and then crystallized from ethanol, whereby 0.07 g (0.12 mmol) of the title compound was obtained as pale yellow crystals (yield: 15.2%).

m.p. 218°–228° C. (dec.).

IR(KBr)cm$^{-1}$: 3415, 1609, 1542, 1315, 1186.

Elemental analysis for $C_{26}H_{29}N_9O_2Cl_2 \cdot 1.8HCl \cdot 3H_2O$: Calculated: C, 45.25; H, 5.37; N, 18.27; Cl, 19.52 Found: C, 45.35; H, 5.35; N, 18.16; Cl, 19.52

EXAMPLE 35
(Compound No. 345)

1H-2-[1-Methyl-4-[4-[N,N-bis(2-chloroethyl) aminophenyl]butyrylamino]imidazol-2-yl] benzimidazole-5-[N-(2-amidinoethyl)]carboxamide hydrochloride Suspended in a mixed solvent of 5 ml of DMF and 4 ml of methanol was 0.20 g (0.51 mmol) of 1H-2-(1-methyl-4-nitroimidazol-2-yl)benzimidazole-5-[N-(2-amidinoethyl)] carboxamide hydrochloride. Using 0.08 g of Pd/C as a catalyst, catalytic hydrogenation was conducted to obtain the corresponding amino derivative. The amino derivative was dissolved, as was, in 5 ml of DMF without purification. To the solution, 0.16 g (0.53 mmol; 1.03 equivalents) of chlorambucil and 76 mg (0.56 mmol; 1.1 equivalents) of HOBt were added successively. The resulting mixture was ice-cooled, followed by the addition of 0.12 g (0.58 mmol; 1.1 equivalents) of DCC. The temperature of the mixture so obtained was allowed to rise back to room temperature, at which the mixture was stirred for 1.5 hours and then allowed to stand overnight. The reaction mixture was concentrated under reduced pressure. The residue was purified by chromatography on a silica gel column (ethyl acetate/IPA/water= 6/2/1→4/2/1; performed twice) and then crystallized from ethanol/ethyl ether, whereby 40 mg (0.061 mmol) of the title compound were obtained as light pink crystals (yield: 12.1%).

m.p. 163°–168° C.

IR(KBr)cm$^{-1}$: 3409, 2924, 1655, 1560, 1543, 1388, 1019.

Elemental analysis for $C_{29}H_{35}N_9O_2Cl_2 \cdot HCl \cdot 2H_2O$: Calculated: C, 50.85; H, 5.89; N, 18.40 Found: C, 50.94; H, 5.79; N, 18.63

EXAMPLE 36
(Compound No. 358)

1H-2-(1-Methyl-4-formylaminoimidazol-2-yl) benzimidazole-5-[N-(2-amidinoethyl)]carboxamide hydrochloride Suspended in a mixed solvent of 5 ml of DMF and 5 ml of methanol was 0.20 g (0.51 mmol) of 1H-2-(1-methyl-4-nitroimidazol-2-yl)benzimidazole-5-[N-(2-amidinoethyl)] carboxamide hydrochloride. Using 0.8 g of Pd/C as a catalyst, catalytic hydrogenation was then conducted. After the Pd/C was filtered off, the methanol was distilled out under reduced pressure. To a DMF solution of the amino derivative obtained above as a crude reaction product, 1-formylimidazole—which had been prepared by dissolving 0.41 g (2.52 mmol) of CDI in 5 ml of THF, adding 0.1 ml (2.65 mmol) of formic acid, and then stirring the resultant mixture for 1 hour—was added under a nitrogen gas atmosphere, ice-cooling and stirring. The temperature of the resulting mixture was allowed to rise back to room temperature, at which the mixture was stirred for 6 hours and then allowed to stand overnight. The thus-obtained mixture was concentrated under reduced pressure. The residue was purified by chromatography on a silica gel column (ethyl acetate/IPA/water=6/2/1). Relevant fractions was further purified on an ODS column (water/5% methanol+acetic acid) and then subjected to gel filtration ("Sephadex G-10", water), whereby 26 mg (0.067 mmol) of the title compound were obtained as amorphous powder (yield: 13.0%).

IR(KBr)cm$^{-1}$: 3256, 1684, 1559, 1541, 1398, 1318

Elemental analysis for $C_{16}H_{18}N_8O_2 \cdot HCl \cdot 2H_2O$: Calculated: C, 45.02; H, 5.43; N, 22.30 Found: C, 45.39; H, 5.28; N, 22.30

EXAMPLE 37
(Compound No. 1608)

1H-2-[4-(Guanidinoacetyl)amino-1-methylimidazol-2-yl]benzimidazole-5-[N-[4-[N,N-bis(2-chloroethyl) amino]phenyl]]carboxamide dihydrochloride (Reaction 1)

1H-2-(1-Methyl-4-nitroimidazol-2-yl] benzimidazole-5-[N-[4-[N,N-bis(2-chloroethyl) amino]phenyl]]carboxamide Dissolved in 5 ml of DMF were 0.17 g (0.59 mmol) of 1H-2-(1-methyl-4-nitroimidazol-2-yl)benzimidazole-5-carboxylic acid and 0.16 g (0.59 mmol; 1.0 equivalent) of N,N-bis(2-chloroethyl)-1,4-phenylenediamine hydrochloride. Under a nitrogen gas stream, ice-cooling and stirring, 0.25 ml (1.79 mmol; 3.0 equivalents) of triethylamine and 0.13 ml (0.86 mmol; 1.5 equivalents) of DECP were added successively to the resultant solution. The thus-obtained mixture was stirred, as was, for 1 hour and then allowed to stand overnight. It was concentrated under reduced pressure. The residue was purified by gel filtration ("Sephadex LH-20", methanol) and then crystallized from ethanol, whereby 0.16 g (0.32 mmol) of the title compound was obtained as yellow crystals (yield: 54.0%).

m.p. 157°–159° C.

(Reaction 2)

1H-2-[4-(Guanidinoacetyl)amino-1-methylimidazol-2-yl]benzimidazole-5-[N-[4-[N,N-bis(2-chloroethyl) amino]phenyl]]carboxamide dihydrochloride Suspended in a mixed solvent of DMF and methanol was 0.16 g (0.32 mmol) of 1H-2-(1-methyl-4-nitroimidazol-2-yl]benzimidazole-5-[N-[4-[N,N-bis(2-chloroethyl)amino] phenyl]]carboxamide, followed by the addition of 0.35 ml of 1N hydrochloric acid. Using 10% Pd/C (wet) as a catalyst, the reactant was hydrogenated into the corresponding amino derivative under normal pressure. To a DMF solution of the amino derivative, 55 μl (0.39 mmol; 1.2 equivalents) of triethylamine, 0.14 g (0.91 mmol; 3.0 equivalents) of guanidinoacetic acid hydrochloride and 0.19 g (0.92 mmol; 3.0 equivalents) of DCC were added successively under a nitrogen gas stream, ice-cooling and stirring. The temperature of the thus-obtained mixture was allowed to rise back to room temperature, at which it was stirred for 9 hours and then allowed to stand overnight. The resulting solid was filtered off and the filtrate was concentrated under reduced pressure. The residue was subjected to gel filtration ("Sephadex LH-20", methanol). Eluted fractions were added with 4N hydrochloric acid/dioxane, concentrated and then crystallized from methanol, whereby 61 mg (0.095 mmol) of the title compound were obtained as yellow crystals (yield: 29.6%).

m.p.>250° C.

IR(KBr)cm$^{-1}$: 3345, 1670, 1542, 1327.

Elemental analysis for $C_{25}H_{28}N_{10}O_2Cl_2 \cdot 2.5HCl \cdot 1.5H_2O$: Calculated: C, 43.53; H, 4.90; N, 20.31; Cl, 23.13 Found: C, 43.43; H, 4.78; N, 20.21; Cl, 23.44

EXAMPLE 38
(Compound No. 424)

1H-2-[2-[4-[4-[N,N-Bis(2-chloroethyl)amino] phenyl]butyrylamino]thiophen-4-yl]benzimidazole-5-[N-(2-amidinoethyl)]carboxamide hydrochloride
(Reaction 1)

1H-2-(2-Nitrothiophen-4-yl)benzimidazole-5-carboxylic acid.

Dissolved in 100 ml of nitrobenzene were 2.0 g (12.7 mmol) of 2-nitrothiophene-4-carboxyaldehyde and 2.0 g (12.8 mmol; 1.0 equivalent) of 3,4-diaminobenzoic acid, followed by stirring under heat over an oil bus which was controlled at 150° C. 32 Hours later, the reaction mixture was cooled to room temperature. The resulting solid was collected by filtration and then washed with IPA and methylene chloride, whereby 2.02 g (7.78 mmol) of the title compound were obtained as ocherous crystals (yield: 61.2%).

m.p.>270° C.
(Reaction 2)

1H-2-(2-Nitrothiophen-4-yl)benzimidazole-5-[N-(2cyanoethyl)]carboxamide

Suspended in 40 ml of DMF were 2.0 g (7.8 mmol) of 1H-2-(2-nitrothiophen-4-yl)benzimidazole-5carboxylic acid, followed by the addition of 1.39 g (8.57 mmol; 1.1 equivalents) of CDI. The resultant mixture was stirred under a nitrogen gas atmosphere at room temperature. 1.5 Hours later, the mixture was ice-cooled, to which 0.63 ml (8.54 mmol; 1.1 equivalents) of β-aminopropionitrile was added. The temperature of the thus-obtained mixture was allowed rise back to room temperature, at which the mixture was allowed to stand overnight. After completion of the reaction was ascertained, the reaction mixture was concentrated under reduced pressure and the residue was washed with IPA, whereby 1.18 g (3.82 mmol) of the title compound were obtained as brown crystals (yield: 49.0%).

m.p.>270° C.
(Reaction 3)

1H-2-(2-Nitrothiophen-4-yl)benzimidazole-5-[N-(2-amidinoethyl)]carboxamide hydrochloride Suspended in 25 ml of ethanol was 0.85 g (2.7 mmol) of 1H-2-(2-nitrothiophen-4-yl)benzimidazole-5-[N-(2-cyanoethyl)]carboxamide. Under ice-cooling, hydrogen chloride gas was bubbled over 1 hour so that the suspension was saturated with hydrogen chloride gas. The temperature of the thus-obtained mixture was allowed to rise back to room temperature, at which the mixture was stirred for additional 2 hours and nitrogen gas was then bubbled for 10 minutes. The resultant mixture was concentrated under reduced pressure. The residue was washed with ethyl ether. The residue was then suspended in 35 ml of ethanol and under ice-cooling, ammonia gas was bubbled for 1 hour until saturation. The temperature of the mixture was allowed to rise back to room temperature, at which the mixture was allowed to stand overnight. The resulting crystals were collected by filtration, whereby 0.84 g (2.13 mmol) of the title compound was collected as brown crystals (yield: 78.8%).

m.p.>275° C.
(Reaction 4)

1H-2-[2-[4-[4-[N,N-Bis(2-chloroethyl)amino]-phenyl]butyrylamino]thiophen-4-yl]benzimidazole-5-[N-(2-amidinoethyl)]carboxamide hydrochloride Dissolved in 4 ml of DMF was 0.15 g (0.38 mmol) of 1H-2-(2-nitrothiophen-4-yl)benzimidazole-5-[N-(2-amidinoethyl)]carboxamide hydrochloride. Using 0.07 g of 10% Pd/C as a catalyst, catalytic hydrogenation was conducted. After the Pd/C was filtered off, the filtrate was ice-cooled under a nitrogen gas atmosphere, followed by the dropwise addition of a solution of 0.13 g (0.43 mmol; 1.1 equivalents) of 4-[4-[N,N-bis(2-chloroethyl)amino]phenyl] butyryl chloride—which had been prepared by adding 0.26 g (2.19 mmol; 5.1 equivalents) of thionyl chloride to 0.13 g (0.43 mmol; 1.1 equivalents) of chlorambucil, allowing the resultant mixture to stand for 5 minutes at room temperature, concentrating the mixture under reduced pressure, evaporating the concentrate with benzene and then repeating the evaporation with benzene once more—in 1 ml of benzene. The temperature of the resultant mixture was allowed to rise back to room temperature, at which the mixture was stirred for 5.3 hours and then allowed to stand overnight. The thus-obtained mixture was concentrated under reduced pressure, purified by chromatography on a silica gel column (ethyl acetate/IPA/water=6/2/1) and then crystallized from ethyl ether, whereby 13 mg (0.02 mmol) of the title compound were obtained as light brown crystals (yield: 5.25%).

m.p.>275° C.

IR(KBr)cm$^{-1}$: 3160, 1637, 1545, 1474, 1289.

EXAMPLE 39
(Compound No. 438)

1H-2-(2-Benzoylaminothiophen-4-yl)benzimidazole-5-[N-(2-amidinoethyl)]carboxamide hydrochloride Dissolved in 20 ml of DMF was 0.40 g (1.0 mmol) of 1H-2-(2-nitrothiophen-4-yl)benzimidazole-5-[N-(2-amidinoethyl)]carboxamide hydrochloride. Using 0.18 g of 10% Pd/C as a catalyst, catalytic hydrogenation was conducted. After the Pd/C was filtered off, the resultant mixture was ice-cooled under a nitrogen gas atmosphere, followed by the successive addition of 0.16 ml (1.15 mmol; 1.1 equivalents) of triethylamine and 0.13 ml (1.13 mmol; 1.1 equivalents) of benzoyl chloride. The temperature of the reaction mixture was allowed to rise back to room temperature. 4.5 Hours later, the reaction mixture was concentrated under reduced pressure. The residue was purified by chromatography on a silica gel column (ethyl acetate/IPA/water= 6/2/1) and then crystallized from ethyl ether. As inclusion of impurities was confirmed by NMR, the product was purified further by gel filtration ("Sephadex LH-20", methanol) and then crystallized from ethyl ether, whereby 24 mg (0.05 mmol) of the title compound were obtained as light brown crystals (yield: 5.0%).

m.p. 220°–223° C.

Elemental analysis for $C_{22}H_{20}N_6SO_2\cdot3H_2O$: Calculated: C, 50.52; H, 5.20; N, 16.07 Found: C, 50.70; H, 5.02; N, 16.20

EXAMPLE 40

(Compound No. 1617)

1H-2-[5-(Guanidinoacetyl)aminothiophen-3-yl] benzimidazole-5-[N-[4-[N,N-bis(2-chloroethyl) amino]phenyl]]carboxamide dihydrochloride (Reaction 1)

1H-2-(5-Nitrothiophen-3-yl)benzimidazole-5-[N-[4-[N,N-bis(2-chloroethyl)amino]phenyl]]carboxamide Dissolved in 10 ml of DMF were 0.30 g (1.17 mmol) of 1H-2-(5-nitrothiophen-3-yl)benzimidazole-5-carboxylic acid and 0.31 g (1.15 mmol; 1.0 equivalent) of N,N-bis(2-chloroethyl)-1,4-phenylenediamine hydrochloride. Under a nitrogen gas stream, ice-cooling and stirring, 0.49 ml (3.51 mmol; 3.0 equivalents) of triethylamine and 0.27 ml (1.78 mmol; 1.5 equivalents) of DECP were added successively. The resultant mixture was stirred, as was, for 8 hours and then allowed to stand overnight. The mixture was concentrated under reduced pressure and methanol was added to the residue. The insoluble solid was filtered off. The filtrate was purified by chromatography on a silica gel column (chloroform/2–4% methanol) and then washed with methanol, whereby 0.11 g (0.22 mmol) of the title compound was obtained as brown crystals (yield: 19.0%).

(Reaction 2)

1H-2-[5-(Guanidinoacetyl)aminothiophen-3-yl] benzimidazole-5-[N-[4-[N,N-bis(2-chloroethyl) amino]phenyl]]carboxamide dihydrochloride Suspended in a mixed solvent of DMF and methanol was 0.10 g (0.20 mmol) of 1H-2-(5-nitrothiophen-3-yl) benzimidazole-5-[N-[4-[N,N-bis(2-chloroethyl)amino] phenyl]]carboxamide, followed by the addition of 0.22 me of 1N hydrochloric acid. Using 0.05 g of 10% Pd/C (wet) as a catalyst, the reactant was hydrogenated into the corresponding amino derivative under normal pressure. To a DMF solution of the amino derivative, 32 μl (0.23 mmol; 1.1 equivalents) of triethylamine, 93 mg (0.61 mmol; 3.0 equivalents) of guanidinoacetic acid hydrochloride and 0.12 g (0.58 mmol, 2.9 equivalents) of DCC were successively added under a nitrogen gas stream, ice-cooling and stirring. The temperature of the thus-obtained mixture was allowed to rise back to room temperature, at which the mixture was stirred for 8 hours and then allowed to stand overnight. The resulting solid was filtered off and the filtrate was concentrated under reduced pressure. DMF was again added to the residue and the resulting crystals were filtered off. The filtrate was concentrated and the residue was subjected to gel filtration ("Sephadex LH-20", methanol). Eluate fractions were added with 4N hydrochloric acid/dioxane, concentrated and then crystallized from ethanol, whereby 9 mg (0.014 mmol) of the title compound were obtained as brown crystals (yield: 7.0%).

m.p.>250° C.

IR(KBr)cm$^{-1}$: 3338, 1653, 1517, 1330, 818.

EXAMPLE 41

(Compound No. 505)

1H-2-[5-[4-[4-[N,N-Bis(2-chloroethyl)amino]phenyl] butyrylamino]thiophen-2-yl]benzimidazole-5-[N-(2-amidinoethyl)]carboxamide hydrochloride (Reaction 1)

Methyl 1H-2-(5-nitrothiophen-2-yl)benzimidazole-5-carboxylate

Suspended in 25 ml of nitrobenzene were 0.50 g (3.18 mmol) of 5-nitro-2-thiophenecarboxyaldehyde and 0.53 g (3.19 mmol; 1.0 equivalent) of methyl 3,4-diaminobenzoate. The resulting mixture was stirred under heat for 28.5 hours over an oil bath which was controlled at 150° C. The solvent was distilled out and the residue was washed with methanol, whereby 0.775 g (2.86 mmol) of the title compound was obtained as ocherous crystals (yield: 89.9%).

m.p.>280° C.

(Reaction 2)

1H-2-(5-Nitrothiophen-2-yl)benzimidazole-5-carboxylic acid

Suspended in 15 ml of methanol was 0.57 g (2.22 mmol) of methyl 1H-2-(5-nitrothiophen-2-yl)benzimidazole-5-carboxylate, followed by the addition of 15 ml of a 1N aqueous solution of sodium hydroxide. The resultant mixture was stirred at 60° C. for 1 hour under heating. The methanol was distilled out under reduced pressure. The remaining aqueous solution was acidified with 4N hydrochloric acid and the resulting crystals were collected by filtration, whereby 0.55 g (2.14 mmol) of the title compound was obtained as dark brown crystals (yield: 96.3%).

m.p.>280° C.

(Reaction 3)

1H-2-(5-Nitrothiophen-2-yl)benzimidazole-5-[N-(2-cyanoethyl)]carboxamide

Dissolved in 45 ml of DMF were 1.5 g (5.83 mmol) of 1H-2-(5-nitrothiophen-2-yl)benzimidazole-5-carboxylic acid, followed by the addition of 1.04 g (6.4 mmol; 1.1 equivalents) of CDI. The resulting mixture was stirred at room temperature under a nitrogen gas atmosphere and 1 hour later, was ice-cooled, to which 0.43 ml (5.8 mmol; 1.0 equivalent) of β-aminopropionitrile was added. The temperature of the thus-obtained mixture was allowed to rise back to room temperature, at which the mixture was stirred for 30 minutes and then allowed to stand overnight. After completion of the reaction was confirmed, the reaction mixture was concentrated under reduced pressure. The residue was purified by chromatography on a silica gel column (methylene chloride/4–10% methanol) and then washed with ethyl ether, whereby 0.53 g (1.7 mmol) of the title compound was obtained as yellow crystals (yield: 29.3%).

m.p. 219°–222° C.

(Reaction 4)

1H-2-(5-Nitrothiophen-2-yl)benzimidazole-5-[N-(2-amidinoethyl)]carboxamide hydrochloride Suspended in 15 ml of ethanol was 0.52 g (1.68 mmol) of 1H-2-(5-nitrothiophen-2-yl)benzimidazole-5-(N-(2-cyanoethyl)]carboxamide, followed by bubbling of hydrogen chloride gas under ice-cooling until saturation for an hour. The temperature of the thus-obtained mixture was allowed to rise back to room temperature and, after the mixture was stirred for 3 hours, the solvent was distilled out under reduced pressure. The residue was washed with ethyl ether and the ethyl ether was then poured out. This procedure was repeated twice. The residue was dissolved in 15 ml of ethanol and under ice-cooling, ammonia gas was bubbled until saturation (for 2 hours). The temperature of the resulting mixture was allowed to rise back to room temperature, at which the mixture was stirred for 1 hour. The solvent was distilled out under reduced pressure and the residue was washed with ethanol, whereby 0.54 g (1.49 mmol) of the title compound was obtained as yellow crystals (yield: 88.6%).

m.p.>280° C.
(Reaction 5)

1H-2-(5-Aminothiophen-2-yl)benzimidazole-5-[N-(2-amidinoethyl)]carboxamide hydrochloride Suspended in a mixed solvent of 5 ml of DMF and 5 ml of methanol was 0.53 g (1.46 mmol) of 1H-2-(5-nitrothiophen-2-yl)benzimidazole-5-[N-(2-amidinoethyl)]carboxamide hydrochloride. Using 0.22 g of Pd/C as a catalyst, catalytic hydrogenation was conducted to convert the reactant into the corresponding amino derivative. This amino derivative was provided for use in the next reaction as in other examples.
(Reaction 6)

1H-2-[5-[4-[4-[N,N-Bis(2-chloroethyl)amino]phenyl]butyrylamino]thiophen-2-yl]benzimidazole-5-[N-(2-amidinoethyl)]carboxamide hydrochloride 1H-2-(5-Aminothiophen-2-yl)benzimidazole-5-[N-(2-amidinoethyl)]carboxamide hydrochloride (half the amount of the amino derivative obtained from 1.46 mmol of the nitro derivative; in the form of a solution dissolved in 3 ml of DMF) was ice-cooled under a nitrogen gas atmosphere, to which a solution of 4-[N,N-bis(2-chloroethyl)amino]phenylbutyryl chloride—which had been synthesized from 0.25 g (0.82 mmol; 1.1 equivalents) of chlorambucil and 0.49 g (4.1 mmol; 5.5 equivalents) of thionyl chloride—in 2 ml of methylene chloride and 0.10 ml (0.72 mmol; 1.0 equivalent) of triethylamine were added successively. The temperature of the thus-obtained mixture was allowed to rise back to room temperature, at which the mixture was stirred for 5 hours and then allowed to stand overnight. The resultant mixture was concentrated under reduced pressure, purified by chromatography on a silica gel column (ethyl acetate/IPA/water=7/2/1→9/2/1→12/2/1; performed three times in total), and then crystallized from ethyl ether, whereby 27 mg (0.044 mmol) of the title compound were obtained as brownish white crystals (yield: 6.0%).

m.p.>275° C.

IR(KBr)cm$^{-1}$: 3220, 2930, 1684, 1541, 1521, 806.

Elemental analysis for $C_{29}H_{33}N_7SO_2Cl_2 \cdot 2HCl \cdot H_2O$: Calculated: C, 49.37; H, 5.29; N, 13.90 Found: C, 49.69; H, 5.29; N, 13.47

EXAMPLE 42
(Compound No. 518)

1H-2-(5-Formylaminothiophen-2-yl)benzimidazole-5-[N-(2-amidinoethyl)]carboxamide hydrochloride 1H-2-(5-Aminothiophen-2-yl)benzimidazole-5-[N-(2-amidinoethyl)]carboxamide hydrochloride (half the amount of the amino derivative synthesized from 1.46 mmol of the nitro derivative; in the form of a solution dissolved in approx. 3 ml of DMF) was ice-cooled under a nitrogen gas atmosphere, to which a solution of formylimidazole—which had been synthesized by adding 0.14 ml (3.71 mmol; 5 equivalents) of formic acid to a solution of 0.59 g (3.63 mmol; 5 equivalents) of CDI in 8 ml of THF and then stirring the resultant mixture for 2 hours)—in 8 ml of THF was added dropwise. The temperature of the thus-obtained mixture was allowed to rise back to room temperature, at which the mixture was stirred for 8.5 hours and then allowed to stand overnight. The resultant mixture was concentrated under reduced pressure. The residue was purified by chromatography on a silica gel column (ethyl acetate/IPA/water= 7/2/1; performed three times) and then crystallized from ethyl acetate/IPA, whereby 10 mg (0.025 mmol) of the title compound were obtained as brown powder (amorphous) (yield: 3.4%).

EXAMPLE 43
(Compound No. 3024)

1H-2-(5-Nitrofuran-2-yl)benzimidazole-5-carboxylic acid

Suspended in 25 ml of nitrobenzene were 0.50 g (3.54 mmol) of 5-nitrofurfural and 0.56 g (3.57 mmol; 1.0 equivalent) of 3,4-diaminobenzoic acid (97%), followed by stirring under heat for 20 hours over an oil bath which was controlled at 150° C. The thus-obtained mixture was ice-cooled and the resulting crystals were collected by filtration, whereby 0.64 g (2.32 mmol) of the title compound was obtained as dark brown crystals. Further, the filtrate was concentrated and washed with methylene chloride, whereby 0.89 g (3.28 mmol) of the title compound was obtained (yield: 92.7%).

m.p.>280° C.

EXAMPLE 44
(Compound No. 672)

1H-2-(5-Benzoylaminopyrrol-2-yl)benzimidazole-5-[N-(2-amidinoethyl)]carboxamide hydrochloride
(Reaction 1)

1H-2-(5-Nitropyrrol-2-yl)benzimidazole-5-carboxylic acid

A solution of 1.03 g (7.35 mmol) of 5-nitropyrrol-2-aldehyde and 1.12 g (7.35 mmol) of 3,4-diaminobenzoic acid in 50 mg of nitrobenzene was heated at 150° C. for 6 hours. After completion of the reaction, the resulting crystals were collected by filtration and washed with IPA. They were recrystallized from DMF-water, whereby 1.28 g of the title compound were obtained as green crystals (yield: 64%).

m.p.>300° C.

IR(KBr)cm$^{-1}$: 3269, 2835, 1665, 1493, 1458, 1350, 1306, 1254, 1137.
(Reaction 2)

1H-2-(5-Nitro-1-methylpyrrol-2-yl)benzimidazole-5-[N-(2-cyanoethyl)]carboxamide CDI (566 mg; 3.49 mmol) was added to a solution of 633 mg (2.33 mmol) of 1H-2-(5-nitropyrrol-2-yl)benzimidazole-5-carboxylic acid in 19 ml of DMF, followed by stirring at room temperature for 30 minutes. After crystals were sufficiently precipitated and full consumption of the raw materials was confirmed by TLC, 489 mg (6.98 mmol) of 3-aminopropionitrile were added dropwise. The resulting mixture was stirred at room temperature for 30 minutes until the crystals were dissolved. After completion of the reaction, the reaction mixture was concentrated and IPA was added. The precipitated crystals were collected and then recrystallized from DMF-water, whereby 608 mg of the title compound were obtained as ocherous crystals (yield: 80%).

m.p. 268°–270° C.

IR(KBr)cm$^{-1}$: 3359, 2252, 1630, 1545, 1351, 1305.
(Reaction 3)

1H-2-(5-Nitropyrrol-2-yl)benzimidazole-5-[N-(2-amidinoethyl)]carboxamide hydrochloride A suspension of 771 mg (2.38 mmol) of 1H-2-(5-nitro-1-methylpyrrol-2-yl)benzimidazole-5-[N-(2-cyanoethyl)]carboxamide in 54 ml of ethanol was saturated with hydrogen chloride gas under ice-cooling. The resultant mixture was stirred at room temperature for 1 hour. After excess hydrogen chloride gas purged with nitrogen gas, the mixture was concentrated and the residue was washed with ethyl ether. The residue was again suspended in 23 ml of a 1:1 mixed solvent of methanol and ethanol, followed by saturated with ammonia gas. As a result, crystals were precipitated subsequent to initial dissolution of the residue. After nitrogen gas was bubbled to purge excess ammonia gas, crystals were collected by filtration and then washed with IPA, whereby 812 mg of the title compound were obtained as pale yellow crystals (yield: 90%).

m.p. 299°–300° C.

IR(KBr)cm$^{-1}$: 3363, 1702, 1636, 1545, 1452, 1405, 1349, 1236, 1193.
(Reaction 4)

1H-2-(5-Benzoylaminopyrrol-2-yl)benzimidazole-5-[N-(2-amidinoethyl)]carboxamide hydrochloride A solution of 153 mg (0.405 mmol) of 1H-2-(5-nitropyrrol-2-yl)benzimidazole-5-[N-(2-amidinoethyl)]carboxamide hydrochloride in 4.6 ml of DMF was catalytically hydrogenated using 76.9 mg of 10% Pd/C as a catalyst, so that the reactant was reduced into the corresponding amino compound. The Pd/C was filtered off. To the filtrate, 56.9 mg (0.405 mmol) of benzoyl chloride were added dropwise at –78° C. under a nitrogen gas atmosphere, followed by stirring for 30 minutes. The reaction mixture was concentrated and the residue was subjected to chromatography on a silica gel column (ethyl acetate/IPA/water=6/2/1), whereby 56.4 mg of the title compound were obtained (yield: 31%).

m.p. 195°–200° C.

IR(KBr)cm$^{-1}$: 3316, 1687, 1638, 1555, 1432, 1307.

EXAMPLE 45

(Compound No. 671)

1H-2-(5-Formylaminopyrrol-2-yl)benzimidazole-5-[N-(2-amidinoethyl)]carboxamide hydrochloride A solution of 102 mg (0.270 mmol) of 1H-2-(5-nitropyrrol-2-yl)benzimidazole-5-[N-(2-amidinoethyl)]carboxamide hydrochloride in 3.1 ml of DMF was catalytically hydrogenated using 10% Pd/C as a catalyst, so that the reactant was reduced into the corresponding amino compound. The Pd/C was filtered off. Added dropwise at –40° C. to the filtrate under a nitrogen gas atmosphere was a THF solution of N-formylimidazole, which THF solution had been prepared by adding 24.9 mg (0.54 mmol) of 98–100% formic acid dropwise at room temperature to a solution of 87.6 mg (0.54 mmol) of CDI in 2.6 ml of THF and then stirring the resultant mixture for 15 minutes. After the thus-obtained mixture was stirred at room temperature for 15 minutes, the reaction mixture was concentrated and then subjected to flush column chromatography (ethyl acetate/IPA/water=6/2/1), whereby 7.2 mg of the title compound were obtained (yield: 7.1%).

m.p. 175°–185° C. (dec.).

IR(KBr)cm$^{-1}$: 3406, 1671, 1630, 1561, 1438, 1319.

EXAMPLE 46

(Compound No. 665)

1H-2-[5-[4-[4-[N,N-Bis(2-chloroethyl)amino]phenyl]butyrylamino]pyrrol-2-yl]benzimidazole-5-[N-(2-amidinoethyl)]carboxamide hydrochloride A solution of 111 mg (0.294 mmol) of 1H-2-(5-nitropyrrol-2-yl)benzimidazole-5-[N-(2-amidinoethyl)]carboxamide hydrochloride in 3.3 ml of DMF was catalytically hydrogenated using 55.8 mg of 10% Pd/C as a catalyst, so that the reactant was reduced into the corresponding amino compound. The Pd/C was filtered off. Added dropwise at –78° C. to the filtrate under a nitrogen gas atmosphere was a 1,2-dichloroethane solution of 4-[4-[N,N-bis(2-chloroethyl)amino]phenyl]butyryl chloride, which 1,2-dichloroethane solution had been prepared by adding 153 mg (1.20 mmol) of oxalyl chloride dropwise at –20° C. to a solution of 122 mg (0.401 mmol) of chlorambucil in 6.1 ml of 1,2-dichloroethane, stirring the resultant mixture overnight at room temperature, concentrating the resultant mixture into dryness and then dissolving the thus-obtained oil in 1.0 ml of 1,2-dichloroethane. The thus-obtained mixture was stirred for 30 minutes. After completion of the reaction, the reaction mixture was concentrated and the residue was subjected to flush column chromatography (ethyl acetate/IPA/water=6/2/1), whereby 45.6 mg of the title compound were obtained (yield: 24%).

m.p. 150°–156° C. (dec.).

IR(KBr)cm$^{-1}$: 3269, 3133, 1655, 1557, 1519, 1438, 1313, 1044.

EXAMPLE 47

(Compound No. 1592)

1H-2-[4-(Guanidinoacetyl)amino-1-methylpyrrol-2-yl]benzimidazole-5-[N-[3-[N-[4-[N,N-bis(2-chloroethyl)amino]phenyl]carboxamido]propyl]]carboxamide hydrochloride (Reaction 1)

4-[[1H-2-(1-Methyl-4-nitropyrrol-2-yl)benzimidazole]-5-carboxamido]butyric acid

Suspended in 10 ml of DMF was 0.30 g (1.05 mmol) of 1H-2-(1-methyl-4-nitropyrrol-2-yl)benzimidazole-5-carboxylic acid, followed by the addition of 0.25 g (1.54 mmol; 1.5 equivalents) of CDI under a nitrogen gas stream. The thus-obtained mixture was stirred, as was, at room temperature for 1.5 hours. The mixture was ice-cooled, to which 0.13 g (1.26 mmol; 1.2 equivalents) of γ-aminobutyric acid was added. The temperature of the mixture was allowed to rise back to room temperature, at which the mixture was stirred for 6.5 hours and then allowed to stand overnight. The mixture was concentrated under reduced pressure and methanol was added to the residue. The resulting crystals were collected by filtration, whereby 0.29 g (0.78 mmol) of the title compound was obtained as yellow crystals (yield: 74.4%).

(Reaction 2)

1H-2-(1-Methyl-4-nitropyrrol-2-yl)benzimidazole-5-[N-[3-[N-[4-[N,N-bis(2-chloroethyl)amino]phenyl]carboxamido]propyl]]carboxamide Dissolved in 10 mL of DMF were 0.24 g (0.65 mmol) of 4-[[1H-2-(1-methyl-4-nitropyrrol-2-yl)benzimidazole]-5- carboxamido]butyric acid and 0.19 g (0.70 mmol; 1.08 equivalents) of 4-[N,N-bis(2-chloroethyl)] phenylenediamine hydrochloride. The resultant mixture was stirred under a nitrogen gas stream and ice-cooling. Successively added were 0.27 ml (1.94 mmol; 3.0 equivalents) of triethylamine and 0.15 ml (0.99 mmol; 1.5 equivalents) of DECP. The temperature of the thus-obtained mixture was allowed to rise back to room temperature, at which the mixture was stirred for 5 hours and then allowed to stand overnight. The resulting mixture was concentrated under reduced pressure and the residue was crystallized from methanol, whereby 0.26 g (0.45 mmol) of the title compound was obtained as pale yellow crystals (yield: 69.3%).
(Reaction 3)

1H-2-[4-(Guanidinoacetyl)amino-1-methylpyrrol-2-yl]benzimidazole-5-[N-[3-[N-[4-[N,N-bis(2-chloroethyl)amino]phenyl]carboxamido]propyl]] carboxamide hydrochloride Using 10% Pd/C (wet) as a catalyst, 0.25 g (0.43 mmol) of 1H-2-(1-methyl-4-nitropyrrol-2-yl)benzimidazole-5-[N-[3-[N-[4-[N,N-bis(2-chloroethyl)amino]phenyl] carboxamido]propyl]]carboxamide was hydrolyzed into the corresponding amino derivative under normal pressure. A DMF solution of the amino derivative was stirred under a nitrogen gas stream and ice-cooling, to which 68 μl (0.49 mmol; 1.1 equivalents) of triethylamine, 0.20 g (1.30 mmol; 3.0 equivalents) of guanidinoacetic acid hydrochloride and 0.27 g (1.31 mmol; 3.0 equivalents) of DCC were added successively. The temperature of the thus-obtained mixture was allowed to rise back to room temperature, at which the mixture was stirred for 4 hours and then allowed to stand overnight. The mixture was concentrated under reduced pressure. The residue was subjected to gel filtration ("Sephadex LH-20", methanol), purified further by chromatography on a silica gel column (ethyl acetate/IPA/water= 6/2/1) and then crystallized from IPA, whereby 88 mg (0.127 mmol) of the title compound were obtained as white crystals (yield: 29.6%).

IR(KBr)cm$^{-1}$: 3317, 1655, 1542, 1518, 1248

Elemental analysis for $C_{30}H_{36}N_{10}O_3Cl_2 \cdot HCl \cdot 3H_2O \cdot 0.5IPA$: Calculated: C, 48.75; H, 6.10; N, 18.05; Cl, 13.70 Found: C, 48.79, H, 5.82; N, 17.67; Cl, 13.67

EXAMPLE 48
(Compound No. 1017)

1H-2-[1-Methyl-4-(guanidinoacetylamino)pyrrol-2-yl]benzimidazole-5-[N-[3-chloro-4-[N,N-bis(2-chloroethyl)amino]phenyl]]carboxamide dihydrochloride (Reaction 1)

4-[N,N-Bis(2-hydroxyethyl)amino]-3-chloro-nitrobenzene

Dissolved in 8 ml of DMSO were 10.0 g (57.0 mmol) of 3-chloro-4-fluronitrobenzene and 8.6 g (82 mmol) of diethanolamine. The thus-obtained mixture was stirred under heat for 2 hours at 140° C., followed by extraction with ethyl acetate. The solvent was distilled out under reduced pressure, whereby 9.5 g of the title compound were obtained as a yellow oil (yield: 64%).
(Reaction 2)

4-[N,N-Bis(2-chloroethyl)amino]-3-chloro-nitrobenzene

Thionyl chloride (6 ml; 82 mmol) was added to a solution of 4.2 g (16.1 mmol) of 4-[N,N-bis(2-hydroxyethyl)]amino-3-chloronitrobenzene in 60 ml of 1,2-dichloroethane. The thus-obtained mixture was stirred under heat for 1 hour at 80° C. and the solvent was then distilled out under reduced pressure, whereby 4.0 g of the title compound were obtained as a yellow oil (yield: 83%).
(Reaction 3)

1H-2-(1-Methyl-4-nitropyrrol-2-yl)benzimidazole-5-[N-[3-chloro-4-[N,N-bis(2-chloroethyl)amino] phenyl]]carboxamide Dissolved in 10 ml of DMF were 200 mg (0.7 mmol) of 1H-2-(1-methyl-4-nitropyrrol-2-yl)benzimidazole-5-carboxylic acid and 3-chloro-4-[N,N-bis(2-chloroethyl)amino]aniline hydrochloride which had been obtained by catalytically hydrogenating 230 mg (0.49 mmol) of 4-[N,N-bis(2-chloroethyl)amino]-3-chloro-nitrobenzene in 20 ml of methanol while using 100 mg of 10% Pd/C as a catalyst. The thus-obtained solution was cooled to 0° C. Under a nitrogen gas atmosphere, were added 117 μl (0.84 mmol) of triethylamine and then 127 μl (0.84 mmol) of DECP. The resultant mixture was stirred, as was, for 40 minutes. The mixture was stirred further for 1 hour at room temperature and then allowed to stand overnight. The solvent was distilled out under reduced pressure. The residue was purified by chromatography on a silica gel column (ethyl acetate/n-hexane=1/1), whereby 210 mg of the title compound were obtained as yellow powder (yield: 51%).
(Reaction 4)

1H-2-[1-Methyl-4-(guanidinoacetylamino)pyrrol-2-yl]benzimidazole-5-[N-[3-chloro-4-[N,N-bis(2-chloroethyl)amino]phenyl]]carboxamide dihydrochloride Dissolved in 10 ml of a 1:1 mixed solvent of DMF and methanol were 200 mg (0.37 mmol) of 1H-2-(1-methyl-4-nitropyrrol-2-yl)benzimidazole-5-[N-[3-chloro-4-[N,N-bis(2-chloroethyl)amino]phenyl]]carboxamide in a reactor, followed by the addition of 200 mg of 10% Pd/C and 420 μl of 1N hydrochloric acid under a nitrogen gas atmosphere. The reactor was purged with hydrogen gas and the mixture was stirred at room temperature for 2 hours. After the Pd/C was filtered off, the filtrate was concentrated and the resultant concentrate was dissolved in DMF to form a DMF solution. To the solution, 62 μl (0.45 mmol) of triethylamine, 172 mg (1.12 mmol) of guanidinoacetic acid hydrochloride and 231 mg (1.12 mmol) of DCC were successively added under ice-cooling. The thus-obtained mixture was stirred at room temperature for 1 hour and then allowed to stand overnight. After the resulting white precipitate was filtered off, the solvent was distilled out under reduced pressure. A 4N hydrochloric acid/dioxane solution was added to the residue, followed by concentration under reduced pressure. The residue was washed with IPA. Yellow powder so obtained was washed further with ethanol, whereby 100 mg of the title compound were obtained as yellow powder (yield: 42%).

IR(KBr)cm$^{-1}$: 3151, 1654, 1500, 1397, 1061, 824

EXAMPLE 49
(Compound No. 1021)

1H-2-[1-Methyl-4-(guanidinoacetylamino)pyrrol-2-yl]benzimidazole-5-[N-[3-fluoro-4-[N,N-bis(2-chloroethyl)amino]phenyl]carboxamide hydrochloride Dissolved in a mixed solvent of 10 ml of DMF and 10 ml of methanol were 150 mg (0.29 mmol) of 1H-2-(1-methyl- 4-nitropyrrol-2-yl)benzimidazole-5-[N-[3-fluoro-4-[N,N-bis(2-chloroethyl)amino]phenyl]carboxamide, followed by the addition of 200 mg of 10% Pd/C and 300 μl of 1N hydrochloric acid under a nitrogen gas atmosphere. Hydrogenation was then conducted at room temperature under normal pressure. After the Pd/C was filtered off, the filtrate was concentrated and the resultant concentrate was dissolved in DMF to form a DMF solution. To the solution, 49 μl (0.29 mmol) of triethylamine, 133 mg (0.87 mmol) of guanidinoacetic acid hydrochloride and 180 mg (0.87 mmol) of DCC were successively added under ice-cooling. Subsequent to the reaction, the reaction mixture was filtered and the filtrate was concentrated. The brown syrupy residue was subjected to chromatography on a gel filtration column ("Sephadex LH-20", methanol). Fluorescent fractions were collected and concentrated, followed by the addition of 4N hydrochloric acid/dioxane. The resulting mixture was concentrated again. The concentrate was washed with methanol, whereby 76.5 mg of the title compound were obtained as yellow powder (yield: 40%).

Elemental analysis for $C_{26}H_{28}Cl_2FN_9O_2 \cdot 2HCl$: Calculated: C, 47.22, H, 4.57; N, 19.06 Found: C, 47.60, H, 4.53; N, 18.81

EXAMPLE 50
(Compound No. 1013)

1H-2-[1-Methyl-4-(guanidinoacetylamino)pyrrol-2-yl]benzimidazole-5-[N-[3-cyano-4-[N,N-bis(2-chloroethyl)amino]phenyl]]carboxamide dihydrochloride (Reaction 1)

1H-2-(1-Methyl-4-nitropyrrol-2-yl)benzimidazole-5-[N-[3-cyano-4-[N,N-bis(2-chloroethyl)amino]phenyl]]carboxamide Dissolved in 5 ml of DMF were 105 mg (0.37 mmol) of 1H-2-(1-methyl-4-nitropyrrol-2-yl)benzimidazole-5-carboxylic acid and 3-cyano-4-[N,N-bis(2-chloroethyl)amino]aniline hydrochloride which had been obtained by hydrogenating a solution of 104 mg (0.36 mmol) of 2-[N,N-bis(2-chloroethyl)amino]-5-nitrobenzonitrile in 10 ml of methanol while using 100 mg of 10% Pd/C. The thus-obtained solution was cooled to 0° C. Under a nitrogen gas atmosphere, were added 61 μl (0.44 mmol) of triethylamine and then 67 μl (0.44 mmol) of DECP. The resultant mixture was stirred, as was, for 30 minutes. After the mixture was stirred at room temperature for additional 2 hours, the solvent was distilled out under reduced pressure. The residue was purified by chromatography on a silica gel column (chloroform/methanol=10/1), whereby 61 mg of the title compound were obtained as yellow powder (yield: 32%).
(Reaction 2)

1H-2-[1-Methyl-4-(guanidinoacetylamino)pyrrol-2-yl]benzimidazole-5-[N-[3-cyano-4-[N,N-bis(2-chloroethyl)amino]phenyl]]carboxamide dihydrochloride Dissolved in 10 ml of a 1:1 mixed solvent of DMF and methanol were 56 mg (0.11 mmol) of 1H-2-(1-methyl-4-nitropyrrol-2-yl)benzimidazole-5-[N-[3-cyano-4-[N,N-bis(2-chloroethyl)amino]phenyl]]carboxamide in a reactor, followed by the addition of 50 mg of 10% Pd/C and 128 μl (1.2 equivalents) of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 18 μl (0.13 mmol) of triethylamine, 50 mg (0.33 mmol) of guanidinoacetic acid hydrochloride and 70 mg (0.34 mmol) of DCC were successively added under ice-cooling. The resultant mixture was stirred at room temperature for 1 hour and then allowed to stand overnight. The resulting white precipitate was filtered off and the solvent was distilled out under reduced pressure. The residue was dissolved in methanol and purified by gel filtration ("Sephadex LH-20", methanol). After the solvent was distilled out under reduced pressure, a 4N hydrochloric acid/dioxane solution was added. The thus-obtained mixture was concentrated again under reduced pressure. The residue was dissolved in methanol, to which ethyl acetate was added to conduct reprecipitation, whereby 27 mg of the title compound were obtained as white powder (yield: 38%).

IR(KBr)cm$^{-1}$: 3146, 2216, 1656, 1506, 1399, 1059, 823

EXAMPLE 51
(Compound No. 1596)

1H-2-[1-Methyl-4-(guanidinoacetylamino)pyrrol-2-yl]benzimidazole-5-[N-[4-[N,N-bis(2-chloroethyl)amino]-2-morphonylcarboxamido]phenyl]carboxamide hydrochloride (Reaction 1)

N-(2-Nitro-5-chlorobenzoyl)morpholine

Dissolved in 20 ml of thionyl chloride were 5.0 g (24.8 mmol) of 2-nitro-5-chlorobenzoic acid, followed by heating for 1.5 hours under reflux. After the reaction, the reaction mixture was concentrated and the residue was dissolved in 10 ml of acetone. The thus-obtained solution was added dropwise to a solution of 4.7 ml (62 mmol) of morpholine in 20 ml of acetone, followed by stirring at room temperature for 2 hours. Subsequent to the reaction, the reaction mixture was concentrated and then extracted with ethyl acetate. The ethyl acetate layer was dried and then concentrated. The residue was recrystallized from ethyl acetate/n-hexane, whereby 5.64 g of the title compound were obtained as white powder (yield: 84%).
(Reaction 2)

N-[2-Nitro-5-[N,N-bis(2-hydroxyethyl)amino] benzoyl]morpholine

Dissolved in 4 ml of DMSO were 1.0 g (3.69 mmol) of N-(2-nitro-5-chlorobenzoyl)morpholine and 1.16 g (11 mmol) of diethanolamine. The resulting mixture was stirred under heat at 140° C. for 3 hours. After the reaction, the reaction mixture was concentrated and the resulting yellow syrup was purified by chromatography on a silica gel column (chloroform/methanol=10/1), whereby 667 mg of the title compound were obtained as yellow powder (yield: 53.5%).
(Reaction 3)

N-[2-Nitro-5-[N,N-bis(2-chloroethyl)amino] benzoyl]morpholine

Dissolved in 5 ml of DMF were 500 mg (1.5 mmol) of N-[2-nitro-5-[N,N-bis(2-hydroxyethyl)amino]benzoyl] morpholine, followed by the dropwise addition of 414 mg (3.6 mmol) of methanesulfonyl chloride under ice-cooling. The thus-obtained mixture was stirred under heat at 70° C. for 1 hour. After the reaction, the reaction mixture was concentrated and the residue was purified by chromatography on a silica gel column (chloroform), whereby 539 mg of the title compound were obtained as yellow powder (yield: 81%).
(Reaction 4)

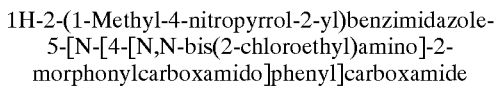

1H-2-(1-Methyl-4-nitropyrrol-2-yl)benzimidazole-5-[N-[4-[N,N-bis(2-chloroethyl)amino]-2-morphonylcarboxamido]phenyl]carboxamide Dissolved in 10 ml of THF were 200 mg (0.56 mmol) of N-[2-nitro-5-[N,N-bis(2-chloroethyl)amino]benzoyl]morpholine, followed by the addition of 200 mg of 10% Pd/C under a nitrogen gas atmosphere. 4N Hydrochloric acid (140 μl) was added, followed by hydrogenation at room temperature under normal pressure. After the Pd/C was filtered off, the filtrate was concentrated. The concentrate was added with 160 mg (0.56 mmol) of 1H-2-(1-methyl-4-nitropyrrol-2-yl)benzimidazole-5-carboxylic acid, followed by the successive addition of 120 μl (0.84 mmol) of DECP and 210 μl (1.5 mmol) of triethylamine. The thus-obtained mixture was allowed to stand overnight. After the reaction, the reaction mixture was concentrated and the resulting black brown syrup was purified by chromatography on a silica gel column (chloroform→chloroform+2% methanol), whereby 100 mg of the title compound were obtained as yellow powder (yield: 31%).
(Reaction 5)

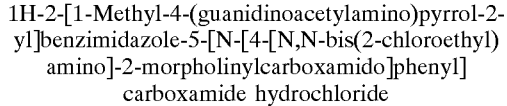

1H-2-[1-Methyl-4-(guanidinoacetylamino)pyrrol-2-yl]benzimidazole-5-[N-[4-[N,N-bis(2-chloroethyl)amino]-2-morpholinylcarboxamido]phenyl]carboxamide hydrochloride Dissolved in a mixed solvent of 10 ml of DMF and 10 ml of methanol were 100 mg (0.17 mmol) of 1H-2-(1-methyl-4-nitropyrrol-2-yl)benzimidazole-5-[N-[4-[N,N-bis(2-chloroethyl)amino]-2-morpholinylcarboxamido]phenyl]carboxamide, followed by the addition of 100 mg of 10% Pd/C and 180 μl of 1N hydrochloric acid under a nitrogen gas atmosphere. Hydrogenation was then conducted at room temperature under normal pressure. After the Pd/C was filtered off, the filtrate was concentrated to form a DMF solution. To the solution, 28 μl (0.17 mmol) of triethylamine, 77 mg (0.50 mmol) of guanidinoacetic acid hydrochloride and 103 mg (0.5 mmol) of DCC were successively added under ice-cooling. The thus-obtained mixture was allowed to stand overnight. Subsequent to the reaction, the reaction mixture was filtered and the filtrate was concentrated. The resulting brown syrupy residue was subjected to chromatography on a gel filtration column ("Sephadex LH-20", methanol). 4N Hydrochloric acid/dioxane was added, followed by concentration again. The residue was washed with methanol, whereby 25 mg of the title compound were obtained as yellow powder (yield: 20%).

EXAMPLE 52
(Compound No. 1042)

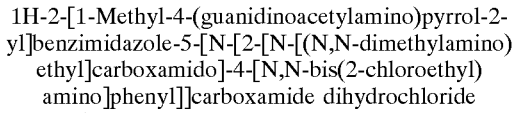

1H-2-[1-Methyl-4-(guanidinoacetylamino)pyrrol-2-yl]benzimidazole-5-[N-[2-[N-[(N,N-dimethylamino)ethyl]carboxamido]-4-[N,N-bis(2-chloroethyl)amino]phenyl]]carboxamide dihydrochloride
(Reaction 1)

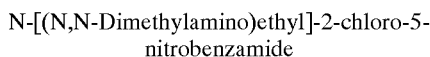

N-[(N,N-Dimethylamino)ethyl]-2-chloro-5-nitrobenzamide

A solution of 10 g (0.050 mmol) of 2-chloro-5-nitrobenzoic acid in 60 ml of THF was cooled over an ice bath, followed by the addition of 10 g (0.064 mmol) of CDI. The thus-obtained mixture was stirred at room temperature for 1 hour. To the solution, 12 ml (0.11 mmol) of N,N-dimethylethylenediamine were added dropwise, followed by stirring at room temperature for 3 hours. After the solvent was distilled out, the residue was dissolved in ethyl acetate. After the solution so obtained was washed with a 10% aqueous solution of sodium hydrogencarbonate, magnesium sulfate was added to the solution to dry the same. The ethyl acetate was distilled out under reduced pressure and the residue was purified by chromatography on a silica gel column (ethyl acetate), whereby 10 g of the title compound were obtained as a colorless oil (yield: 74%).
(Reaction 2)

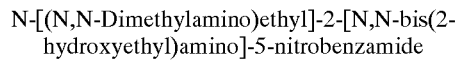

N-[(N,N-Dimethylamino)ethyl]-2-[N,N-bis(2-hydroxyethyl)amino]-5-nitrobenzamide

Diethanolamine (5 g; 48.6 mmol) was added to a solution of 5 g (18.4 mmol) of N-[(N,N-dimethylamino)ethyl]-2-chloro-5-nitrobenzamide in 10 ml of DMSO, followed by stirring at 150° C. for 3.5 hours. After the resulting mixture was cooled to room temperature, it was extracted with ethyl acetate. Magnesium sulfate was added to the extract to dry the same, and the solvent was then distilled out under reduced pressure. The residue was purified by chromatography on a silica gel column (ethyl acetate/methanol=1/0→1/1), whereby 2.6 g of the title compound were obtained as a colorless oil (yield: 38%).
(Reaction 3)

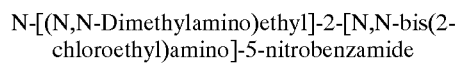

N-[(N,N-Dimethylamino)ethyl]-2-[N,N-bis(2-chloroethyl)amino]-5-nitrobenzamide

Triethylamine (4.5 ml; 32 mmol) was added to a solution of 2.6 g (0.76 mmol) of N-[(N,N-dimethylamino)ethyl]-2-[N,N-bis(2-hydroxyethyl)amino]-5-nitrobenzamide in 20 ml of methylene chloride, followed by cooling over an ice bath. The thus-obtained solution was added with 1.8 ml (23 mmol) of mesyl chloride, followed by stirring at room temperature for 3 hours. After the reaction mixture was washed with a saturated aqueous solution of sodium hydrogencarbonate, magnesium sulfate was added to the organic layer to dry the same. The solvent was distilled out under reduced pressure. The residue was dissolved in 10 ml of DMF, to which 5 g of sodium chloride were added. The resulting mixture was then stirred at 150° C. for 30 minutes. After the thus-obtained mixture was cooled to room temperature, the sodium chloride was filtered off and the solvent was distilled out under reduced pressure. The residue was purified by chromatography on a silica gel column (chloroform/methanol=10/1), whereby 0.95 g of the title compound was obtained as yellow powder (yield: 33%).
(Reaction 4)

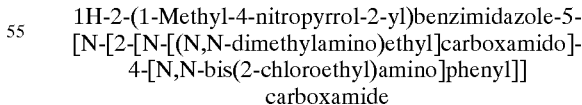

1H-2-(1-Methyl-4-nitropyrrol-2-yl)benzimidazole-5-[N-[2-[N-[(N,N-dimethylamino)ethyl]carboxamido]-4-[N,N-bis(2-chloroethyl)amino]phenyl]]carboxamide Dissolved in 10 ml of DMF were 500 mg (1.8 mmol) of 1H-2-(1-methyl-4-nitropyrrol-2-yl)benzimidazole-5-carboxylic acid and 2-[N-[(N,N-dimethylamino)ethyl]carboxamido]-4-[N,N-bis(2-chloroethyl)amino]aniline hydrochloride which had been obtained by catalytically hydrogenating 200 mg (0.53 mmol) of N-[(N,N-dimethylamino)ethyl]-5-[N,N-bis(2-chloroethyl)amino]-2-nitrobenzamide in 10 ml of methanol. The thus-obtained solution was cooled to 0° C. Added under a nitrogen gas atmosphere were 241 μl (1.8 mmol) of triethylamine and then 265 μl (1.8 mmol) of DECP. The resulting mixture was stirred, as was, for 30 minutes. The mixture was stirred further for 1 hour at room temperature and then allowed to stand overnight. The solvent was distilled out under reduced pressure and the residue was purified by chromatography on a silica gel column (chloroform/methanol=1/1), whereby 96 mg of the title compound were obtained as yellow powder (yield: 30%).
(Reaction 5)

1H-2-(1-Methyl-4-guanidinoacetylamino)pyrrol-2-yl)benzimidazole-5-[N-[2-[N-[(N,N-dimethylamino) ethyl]carboxamido]-4-[N,N-bis(2-chloroethyl) amino]phenyl]]carboxamide dihydrochloride Dissolved in a 1:1 mixed solvent of DMF and methanol in a reactor were 96 mg (0.16 mmol) of 1H-2-(1-methyl-4-nitropyrrol-2-yl)benzimidazole-5-[N-[2-[N-[(N,N-dimethylamino)ethyl]carboxamido]-4-[N,N-bis(2-chloroethyl)amino]phenyl]]carboxamide, followed by the addition of 100 mg of 10% Pd/C and 600 μl of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 26 μl (0.19 mmol) of triethylamine, 72 mg (0.47 mmol) of guanidinoacetic acid hydrochloride, 97 mg (0.47 mmol) of DCC and 36 mg (0.24 mmol) of HOBt were successively added under ice-cooling. The thus-obtained mixture was stirred at room temperature for 1 hour and then allowed to stand overnight. The resulting white precipitate was filtered off and the solvent was distilled out under reduced pressure. The residue was purified by chromatography on a silica gel column (ethyl acetate/IPA/water=4/2/1), whereby 50 mg of the title compound were obtained as yellow powder (yield: 42%).

IR(KBr)cm$^{-1}$: 1654, 1525, 1396, 1063, 821

EXAMPLE 53
(Compound No. 1584)

1H-2-[1-Methyl-4-(arginylamino)pyrrol-2-yl] benzimidazole-5-[N-[4-[N,N-bis(2-chloroethyl) amino]phenyl]]carboxamide hydrochloride
(Reaction 1)

1H-2-[1-Methyl-4-[[N-t-butoxycarbonyl)arginyl] amino]pyrrol-2-yl]benzimidazole-5-[N-[4-[N,N-bis (2-chloroethyl)amino]phenyl]]carboxamide hydrochloride Dissolved in a mixed solvent of 3 ml of DMF and 3 ml of methanol was 0.41 g (0.82 mmol) of 1H-2-(1-methyl-4-nitropyrrol-2-yl)benzimidazole-5-[N-[4-[N,N-bis(2-chloroethyl)amino]phenyl]]carboxamide, followed by the addition of 0.21 ml of 4N hydrochloric acid. Using 0.18 g of 10% Pd/C as a catalyst, the reactant was converted to the corresponding amino derivative by hydrogenation under normal pressure. A DMF solution of the amino derivative was stirred under a nitrogen gas stream and ice-cooling, to which 0.12 ml (0.86 mmol; 1.05 equivalents) of triethylamine, 0.51 g (1.64 mmol; 2.0 equivalents) of N-Boc arginine and 0.34 g (1.65 mmol; 2.0 equivalents) of DCC were added successively. The thus-obtained mixture was stirred, as was, for 2 hours and then allowed to stand overnight. The resulting crystals were filtered off and the filtrate was concentrated under reduced pressure. The residue was purified by chromatography on a silica gel column (ethyl acetate/IPA/water=7/2/1 and then chloroform/ 15–20% methanol; performed twice in total) and was then crystallized from ether, whereby 80 mg (0.11 mmol) of the title compound were obtained as light brown crystals (yield: 12.8%).
(Reaction 2)

1H-2-[1-Methyl-4-(arginylamino)pyrrol-2-yl] benzimidazole-5-[N-[4-[N,N-bis(2-chloroethyl) amino]phenyl]]carboxamide hydrochloride Dissolved in 4 ml of ethanol was 1H-2-[1-methyl-4-[[N-t-butoxycarbonyl)arginyl]amino]pyrrol-2-yl] benzimidazole-5-[N-[4-[N,N-bis(2-chloroethyl)amino] phenyl]]carboxamide, followed by the addition of 1 ml of 4N hydrochloric acid/dioxane. The thus-obtained mixture was stirred at room temperature for 5 hours and then concentrated under reduced pressure. The residue was subjected to gel filtration ("Sephadex LH-20", methanol) and then crystallized from acetonitrile, whereby 50 mg (0.71 mmol) of the title compound were obtained as yellow crystals (yield: 67.6%).

m.p.>275° C.

IR(KBr)cm$^{-1}$: 3384, 1654, 1541, 1518

Elemental analysis for $C_{29}H_{36}N_{10}O_2Cl_2 \cdot 2HCl \cdot 4.5H_2O$: Calculated: C, 42.58; H, 5.91; N, 17.12 Found: C, 43.09, H, 5.76; N, 16.84

EXAMPLE 54
(Compound No. 1585)

1H-2-[1-Methyl-4-[(4-benzylpiperazinyl) acetylamino]pyrrol-2-yl]benzimidazole-5-[N-[4-[N, N-bis(2-chloroethyl)amino]phenyl]]carboxamide In a mixed solvent of 5 ml of DMF and 5 ml of methanol, 0.31 g (0.62 mmol) of 1H-2-(1-methyl-4-nitropyrrol-2-yl) benzimidazole-5-[N-[4-[N,N-bis(2-chloroethyl)]amino] phenyl]]carboxamide was dissolved, followed by the addition of 0.7 ml of 1N hydrochloric acid. Using 0.14 g of 10% Pd/C (wet) as a catalyst, the resultant mixture was hydrogenated under normal pressure so that it was converted to the corresponding amino derivative. A solution of the amino derivative in DMF was stirred under a nitrogen gas atmosphere and ice-cooling. To the reaction mixture, 0.1 ml (0.72 mmol; 1.2 equivalents) of triethylamine and 2-(4-benzylpiperazino)acetylimidazole, which had been prepared by dissolving 0.47 g of 2-(4-benzylpiperazino)acetic acid (with some impurities) and 0.15 g (0.93 mmol) of CDI in 5 ml of DMF, were added. The mixture was stirred for 4 hours and was then allowed to stand overnight as was. The thus-obtained mixture was concentrated under reduced pressure and the residue was purified by chromatography on a silica gel column (chloroform/4% methanol). The reaction product was recrystallized from ethyl ether, whereby 0.25 g (0.36 mmol) of the title compound was obtained as light red crystals (yield: 58.6%).

m.p. 185°–195° C. (dec.).

IR(KBr)cm$^{-1}$: 3284, 1654, 1518, 1327, 815

Elemental analysis for $C_{36}H_{40}N_8O_2Cl_2 \cdot H_2O$: Calculated: C, 61.27; H, 6.00; N, 15.88 Found: C, 61.14, H, 5.75; N, 15.95

EXAMPLE 55
(Compound No. 1576)

1H-2-[1-Methyl-4-[(piperazinylacetyl)amino]pyrrol-2-yl]benzimidazole-5-[N-[4-[N,N-bis(2-chloroethyl) amino]phenyl]]carboxamide In a mixed solvent of 3 ml of DMF and 3 ml of methanol, 0.24 g (0.35 mmol) of 1H-2-[1-methyl-4-[(4- benzylpiperazinyl)acetylamino]pyrrol-2-yl]benzimidazole-5-[N-[4-[N,N-bis(2-chloroethyl)amino]phenyl]]carboxamide was suspended. Using 0.12 g of 10% Pd/C (wet) as a catalyst, catalytic hydrogenation was conducted. Eleven hours later, the reaction was terminated even though some raw materials still remained. After Pd/C was filtered off, the filtrate was subjected to gel filtration ("Sephadex LH-20", methanol). To the fraction so eluted, 4N hydrochloric acid/dioxane was added, followed by crystallization from ethanol. As the crystals still contained some impurities, they were purified further by chromatography on a silica gel column (DMF/toluene=1/1) and crystallized from ethyl ether, whereby 103 mg (0.17 mmol) of the title compound were obtained as yellowish white crystals (yield: 49.1%).

m.p.>250° C.

IR(KBr)cm$^{-1}$: 3401, 1654, 1518, 815

Elemental analysis for $C_{29}H_{34}N_8O_2Cl_2.2HCl.1.5H_2O.1.5EtOH$: Calculated: C, 50.01: H, 5.88; N, 15.55 Found: C, 49.94, H, 5.46; N, 15.62

EXAMPLE 56
(Compound No. 1590)

1H-2-[1-Methyl-4-[2-imidazolylcarboxamido)-pyrrol- 2-yl]benzimidazole-5-[N-[4-[N,N-bis(2-chloroethyl)amino]phenyl]]carboxamide In a mixed solvent of 3 ml of DMF and 3 ml of methanol, 0.20 g (0.40 mmol) of 1H-2-(1-methyl-4-nitropyrrol-2-yl)benzimidazole-5-[N-[4-[N,N-bis(2-chloroethyl)amino]phenyl]]carboxamide was dissolved, followed by the addition of 0.5 ml of 1N hydrochloric acid. Using 0.10 g of 10% Pd/C (wet) as a catalyst, the resultant mixture was hydrogenated under normal pressure so that it was converted to the corresponding amino derivative. A solution of the amino derivative in DMF was stirred under a nitrogen gas atmosphere and ice-cooling. To the reaction mixture, 68 μl (0.49 mmol; 1.2 equivalents) of triethylamine, 0.11 g (0.98 mmol; 2.5 equivalents) of imidazole-2-carboxylic acid, 59 mg (0.44 mmol; 1.1 equivalents) of HOBt and 92 mg (0.45 mmol; 1.1 equivalents) of DCC were added. The temperature of the resultant mixture was allowed to rise back to room temperature, at which the mixture was stirred for 4 hours. The reaction mixture was then allowed to stand overnight. After the solid so obtained was filtered off, the filtrate was concentrated under reduced pressure. The residue was purified by chromatography on a silica gel column (chloroform/4–8% methanol). Eluted fractions were concentrated and the residue was added with 4N hydrochloric acid/dioxane. The resulting solution was concentrated and was then crystallized from methanol, whereby 74 mg (0.13 mmol) of the title compound was obtained as light brown crystals (yield: 32.7%).

m.p.>260° C.>.

IR(KBr)cm$^{-1}$: 3365, 1684, 1592, 1517, 1398, 1329, 818

Elemental analysis for $C_{27}H_{26}N_8O_2Cl_2.2HCl.2.5H_2O$: Calculated: C, 47.45; H, 4.87; N, 16.40 Found: C, 47.43, H, 4.98; N, 16.30

EXAMPLE 57
(Compound No. 1589)

1H-2-[1-Methyl-4-[[3-(imidazol-1-yl)propionyl]amino]pyrrol-2-yl]benzimidazole-5-[N-[4-[N,N-bis(2-chloroethyl)]amino]phenyl]carboxamide In a mixed solvent of 3 ml of DMF and 3 ml of methanol, 0.20 g (0.40 mmol) of 1H-2-(1-methyl-4-nitropyrrol-2-yl)benzimidazole-5-[N-[4-[N,N-bis(2-chloroethyl)amino]phenyl]]carboxamide was dissolved, followed by the addition of 0.50 ml of 1N hydrochloric acid. Using 0.10 g of 10% Pd/C (wet) as a catalyst, the resultant mixture was hydrogenated under normal pressure so that it was converted to the corresponding amino derivative. A solution of the amino derivative in DMF was stirred under a nitrogen gas atmosphere and ice-cooling. To the reaction mixture, 75 μl (0.54 mmol; 1.3 equivalents) of triethylamine and a solution of 3-(imidazol-1-yl)propionylimidazole in DMF, which had been prepared in advance by dissolving 0.15 g (0.60 mmol) of 3-(4-benzylpiperazinyl)propionic acid and 0.12 g (0.74 mmol) of CDI in 3 ml of DMF and stirring the solution at room temperature for 2.5 hours, were added successively. The temperature of the resultant mixture was allowed to rise back to room temperature, at which the mixture was stirred for 4.5 hours. The reaction mixture was concentrated under reduced pressure. The residue was purified by chromatography on a silica gel column (ethyl acetate/IPA/water=6/2/1) and crystallized from ethyl acetate, whereby 103 mg (0.17 mmol) of the title compound were obtained as light brown crystals (yield: 42.5%).

m.p.>260° C.

IR(KBr)cm$^{-1}$: 3287, 1636, 1518, 1328, 1239, 815

Elemental analysis for $C_{29}H_{30}Cl_2N_8O_2.HCl$: Calculated: C, 55.29; H, 4.96; N, 17.79 Found: C, 54.94, H, 5.07; N, 17.81

EXAMPLE 58
(Compound No. 1604)

1H-2-[1-Methyl-4-furoylaminopyrrol-2-yl]benzimidazole-5-[N-[3-[N-ethyl,N-(2-chloroethyl)amino]phenyl]carboxamide (Reaction 1)

3-Nitroacetanilide

To 10 g (72 mmol) of 3-nitroaniline, 10 ml (106 mmol) of acetic anhydride were added, followed by stirring. White crystals were precipitated with exotherm. After stirring for 10 minutes, ice water was poured into the reaction mixture. The crystals were dissolved in chloroform, followed by washing successively with 1N hydrochloric acid, a saturated aqueous solution of sodium hydrogencarbonate and saturated saline. The organic layer was dried over anhydrous magnesium sulfate and then the solvent was distilled out under reduced pressure. The residue was washed with ethyl ether, whereby 11.6 g of white powder were obtained (yield: 89%).

(Reaction 2)

3-Nitro-N-ethylaniline

To a solution of 8 g (44 mmol) of 3-nitroacetanilide in 200 ml of dry THF, a solution of 5.5 ml (58 mmol) of borane dimethyl sulfide complex in 5 ml of THF was added, followed by stirring at 80° C. for 4 hours. To the reaction mixture, 3 ml (32 mmol) of borane dimethyl sulfide complex were further added, followed by stirring at 80° C. for 3 hours. After 1N hydrochloric acid was added to the reaction mixture until the solution became uniform, the solvent was concentrated under reduced pressure. To the residue, a 10N aqueous solution of sodium hydroxide was added, followed by extraction with chloroform. The extract was washed with saturated saline and then dried over magnesium sulfate. The solvent was distilled out under reduced pressure. The residue was purified by chromatography on a column (ethyl acetate/ n-hexane=4/1), whereby 6.6 g of the title compound were obtained as brown powder (yield: 89%).
(Reaction 3)

3-[[N-Ethyl,N-(2-hydroxyethyl)]amino]nitrobenzene

In 40 ml of a 30% aqueous solution of acetic acid, 6.0 g (39.1 mmol) of 3-(N-ethyl)aminonitrobenzene were dissolved, followed by the addition of 11.5 g (261 mmol) of ethylene oxide under a nitrogen gas atmosphere. The resultant mixture was stirred overnight at room temperature. After completion of the reaction, the reaction mixture was extracted with ethyl acetate. The ethyl acetate layer was dried and concentrated, whereby 5.27 g of the title compound were obtained as a brown syrup (yield: 64.1%).
(Reaction 4)

3-[[N-Ethyl,N-(2-chloroethyl)]amino]nitrobenzene

In 50 ml of benzene, 3.0 g (14.3 mmol) of 3-[[N-ethyl, N-(2-hydroxyethyl)]amino]nitrobenzene were dissolved, followed by the addition of 4.1 g (29.2 mmol) of thionyl chloride. The resultant mixture was stirred at 60° C. for one hour. After completion of the reaction, the reaction mixture was concentrated and recrystallized from ethyl acetate/n-hexane, whereby 3.18 g of the title compound were obtained as yellow powder (yield: 97%).
(Reaction 5)

3-[N-Ethyl,N-2-chloroethyl)]aminoaniline

In 20 ml of concentrated hydrochloric acid, 640 mg (2.8 mmol) of 3-[[N-ethyl,N-(2-chloroethyl)]amino] nitrobenzene were dissolved, followed by the addition of 2.5 g (11 mmol) of thionyl tin chloride dihydrate. The resultant mixture was stirred under reflux for 2 hours. After completion of the reaction, ammonia water was added to the reaction mixture, followed by extraction with ethyl acetate. The ethyl acetate layer was dried and concentrated, whereby a pale yellow syrup was obtained. To the syrup, 4N hydrochloric acid/dioxane was added, whereby 624 mg of the title compound were obtained as a yellow syrup (yield: 82%).
(Reaction 6)

1H-2-(1-Methyl-4-nitropyrrol-2-yl)benzimidazole-5-[N-[3-[[N-ethyl,N-(2-chloroethyl)]amino]phenyl]]carboxamide In 30 ml of DMF, 658 mg (2.3 mmol) of 1H-2-(1-methyl-4-nitropyrrol-2-yl)benzimidazole-5-carboxylic acid and 624 mg (2.3 mmol) of 3-[N-ethyl,N-(2-chloroethyl)] aminoaniline were dissolved. Under ice cooling, 530 µl (3.5 mmol) of DECP and 960 µl (6.9 mmol) of triethylamine were added to the resultant solution by using a syringe. After ice cooling for two hours, the reaction mixture was allowed to stand overnight at room temperature. After completion of the reaction, the reaction mixture was concentrated and the dark brown residue in the form of syrup was purified by chromatography on a silica gel column (chloroform→2% methanol/chloroform). Relevant fractions were collected and concentrated, whereby 428 mg of the title compound were obtained as yellow powder (yield: 40%).
(Reaction 7)

1H-2-(1-Methyl-4-furoylaminopyrrolyl-2-yl) benzimidazole-5-[N-[3-[[N-ethyl,N-(2-chloroethyl)] amino]phenyl]]carboxamide In 10 ml of DMF and 10 ml of methanol, 200 mg (0.43 mmol) of 1H-2-(1-methyl-4-nitropyrrol-2-yl) benzimidazole-5-[N-[3-[[N-ethyl,N-(2-chloroethyl)]amino] phenyl]]carboxamide were dissolved. To the resultant solution, 250 mg of 10% Pd/C and 500 µl of 1N hydrochloric acid were added under a nitrogen stream, followed by hydrogenation at ordinary temperature under normal pressure. After Pd/C was filtered off, the filtrate was concentrated to form a DMF solution. To the solution, 120 µl of triethylamine and a solution of 56.2 mg (0.43 mmol) of furoyl chloride in methylene chloride were added successively under ice cooling. The resultant solution was allowed to stand overnight. After completion of the reaction, the reaction mixture was concentrated. The dark brown residue in the form of syrup was purified by chromatography on a silica gel column (chloroform/methanol=30/1), whereby 149 mg of the title compound were obtained as white powder (yield: 66%).

Elemental analysis for $C_{28}H_{27}ClN_6O_3 \cdot 1.5H_2O$: Calculated: C, 60.27; H, 5.42; N, 15.06 Found: C, 60.51, H, 5.12; N, 15.41

EXAMPLE 59
(Compound No. 1480)

1H-2-[1-Methyl-4-(2-pyrrolcarboxamido)pyrrol-2-yl]benzimidazole-5-[N-[4-[N,N-bis(2-chloroethyl) amino]phenyl]]carboxamide hydrochloride To a solution of 40 mg (0.36 mmol) of 2-pyrrolecarboxylic acid in 10 ml of benzene, 0.1 ml (1.4 mmol) of thionyl chloride was added in a reactor, followed by stirring under heat at 100° C. for 2 hours. After the solvent was distilled out under reduced pressure, a small amount of benzene was added to the residue. Distillation was repeated twice under reduced pressure. The acid chloride so obtained was immediately provided for use in the next reaction. In 10 ml of a 1:1 mixed solvent of DMF and methanol, 150 mg (0.30 mmol) of 1H-2-(1-methyl-4-nitropyrrol-2-yl)benzimidazole-5-[N-[4-[N,N-bis(2-chloroethyl)amino]phenyl]]carboxamide were dissolved, followed by the addition of 150 mg of 10% Pd/C and 360 µl of 1N hydrochloric acid under a nitrogen gas atmosphere. The reactor was purged with a hydrogen gas, followed by stirring at room temperature for 2 hours. After Pd/C was filtered off, the filtrate was concentrated to form a DMF solution. To the solution, 62 µl (0.45 mmol) of triethylamine and 2-pyrrolecarboxylic acid chloride, which had been synthesized in advance, were successively added. The resultant mixture was stirred at room temperature for one hour. The reaction mixture was added with 5 ml of methanol and was then allowed to stand overnight. The solvent was distilled out under reduced pressure. The residue was purified by chromatography on a silica gel column (chloroform/methanol=95/5), whereby 50 mg of the title compound were obtained as white powder (yield: 30%).

IR(KBr)cm$^{-1}$: 3148, 1636, 1518, 1419, 812, 756

EXAMPLE 60
(Compound No. 1520)

1H-2-[1-Methyl-4-[3-(methylthio)propionylamino] pyrrol-2-yl]benzimidazole-5-[N-[4-[N,N-bis(2-chloroethyl)amino]phenyl]]carboxamide In a mixed solvent of 3 ml of DMF and 3 ml of methanol, 0.20 g (0.40 mmol) of 1H-2-(1-methyl-4-nitropyrrol-2-yl) benzimidazole-5-[N-[4-[N,N-bis(2-chloroethyl)amino] phenyl]]carboxamide were dissolved, followed by the addition of 0.45 ml of 1N hydrochloric acid. Using 0.10 g of 10%

Pd/C (wet) as a catalyst, hydrogenation was conducted under normal pressure to obtain the corresponding amino derivative. A solution of the amino derivative in DMF was stirred under a nitrogen gas stream and ice cooling. To the reaction mixture, 67 μl (0.48 mmol; 1.2 equivalents) of triethylamine and a DMF solution of 3-(methylthio) propionylimidazole, which had been prepared by dissolving 0.06 g (0.50 mmol; 1.2 equivalents) of 3-(methylthio) propionic acid and 95 mg (0.59 mmol; 1.4 equivalents) of CDI in 3 ml of DMF, were added. The temperature of the resultant mixture was allowed to rise back to room temperature, at which the mixture was stirred for 4 hours. The reaction mixture was then allowed to stand overnight, followed by concentration under reduced pressure. The residue was purified by chromatography on a silica gel column (chloroform/4% methanol) and crystallized from ethyl acetate-ethyl ether, whereby 164 mg (0.29 mmol) of the title compound were obtained as light brown crystals (yield: 71.6%).

IR(KBr)cm$^{-1}$: 3275, 1642, 1518, 1327, 813

Elemental analysis for $C_{27}H_{30}Cl_2N_6O_2S$: Calculated: C, 56.54; H. 5.27; N: 14.65, Cl: 12.36 Found: C, 56.12, H, 5.22; N, 14.30, Cl: 12.30

EXAMPLE 61
(Compound No. 1527)

1H-2-[1-Methyl-4-[3-(methylthio)propionylamino] pyrrol-2-yl]benzimidazole-5-[N-[3-chloro-4-[N,N-bis(2-chloroethyl)amino]phenyl]]carboxamide In 10 ml of a 1:1 mixed solvent of DMF and methanol, 201 mg (0.38 mmol) of 1H-2-[1-methyl-4-nitropyrrol-2-yl] benzimidazole-5-[N-[3-chloro-4-[N,N-bis(2-chloroethyl) amino]phenyl]]carboxamide were dissolved in a reactor, followed by the addition of 200 mg of 10% Pd/C and 412 μl of 1N hydrochloric acid under a nitrogen gas atmosphere. The reactor was purged with a hydrogen gas, followed by stirring at room temperature for 2 hours. After Pd/C was filtered off, the filtrate was concentrated to form a DMF solution. To the solution, 78 μl (0.56 mmol) of triethylamine and a solution of an active intermediate, which had been prepared in advance by reacting 135 mg (1.12 mmol) of 3-(methylthio)propionic acid with 182 mg (1.12 mmol) of CDI, in 5 ml of DMF were added and the resultant mixture was allowed to stand overnight. The solvent was distilled out under reduced pressure. The residue so obtained was purified by chromatography on a silica gel column (chloroform/methanol=96/4). Further purification was conducted by chromatography on a silica gel column (ethyl acetate/n-hexane=3/1), whereby 45 mg of the title compound were obtained as white powder (yield: 20%).

EXAMPLE 62
(Compound No. 1528)

1H-2-[1-Methyl-4-[3-(methylthio)propionylamino] pyrrol-2-yl]benzimidazole-5-[N-[3-fluoro-4-[N,N-bis(2-chloroethyl)amino]phenyl]]carboxamide
(Reaction 1)

3-Fluoro-4-[N,N-bis(2-hydroxyethyl)] aminonitrobenzene

In 4 ml of DMSO, 5.0 g (31.4 mmol) of 3,4-difluoronitrobenzene and 8.3 g (78.5 mmol) of diethanolamine were dissolved, followed by stirring under heat at 140° C. for one hour. After completion of the reaction, the reaction mixture was extracted with ethyl acetate. The ethyl acetate layer was dried and concentrated. To the reddish brown syrup so obtained, n-hexane/ethyl acetate was added for crystallization, whereby 6.93 g of the title compound were obtained as yellow powder (yield: 90%).
(Reaction 2)

3-Fluoro-4-[N,N-bis(2-chloroethyl)] aminonitrobenzene

In 12 ml of DMF, 1.3 g (5.32 mmol) of 3-fluoro-4-[N,N-bis(2-hydroxyethyl)amino]nitrobenzene were dissolved, followed by the dropwise addition of 1.47 g (12.8 mmol) of methanesulfonyl chloride under ice cooling. The resultant mixture was stirred under heat at 70° C. for one hour. After completion of the reaction, the reaction mixture was concentrated. The yellow syrup so obtained was purified by chromatography on a silica gel column (chloroform). The relevant fractions were concentrated and then crystallized from n-hexane/ethyl acetate, whereby 1.2 g of the title compound were obtained as yellow powder (yield: 81%).
(Reaction 3)

1H-2-(1-Methyl-4-nitropyrrol-2-y)benzimidazole-5-[N-[3-fluoro-4-[N,N-bis(2-chloroethyl)amino] phenyl]]carboxamide In 10 ml of THF, 500 mg (1.78 mmol) of 3-fluoro-4-[N, N-bis(2-chloroethyl)amino]nitrobenzene were dissolved. To the resultant solution, 200 mg of 10% Pd/C were added under a nitrogen gas atmosphere, followed by the addition of 450 μl of 4N hydrochloric acid. The resultant mixture was hydrogenated under normal pressure at ordinary temperature. After Pd/C was filtered off, the filtrate was concentrated. To the concentrate, 510 mg (1.78 mmol) of 1H-2-(1-methyl-4-nitropyrrol-2-yl)benzimidazole-5-carboxylic acid were added, followed by the successive addition of 468 μl (2.67 mmol) of DECP and 740 μl (5.34 mmol) of triethylamine. The resultant mixture was allowed to stand overnight. After completion of the reaction, the reactant was concentrated. The dark brown syrup so obtained was purified by chromatography on a silica gel column (chloroform→chloroform+2% methanol), whereby 325.6 mg of the title compound were obtained as yellow powder (yield: 35%).
(Reaction 4)

1H-2-[1-Methyl-4-[3-(methylthio)propionylamino] pyrrol-2-yl]benzimidazole-5-[N-[3-fluoro-4-[N,N-bis(2-chloroethyl)amino]phenyl]]carboxamide In 10 ml of DMF and 10 ml of methanol, 150 mg (0.29 mmol) of 1H-2-(1-methyl-4-nitropyrrol-2-yl) benzimidazole-5-[N-[3-fluoro-4-[N,N-bis(2-chloroethyl) amino]phenyl]]carboxamide were dissolved. To the resultant solution, 200 mg of 10% Pd/C were added under a nitrogen gas atmosphere, followed by the addition of 320 μl of 1N hydrochloric acid. Hydrogenation was conducted under normal pressure at ordinary temperature. After Pd/C was filtered off, the filtrate was concentrated to form a DMF solution. To the solution, 49 μl (0.29 mmol) of triethylamine and a solution of an active intermediate, which had been prepared in advance by reacting 105 mg (0.87 mmol) of 3-(methylthio)propionic acid with 141 mg (0.87 mmol) of CDI, in 5 ml of DMF were added under ice cooling. The resulting solution was then allowed to stand overnight. After completion of the reaction, the reaction mixture was concentrated. The residue in the form of brown syrup was purified by chromatography on a silica gel column (chloroform/methanol=95/5). The concentrate was washed with n-hexane/chloroform, whereby 115 mg of the title compound were obtained as pale yellow powder (yield: 67%).

Elemental analysis for $C_{27}H_{29}Cl_2FN_6O_2S.H_2O$: Calculated: C, 53.20; H, 5.13; N, 13.79 Found: C, 53.62; H, 4.95; N, 13.79

EXAMPLE 63
(Compound No. 1524)

1H-2-[1-Methyl-4-[3-(methylthio)propionylamino]
pyrrol-2-yl]benzimidazole-5-[N-[3-methyl-4-[N,N-
bis(2-chloroethyl)amino]phenyl]]carboxamide In 10 ml of a 1:1 mixed solvent of DMF and methanol, 200 mg (0.39 mmol) of 1H-2-(1-methyl-4-nitropyrrol-2-yl) benzimidazole-5-[N-[3-methyl-4-[N,N-bis(2-chloroethyl) amino]phenyl]]carboxamide were dissolved in a reactor, followed by the addition of 150 mg of 10% Pd/C and 427 μl of 1N hydrochloric acid under a nitrogen gas atmosphere. The reactor was purged with a hydrogen gas, followed by stirring at room temperature for 2 hours. After Pd/C was filtered off, the filtrate was concentrated to form a DMF solution. To the solution, 65 μl (0.46 mmol) of triethylamine and a solution of an active intermediate, which had been prepared in advance by reacting 140 mg (1.17 mmol) of 3-(methylthio)propionic acid with 200 mg (1.23 mmol) of CDI, in 5 ml of DMF were added, followed by stirring at room temperature for 3 hours. The reaction mixture was allowed to stand overnight. The solvent was distilled out under reduced pressure. The residue so obtained was purified by chromatography on a silica gel column (chloroform/methanol=95/5), whereby 195 mg of the title compound were obtained as white powder (yield: 86%).

IR(KBr)cm$^{-1}$: 3163, 1654, 1509, 1397, 1063, 805

EXAMPLE 64
(Compound No. 1530)

1H-2-[1-Methyl-4-[3-(methylthio)propionylamino]
pyrrol-2-yl]benzimidazole-5-[N-[2-methyl-4-[N,N-
bis(2-chloroethyl)amino]phenyl]]carboxamide 1H-2-(1-Methyl-4-nitropyrrol-2-yl)benzimidazole-5-[N-[2-methyl-4-[N,N-bis(2-chloroethyl)amino]phenyl]] carboxamide (102 mg; 0.20 mmol) was dissolved in 10 ml of a 1:1 mixed solvent of DMF and methanol in a reactor, followed by the addition of 100 mg of 10% Pd/C and 218 μl of 1N hydrochloric acid under a nitrogen gas atmosphere. The reactor was purged with a hydrogen gas, followed by stirring at room temperature for 2 hours. After Pd/C was filtered off, the filtrate was concentrated to form a DMF solution. To the solution, 55 μl (0.39 mmol) of triethylamine and a solution of an active intermediate, which had been prepared in advance by reacting 71 mg (0.59 mmol) of 3-(methylthio)propionic acid and 96 mg (0.59 mmol) of CDI, in 5 ml of DMF were added under ice cooling. The reaction mixture was then allowed to stand overnight. The solvent was distilled out under reduced pressure. The residue so obtained was purified by chromatography on a silica gel column (chloroform/methanol=96/4), whereby 100 mg of the title compound were obtained as white powder (yield: 86%).

EXAMPLE 65
(Compound No. 1529)

1H-2-[1-Methyl-4-[3-(methylthio)propionylamino]
pyrrol-2-yl]benzimidazole-5-[N-[3-trifluoromethyl-
4-(N,N-bis(2-chloroethyl)amino]phenyl]]
carboxamide (Reaction 1)

3-Trifluoromethyl-4-[N,N-bis(2-hydroxyethyl)
amino]nitrobenzene

2-Fluoro-5-nitrobenzotrifluoride (5.0 g; 23.9 mmol) and 6.0 g (57.1 mmol) of diethanolamine were dissolved solved in 30 ml of DMSO, followed by stirring under heat at 140° C. for 5 hours. The reaction mixture was extracted with ethyl acetate and the extract was then dried over magnesium sulfate. The brown oil so obtained was purified by chromatography on a silica gel column (chloroform/ methanol=10/1), whereby 565 mg of the title compound were obtained as yellow powder (yield: 8%).
(Reaction 2)

3-Trifluoromethyl-4-[N,N-bis(2-chloroethyl)]amino]
nitrobenzene

3-Trifluoromethyl-4-[N,N-bis(2-hydroxyethyl)amino] nitrobenzene (0.556 g; 1.89 mmol) was dissolved in 5 ml of DMF. Methanesulfonyl chloride (0.52 g; 4.53 mmol) was added to the resultant solution, followed by stirring under heat at 70° C. for one hour. After completion of the reaction, the reaction mixture was concentrated. The brown syrup so obtained was purified by chromatography on a silica gel column (chloroform), whereby 434 mg of the title compound were obtained as yellow powder (yield: 70%).
(Reaction 3)

1H-2-(1-Methyl-4-nitropyrrol-2-yl)benzimidazole-5-
[N-[3-trifluoromethyl-4-[N,N-bis(2-chloroethyl)
amino]phenyl]]carboxamide 1H-2-(1-Methyl-4-nitropyrrol-2-yl)benzimidazole-5-carboxylic acid (375 mg; 1.33 mmol) and 3-trifluoromethyl-4-[N,N-bis(2-chloroethyl)amino]aniline hydrochloride, which had been obtained by catalytic hydrogenation of a solution of 434 mg (1.31 mmol) of 3-trifluoromethyl-4-[N,N-bis(2-chloroethyl)amino]nitrobenzene in 10 ml of methanol by using Pd/C as a catalyst, were dissolved in 10 ml of DMF, followed by cooling to 0° C. Under a nitrogen gas atmosphere, the reaction mixture was added with 320 μl (2.3 mmol) of triethylamine and then with 220 μl (1.45 mmol) of DECP, followed by stirring for 30 minutes as was. After stirring for further two hours at room temperature, the solvent was distilled out under reduced pressure. The residue was purified by chromatography on a silica gel column (chloroform/methanol=10/1), whereby 159 mg of the title compound were obtained as yellow powder (yield: 32%).
(Reaction 4)

1H-2-[1-Methyl-4-[3-(methylthio)propionylamino]
pyrrol-2-yl]benzimidazole-5-[N-[3-trifluoromethyl-
4-[N,N-bis(2-chloroethyl)amino]phenyl]]
carboxamide 1H-2-(1-Methyl-4-nitropyrrol-2-yl)benzimidazole-5-[N-[3-trifluoromethyl-4-[N,N-bis(2-chloroethyl)amino]phenyl] ]carboxamide (116 mg; 0.20 mmol) was dissolved in 8 ml of a 1:1 mixed solvent of DMF and methanol in a reactor, followed by the addition of 100 mg of 10% Pd/C and 224 μl of 1N hydrochloric acid under a nitrogen gas atmosphere. The reactor was purged with a hydrogen gas, followed by stirring at room temperature for 2 hours. After Pd/C was filtered off, the filtrate was concentrated to form a DMF solution. To the solution, 60 μl (0.43 mmol) of triethylamine and a solution of an active intermediate, which had been prepared in advance by reacting 73 mg (0.61 mmol) of 3-(methylthio)propionic acid with 100 mg (0.62 mmol) of CDI, in 5 ml of DMF were added under ice cooling. The resultant solution was stirred at room temperature for 6 hours and was then allowed to stand overnight. The solvent was distilled out under reduced pressure. The residue so obtained was purified by chromatography on a silica gel column (chloroform/methanol=95/5), whereby 90 mg of the title compound were obtained as white powder (yield: 69%).

EXAMPLE 66
(Compound No. 1601)

1H-2-[1-Methyl-4-[3-(methylthio)propionylamino] pyrrol-2-yl]benzimidazole-5-[N-[4-[N,N-bis(2-chloroethyl)amino]benz-2-oxa-1,3-diazolyl]] carboxamide (Reaction 1)

4-[N,N-Bis(2-hydroxyethyl)amino]-7-nitrobenz-2-oxa-1,3-diazole

4-Chloro-7-nitrobenz-2-oxa-1,3-diazole (5.0 g; 25 mmol) and 6.6 g (63 mmol) of diethanolamine were dissolved in 4 ml of DMSO. The resultant solution was stirred under heat at 140° C. for 2 hours, followed by extraction with ethyl acetate. The solvent was distilled out under reduced pressure, whereby 5.8 g of the title compound were obtained as orange powder (yield: 87%).

(Reaction 2)

4-[N,N-Bis(2-chloroethyl)amino]-7-nitrobenz-2-oxa-1,3-diazole

4-[N,N-Bis(2-hydroxyethyl)amino]-7-nitrobenz-2-oxa-1,3-diazole (1.0 g; 3.7 mmol) was dissolved in 10 ml of DMF, followed by the addition of 2 ml (9.0 mmol) of methanesulfonyl chloride. The resultant mixture was stirred under heat at 70° C. for one hour. The solvent was distilled out under reduced pressure. The brown oil so obtained was purified by chromatography on a silica gel column (chloroform:methanol=97:3), whereby 917 mg of the title compound were obtained as orange powder (yield: 81%).

(Reaction 3)

1H-2-(1-Methyl-4-nitropyrrol-2-yl)benzimidazole-5-[N-[4-[N,N-bis(2-chloroethyl)amino]benz-2-oxa-1,3-diazolyl]]carboxamide 1H-2-(1-Methyl-4-nitropyrrol-2-yl)benzimidazole-5-carboxylic acid (243 mg: 0.85 mmol) and 4-[N,N-bis(2-chloroethyl)amino]-7-aminobenz-2-oxa-1,3-diazole hydrochloride, which had been obtained by catalytic hydrogenation of a solution of 300 mg (0.85 mmol) of 4-[N,N-bis(2-chloroethyl)amino]-7-nitrobenz-2-oxa-1,3-diazole in 10 ml of methanol by using Pd/C as a catalyst, were dissolved in 5 ml of DMF, followed by cooling to 0° C. To the reaction mixture, 355 μl (2.6 mmol) of triethylamine and then 193 μl (1.3 mmol) of DECP were added under a nitrogen atmosphere, followed by stirring for 30 minutes as was. Stirring was conducted for further 2 hours at room temperature. The solvent was distilled off under reduced pressure. The residue so obtained was purified by chromatography on a silica gel column (chloroform/methanol=10/1), whereby 175 mg of the title compound were obtained as orange powder (yield: 38%).

(Reaction 4)

1H-2-[1-Methyl-4-[3-(methylthio)propionylamino] pyrrol-2-yl]benzimidazole-5-[N-[4-[N,N-bis(2-chloroethyl)amino]benz-2-oxa-1,3-diazolyl]] carboxamide 1H-2-(1-Methyl-4-nitropyrrol-2-yl)benzimidazole-5-[N-[4-[N,N-bis(2-chloroethyl)amino]benz-2-oxa-1,3-diazolyl]] carboxamide (169 mg; 0.31 mmol) was dissolved in 10 ml of a 1:1 mixed solvent of DMF and methanol in a reactor, followed by the addition of 150 mg of 10% Pd/C and 342 μl of 1N hydrochloric acid under a nitrogen gas atmosphere. The reactor was purged with a hydrogen gas, followed by stirring at room temperature for 2 hours. After Pd/C was filtered off, the filtrate was concentrated to form a DMF solution. To the solution, 52 μl (0.37 mmol) of triethylamine and a solution of an active intermediate, which had been prepared in advance by reacting 112 mg (0.93 mmol) of 3-(methylthio)propionic acid with 151 mg (0.93 mmol) of CDI, in 5 ml of DMF were added under ice cooling. The reaction mixture was then allowed to stand overnight. The solvent was distilled out under reduced pressure. The residue so obtained was purified by chromatography on a silica gel column (chloroform/methanol=96/4). The solvent was distilled out under reduced pressure. The residue was dissolved in ethyl acetate, followed by the addition of ethyl ether to cause re-precipitation, whereby 89 mg of the title compound were obtained as orange powder (yield: 46%).

IR(KBr)cm$^{-1}$: 3134, 1654, 1535, 1289, 811, 743

EXAMPLE 67
(I$^-$ salt of Compound No. 1056)

2-[N-[1-Methyl-2-[5-[N-[4-[N,N-bis(2-chloroethyl) amino]phenyl]]carbamoyl]-1H-benzimidazol-2-yl] pyrrol-4-yl]carbamoylethyl-dimethylsulfonium iodide 1H-2-[1-Methyl-4-[3-(methylthio)propionylamino] pyrrol-2-yl]benzimidazole-5-[N-[4-[N,N-bis(2-chloroethyl) amino]phenyl]]carboxamide (76 mg; 0.13 mmol) was dissolved in 0.5 ml of 80% formic acid, 0.25 ml of acetic acid and 0.2 ml of methyl iodide. The resultant solution was stirred at room temperature for 9 hours under shading and was then allowed to stand overnight. The reaction mixture was added with methanol, followed by concentration under reduced pressure. The concentrate was evaporated with ethanol and to the residue, IPA was added. The solid so obtained was collected by filtration, whereby 54 mg (0.075 mmol) of the title compound were obtained as a light brown hygroscopic solid (yield: 58.1%). The filtrate was concentrated further and treated with ethyl acetate, whereby 22 mg (0.031 mmol) of the title compound were obtained (yield: 23.7%). The total amount of the title compounds so obtained was 76 mg (0.106 mmol; yield: 81.8%).

IR(KBr)cm$^{-1}$: 3397, 1648, 1517, 1327, 814

Elemental analysis for $C_{28}H_{33}Cl_2IN_6O_2S$: Calculated: C, 47.01; H, 4.84; N, 11.75 Found: C, 46.97; H, 4.84, N, 11.78

EXAMPLE 68
(I$^-$ salt of Compound No. 1076)

2-[N-[1-Methyl-2-[5-[N-[3-fluoro-4-[N,N-bis(2-chloroethyl)amino]phenyl]]carbamoyl]-1H-benzimidazol-2-yl]pyrrol-4-yl]carbamoylethyl-dimethylsulfonium iodide 1H-2-[1-Methyl-4-[3-(methylthio)propionylamino] pyrrol-2-yl]benzimidazole-5-[N-[3-fluoro-4-[N,N-bis(2-chloroethyl)amino]]phenyl]carboxamide (100 mg; 0.19 mmol) was dissolved in 1 ml of 80% formic acid, 0.5 ml of acetic acid and 0.4 ml of methyl iodide. The resultant solution was stirred at room temperature for two nights under shading. After completion of the reaction, the reaction mixture was added with methanol and was evaporated with methanol three times. The residue was washed with ethanol, whereby 100 mg of the title compound were obtained as pale yellow powder (yield: 98%).

Elemental analysis for $C_{28}H_{32}Cl_2FIN_6O_2 \cdot H_2O$: Calculated: C, 44.75; H, 4.56; N, 11.18 Found: C, 44.60; H, 4.59; N, 10.83

EXAMPLE 69
(I⁻ salt of Compound No.1060)

2-[N-[1-Methyl-2-[5-[N-[3-methyl-4-[N,N-bis(2-chloroethyl)amino]phenyl]]carbamoyl]-1H-benzimidazol-2-yl]pyrrol-4-yl]carbamoylethyl-dimethylsulfonium iodide 1H-2-[1-Methyl-4-[3-(methylthio)propionylamino]pyrrol-2-yl]benzimidazole-5-[N-[3-methyl-4-[N,N-bis(2-chloroethyl)amino]phenyl]]carboxamide (40 mg; 0.068 mmol) was added to a mixed solvent of 240 μl of 80% of formic acid and 120 μl of acetic acid. To the resultant solution, 210 μl of methyl iodide were added, followed by stirring at room temperature for 7 hours under shading. The reaction mixture was allowed to stand overnight. Methanol was added and the solvent was distilled out under reduced pressure. To the residue, toluene was added. Distillation was repeated three times under reduced pressure. The residue was washed with IPA, whereby 35 mg of the title compound were obtained as pale yellow powder (yield: 70%).

IR(KBr)cm⁻¹: 3254, 1648, 1510, 1307, 803, 744

EXAMPLE 70
(I⁻ salt of Compound No. 1079)

2-[N-[1-Methyl-2-[5-[N-[2-methyl-4-[N,N-bis(2-chloroethyl)amino]phenyl]]carbamoyl]-1H-benzimidazol-2-yl]pyrrol-4-yl]carbamoylethyl-dimethylsulfonium iodide 1H-2-[1-Methyl-4-[3-(methylthio)propionylamino]pyrrol-2-yl]benzimidazole-5-[N-[2-methyl-4-[N,N-bis(2-chloroethyl)amino]phenyl]]carboxamide (84 mg; 0.14 mmol) was dissolved in a mixed solvent of 500 μl of 80% formic acid and 250 μl of acetic acid. To the resultant solution, 210 μl of methyl iodide were added, followed by stirring at room temperature for 4 hours under shading. The reaction mixture was allowed to stand overnight. Methanol was added and the solvent D was distilled out under reduced pressure. Toluene was added to the residue and the distillation was repeated three times under reduced pressure. The residue was washed with ethyl acetate, whereby 99 mg of the title compound were obtained as white powder (yield: 95%).

IR(KBr)cm⁻¹: 3245, 1654, 1512, 1306, 802, 745

EXAMPLE 71
(Cl⁻ salt of Compound No. 1077)

2-[N-[1-Methyl-2-[5-[N-[3-trifluoromethyl-4-[N,N-bis(2-chloroethyl)amino]phenyl]]carbamoyl]-1H-benzimidazol- 2-yl]pyrrol-4-yl]carbamoylethyl-dimethylsulfonium chloride 1H-2-[1-Methyl-4-[3-(methylthio)propionylamino]pyrrol-2-yl]benzimidazole-5-[N-[3-trifluoromethyl-4-[N,N-bis(2-chloroethyl)amino]phenyl]]carboxamide (86 mg; 0.13 mmol) was dissolved in a mixed solvent of 500 μl of 80% formic acid and 250 μl of acetic acid. To the resultant solution, 210 μl of methyl iodide were added, followed by stirring at room temperature for one hour under shading. The reaction mixture was allowed to stand overnight. To the reaction mixture, further 210 μl of methyl iodide were added, followed by stirring at room temperature for 8 hours. The reaction mixture was allowed to stand overnight. Methanol was added and the solvent was distilled out under reduced pressure. Toluene was added to the residue and the distillation was repeated twice under reduced pressure. The residue was dissolved in methanol and passed through an ion-exchange column ("DOWEX" 1×8, Cl⁻ type), whereby iodine ions as counter ions were exchanged by chlorine ions. The solvent was distilled out under reduced pressure. The residue so obtained was washed with methanol, whereby 75 mg of the title compound were obtained as white powder (yield: 81%).

IR(KBr)cm⁻¹: 3240, 1656, 1541, 1418, 1319, 1048, 747

EXAMPLE 72
(Cl⁻ salt of Compound No.1602)

2-[N-[1-Methyl-2-[5-[N-[4-[N,N-bis(2-chloroethyl)amino]benz-2-oxa-1,3-diazolyl]]carbamoyl]-1H-benzimidazol-2-yl]pyrrol-4-yl]carbamoylethyl-dimethylsulfonium chloride 1H-2-1-Methyl-4-[3-(methylthio)propionylamino]pyrrol-2-yl]benzimidazole-5-[N-[4-[N,N-bis(2-chloroethyl)amino]benz-2-oxa-1,3-diazolyl]]carboxamide (50 mg; 0.081 mmol) was dissolved in a mixed solvent of 300 μl of 80% formic acid and 150 μl of acetic acid. To the resultant solution, 260 μl (4.2 mmol) of methyl iodide were added, followed by stirring at room temperature for 7 hours under shading. The reaction mixture was allowed to stand for two nights. Methanol was added and the solvent was distilled out under reduced pressure. Toluene was added to the residue and the distillation was repeated twice under reduced pressure. The residue was dissolved in methanol and passed through an ion-exchange resin ("DOWEX" 1×8, Cl⁻ type), whereby iodine ions as counter ions were exchanged by chlorine ions. The solvent was distilled out under reduced pressure. The residue so obtained was washed with methanol, whereby 39 mg of the title compound were obtained as orange powder (yield: 72%).

IR(KBr)cm⁻¹: 3228, 1660, 1534, 1419, 1290, 813, 740

EXAMPLE 73
(Cl⁻ salt of Compound No. 1072)

2-[N-[1-Methyl-2-[5-[N-[3-chloro-4-[N,N-bis(2-chloroethyl)amino]phenyl]]carbamoyl]-1H-benzimidazol-2-yl]pyrrol-4-yl]carbamoylethyl-dimethylsulfonium chloride 1H-2-[1-Methyl-4-[3-(methylthio)propionylamino]pyrrol-2-yl]benzimidazole-5-[N-[3-chloro-4-[N,N-bis(2-chloroethyl)amino]phenyl]]carboxamide (40 mg; 0.066 mmol) was dissolved in a mixed solvent of 240 μl of 80% formic acid and 120 μl of acetic acid. To the resultant solution, 210 μl of methyl iodide were added, followed by stirring at room temperature for 8 hours under shading. The reaction mixture was allowed to stand overnight. Methanol was added and the solvent was distilled out under reduced pressure. Toluene was added to the residue and the distillation was repeated twice under reduced pressure. The residue was dissolved in methanol and passed through an ion-exchange resin ("DOWEX" 1×8, Cl⁻ type), whereby iodine ions as counter ions were exchanged by chlorine ions. The solvent was distilled out under reduced pressure. The residue so obtained was washed with methanol/ethanol, whereby 38 mg of the title compound were obtained as white powder (yield: 87%).

IR(KBr)cm$^{-1}$: 3248, 1656, 1499, 1394, 1307, 826, 746

EXAMPLE 74
(Cl$^-$ salt of Compound No. 1076)

2-[N-[1-Methyl-2-[5-[N-[3-fluoro-4-[N,N-bis(2-chloroethyl)amino]phenyl]]carbamoyl]-1H-benzimidazol-2-yl pyrrol-4-yl]carbamoylethyl-dimethylsulfonium chloride 2-[N-[1-Methyl-2-[5-[N-[3-fluoro-4-[N,N-bis(2-chloroethyl)amino]phenyl]]carbamoyl]-1H-benzimidazol-2-yl]pyrrol-4-yl]carbamoylethyl-dimethylsulfonium iodide (100 mg; 0.17 mmol) was dissolved in methanol. The solution was subjected to chromatography on an anion exchange resin ("DOWEX" 1×8, Cl$^-$ type), whereby iodine ions as counter ions were exchanged by chlorine ions. After elution, the residue was washed with methanol, whereby 20 mg of the title compound were obtained as white powder (yield: 19%).

EXAMPLE 75
(Cl$^-$ salt of Compound No. 1060)

2-[N-[1-Methyl-2-[5-[N-[3-methyl-4-[N,N-bis(2-chloroethyl)amino]phenyl]]carbamoyl]-1H-benzimidazol-2-yl]pyrrol-4-yl]carbamoylethyl-dimethylsulfonium chloride 1H-2-[1-Methyl-4-[3-(methylthio)propionylamino]pyrrol-2-yl]benzimidazole-5-[N-[3-methyl-4-[N,N-bis(2-chloroethyl)amino]phenyl]]carboxamide (100 mg; 0.17 mmol) was dissolved in a mixed solvent of 600 μl of 80% formic acid and 300 μl of acetic acid. To the resultant solution, 250 μl of methyl iodide were added, followed by stirring at room temperature for 6 hours under shading. The reaction mixture was allowed to stand overnight. The reaction mixture was stirred at room temperature for further 10 hours and was allowed to stand overnight again. Methanol was added and the solvent was distilled out under reduced pressure. Toluene was added to the residue and the distillation was repeated twice under reduced pressure. The residue was dissolved in methanol and passed through an ion-exchange column ("DOWEX" 1×8, Cl$^-$ type), whereby iodine ions as counter ions were exchanged by chlorine ions. The solvent was distilled out under reduced pressure. The residue so obtained was washed with methanol, whereby 60 mg of the title compound were obtained as white powder (yield: 55%).

IR(KBr)cm$^{-1}$: 3248, 1648, 1512, 1307, 803, 742

EXAMPLE 76
(Cl$^-$ salt of Compound No. 1079)

2-[N-[1-Methyl-2-[5-[N-[2-methyl-4-[N,N-bis(2-chloroethyl)amino]phenyl]]carbamoyl]-1H-benzimidazol-2-yl)pyrrol-4-yl]carbamoylethyl-dimethylsulfonium chloride 2-[N-[1-Methyl-2-[5-[N-[2-methyl-[N,N-bis(2-chloroethyl)amino]phenyl]]carbamoyl]-1H-benzimidazol-2-yl]pyrrol-4-yl]carbamoylethyl-dimethylsulfonium iodide (50 mg; 0.068 mmol) was dissolved in methanol. The resultant solution was subjected to chromatography on an ion-exchange column ("DOWEX" 1×8, Cl$^-$ type) to exchange iodine ions as counter ions to chlorine ions, whereby 34 mg of the title compound were obtained as white powder (yield: 78%).

IR(KBr)cm$^{-1}$: 3247, 1654, 1509, 1307, 802, 745

EXAMPLE 77
(Compound No. 1904)

1H-2-[1-Methyl-4-(methylthioacetylamino)pyrrol-2-yl]benzimidazol-5-[N-[4-[N,N-bis(2-chloroethyl)amino]phenyl]]carboxamide 1H-2-(1-Methyl-4-nitropyrrol-2-yl)benzimidazole-5-[N-[4-[N,N-bis(2-chloroethyl)amino]phenyl]]carboxamide (150 mg; 0.30 mmol) was dissolved in 10 ml of DMF and 10 ml of methanol, followed by the addition of 200 mg of 10% Pd/C and 320 μl of 1N hydrochloric acid. The resultant solution was hydrogenated under normal pressure at room temperature. After the Pd/C was filtered off, the filtrate was concentrated to form a DMF solution. To the solution, 50 μl (0.30 mmol) of triethylamine and a solution of an active intermediate, which had been obtained in advance by reacting 96 mg (0.90 mmol) of methylthioacetic acid and 146 mg (0.90 mmol) of CDI, in 5 ml of DMF were added under ice cooling. The thus-obtained mixture was allowed to stand overnight. The reaction mixture was then concentrated. The brown oil so obtained was purified by chromatography on a silica gel column (chloroform/methanol=95/5), followed by washing with ether/chloroform, whereby 101 mg of the title compound were obtained as pale yellow powder (yield: 59%).

IR(KBr)cm$^{-1}$: 3274, 2960, 2918, 1647, 1558, 1517, 1326,

EXAMPLE 78
(I' salt of Compound 1336)

2-[N-[1-Methyl-2-[5-[N-[4-[N,N-bis(2-chloroethyl)amino]phenyl]]carbamoyl]-1H-benzimidazol-2-yl]pyrrol-4-yl]carbamoylmethyl-dimethylsulfonium iodide Dissolved in a mixed solvent of 0.5 ml of 80% formic acid and 0.25 ml of acetic acid were 100 mg (0.19 mmol) of 1H-2-[1-methyl-4-(methylthioacetylamino)pyrrol-2-yl]benzimidazol-5-[N-[4-[N,N-bis(2-chloroethyl)amino]phenyl]]carboxamide, followed by the addition of 0.4 ml of methyl iodide. The resultant mixture was stirred at room temperature for 4 days under shading. The reaction mixture so obtained was purified by chromatography on a gel filtration column ("Sephadex LH-20", methanol) and then, washed with methanol, whereby 68.5 mg of the title compound were obtained as white powder (yield: 55%).

IR(KBr)cm$^{-1}$: 3398, 1654, 1578, 1518, 1325, 816

EXAMPLE 79
(Compound No. 1944)

1H-2-[1-Methyl-4-(2-pyridylacetyl)aminopyrrol-2-yl]benzimidazol-5-[N-(4-[N,N-bis(2-chloroethyl)amino]phenyl]]carboxamide 1H-2-(1-Methyl-4-nitropyrrol-2-yl)benzimidazole-5-[N-[4-[N,N-bis(2-chloroethyl)amino]phenyl]]carboxamide (150 mg; 0.30 mmol) was dissolved in a mixed solvent of 10 ml of DMF and 10 ml of methanol, followed by the addition of 200 mg of 10% Pd/C and 320 μl of 1N hydrochloric acid. The resultant solution was hydrogenated under normal pressure at room temperature. After the Pd/C was filtered off, the filtrate was concentrated to form a DMF solution. To the solution, 50 μl (0.30 mmol) of triethylamine and a solution of an active intermediate, which had been obtained in advance by reacting 156 mg (0.90 mmol) of 2-pyridylacetic acid hydrochloride and 146 mg (0.90 mmol) of CDI, in 5 ml of DMF were added under ice cooling. The thus-obtained mixture was allowed to stand overnight. The reaction mixture was then concentrated. The brown oil so obtained was purified by chromatography on a silica gel column (chloroform/methanol=10/1), followed by washing with ether/chloroform, whereby 107 mg of the title compound were obtained as pale yellow powder (yield: 61%).

IR(KBr)cm$^{-1}$: 3270, 2958, 1647, 1594, 1518, 1327, 815

EXAMPLE 80
(Compound No. 1952)

1H-2-[1-Methyl-4-(4-pyridylacetyl)aminopyrrol-2-yl]benzimidazol-5-[N-[4-[N,N-bis(2-chloroethyl)amino]phenyl]]carboxamide In a reactor, 300 mg (0.60 mmol) of 1H-2-(1-methyl-4-nitropyrrol-2-yl)benzimidazole-5-[N-[4-[N,N-bis(2-chloroethyl)amino]phenyl]]carboxamide were dissolved in 10 ml of a 1:1 mixed solvent of DMF and methanol, followed by the addition of 200 mg of 10% Pd/C and 718 µl of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 100 µl (0.72 mmol) of triethylamine and a solution of an active intermediate, which had been prepared in advance by reacting 311 mg (1.8 mmol) of 4-pyridineacetic acid with 291 mg (1.8 mmol) of CDI, in 5 me of DMF were added and the resultant mixture was allowed to stand overnight. The solvent was distilled out under reduced pressure. The residue so obtained was purified by chromatography on a silica gel column (chloroform/methanol=10/1→8/2). The solvent was distilled under reduced pressure, followed by reprecipitation with methanol and ethyl acetate, whereby 190 mg of the title compound were obtained as white powder (yield: 54%).

IR(KBr)cm$^{-1}$: 3280, 1638, 1518, 1328, 815, 716

Elemental analysis for $C_{30}H_{29}Cl_2N_7O_2.H_2O$: Calculated: C, 59.31; H, 4.98; N, 16.14 Found: C, 59.31; H, 5.11; N, 16.04

EXAMPLE 81
(Compound No. 1424)

1H-2-[1-Methyl-4-(3-pyridylacetylamino)pyrrol-2-yl]benzimidazol-5-[N-[4-[N,N-bis(2-chloroethyl)amino]phenyl]]carboxamide hydrochloride In a reactor, 400 mg (0.80 mmol) of 1H-2-(1-methyl-4-nitropyrrol-2-yl)benzimidazole-5-[N-[4-[N,N-bis(2-chloroethyl)amino]phenyl]]carboxamide were dissolved in 10 ml of a 1:1 mixed solvent of DMF and methanol, followed by the addition of 300 mg of 10% Pd/C and 1.2 ml of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 133 µl (0.95 mmol) of triethylamine and a solution of an active intermediate, which had been prepared in advance by reacting 416 mg (2.4 mmol) of 3-puridineacetic acid with 388 mg (2.4 mmol) of CDI, in 5 ml of DMF were added and the resultant mixture was allowed to stand overnight. The solvent was distilled out under reduced pressure. The residue so obtained was purified by chromatography on a silica gel column (chloroform/methanol=95/5). The solvent was distilled under reduced pressure, followed by reprecipitation with methanol and ethyl acetate, whereby 270 mg of the title compound were obtained as white powder (yield: 54%).

IR(KBr)cm$^{-1}$: 3096, 1648, 1516, 1327, 814, 711

Elemental analysis for $C_{30}H_{29}Cl_2N_7O_2.H_2O$: Calculated: C, 59.31; H, 4.98; N, 16.14 Found: C, 59.19; H, 4.88; N, 15.83

EXAMPLE 82
(Cl$^-$ salt of Compound No. 1440)

3-[[N-[1-Methyl-2-[5-[N-[4-[N,N-bis(2-chloroethyl)amino]phenyl]]carbamoyl]-1H-benzimidazol-2-yl]pyrrol-4-yl]carbamoylmethyl]pyridinium chloride 1H-2-(1-Methyl-4-nitropyrrol-2-yl)benzimidazol-5-[N-[4-[N,N-bis(2-chloroethyl)amino]phenyl]]carboxamide (79 mg; 0.13 mmol) was dissolved in 50 ml of acetone. To the solution, 5 ml of methyl iodide were added, followed by stirring at room temperature for 2 days. After the solvent was distilled out under reduced pressure, the residue was purified by chromatography on a silica gel column (ethyl acetate/IPA/water/acetic acid =3/2/1/0→6/4/2/1). The solid so obtained was dissolved in methanol and passed through an ion-exchange resin ("DOWEX" 1×8, Cl$^-$ type), whereby counter ions were exchanged by chlorine ions. The ion-exchanged solution was purified further by chromatography on a gel filtration column ("Sephadex LH-20", methanol), whereby 47 mg of the title compound were obtained as pale yellow powder (yield: 58%).

IR(KBr)cm$^{-1}$: 3243, 1638, 1518, 1328, 816, 745

EXAMPLE 83
(Cl$^-$ salt of Compound No. 1716)

2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-trimethylammonium chloride 1H-2-[1-Methyl-4-[3-(N,N-dimethylamino)propionylamino]pyrrol-2-yl]benzimidazol-5-[N-[4-[N,N-bis(2-chloroethyl)amino]phenyl]]carboxamide (150 mg; 0.25 mmol) was dissolved in 5 ml of methanol. To the solution, 39 mg (0.37 mmol) of sodium carbonate and 70 mg (0.56 mmol) of dimethyl sulfate were added, followed by stirring at room temperature for two nights. After the solvent was distilled out under reduced pressure, the residue was purified by chromatography on a silica gel column (ethyl acetate/IPA/water/ acetic acid 3/2/1/0→6/4/2/1). The solid so obtained was dissolved in methanol and passed through an ion-exchange resin ("DOWEX" 1×8, Cl$^-$ type), whereby counter ions were exchanged by chlorine ions. The ion-exchanged solution was purified further by chromatography on a gel filtration column ("Sephadex LH-20", methanol), whereby 72 mg of the title compound were obtained as pale yellow powder (yield: 46%).

IR(KBr)cm$^{-1}$: 3261, 1648, 1518, 1328, 817

EXAMPLE 84
(Compound No. 1522)

1H-2-[1-Methyl-4-[3-(methylthio)propionyl]aminopyrrol-2-yl]benzimidazole-5-[N-[2-[4-[N,N-bis(2-chloroethyl)amino]phenyl]ethyl]]carboxamide In a mixed solvent of 4 ml of DMF and 3 ml of methanol, 0.25 g (0.47 mmol) of 1H-2-(1-methyl-4-nitropyrrol-2-yl)benzimidazole-5-[N-[2-[4-[N,N-bis(2-chloroethyl)amino]phenyl]ethyl]]carboxamide was dissolved. Using 10% Pd/C (wet) as a catalyst, the resultant mixture was hydrogenated under normal pressure so that it was converted to the corresponding amino derivative. The solvent was concentrated and the DMF solution so obtained was stirred under a nitrogen gas stream and ice-cooling. To the reaction mixture, 75 μl (0.54 mmol; 1.1 equivalents) of triethylamine and a solution of 3-(methylthio)propionylimidazole, which had been prepared from 0.07 g (0.58 mmol) of 3-(methylthio)propionic acid and 0.12 g (0.74 mmol; 1.3 equivalents) of CDI, in 4 ml of DMF were added successively. The temperature of the resultant mixture was allowed to rise back to room temperature, at which the mixture was stirred for 4 hours. The reaction mixture was then allowed to stand overnight, followed by concentration under reduced pressure. The residue so obtained was purified by chromatography on a silica gel column (chloroform/4% methanol) and crystallized from ethyl ether, whereby 0.19 g (0.32 mmol) of the title compound was obtained as reddish white crystals (yield: 67.2%).

m.p. 152°–155° C.

IR(KBr)cm$^{-1}$; 3270, 2925, 1618, 1542, 1519, 1349, 1303

EXAMPLE 85
(I⁻ salt of Compound No. 1058)

2-[N-[1-Methyl-2-[5-[N-[2-[4-[N,N-bis(2-chloro ethyl)amino]phenyl]ethyl]carbamoyl]-1H-benzimidazol-2-yl]pyrrol-4-yl]carbamoylethyl-dimethylsulfonium iodide 1H-2-[1-Methyl-4-[3-(methylthio)propionyl]aminopyrrol-2-yl]benzimidazole-5-[N-[2-[4-[N,N-bis(2-chloroethyl)amino]phenyl]ethyl]]carboxamide (0.10 g; 0.17 mmol) was dissolved in 0.5 ml of 80% formic acid, 0.25 ml of acetic acid and 0.2 ml of methyl iodide. The resultant solution was allowed to stand overnight at room temperature under shading. The reaction mixture was then concentrated under reduced pressure. The residue so obtained was subjected to gel filtration ("Sephadex LH-20", methanol) and then, crystallized from ethyl ether, whereby 99 mg (0.13 mmol) of the title compound were obtained as reddish white amorphous powder (yield: 78.3%).

IR(KBr)cm$^1$: 3414, 1618, 1543, 1347, 1308

EXAMPLE 86
(Compound No. 1005)

1H-2-[1-Methyl-4-(2-guanidinoacetylamino)pyrrol-2-yl]benzimidazole-5-[N-[3-methyl-4-[N,N-bis(2-chloroethyl)amino]phenyl]]carboxamide dihydrochloride (Reaction 1)

3-Methyl-4-[N,N-bis(2-hydroxyethyl)amino] nitrobenzene

In 30 ml of DMSO, 4.0 g (25.8 mmol) of 2-fluoro-5-nitrotoluene and 7.0 g (67 mmol) of diethanolamine were dissolved. The resultant solution was stirred under heat at 140° C. for 6.5 hours, followed by extraction with ethyl acetate. The solvent was distilled out under reduced pressure. The residue so obtained was washed with ethyl acetate, whereby 5.2 g of the title compound were obtained as yellow powder (yield: 84%).

(Reaction 2)

3-Methyl-4-[N,N-bis(2-chloroethyl)amino] nitrobenzene

To a solution of 2.0 g (8.3 mmol) of 3-methyl-4-[N,N-bis(2-hydroxyethyl)amino]nitrobenzene in 20 ml of benzene, 3 ml (40 mmol) of thionyl chloride were added. After the resultant mixture was stirred under heat at 80° C. for 2 hours, the solvent was distilled out under reduced pressure. The residue so obtained was purified by chromatography on a silica gel column (ethyl acetate/n-hexane=1/1), whereby 2.0 g of the title compound were obtained as yellow powder (yield: 92%).

(Reaction 3)

1H-2-(1-Methyl-4-nitropyrrol-2-yl)benzimidazole-5-[N-[3-methyl-4-[N,N-bis(2-chloroethyl)amino] phenyl]]carboxamide A solution of 280 mg (0.98 mmol) of 1H-2-(1-methyl-4-nitropyrrol-2-yl)benzimidazole-5-carboxylic acid and 3-methyl-4-[N,N-bis(2-chloroethyl)amino]aniline hydrochloride, which had been derived from its corresponding nitro compound, in 10 ml of DMF was cooled to 0° C. Under a nitrogen gas atmosphere, 320 μl (2.3 mmol) of triethylamine and then 220 μl (1.45 mmol) of DECP were added to the resultant solution, followed by stirring for 30 minutes as was. After the stirring was conducted for further two hours at room temperature, the solvent was distilled out under reduced pressure. The residue so obtained was purified by chromatography on a silica gel column (chloroform/methanol=10/1), whereby 159 mg of the title compound were obtained as yellow powder (yield: 32%).

(Reaction 4)

1H-2-[1-Methyl-4-(2-guanidinoacetylamino)pyrrol-2-yl]benzimidazole-5-[N-[3-methyl-4-[N,N-bis(2-chloroethyl)amino]phenyl]]carboxamide dihydrochloride In a reactor, 150 mg (0.29 mmol) of 1H-2-(1-methyl-4-nitropyrrol-2-yl)benzimidazole-5-[N-[3-methyl-4-[N,N-bis (2-chloroethyl)amino]phenyl]]carboxamide were dissolved in 10 ml of a 1:1 mixed solvent of DMF and methanol, followed by the addition of 120 mg of 10% Pd/C and 350 μl of 1N hydrochloric acid under a nitrogen gas atmosphere. The reactor was purged with hydrogen gas. The resultant mixture was stirred at room temperature for 2 hours. After the Pd/C was filtered off, the filtrate was concentrated to form a DMF solution. To the solution, 49 μl (0.35 mmol) of triethylamine, 134 mg (0.87 mmol) of guanidineacetic acid hydrochloride and 180 mg (0.87 mmol) of DCC were added successively under ice cooling, followed by stirring at room temperature for one hour. The reaction mixture was then allowed to stand overnight. White powder was removed by filtration, followed by concentration under reduced pressure. To the residue so obtained, a 4N hydrochloric acid/dioxane solution was added and the resultant mixture was concentrated under reduced pressure. The residue was washed with methanol, whereby 70 mg of the title compound were obtained as yellow powder (yield: 29%).

IR(KBr)cm$^{-1}$: 3378, 1655, 1510, 1310, 1242, 806

EXAMPLE 87
(Compound No. 1260)

1H-2-[1-Methyl-4-[4-(N,N-dimethylamino) butyrylamino]pyrrol-2-yl]benzimidazole-5-[N-[3-methyl-4-[N,N-bis(2-chloroethyl)amino]phenyl]] carboxamide dihydrochloride 1H-2-(1-Methyl-4-nitropyrrol-2-yl)benzimidazole-5-[N-[3-methyl-4-[N,N-bis(2-chloroethyl)amino]phenyl]] carboxamide (237 mg; 0.46 mmol) was dissolved in 10 ml of a 1:1 mixed solvent of DMF and methanol in a reactor, followed by the addition of 200 mg of 10% Pd/C and 1 ml of 1N hydrochloric acid under a nitrogen gas atmosphere. The reactor was purged with hydrogen gas. The resultant mixture was stirred at room temperature for 2 hours. After the Pd/C was filtered off, the filtrate was concentrated to form a DMF solution. To the solution, 77 µl (0.56 mmol) of triethylamine, 230 mg (1.4 mmol) of N,N-dimethylaminobutyric acid hydrochloride and 285 mg (1.4 mmol) of DCC were added successively under ice cooling, followed by stirring at room temperature for one hour. The reaction mixture was then allowed to stand overnight. White powder was removed from the reaction mixture by filtration, followed by concentration under reduced pressure. The residue so obtained was purified by chromatography on a silica gel column (ethyl acetate/IPA/water=5/2/1), whereby 60 mg of the title compound were obtained as white powder (yield: 21%).

EXAMPLE 88
(Compound No. 1464)

1H-2-(1-Methyl-4-furoylaminopyrrol-2-yl)benzimidazole-5-[N-[4-[N,N-bis(2-chloroethyl)amino]phenyl]]carboxamide 1H-2-(1-Methyl-4-nitropyrrol-2-yl)benzimidazole-5-[N-[4-[N,N-bis(2-chloroethyl)amino]phenyl]]carboxamide (250 mg; 0.50 mmol) was dissolved in a mixed solvent of 10 ml of DMF and 10 ml of methanol, followed by the addition of 250 mg of 10% Pd/C and 500 µl of 1N hydrochloric acid under a nitrogen gas stream. The hydrogenation was conducted under normal pressure at room pressure. After the Pd/C was filtered off, the filtrate was concentrated to form a DMF solution. To the solution, 140 µl of triethylamine and a solution of 65.2 mg (0.50 mmol) of furoyl chloride in methylene chloride were added successively under ice cooling. The reaction mixture was then allowed to stand overnight, followed by concentration under reduced pressure. The dark brown residue so obtained in the form of oil was purified by chromatography on a silica gel column (chloroform/methanol=20/1), whereby 191 mg of the title compound were obtained as pale yellow powder (yield: 67%).

IR(KBr)cm$^{-1}$: 3276, 2958, 1643, 1594, 1518, 1327, 814, 758

EXAMPLE 89
(Compound No. 2089)

1H-2-[1-Methyl-4-[4-[N-ethyl,N-(2-chloroethyl)amino]benzoylamino]pyrrol-2-yl]benzimidazole-5-[N-[4-[N-ethyl,N-(2-chloroethyl)amino]phenyl]]carboxamide hydrochloride (Reaction 1)

4-[N-Ethyl,N-(2-hydroxyethyl)amino]nitrobenzene

In 30 ml of DMSO, 5.0 g (35.4 mmol) of 4-fluoronitrobenzene and 6 g (67.3 mmol) of 2-(ethylamino)ethanol were dissolved. The resultant solution was stirred under heat at 140° C. for 4 hours, followed by extraction with ethyl acetate. The solvent was distilled out under reduced pressure, followed by washing with ethyl acetate, whereby 6.3 g of yellow powder were obtained (yield: 85%).

(Reaction 2)

4-[N-Ethyl,N-(2-chloroethyl)amino]nitrobenzene

To a solution of 3.0 g (14.3 mmol) of 4-[N-ethyl,N-(2-hydroxyethyl)amino]nitrobenzene in 20 ml of chloroform, 2.1 ml (28.8 mmol) of thionyl chloride were added. After the resultant mixture was stirred under heat at 80° C. for 2 hours, the solvent was distilled out under reduced pressure. The residue was purified by chromatography on a silica gel column (ethyl acetate/n-hexane=1/1), whereby 3.0 g of yellow powder were obtained (yield: 92%).

IR(KBr)cm$^{-1}$: 2975, 1598, 1310, 1277, 1115, 825, 725

(Reaction 3)

4-[N-Ethyl,N-(2-chloroethyl)amino]aniline hydrochloride

To a solution of 3.0 g (13.1 mmol) of 4-[N-ethyl,N-(2-chloroethyl)amino]nitrobenzene in 70 ml of a concentrated hydrochloric acid, 10 g of tin chloride were added. The resultant mixture was refluxed under heat for 3 hours, followed by treatment with aqueous ammonia and extraction with chloroform. The solvent was distilled out under reduced pressure. A solution of 4N hydrochloric acid/dioxane was added to the residue, followed by washing with IPA, whereby 3.1 g of the powder were obtained (yield: 100%).

(Reaction 4)

1H-2-(1-Methyl-4-nitropyrrol-2-yl)benzimidazole-5-[N-[4-[N-ethyl,N-(2-chloroethyl)amino]phenyl]]carboxamide A solution of 400 mg (1.40 mmol) of 1H-2-(1-methyl-4-nitropyrrol-2-yl)benzimidazole-5-carboxylic acid and 329 mg (1.40 mmol) of 4-[N-ethyl,N-(2-chloroethyl)amino]aniline hydrochloride in 10 ml of DMF was cooled to 0° C. Under a nitrogen gas atmosphere, 400 µl (2.89 mmol) of triethylamine and then 350 µl (2.31 mmol) of DECP were added to the resultant solution, followed by stirring for 30 minutes as was. The reaction mixture was stirred for further 2 hours at room temperature. The solvent was then distilled out under reduced pressure. The residue was purified by chromatography on a silica gel column (chloroform/methanol=10/1), whereby 240 mg of yellow powder were obtained (yield: 37%).

(Reaction 5)

4-[N-Ethyl,N-(2-hydroxyethyl)amino]benzonitrile

A solution of 10 g (82.6 mmol) of 4-fluorobenzonitrile and 15 g (0.17 mmol) of 2-(ethylamino)ethanol in 30 ml of DMSO was stirred under heat at 140° C. for 3 hours, followed by extraction with ethyl acetate. The solvent was distilled out under reduced pressure, followed by washing with ethyl acetate, whereby 6.9 g of white powder were obtained (yield: 44%).

IR(KBr)cm$^{-1}$: 3456, 2221, 1609, 1530, 1407, 1357, 1177, 1043, 822

(Reaction 6)

4-[N-Ethyl,N-(2-chloroethyl)amino]benzonitrile

To a solution of 6.0 g (31.5 mmol) of 4-[N-ethyl,N-(2-hydroxyethyl)amino]nitrobenzene in 50 ml of chloroform, 5 ml (68.5 mmol) of thionyl chloride were added. After the resultant mixture was stirred under heat at 70° C. for 3 hours, the solvent was distilled out under reduced pressure. The residue so obtained was purified by chromatography on a silica gel column (ethyl acetate), whereby 5.0 g of white powder were obtained (yield: 76%).

(Reaction 7)

4-[N-Ethyl,N-(2-chloroethyl)amino]benzoic acid

To a solution of 2.5 g (12.0 mmol) of 4-[N-ethyl,N-(2-chloroethyl)amino]benzonitrile in 25 ml of ethanol, 25 ml of concentrated hydrochloric acid were added, followed by reflux under heat for 12 hours. The reaction mixture was allowed to cool down. Sodium carbonate was then added to basify the solution, followed by washing with chloroform. The water layer was acidified with concentrated hydrochloric acid and then extracted with chloroform. The solvent was distilled out under reduced pressure, followed by washing with IPA, whereby 1.1 g of white powder were obtained (yield: 40%).
(Reaction 8)

1H-2-[1-Methyl-4-[4-[N-ethyl,N-(2-chloroethyl) amino]benzoylamino]pyrrol-2-yl]benzimidazole-5-[N-[4-[N-ethyl,N-(2-chloroethyl)amino]phenyl]] carboxamide hydrochloride To a solution of 166 mg (0.73 mmol) of 4-[N-ethyl,N-(2-chloroethyl)amino]benzoic acid in 10 ml of benzene, 0.6 ml (8.2 mmol) of thionyl chloride was added, followed by stirring under heat at 90° C. for 1.5 hours. The solvent was distilled out under reduced pressure. A small amount of benzene was added to the residue, followed by distillation under reduced pressure. This operation was repeated twice. The acid chloride so obtained was immediately provided for use in the next reaction. In 10 ml of a 1:1 mixed solvent of DMF and methanol, 200 mg (0.43 mmol) of 1H-2-(1-methyl-4-nitropyrrol-2-yl)benzimidazole-5-[N-[4-[N-ethyl, N-(2-chloroethyl)amino]phenyl]]carboxamide were dissolved, followed by the addition of 200 mg of 10% Pd/C and 520 μl of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 120 μl (0.87 mmol) of triethylamine and the acid chloride, which had been synthesized above, were added successively under ice cooling. The resultant mixture was stirred at room temperature for one hour, followed by the addition of 5 ml of methanol. The solvent was distilled out under reduced pressure. The residue was purified by chromatography on a silica gel column (chloroform/ methanol=98/2), whereby 170 mg of the title compound were obtained as pale yellow powder (yield: 61%).

IR(KBr)cm$^{-1}$: 3422, 1973, 1606, 1519, 1271, 816

Elemental analysis for $C_{28}H_{27}Cl_2N_7O_2 \cdot 1.5H_2O$: Calculated: C, 56.86; H, 5.11; N, 16.57 Found: C, 57.28; H, 4.91; N, 16.21

EXAMPLE 90
(Compound No. 1048)

1H-2-[1-Methyl-4-(2-guanidinoacetylamino)pyrrol-2-yl]benzimidazol-5-[N-[4-[N-ethyl,N-(2-chloroethyl)amino]phenyl]]carboxamide dihydrochloride 1H-2-(1-Methyl-4-2-nitropyrrol-2-yl)benzimidazol-5-[N-[4-(N-ethyl,N-(2-chloroethyl)amino]phenyl]] carboxamide (150 mg: 0.32 mmol) was dissolved in 10 ml of a 1:1 mixed solvent of DMF and methanol in a reactor, followed by the addition of 150 mg of 10% Pd/C and 353 μl of 1N hydrochloric acid under a nitrogen gas atmosphere. The reactor was purged with hydrogen gas and the resultant mixture was stirred at room temperature for 2 hours. After the Pd/C was filtered off, the filtrate was concentrated to form a DMF solution. To the solution, 54 μl (0.39 mmol) of triethylamine, 150 mg (0.98 mmol) of guanidineacetic acid hydrochloride and 199 mg (0.97 mmol) of DCC were added successively under ice cooling, followed by stirring at room temperature for one hour. The reaction mixture was allowed to stand overnight. White powder was removed by filtration, followed by concentration under reduced pressure. The residue so obtained was dissolved in methanol and to the solution, a solution of 4N hydrochloric acid/dioxane was added. Concentration was conducted again under reduced pressure. The residue was then washed with methanol, whereby 115 mg of the title compound were obtained as yellow powder (yield: 63%).

IR(KBr)cm$^{-1}$: 3153, 1664, 1549, 1398, 1324, 826

EXAMPLE 91
(Compound No. 1049)

1H-2-[1-Methyl-4-(guanidinoacetylamino)pyrrol-2-yl]benzimidazol-5-[N-[3-[N-ethyl,N-(2-chloroethyl) amino]phenyl]]carboxamide hydrochloride 1H-2-(1-Methyl-4-nitropyrrol-2-yl)benzimidazol-5-[N-[3-[N-ethyl,N-(2-chloroethyl)amino]phenyl]]carboxamide (200 mg: 0.43 mmol) was dissolved in 10 ml of DMF and 10 ml of methanol, followed by the addition of 200 mg of 10% Pd/C and 500 μl of 1N hydrochloric acid under a nitrogen gas atmosphere. The hydrogenation was conducted at room temperature under normal pressure. After the Pd/C was filtered off, the filtrate was concentrated to form a DMF solution. To the solution, 75 μl of triethylamine, 197 mg (1.3 mmol) of guanidine hydrochloride and 265 mg (1.3 mmol) of DCC were added successively under ice cooling. The resultant mixture was allowed to stand overnight. After the reaction, the reaction mixture was filtered and concentrated. The dark brown oil so obtained was purified by chromatography on a gel filtration column ("Sephadex LH-20", methanol), whereby 136 mg of the title compound were obtained as white powder (yield: 56%).

EXAMPLE 92
(Compound No. 1009)

1H-2-[1-Methyl-4-(guanidinoacetylamino)pyrrol-2-yl]benzimidazole-5-[N-[3-methoxy-4-[N,N-bis(2-chloroethyl)amino]phenyl]]carboxamide dihydrochloride (Reaction 1)

3-Methoxy-4-(N,N-bis(2-hydroxyethyl)amino] nitrobenzene

To a suspension of 5.0 g (29.7 mmol) of 2-methoxy-5-nitroaniline in 30 ml of 30% acetic acid, 20.0 g of ethylene oxide were added dropwise under ice cooling, followed by stirring for one hour. The reaction mixture was stirred further at room temperature overnight, followed by stirring at room temperature for 2 hours while nitrogen gas was blown into the mixture. Sodium bicarbonate was then added to neutralize the reaction mixture, followed by the addition of salt until saturation. The resultant mixture was extracted with ethyl acetate. After the extract was dried over magnesium sulfate, the solvent was distilled out under reduced pressure. The residue was purified by chromatography on a silica gel column (methylene chloride/ethyl acetate=1/1→0/1), whereby 500 mg of yellow powder were obtained (yield: 6.6%).
(Reaction 2)

3-Methoxy-4-[N,N-bis(2-chloroethyl)amino] nitrobenzene

To a solution of 0.48 g (1.9 mmol) of 3-methoxy-4-[N,N-bis(2-hydroxyethyl)amino]nitrobenzene in 20 ml of benzene, 1 ml (14 mmol) of thionyl chloride were added. After the resultant mixture was stirred under heat at 90° C. for 3 hours, the solvent was distilled out under reduced pressure. The yellow oil so obtained was purified by chromatography on a silica gel column (ethyl acetate/n-hexane= 1/1), whereby 350 mg of yellow powder were obtained (yield: 64%).
(Reaction 3)

1H-2-(1-Methyl-4-nitropyrrol-2-yl)benzimidazole-5-[N-[3-methoxy-4-[N,N-bis(2-chloroethyl)amino]phenyl]]carboxamide

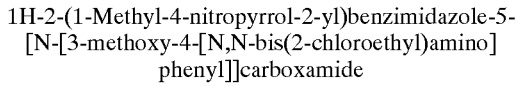

In a reactor, 144 mg (0.49 mmol) of 3-methoxy-4-[N,N-bis(2-chloroethyl)amino]nitrobenzene were dissolved in a mixed solvent of 10 ml of methanol and 2 me of tetrahydrofuran, followed by the addition of 150 mg of 10% Pd/C under a nitrogen gas atmosphere. The reactor was purged with hydrogen gas, followed by stirring at room temperature for one hour. After completion of the reaction, the reactor was purged with nitrogen gas, followed by stirring for 30 minutes. The 10% Pd/C was then filtered off. To the thus-obtained methanol solution, 200 μl of a solution of 4N hydrochloric acid/dioxane were added, whereby 3-methoxy-4-[N,N-bis(2-chloroethyl)amino]aniline hydrochloride were obtained. The hydrochloride was provided for use in the next reaction. In 5 ml of DMF, 200 mg (0.7 mmol) of 1H-2-(1-methyl-4-nitropyrrol-2-yl)benzimidazole-5-carboxylic acid and the 3-methoxy-4-[N,N-bis(2-chloroethyl)amino]aniline hydrochloride were dissolved, followed by cooling to 0° C. To the resulting solution, 102 μl (0.74 mmol) of triethylamine and then 112 μl (0.74 mmol) of DECP were added under a nitrogen gas atmosphere, followed by stirring for 20 minutes as was. The reaction mixture was stirred at room temperature for further one hour and was then allowed to stand overnight. The solvent was distilled out under reduced pressure. The residue so obtained was purified by chromatography on a silica gel column (ethyl acetate/n-hexane=1/1), whereby 80 mg of yellow powder were obtained (yield: 31%).
(Reaction 4)

1H-2-[1-Methyl-4-(guanidinoacetylamino)pyrrol-2-yl]benzimidazole-5-[N-[3-methoxy-4-[N,N-bis(2-chloroethyl)amino]phenyl]]carboxamide dihydrochloride

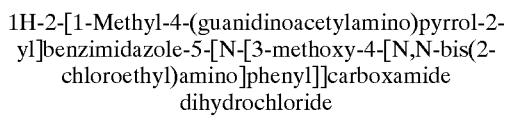

In a reactor, 73 mg (0.14 mmol) of 1H-2-(1-methyl-4-nitropyrrol-2-yl)benzimidazol-5-[N-[3-methoxy-4-[N,N-bis(2-chloroethyl)amino]phenyl]carboxamide were dissolved in 10 ml of a 1:1 mixed solvent of DMF and methanol, followed by the addition of 70 mg of 10% Pd/C and 151 μl of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 23 μl (0.17 mmol) of triethylamine, 65 mg (0.42 mmol) of guanidineacetic acid hydrochloride and 85 mg (0.41 mmol) of DCC were successively added under ice cooling, followed by stirring at room temperature for one hour. The reaction mixture was allowed to stand overnight. White powder was removed by filtration and the filtrate was concentrated under reduced pressure. To the residue so obtained, a solution of 4N hydrochloric acid/dioxane was added, followed by concentration under reduced pressure. The residue was washed with ethanol/IPA, whereby 55 mg of the title compound were obtained as yellow powder (yield: 59%).

EXAMPLE 93
(Compound No. 1024)

1H-2-[1-Methyl-4-(guanidinoacetylamino)pyrrol-2-yl]benzimidazole-5-[N-[2-methyl-4-[N,N-bis(2-chloroethyl)amino]phenyl]]carboxamide dihydrochloride

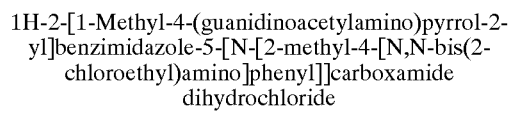

(Reaction 1)

2-Methyl-4-[N,N-bis(2-hydroxyethyl)amino]nitrobenzene

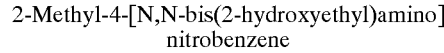

In 8 ml of DMSO, 5.0 g (64.5 mmol) of 2-nitro-5-fluorotoluene and 8.2 g (78 mmol) of diethanolamine were dissolved. The resultant solution was stirred under heat at 140° C. for 7 hours, followed by extraction with ethyl acetate. After the solvent was distilled out under reduced pressure, the residue was washed with ethyl acetate, whereby 10.1 g of yellow powder were obtained (yield: 65%).
(Reaction 2)

2-Methyl-4-[N,N-bis(2-chloroethyl)amino]nitrobenzene

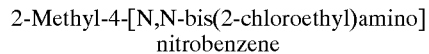

To a solution of 1.0 g (4.2 mmol) of 2-methyl-4-[N,N-bis(2-hydroxyethyl)amino]nitrobenzene in 20 ml of benzene, 5 ml (69 mmol) of thionyl chloride were added. The resultant mixture was stirred under heat at 80° C. for 6 hours, the solvent was distilled out under reduced pressure. The residue so obtained was purified by chromatography on a silica gel column (chloroform), whereby 735 mg of yellow powder were obtained (yield: 64%).
(Reaction 3)

1H-2-(1-Methyl-4-nitropyrrol-2-yl)benzimidazole-5-[N-[2-methyl-4-[N,N-bis(2-chloroethyl)amino]phenyl]]carboxamide

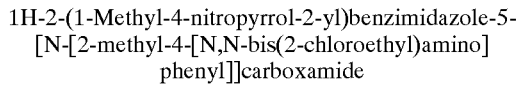

In a reactor, 300 mg (1.1 mmol) of 2-methyl-4-[N,N-bis(2-chloroethyl)amino]nitrobenzene were dissolved in a mixed solvent of 5 ml of methanol and 2 ml of tetrahydrofuran, followed by the addition of 200 mg of 10% Pd/C under a nitrogen gas atmosphere. The reactor was purged with hydrogen gas, followed by stirring at room temperature for one hour. After completion of the reaction, the reactor was purged with nitrogen gas, followed by stirring for 30 minutes. The 10% Pd/C was then filtered off. To the thus-obtained methanol solution, 400 μl of a solution of 4N hydrochloric acid/dioxane were added, whereby 2-methyl-4-[N,N-bis(2-chloroethyl)amino]aniline hydrochloride was obtained. In 10 ml of DMF, 309 mg (1.1 mmol) of 1H-2-(1-methyl-4-nitropyrrol-2-yl)benzimidazole-5-carboxylic acid and the 2-methyl-4-[N,N-bis(2-chloroethyl)amino]aniline hydrochloride obtained above were dissolved, followed by cooling to 0° C. Under a nitrogen gas atmosphere, 330 μl (2.4 mmol) of triethylamine and then 197 μl (1.3 mmol) of DECP were added to the resultant solution, followed by stirring for 20 minutes as was. Stirring was conducted for further 15 minutes at room temperature. The reaction mixture was then allowed to stand overnight. The solvent was distilled out under reduced pressure. The residue so obtained was purified by chromatography on a silica gel column (ethyl acetate/n-hexane=1/1), whereby 329 mg of yellow powder were obtained (yield: 59%).
(Reaction 4)

1H-2-[1-Methyl-4-(guanidinoacetylamino)pyrrol-2-yl]benzimidazole-5-[N-[2-methyl-4-[N,N-bis(2-chloroethyl)amino]phenyl]]carboxamide dihydrochloride

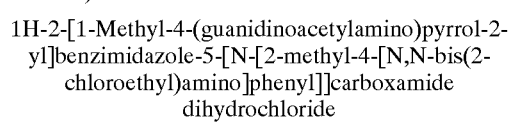

In a reactor, 100 mg (0.19 mmol) of 1H-2-(1-methyl-4-nitropyrrol-2-yl)benzimidazole-5-[N-[2-methyl-4-[N,N-bis (2-chloroethyl)amino]phenyl]]carboxamide were dissolved in 10 ml of a 1:1 mixed solvent of DMF and methanol, followed by the addition of 90 mg of 10% Pd/C and 220 μl of 1N hydrochloric acid under a nitrogen gas atmosphere. The reactor was purged with hydrogen gas, followed by stirring at room temperature for 2 hours. After the Pd/C was filtered off, the filtrate was concentrated to form a DMF solution. To the solution, 32 μl (0.23 mmol) of triethylamine, 89 mg (0.58 mmol) of guanidineacetic acid hydrochloride and 120 mg (0.58 mmol) of DCC were successively added under ice cooling, followed by stirring at room temperature for one hour. The reaction mixture was allowed to stand overnight. White powder was removed by filtration and the filtrate was concentrated under reduced pressure. To the residue so obtained, a solution of 4N hydrochloric acid/dioxane was added, followed by concentration under reduced pressure. The residue was washed with methanol, whereby 84 mg of the title compound were obtained as yellow powder (yield: 66%).

EXAMPLE 94
(Compound No. 1256)

1H-2-[1-Methyl-4-[4-(N,N-dimethylamino) butyrylamino]pyrrol-2-yl]benzimidazole-5-[N-[4-[N, N-bis-(2-chloroethyl)amino]phenyl]]carboxamide hydrochloride Dissolved in a mixed solvent of 3 ml of DMF and 3 ml of methanol was 0.28 g (0.55 mmol) of 1H-2-(1-methyl-4-nitropyrrol-2-yl)benzimidazole-5-[N-[4-[N,N-[bis(2-chloroethyl)amino]phenyl]]carboxamide, followed by the addition of 0.14 ml of 4N hydrochloric acid. Using 0.13 g of 10% Pd/C as a catalyst, the reactant was converted to the corresponding amino derivative by hydrogenation under normal pressure. A DMF solution of the amino derivative was stirred under a nitrogen gas stream and ice-cooling, to which 0.16 ml (1.15 mmol; 2.0 equivalents) of triethylamine and a solution of 4-(N,N-dimethylamino)butyrylchloride in methylene chloride, which had been prepared from 0.14 g (0.84 mmol) of 4-(N,N-dimethylamino)butyric acid hydrochloride, were add successively. The resultant mixture was stirred, as was, for 2 hours and then allowed to stand overnight. The crystals were filtered off and the filtrate was concentrated under reduced pressure. The residue was purified by chromatography on a silica gel column (ethyl acetate/IPA/water=6/2/1; performed twice in total) and was then crystallized from ether-IPA, whereby 0.14 g (0.23 mmol) of the title compound were obtained as pale brown crystals (yield: 41.3%).

IR(KBr)cm$^{-1}$: 3421, 1647, 1636, 1541, 1521

ESI-mass spectrum: m/z ($C_{29}H_{35}N_7O_2Cl_2$) 583.22, Found: 583.85

EXAMPLE 95
(Compound No. 1488)

1H-2-[4-(4-aminobuturylamino)-1-methylpyrrol-2-yl]benzimidazole-5-[N-[4-[N,N-bis(2-chloroethyl) amino]phenyl]]carboxamide (Reaction 1)

1H-2-[1-methyl-4-[4-(benzyloxycarbonylamino) butyrylamino]pyrrol-2-yl]benzimidazole-5-(N-[4-[N, N-bis(2-chloroethyl)amino]phenyl]]carboxamide 1H-2-(1-Methyl-4-nitropyrrol-2-yl)benzimidazole-5-[N-[4-[N,N-bis(2-chloroethyl)amino]phenyl]]carboxamide (0.20 g; 0.40 mmol) was dissolved in a mixed solvent of 3 ml of DMF and 3 ml of methanol, followed by the addition of 0.1 ml of 4N hydrochloric acid. Using 0.14 g of 10% Pd/C as a catalyst, hydrogenation was conducted under normal pressure so that the reactant was converted to its corresponding amino derivative. The DMF solution of the amino derivative was stirred under a nitrogen gas stream and ice cooling, to which 60 μl (0.43 mmol; 1.08 equivalents) of triethylamine and N-[4-(benzyloxycarbonylamino)butyryl] imidazole, which had been prepared from 0.14 g (0.59 mmol; 1.5 equivalents) of 4-(benzyloxycarbonylamino) butyric acid and 0.10 g (0.62 mmol; 1.5 equivalents) of CDI in 3 ml of DMF, were added. The resultant mixture was stirred, as was, for 4 hours and then allowed to stand overnight. The reaction mixture was concentrated under reduced pressure. The residue was purified by chromatography on a silica gel column (chloroform/methanol=96/4) and crystallized from ethyl ether, whereby 0.18 g (0.25 mmol) of the title compound were obtained as pale ocherous crystals (yield: 63.7%).

m.p. 118°–121° C.

(Reaction 2)

1H-2-[4-(4-Aminobutyrylamino)-1-methylpyrrol-2-yl]benzimidazole-5-[N-[4-[N,N-bis(2-chloroethyl) amino]phenyl]]carboxamide 1H-2-[4-[4-(Benzyloxycarbonylamino)butyrylamino]-1-methylpyrrol-2-yl]benzimidazole-5-[N-[4-[N,N-bis(2-chloroethyl)amino]phenyl]]carboxamide (0.15 g; 0.2 mmol) was suspended in methanol, followed by the addition of 60 μl (0.24 mmol) of 4N hydrochloric acid/dioxane. Using 0.07 g of 10% Pd/C as a catalyst, the resultant suspension was hydrogenated under normal pressure. After completion of the reaction was confirmed, the reaction mixture was concentrated under reduced pressure. The residue was added with 4N hydrochloric acid/dioxane, followed by concentration. The concentrate was crystallized from IPA, whereby 0.10 g (0.17 mmol) of the title compound were obtained as yellow crystals (yield: 76.7%).

IR(KBr)cm$^{-1}$: 3364, 3067, 1649, 1567, 1517, 1396, 1330, 1060, 818

EXAMPLE 96
(Compound No. 1536)

1H-2-[1-Methyl-4-(4-morpholinecarbonyl) aminopyrrol-2-yl]benzimidazole-5-[N-[4-[N,N-bis (2-chloroethyl)amino]phenyl]]carboxamide 1H-2-(1-Methyl-4-nitropyrrol-2-yl)benzimidazole-5-[N-[4-[N,N-bis(2-chloroethyl)amino]phenyl]]carboxamide (0.15 g; 0.30 mmol) was dissolved in a mixed solvent of 3 ml of DMF and 4 ml of methanol, followed by the addition of 0.4 ml of 1N hydrochloric acid. Using 0.08 g of 10% Pd/C as a catalyst, hydrogenation was conducted under normal pressure so that the reactant was converted to its corresponding amino derivative. The DMF solution of the amino derivative was stirred under a nitrogen gas atmosphere and ice cooling, to which 0.10 ml (0.72 mmol; 2.4 equivalents) of triethylamine and 50 μl (0.43 mmol; 1.4 equivalents) of 4-morpholinecarbonylchloride were added. The temperature of the resultant mixture was allowed to rise back to room temperature, at which the mixture was stirred for 2.5 hours. The reaction mixture was concentrated under reduced pressure. The residue was purified by chromatography on a silica gel column (chloroform/methanol=92/8) and crystallized from ethyl ether, whereby 0.1 g (0.17 mmol) of the title compound were obtained as reddish white crystals (yield: 57.0%).

IR(KBr)cm$^{-1}$: 3421, 1636, 1518, 1256

Elemental analysis for $C_{28}H_{31}N_7O_3Cl_2 \cdot H_2O$: Calculated: C, 55.82; H, 5.52; N, 16.27 Found: C, 55.58; H, 5.39; N, 16.09

EXAMPLE 97
(Compound No. 1047)

1H-2-[1-Methyl-4-(guanidinoacetylamino)pyrrol-2-yl]benzimidazole-5-[N-[3-[N,N-bis(2-chloroethyl)amino]phenyl]]carboxamide dihydrochloride (Reaction 1)

3-[N,N-Bis(2-chloroethyl)amino]aniline hydrochloride

3-[N,N-Bis(2-chloroethyl)amino]nitrobenzene (2.0 g; 7.6 mmol) was dissolved in 35 ml of concentrated hydrochloric acid, followed by the addition of 6.9 g (30.6 mmol; 4.0 equivalents) of tin(II) chloride dihydrate. The resultant mixture was stirred under heat for 1 hour over an oil bath controlled at 100° C. The reaction mixture was allowed to cool down to room temperature, followed by dilution with water. The diluted solution was basified with concentrated aqueous ammonia and then extracted twice with ethyl acetate. The extract was dried over sodium sulfate and then concentrated under reduced pressure. The residue so obtained was added with 4N hydrochloric acid/dioxane and concentrated. The concentrate was then crystallized from a small amount of methanol/ether, whereby 1.97 g (7.3 mmol) of the title compound were obtained as yellow crystals (yield: 96.1%).

m.p. 195°–201° C.

(Reaction 2)

1H-2-(1-Methyl-4-nitropyrrol-2-yl)benzimidazole-5-[N-[3-[N,N-bis(2-chloroethyl)amino]phenyl]] carboxamide 1H-2-(1-Methyl-4-nitropyrrol-2-yl)benzimidazole-5-carboxylic acid (0.40 g; 1.4 mmol) and 0.38 g (1.4 mmol; 1.0 equivalent) of 3-[N,N-bis(2-chloroethyl)amino]aniline hydrochloride were suspended in 10 ml of DMF, followed by stirring under a nitrogen gas stream and ice cooling. To the reaction mixture, 0.60 ml (4.3 mmol, 3.1 equivalents) of triethylamine and 0.32 ml (2.1 mmol; 1.5 equivalents) of DECP were successively added. The resultant mixture was stirred, as was, for 3.5 hours and the allowed to stand overnight. The reaction mixture was then concentrated under reduced pressure. The residue was purified by chromatography on a silica gel column (chloroform/methanol= 98/2), followed by crystallization from IPA-n-hexane, whereby 0.41 g (0.82 mol) of the title compound were obtained as yellow powder (yield: 58.4%).

(Reaction 3)

1H-2-[4-(guanidinoacetyl)amino-1-methyl-pyrrol-2-yl]benzimidazole-5-[N-[3-[N,N-bis(2-chloroethyl)amino]phenyl]]carboxamide dihydrochloride 1H-2-(1-Methyl-4-nitropyrrol-2-yl)benzimidazole-5-[N-[3-[N,N-bis(2-chloroethyl)amino]phenyl]]carboxamide (0.20 g: 0.40 mmol) was dissolved in a mixed solvent of DMF and methanol, followed by the addition of 0.46 ml of 1N hydrochloric acid. Using 0.11 g of 10% Pd/C as a catalyst, hydrogenation was conducted under normal pressure so that the reactant was converted to its corresponding amino derivative. The DMF solution of the amino derivative was stirred under a nitrogen gas stream and ice cooling, to which 64 μl (0.46 mmol; 1.1 equivalents), 0.18 g (1.17 mmol; 2.9 equivalents) of guanidineacetic acid hydrochloride and 0.25 g (1.21 mmol; 3.0 equivalents) of DCC were successively added. The temperature of the resultant mixture was allowed to rise back to room temperature, at which the mixture was stirred for 5 hours. The reaction mixture was allowed to stand overnight. After the solid so obtained was filtered off, the filtrate was concentrated under reduced pressure. The residue was purified by chromatography on a gel filtration column ("Sephadex LH-20", methanol). Eluted fractions were added with 4N hydrochloric acid/dioxane, concentrated and then washed with ethanol, whereby 0.14 g (0.21 mmol) of the title compound were obtained as white crystals (yield: 53.2%).

m.p. >250° C.

IR(KBr)cm$^{-1}$: 3154, 1657, 1608, 1547, 1497

Elemental analysis for $C_{26}H_{29}N_9O_2Cl_2 \cdot 2HCl \cdot 2.5H_2O$: Calculated: C, 45.36; H, 5.27; N, 18.31; Cl, 20.60 Found: C, 45.67; H, 5.21; N, 18.50 Cl, 20.73

EXAMPLE 98
(Cl$^-$ salt of Compound No. 1056)

2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium chloride In methanol, 80 mg of 2-[N-[1-methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium iodide (I$^-$ salt of Compound No. 1056) were dissolved. The resulting solution was subjected to ion-exchange chromatography ("DOWEX" 1×8, Cl type), whereby I$^-$ ions as counter ions were exchanged by Cl$^-$ ions. The resulting solution was then purified by gel filtration ("Sephadex LH-20"; methanol), whereby 45 mg of the target product were obtained as pale yellow powder (yield: 64.5%).

IR(KBr)cm$^{-1}$: 3418, 1648, 1517, 1417, 1328, 1181, 815

Test 1

To investigate bonding of these compounds with DNA, changes in Tm (melting temperature) were measured. With respect of each of these compounds, the measurement was conducted by determining the difference between Tm measured when a citrated buffer solution of an A(adenine)-T (thymine) DNA copolymer was added with the compound and that measured when the compound was not added. For the measurement, a spectrophotometer ("HITACHI U-3200 MODEL") was used and for temperature control, "HITACHI SPR-10 MODEL" was used. The results are presented in Table 5.

As a result, the pyrrolylbenzimidazole skeleton according to the present invention or a compound having the skeleton as its partial structure was proved to have property to bond to DNA.

Table 5 Effects of Invention Compounds on Tm

TABLE 5

Effects of Invention Compounds on Tm

| Comp'd. No. | ΔTm(°C.) |
| --- | --- |
| 318 | 7 |

TABLE 5-continued

Effects of Invention Compounds on Tm

| Comp'd. No. | ΔTm(°C.) |
|---|---|
| 4 | 17 |
| Distamycin | 10 |

Test 2

A description will next be made of antitumor activities of these compounds. Antitumor activities of representative compounds are shown in Table 6. Their antitumor activities were determined by measuring their in vitro inhibition of proliferation of tumored cells. Namely, mouse B16 melanoma cells were spread over a 96-well culture plate. One day later, each drug was applied. The melanoma cells were then incubated for 3 days in 5% $CO_2$ at 37° C. Following the method reported in Cancer Res., 48, 589–601(1988), the concentration of the drug required to induce 50% inhibition on the proliferation was determined. As a comparative example, the results obtained from the application of distamycin are also shown.

TABLE 6

Antitumor Activity

| Compound | 50% Inhibition (μg/mL) |
|---|---|
| 1 | 0.23 |
| 2 | 0.25 |
| 3 | 0.019 |
| 4 | 0.04 |
| 6 | 0.02 |
| 13 | 0.01 |
| 14 | 0.57 |
| 15 | 0.057 |
| 16 | 0.6 |
| 129 | 0.18 |
| 223 | 1.1 |
| 247 | 2.6 |
| 260 | 0.034 |
| 305 | 4.2 |
| 310 | 0.76 |
| 318 | 19.8 |
| 326 | 12.0 |
| 336 | 0.24 |
| 342 | 0.78 |
| 342 | 0.045 |
| 424 | 0.08 |
| 438 | 42.8 |
| 1001 | 0.53 |
| 1003 | 0.018 |
| 1004 | 0.047 |
| 1005 | 0.65 |
| 1009 | 2.31 |
| 1013 | 0.34 |
| 1017 | 0.78 |
| 1024 | 0.586 |
| 1042 | 3.49 |
| 1047 | 0.0946 |
| 1048 | 5.58 |
| 1049 | 0.274 |
| 1056 | 0.25 |
| 1072 | 0.51 |
| 1076 (I' salt) | 0.51 |
| 1076 (Cl' salt) | 0.45 |
| 1077 | 0.29 |
| 1208 | 2.05 |
| 1256 | 4.67 |
| 1260 | 3.1 |
| 1464 | 0.033 |
| 1480 | 0.16 |
| 1488 | 2.85 |
| 1520 | 0.33 |
| 1524 | 0.6 |
| 1528 | 0.22 |
| 1536 | 0.53 |
| 1585 | 0.1 |
| 1589 | 0.41 |
| 1590 | 0.53 |
| 1592 | 0.61 |
| 1604 | 0.43 |
| 1617 | 0.12 |
| 2001 | 0.005 |
| 2089 | 0.0057 |
| Distamycin | 36.0 |

Test 3

In vivo antitumor activities of these compounds were also studied. P388 leukemia cells ($10^6$ cells/mouse) were intraperitoneally transplanted to female $CDF_1$ mice. One, five and nine days later, each compound was intraperitoneally administered (at 1, 3 or 10 mg/kg) to the mice. As a blank test, 5% glucose was intraperitoneally administered at 10 ml/kg to mice. Based on the group of the mice in the blank test as a control group, the effects of the individual drugs are shown in terms of ILS. The term "ILS" is represented by the following formula:

$$ILS = \frac{\text{Number of survived days of a group subjected to drug test} - \text{Number of survived days of the control group}}{\text{Number of survived days of the control group}} \times 100$$

When test animals survived 8 weeks after the administration, the number of those survived was recorded without calculation of ILS. The results are shown in Table 7.

TABLE 7

Antitumor Activity in vivo

| Compound | Concentration administered (μg/mL) | ILS | Survived After 8 weeks/ Tested Animals |
|---|---|---|---|
| 1 | 1 | 38 | |
| 2 | 1 | 59 | 2/5 (3) |
| 6 | 1 | 94 | |
| 13 | 1 | 123 | 3/5 (3) |
| 305 | 10 | 22 | |
| 310 | 1 | 88 | |
| 1001 | 10 | 115 | |
| 2001 | 10 | 47 | |

The number in parentheses indicate the concentration of compound corresponds

Test 4

Prepared was a $1 \times 10^7$ cells/ml suspension of Colon 26 mouse colon cancer cells in HBSS (Hanks' Balanced Salt Solution). A 0.1 ml portion of the cell suspension was subcutaneously transplanted to a lateroabdominal part of each female $CDF_1$ mouse. After the body weight of the mouse was measured on the following day of the transplantation of the tumor, a solution of a compound (5% glucose solution containing 5% of "Tween 80") was administered into the caudal vein of the mouse. On day 15, a tumor was excised and its weight was measured.

The percentage of the average tumor weight of each experiment group as calculated by supposing that the average tumor weight of the control group not administered with any drug was 100% was calculated as a T/C value.

The results are presented in Table 8. Corresponding to each compound number, its T/C value is shown. The number in parentheses indicates the concentration of the drug when the T/C value was indicated.

TABLE 8

The results of Test 4

| table 8 Compound | T/C (%) (Concn.mg/Kg) |
|---|---|
| 1 | 29 (2) |
| 1001 | 7 (6) |
| 1003 | 41 (0.3) |
| 1005 | 20 (15) |
| 1009 | 29 (10) |
| 1013 | 58 (3) |
| 1017 | 30 (3) |
| 1024 | 61 (10) |
| 1056 | 1 (15) |
| 1256 | 60 (15) |
| Adriamycin | 40 (20) |

Advantages of the Invention

As is evident from the tests, the compounds according to the present invention act on DNA and are useful as anticancer agents.

We claim:

1. A compound represented by the following chemical formula (1) or a pharmacologically acceptable salt thereof:

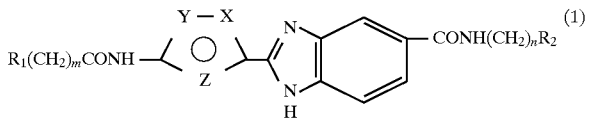

wherein X, Y and Z each independently means CH, N, NH, N(CHD)$_t$CH$_3$, S or O with the proviso that X, Y and Z do not al have the same meaning at the same time and t is an integer of 0–5, m and n are integers of 0–5, R$_1$ and R$_2$ each independently means a hydrogen atom, a C$_{1-20}$ alkyl group, a C$_{1-10}$ haloalkyl group, a C$_{1-10}$ alkoxyl group, a hydroxyl group, a C$_{1-10}$ alkylthio group, a substituted or unsubstituted amino group, a substituted or unsubstituted ammonium group, a substituted or unsubstituted sulfonium group, a substituted or unsubstituted phenyl group, a substituted or unsubstituted 5-membered heterocycle; a substituted or unsubstituted 6-membered heterocycle, a substituted or unsubstituted fused heterocycle substituted or unsubstituted amindino group, a substituted or unsubstituted guanidino group, an amino acid residual group, or a group represented by the following chemical formula (2)

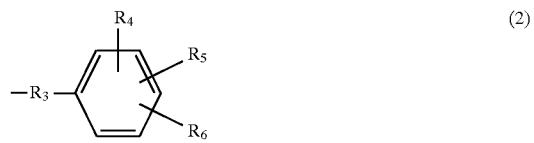

wherein R$_3$ means (CH$_2$)$_r$ or (CH$_2$)$_r$O in which r stands for an integer of 0–5 and the O atom is located closer to the phenyl group, R$_4$ means a hydrogen atom, a C$_{1-10}$ alkyl group, a C$_{1-10}$ alkoxyl group, a halogen atom, a trifluoromethyl group, a cyano group, an amidino group, a guanidino group, a carboxyl group or —COR$_7$ in which R$_7$ means C$_{1-5}$ alkyl group, an alkylamino group which may be substituted by a substituted amino group, an amino group which may be substituted by a substituted or unsubstituted phenyl group, or a substituted or unsubstituted benzylamino group, R$_5$ means a hydrogen atom, a C$_{1-10}$ alkyl group, a C$_{1-10}$ alkyoxyl group, a halogen atom, or —(CH$_2$)$_p$N(R$_8$)$_2$ or —(CH$_2$)$_p$NR$_8$R$_9$ in which p stand for an integer of 0–5 or R$_4$ or R$_5$ may form a ring when R$_4$ and R$_5$ take mutually adjacent positions, R$_6$ means a hydrogen atom, —(CH$_2$)$_p$N (R$_8$)$_2$ or —(CH$_2$)$_p$NR$_8$R$_9$ wherein in each case of R$_5$ and R$_6$, R$_8$ means —CH$_2$CH$_2$W, R$_9$ means a C$_{1-5}$ alkyl group or a mesyl group, W means a halogen atom, a hydroxyl group, a mesyloxy group, a tosyloxy group or —OCOR$_7$ in which R$_7$ and p have the same meanings as defined above.

2. A compound according to claim 1, wherein the 5-membered ring containing X, Y and Z is selected from any one of pyrrole, 1-methylpyrrole, imidazole, 1-methylimidazole, furan and thiophene.

3. A compound or a pharmacologically acceptable salt thereof according to claim 2, wherein R$_1$ means a C$_{1-10}$ haloalkyl group or a group represented by the chemical formula (2).

4. A compound or a pharmacologically acceptable salt thereof according to claim 2, wherein R$_2$ means a C$_{1-10}$ haloalkyl group or a group represented by the chemical formula (2).

5. A compound or a pharmacologically acceptable salt thereof according to claim 3, wherein R$_2$ means a C$_{1-10}$ haloalkyl group or a group represented by the chemical formula (2).

6. A compound or a pharmacologically acceptable salt thereof according to claim 3, wherein R$_2$ means a substituted or unsubstituted amino, guanidino or amidino group.

7. A compound or a pharmacologically acceptable salt thereof according to claim 6, wherein R$_2$ means an unsubstituted amino, guanidino or amidino group.

8. A compound or pharmacologically acceptable salt thereof according to claim 4, wherein R$_1$ means a substituted or unsubstituted amino, guanidino or amidino group.

9. A compound or pharmacologically acceptable salt thereof according to claim 8, wherein R$_1$ means an unsubstituted amino, guanidino or amidino group.

10. A compound or pharmacologically acceptable salt thereof according to claim 4, wherein R$_1$ means a substituted or unsubstituted ammonium or sulfonium group.

11. A compound or pharmacologically acceptable salt thereof according to claim 10, wherein R$_1$ is a trimethylammonium, N-methylpicoryl or dimethylsulfonium group.

12. A compound or pharmacologically acceptable salt thereof according to claim 4, wherein R$_1$ means a C$_{1-10}$ alkylthio group.

13. A pharmaceutical composition comprising as an active ingredient the compound or the pharmacologically acceptable salt thereof according to claim 1.

14. An anticancer composition comprising as an active ingredient the compound or the pharmacologically acceptable salt thereof according to claim 1.

15. An antiviral composition comprising as an active ingredient the compound or the pharmacologically acceptable salt thereof according to claim 1.

16. An antimicrobial composition comprising as an active ingredient the compound or the pharmacologically acceptable salt thereof according to claim 1.

17. A process for preparing a compound represented by the chemical formula (1), which comprises reacting a compound represented by the chemical formula (7) with a carboxylic acid derivative represented by the chemical formula (8):

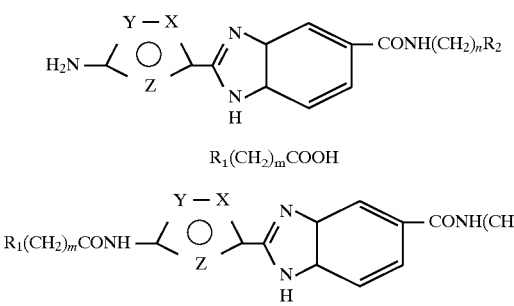

$$H_2N\underset{Z}{\overset{Y-X}{\diagdown\!\!O\!\!\diagup}}\overset{N}{\underset{N\atop H}{\diagdown\!\!\diagup}}-CONH(CH_2)_nR_2 \quad (7)$$

$$R_1(CH_2)_mCOOH \quad (8)$$

$$R_1(CH_2)_mCONH\underset{Z}{\overset{Y-X}{\diagdown\!\!O\!\!\diagup}}\overset{N}{\underset{N\atop H}{\diagdown\!\!\diagup}}-CONH(CH_2)_nR_2 \quad (1)$$

wherein X, Y and Z each independently means CH, N, NH, N(CH$_2$)$_t$CH$_3$, S or O with the proviso that X, Y and Z do not all have the same meaning at the same time and t is an integer of 0–5, m and n are integers of 0–5, R$_1$ and R$_2$ each independently means a hydrogen atom, a C$_{1-20}$ alkyl group, a C$_{1-10}$ haloalkyl group, a C$_{1-10}$ alkoxyl group, a hydroxyl group, a C$_{1-10}$ alkylthio group, a substituted or unsubstituted amino group, a substituted or unsubstituted ammonium group, a substituted or unsubstituted sulfonium group, a substituted or unsubstituted phenyl group, a substituted or unsubstituted 5-membered heteroring, a substituted or unsubstituted 6-membered heteroring, a substituted or unsubstituted fused heteroring, substituted or unsubstituted amidino group, a substituted or unsubstituted guanidino group, an amino acid residual group, or a group represented by the chemical formula (2):

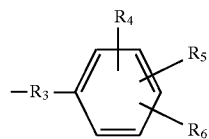

(2)

wherein R$_3$ means (CH$_2$)$_r$ or (CH$_2$)$_r$O in which r stands for an integer of 0–5 and the O atom is located closer to the phenyl group, R$_4$ means a hydrogen atom, a C$_{1-10}$ alkyl group, a C$_{1-10}$ alkoxyl group, a halogen atom, a trifluoromethyl group, a cyano group, an amidino group, a guanidino group, a carboxyl group or —COR$_7$ in which R$_7$ means a C$_{1-5}$ alkyl group, an alkylamino group which may be substituted by a substituted or unsubstituted amino group, an amino group which may be substituted by a substituted or unsubstituted phenyl group, or a substituted or unsubstituted benzylamino group, R$_5$ means a hydrogen atom, a C$_{1-10}$ alkyl group, a C$_{1-10}$ alkoxyl group, a halogen atom, or —(CH$_2$)$_p$N(R$_8$)$_2$ or —(CH$_2$)$_p$NR$_8$R$_9$ in which p stands for an integer of 0–5, or R$_4$ and R$_5$ may form a ring when R$_4$ and R$_5$ take mutually adjacent positions, R$_6$ means a hydrogen atom, —(CH$_2$)$_p$N(R$_8$)$_2$ or —(CH$_2$)$_p$NR$_8$R$_9$ wherein in each case of R$_5$ and R$_6$, R$_8$ means —CH$_2$CH$_2$W, R$_9$ means a C$_{1-5}$ alkyl group or a mesyl group, W means a halogen atom, a hydroxyl group, a mesyloxy group, a tosyloxy group or —OCOR$_7$ in which R$_7$ and p have the same meaning as defined above.

18. A preparation process according to claim 17, wherein the 5-membered ring containing X, Y and Z is selected from any one of pyrrole, 1-methylpyrrole, imidazole, 1-methylimidazole, furan and thiophene.

\* \* \* \* \*

UNITED STATES PATENT AND TRADEMARK OFFICE
CERTIFICATE OF CORRECTION

PATENT NO. : 5,852,011

Page 1 of 2

DATED: : December 22, 1998

INVENTOR(S) : Akio MATSUNAGA et al

It is certified that error appears in the above-identified patent and that said Letters Patent is hereby corrected as shown below:

On the title page: Item [56] insert the following:

U.S. PATENT DOCUMENTS 5,273,991    12/93    Lee

FOREIGN PATENT DOCUMENTS 246868         11/87    Europe
WO93/13739   7/93     WIPO
6-92933        4/94     Japan

OTHER DOCUMENTS

M. Alley et al, "Feasibility of Drug Screening with Panels of Human Tumor Cell Lines Using a Microculture Tetrazolium Assay", Cancer Research", 48, 589-601, February 1, 1988.

G. Gravatt et al, "DNA-Directed Alkylating Agents, 4,4-Anilinoquinoline-Based Minor Groove Directed Aniline Mustards", J. Med. Chem., 34, 1552-1561, 1991.

B. Palmer et al, "Hypoxia-Selective Antitumor Agents. 3. Relationships Between Structure and Cytotoxicity against Cultured Tumor Cells for Substituted N,N-Bis(2-chloroethyl)anilines", J. Med. Chem., 33, 112-121, 1990.

J.L. Everett, "Aryl-2-halogenoalkylamines. Part II", J. Chem. Soc., 1972-1983, 1949.

K. Valu et al, "DNA-Directed Akylating Agents. 3. Structure-Activity Relationships for Acridine-Linked Aniline Mustards: Consequences of Varying the Length of the Linker Chain", J. Med. Chem., 33, 3014-3019, 1990.

K. Fukui et al, "Methioninemethylsulfonium Salts", Synthesis of Monomeric Silanes, Vol. 25, 804-807, 1960.

E. Nishiwaki et al, "Efficient Synthesis of Oligo-N-Methylpyrrolecarboxamides and Related Compounds", Heteroxycles, Vol. 27, 1945-1952, 1988.

UNITED STATES PATENT AND TRADEMARK OFFICE
CERTIFICATE OF CORRECTION

PATENT NO. : 5,852,011

DATED : December 22, 1998

INVENTOR(S) : Akio MATSUNAGA et al

It is certified that error appears in the above-identified patent and that said Letters Patent is hereby corrected as shown below:

OTHER DOCUMENTS

M. Bialer et al, "A Total Synthesis of Distamycin A, an Antiviral Antibiotic", Tetrahedron, Vol. 34, 2389-2391, 1978.

B. Yadagiri et al, "Convenient Routes to Substituted Benzimidazoles and Imidazolo[4,5-b]Pyridines Using Nitrobenzene as Oxidant", Synthetic Communication, 20(7), 955-963, 1990.

A. Ramirez et al, "Structure and Synthesis of Distamycin A", Nature, Vol. 203, 1064-1065, 1964.

B. Baker et al, "Sequence-Specific Cleavage of Double-Helical DNA, N-Bromoacetyldistamycin", J. Am. Chem. Soc., 107, 8266-8268, 1985.

F. Arcamone et al, "Synthesis, DNA-Binding Properties, and Antitumor Activity of Novel Distamycin Derivatives", J. Med. Chem., 32, 774-778, 1989.

IN THE CLAIMS:

In claim 1, line 37, delete "N(CHD)$_x$CH$_3$" and insert --N(CH$_2$)$_x$CH$_3$--

Signed and Sealed this

Fourth Day of January, 2000

Attest:

Attesting Officer

*Acting Commissioner of Patents and Trademarks*